United States Patent
Link et al.

(10) Patent No.: US 6,576,630 B1
(45) Date of Patent: Jun. 10, 2003

(54) COMPOUNDS AND COMPOSITIONS AS PROTEASE INHIBITORS

(75) Inventors: John O. Link, San Francisco, CA (US); Arnold J. Martelli, Burlingame, CA (US); Valeri Martichonok, San Francisco, CA (US); John W. Patterson, Mountain View, CA (US); Oliver L. Saunders, Burlingame, CA (US); Sheila Zipfel, Palo Alto, CA (US)

(73) Assignee: AXYS Pharmaceuticals, Inc., So. San Francisco, CA (US)

( * ) Notice: Subject to any disclaimer, the term of this patent is extended or adjusted under 35 U.S.C. 154(b) by 0 days.

(21) Appl. No.: 09/525,507

(22) Filed: Mar. 15, 2000

Related U.S. Application Data

(60) Provisional application No. 60/124,421, filed on Mar. 15, 1999.

(51) Int. Cl.[7] .................... C07D 263/56; C07D 263/34; C07D 413/12; A61K 31/42; A61D 37/00
(52) U.S. Cl. .................. 514/233.8; 514/253.1; 514/255.05; 514/318; 514/321; 514/338; 514/375; 544/124; 544/138; 544/369; 544/405; 546/193; 546/195; 546/271.5; 548/217
(58) Field of Search ................. 544/124, 138, 544/369, 405; 546/193, 198, 271.5, 271.4; 514/232.8, 253.1, 255.05, 321, 338, 318, 375; 548/217

(56) References Cited

U.S. PATENT DOCUMENTS

| | | | |
|---|---|---|---|
| 5,847,135 A | * 12/1998 | Bemis | 544/264 |
| 5,874,424 A | * 2/1999 | Batchelor et al. | |
| 6,004,933 A | 12/1999 | Spruce et al. | 514/17 |
| 6,022,861 A | * 2/2000 | Scarborough et al. | 514/18 |
| 6,114,310 A | * 9/2000 | Chamberland et al. | |

FOREIGN PATENT DOCUMENTS

| | | |
|---|---|---|
| EP | 0291234 | 11/1988 |
| EP | 0376012 | 7/1990 |
| WO | WO 96/21655 | 7/1996 |
| WO | WO 98/49190 | 11/1996 |
| WO | WO 96/40744 | 12/1996 |
| WO | WO 98/01428 | 1/1998 |
| WO | WO 98/05336 | 2/1998 |
| WO | WO 98/08802 | 3/1998 |
| WO | WO 98/21188 | 5/1998 |
| WO | WO 00/51998 | 9/2000 |
| WO | WO 00/51998 A1 * | 9/2000 |

OTHER PUBLICATIONS

Jeffrey A. Cohen et al., "Therapy of relapsing multiple sclerosis. Treatment approaches for nonresponders", *Journal of Neuroimmunology*, 98: 29–36 (1999).

D. Hallegua et al., "Cyclosporine for lupus membranous nephritis: experience with ten patients and review of the literature", *Lupus*, 9: 241–251 (2000).

C.H. Polman, BMJ Uitdehaag, "Drug treatment of multiple sclerosis", *BMJ*, 321: 19–26 (2000).

Richard J. Riese et al., "Essential Role for Cathesin S in MHC Class II–Associated Invariant Chain Processing and Peptide Loading", *Immunity*, 4: 357–366 (Apr. 1996).

Mamoru Suzuki et al., "Synthesis of 2–Aryl–4(3–thienyl)imidazole Derivatives with Antinflammatory Properties [1]", *Chem. Pharm. Bull*, 34(8): 3111–3120 (1996).

Tamon Moriya et al., "Synthesis and Hypolipidemic Activities of 5–Thienyl–4–oxazoleacetic Acid Derivatives[1"] *J. Med. Chem.*, 29: 333–341 (1986).

Ming Tao et al., "Inhibition of Calpain By Peptidyl Heterocycles", *Bioorganic & Medicinal Chemnistry Letters*, 6:24 3009–3112 (1996).

Julian Adams et al., "Potent and Selective Inhibitors of the Proteasom: Dipeptidyl Boronic Acids", *Biooganic & Medicinal Chemistry Letters*, 8: 333–338 (1998).

Edwards et al., "Design, Synthesis, and Kinetic Evaluation of a Unique Class of Elastase Inhibitors, the Peptidyl a–Ketobenzoxazoles, and the X–ray Crystal Structure of the Covalent Complex between Porcine Pancreatic Elastase and Ac–Ala–Pro–Val–2–Benzoxazole" Journal of American Chemical Society, vol. 114, No. 5, p 1854–1863 (1992).

Tsutsumi, et al., "Synthesis and Structure–Activity Relationships of Peptidyl a–Keto Heterocycles as Novel Inhibitors of Prolyl Endopeptidase" Journal of Medicinal Chemistry, vol. 37, No. 21, p 3492–3502 (1994).

Ogilvie W. et al."Peptidomimetic inhibitors of the human cytomegalovirus protease" Journal of Medicinal Chemistry vol. 40 No. 25 (1997).

Evoli, A. et al, Drugs, 1996, 52(5), 662–70, abstract only.*
Heitmiller, R.F., Semin. Thorac. Cardiovasc. Surg., 1999, 11(1), 41–6, abstract only.*
Polman, C.H. et al, BMJ 2000, 321, 490–4.*
Cohen, J.A. et al, J. Neuroimmun., 1999, 98 29–36.*
Levy, E.G., Baillieres Clin. Endocrinol. Metab., 1997, 11(3) 585–595.*
Hallegua, D. et al, Lupus, 2000, 9, 241–251.*
Khamashta, M.A. et al, Expert. Opin. Investig. Drugs, 2000, 9(7), 1581–93.*
Ogilvie, W. et al, J. Med. Chem., 1997, 40, 4113–4135.*

* cited by examiner

Primary Examiner—Richard L. Raymond
Assistant Examiner—Thomas McKenzie
(74) Attorney, Agent, or Firm—Townsend and Townsend and Crew LLP

(57) ABSTRACT

The present invention relates to novel alkanoyl-substituted heterocyclic derivatives which are cysteine protease inhibitors; the pharmaceutically acceptable salts and N-oxides thereof; their uses as therapeutic agents and the methods of their making.

16 Claims, No Drawings

COMPOUNDS AND COMPOSITIONS AS PROTEASE INHIBITORS

This application claims the benefit under U.S.C. Sec 119 (e)(1) of prior filed U.S. Provisional Application No. 60/124, 421 filed Mar. 15, 1999.

THE INVENTION

This application relates to compounds and compositions for treating diseases associated with cysteine protease activity, particularly diseases associated with activity of cathepsins B, K, L or S.

DESCRIPTION OF THE FIELD

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g. as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteo arthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in ososteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

In view of the number of diseases wherein it is recognized that an increase in cysteine protease activity contributes to the pathology and/or symptomatology of the disease, molecules which are shown to inhibit the activity of this class of enzymes, in particular molecules which are inhibitors of cathepsins B, K, L and/or S, will be useful as therapeutic agents.

SUMMARY OF THE INVENTION

In one particular embodiment, the present invention relates to protease inhibitors of Formula I:

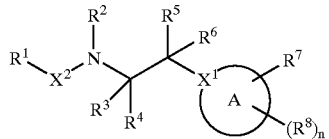

in which:
A comprises a heteromonocyclic ring containing 5 to 6 ring member atoms or a fused heteropolycyclic ring system containing 8 to 14 ring member atoms, wherein each ring contains 5 to 7 ring member atoms, $X^1$ is a ring member carbon atom and each ring member atom other than $X^1$ is a carbon atom or a heteroatom, with the proviso that (i) at least one ring member atom is a heteroatom and (ii) when A is a heteromonocyclic radical containing 5 ring member atoms, no more than two of the ring member atoms comprising A are heteroatoms;

n is 0, 1, 2 or 3;

$X^1$ is =C— or —CH—;

$X^2$ is a bond or a divalent group of Formula (a) or (b):

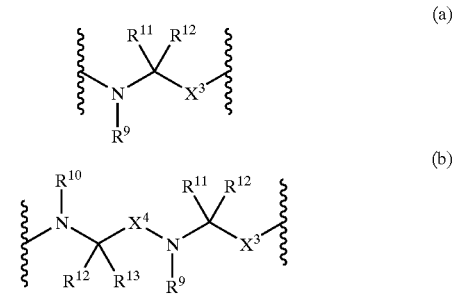

wherein:
$X^3$ and $X^4$ independently are —C(O)— or —CH$_2$S(O)$_2$—

$R^9$ and $R^{10}$ independently are hydrogen, $(C_{1-6})$alkyl or as defined below;

$R^{11}$ at each occurrence independently is hydrogen or $(C_{1-6})$alkyl;

$R^{12}$ and $R^{13}$ independently are (i) $(C_{1-6})$alkyl optionally substituted with cyano, halo, nitro, —NR$^{14}$R$^{14}$, —NR$^{14}$C(O)OR$^{14}$, —NR$^{14}$C(O)NR$^{14}$R$^{14}$, —NR$^{14}$C(NR$^{14}$)NR$^{14}$R$^{14}$, —OR$^{14}$, —SR$^{14}$, —C(O)OR$^{14}$, —C(O)NR$^{14}$R$^{14}$, —S(O)$_2$NR$^{14}$R$^{14}$, —P(O)(OR$^{14}$)OR$^{14}$, —OP(O)(OR$^{14}$)OR$^{14}$, —NR$^{14}$C(O)R$^{15}$, —S(O)R$^{15}$, —S(O)$_2$R$^{15}$, —C(O)R$^{15}$, —OR$^{16}$, —SR$^{16}$, —S(O)R$^{16}$, —S(O)$_2$R$^{16}$, —C(O)R$^{16}$, —C(O)OR$^{16}$, —OC(O)R$^{16}$, —NR$^{16}$R$^{17}$, —NR$^{17}$C(O)R$^{16}$, —NR$^{17}$C(O)OR$^{16}$, —C(O)NR$^{16}$R$^{17}$, —S(O)$_2$NR$^{16}$R$^{17}$, —NR$^{17}$C(O)NR$^{16}$R$^{17}$ or —NR$^{17}$C(NR$^{17}$)NR$^{16}$R$^{17}$, wherein R$^{14}$ at each occurrence independently is hydrogen, $(C_{1-6})$alkyl or halo-substituted $(C_{1-3})$alkyl, R$^{15}$ is $(C_{1-6})$alkyl or halo-substituted $(C_{1-3})$alkyl, halo, $(C_{1-6})$alkyl or R$^{16}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl and R$^{17}$ is hydrogen or $(C_{1-6})$alkyl, and wherein within R$^{16}$ said cycloalkyl, heterocycloalkyl, aryl, heteroaryl, polycycloaryl or heterpolycycloaryl ring optionally is substituted by a group selected from —$R^{18}$, —$X^5OR^{18}$, —$X^5SR^{18}$, —$X^5S(O)R^{18}$, —$X^5S(O)_2R^{18}$, —$X^5C(O)R^{18}$, —$X^5C(O)OR^{18}$, —$X^5OC(O)R^{18}$, —$X^5NR^{18}R^{19}$, —$X^5NR^{19}C(O)R^{18}$, —$X^5NR^{19}C(O)OR^{18}$, —$X^5C(O)NR^{18}R^{19}$, —$X^5S(O)_2NR^{18}R^{19}$, —$X^5NR^{19}C(O)NR^{18}R^{19}$ or —$X^5NR^{19}C(NR^{19})NR^{18}R^{19}$, wherein $X^5$ is a bond or $(C_{1-6})$alkylene, $R^{18}$ is hydrogen or $(C_{1-6})$alkyl and $R^{19}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl, or (ii) a group selected from $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl and hetero$(C_{8-12})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from —$R^{18}$, —$X^5OR^{18}$, —$X^5SR^{18}$, —$X^5S(O)R^{18}$, —$X^5S(O)_2R^{18}$, —$X^5C(O)R^{18}$, —$X^5C(O)OR^{18}$, —$X^5OC(O)R^{18}$, —$X^5NR^{18}R^{19}$, —$X^5NR^{19}C(O)R^{18}$, —$X^5NR^{19}C(O)OR^{18}$, —$X^5C(O)NR^{18}R^{19}$, —$X^5S(O)_2NR^{18}R^{19}$, —$X^5NR^{19}C(O)NR^{18}R^{19}$ or —$X^5NR^{19}C(NR^{19})NR^{18}R^{19}$, wherein $X^5$, $R^{18}$ and $R^{19}$ are as defined above; wherein within $R^{12}$ and/or $R^{13}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above; or $R^{12}$ together with $R^9$ and/or $R^{13}$ together with $R^{10}$ form trimethylene, tetramethylene or phenylene-1,2-dimethylene, optionally substituted with 1 to 3 radicals independently selected from $(C_{1-6})$alkyl, $(C_{1-6})$alkylidene, cyano, halo, halo-substituted $(C_{1-4})$alkyl, nitro, oxo, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^{55}NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above; and $R^1$ is —$X^6X^7R^{20}$, wherein $X^6$ is —C(O)—, —C(O)C(O)— or —S(O)_2—, $X^7$ is a bond, —O— or —$NR^{21}$—, wherein $R^{21}$ is hydrogen or $(C_{1-6})$alkyl, and $R^{20}$ is (i) $(C_{1-6})$alkyl optionally substituted by cyano, halo, nitro, —$NR^{14}R^{14}$, —$NR^{14}C(O)OR^{14}$, —$NR^{14}C(O)NR^{14}R^{14}$, —$NR^{14}C(NR^{14})NR^{14}R^{14}$, —$OR^{14}$, —$SR^{14}$, —$C(O)OR^{14}$, —$C(O)NR^{14}R^{14}$, —$S(O)_2NR^{14}R^{14}$, —$P(O)(OR^{14})OR^{14}$, —$OP(O)(OR^{14})OR^{14}$, —$NR^{14}C(O)R^{15}$, —$S(O)R^{15}$, —$S(O)_2R^{15}$, —$C(O)R^{15}$, —$OR^{22}$, —$SR^{22}$, —$S(O)R^{22}$, —$S(O)_2R^{22}$, —$C(O)R^{22}$, —$C(O)OR^{22}$, —$C(O)NR^{22}R^{23}$, —$NR^{22}R^{23}$, —$NR^{23}C(O)R^{22}$, —$NR^{23}C(O)OR^{22}$, —$NR^{23}C(O)NR^{22}R^{23}$ or —$NR^{23}C(NR^{23})NR^{22}R^{23}$, wherein $R^{14}$ and $R^{15}$ are as defined above, $R^{22}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-6})$alkyl or hetero$(C_{8-12})$bicycloaryl$(C_{0-6})$alkyl and $R^{23}$ at each occurrence independently is hydrogen or $(C_{1-6})$alkyl, or (ii) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-6})$alkyl or hetero$(C_{8-12})$bicycloaryl$(C_{0-6})$alkyl or (iii) $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl, wherein said cycloalkyl, heterocycloalkyl, phenyl or heteroaryl is substituted by —$R^{24}$, —$X^5OR^{24}$, —$X^5SR^{24}$, —$X^5S(O)R^{24}$, —$X^5S(O)_2R^{24}$, —$X^5C(O)R^{24}$, —$X^5C(O)OR^{24}$ —$X^5C(O)NR^{24}R^{25}$, —$X^5NR^{24}R^{25}$, —$X^5NR^{25}C(O)R^{24}$, —$X^5NR^{25}C(O)OR^{24}$, —$X^5NR^{25}C(O)NR^{24}R^{25}$ or —$X^5NR^{25}C(NR^{25})NR^{24}R^{25}$, wherein $X^5$ is as defined above, $R^{24}$ is $(C_{3-6})$cycloalkyl$(C_{0-6})$alkyl, hetero$(C_{3-6}$cycloalkyl$(C_{0-6})$alkyl, phenyl$(C_{0-6})$alkyl or hetero$(C_{5-6})$aryl$(C_{0-6})$alkyl and $R^{25}$ at each occurrence independently is hydrogen or $(C_{1-6})$alkyl; wherein within $R^1$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above; or when $X^2$ is a divalent group of formula (a) or (b) then $R^1$ may also represent hydrogen, carboxy, oxalo or carbamoyl;

$R^2$ is hydrogen or $(C_{1-6})$alkyl;

$R^3$ is (i) $(C_{1-6})$alkyl optionally substituted with cyano, halo, nitro, —$SR^{26}$, —$C(O)OR^{26}$, —$C(O)NR^{26}R^{26}$, —$P(O)(OR^{26})OR^{26}$, —$OP(O)(OR^{26})OR^{26}$, —$S(O)R^{27}$, —$S(O)_2R^{27}$ or —$C(O)R^{27}$, wherein $R^{26}$ at each occurrence independently is hydrogen, $(C_{1-6})$alkyl or halo-substituted $(C_{1-3})$alkyl and $R^{27}$ is $(C_{1-6})$alkyl or halo-substituted $(C_{1-3})$alkyl, or (ii) $(C_{5-6})$cycloalkyl$(C_{2-3})$alkyl, hetero$(C_{3-6})$cycloalkyl$(C_{2-3})$alkyl, $(C_{6-12})$aryl$(C_{2-3})$alkyl or hetero$(C_{5-6})$aryl$(C_{2-3})$alkyl, wherein said cycloalkyl, heterocycloalkyl, aryl or heteroaryl optionally is substituted further with 1 to 5 radicals independently selected from $(C_{1-6})$alkyl, $(C_{1-6})$alkylidene, cyano, halo, halo-substituted $(C_{1-4})$alkyl, nitro, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above, provided that when $R^3$ is unsubstituted $(C_{1-5})$alkyl and $R^4$ is hydrogen or unsubstituted $(C_{1-5})$alkyl, then $X^2$ may not represent (i) a bond when $R^1$ is —$C(O)R^{20}$, —$C(O)_2R^{20}$ or —$S(O)_2R^{20}$ in which $R^{20}$ is $(C_{1-6})$alkyl, phenyl$(C_{1-4})$alkyl, phenyl, $(C_{3-7})$cycloalkyl, camphan-10-yl, naphth-1-yl, naphth-2-yl, phenyl substituted by one or more of $(C_{1-4})$alkyl, perfluoro$(C_{1-4})$alkyl, $(C_{1-4})$alkoxy, hydroxy, halo, amido, nitro, amino, $(C_{1-4})$alkylamino, $(C_{1-4})$dialkylamino, carboxy or $(C_{1-4})$alkoxycarbonyl, or naphth-1-yl or naphth-2-yl substituted by one or more of $(C_{1-4})$alkyl, perfluoro$(C_{1-4})$alkyl, $(C_{1-4})$alkoxy, hydroxy, halo, amido, nitro, amino, carboxy or $(C_{1-4})$alkoxycarbonyl or (ii) a divalent group of formula (a) or (b) in which the moiety $R^{12}$ is methyl, isopropyl, n-butyl, sec-butyl, tert-butyl, 1-methylpropyl, benzyl, naphth-1-ylmethyl, naphth-2-ylmethyl, thien-2-ylmethyl, thien-3-ylmethyl, or wherein $R^9$ and $R^{12}$ form ethylene, trimethylene, hydroxy-substituted trimethylene, tetramethylene or phenylene-1,2-dimethylene; or $R^3$ and $R^4$ taken together with the carbon atom to which both $R^3$ and $R^4$ are attached form $(C_{3-8})$cycloalkylene or $(C_{3-8})$heterocycloalkylene, wherein said cycloalkylene or heterocycloalkylene is optionally substituted with 1 to 3 radicals independently selected from $(C_{1-6})$alkyl, $(C_{1-6})$alkylidene, cyano, halo, halo-substituted $(C_{1-4})$alkyl, nitro, $—X^5NR^{14}C(O)OR^{14}$, $—X^5NR^{14}C(O)NR^{14}R^{14}$, $—X^5NR^{14}C(NR^{14})NR^{14}R^{14}$, $—X^5OR^{14}$, $—X^5SR^{14}$, $—X^5C(O)OR^{14}$, $—X^5C(O)NR^{14}R^{14}$, $—X^5S(O)_2NR^{14}R^{14}$, $—X^5P(O)(OR^{14})OR^{14}$, $—X^5OP(O)(OR^{14})OR^{14}$, $—X^5NR^{14}C(O)R^{15}$, $—X^5S(O)R^{15}$, $—X^5S(O)_2R^{15}$ and $—X^5C(O)R^{15}$, wherein $X^5$, $R^{14}$ and $R^{15}$ are as defined above;

$R^4$ is hydrogen, $(C_{1-6})$alkyl or as defined above;

$R^5$ is hydrogen and $R^6$ is hydroxy or $R^5$ and $R^6$ together form oxo;

$R^7$ is a group selected from cyano, halo, nitro, $—R^{29}$, $—X^5NR^{29}R^{30}$, $—X^5NR^{30}C(O)OR^{29}$, $—X^5NR^{30}C(O)NR^{29}R^{30}$, $—X^5NR^{30}C(NR^{30})NR^{29}R^{30}$, $—X^5OR^{29}$, $—X^5SR^{29}$, $—X^5C(O)OR^{29}$, $—X^5C(O)NR^{29}R^{30}$, $—X^5S(O)_2NR^{29}R^{30}$, $—X^5P(O)(OR^{30})OR^{29}$, $—X^5OP(O)(OR^{29})OR^{29}$, $—X^5NR^{30}C(O)R^{31}$, $—X^5S(O)R^{31}$, $—X^5S(O)_2R^{31}$ and $—X^5C(O)R^{31}$, wherein $X^5$ is as defined above, $R^{29}$ is hydrogen or $—R^{31}$, $R^{30}$ at each occurrence is hydrogen or $(C_{1-6})$alkyl and $R^{31}$ is $(C_{1-6})$alkyl, $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl or hetero$(C_{5-12})$aryl$(C_{0-6})$alkyl, wherein within $R^7$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, $—X^5NR^{14}R^{14}$, $—X^5NR^{14}C(O)OR^{14}$, $—X^5NR^{14}C(O)NR^{14}R^{14}$, $—X^5NR^{14}C(NR^{14})NR^{14}R^{14}$, $—X^5OR^{14}$, $—X^5SR^{14}$, $—X^5C(O)OR^{14}$, $—X^5C(O)NR^{14}R^{14}$, $—X^5S(O)_2NR^{14}R^{14}$, $—X^5P(O)(OR^{14})OR^{14}$, $—X^5OP(O)(OR^{14})OR^{14}$, $—X^5NR^{14}C(O)R^{15}$, $—X^5S(O)R^{15}$, $—X^5S(O)_2R^{15}$ and $—X^5C(O)R^{15}$, wherein $X^5$, $R^{14}$ and $R^{15}$ are as defined above; and $R^8$ at each occurrence independently is selected from $(C_{1-6})$alkyl, $(C_{1-6})$alkylidene, cyano, halo, halo-substituted $(C_{1-4})$alkyl, nitro, $—X^5NR^{14}R^{14}$, $—X^5NR^{14}C(O)OR^{14}$, $—X^5NR^{14}C(O)NR^{14}R^{14}$, $—X^5NR^{14}C(NR^{14})NR^{14}R^{14}$, $—X^5OR^{14}$, $—X^5SR^{14}$, $—X^5C(O)OR^{14}$, $—X^5C(O)NR^{14}R^{14}$, $—X^5S(O)_2NR^{14}R^{14}$, $—X^5P(O)(OR^{14})OR^{14}$, $—X^5OP(O)(OR^{14})OR^{14}$, $—X^5NR^{14}C(O)R^{15}$, $—X^5S(O)R^{15}$, $—X^5S(O)_2R^{15}$ and $—X^5C(O)R^{15}$, wherein $X^5$, $R^{14}$ and $R^{15}$ are as defined above; and the N-oxide derivatives, prodrug derivatives, protected derivatives, individual isomers and mixtures of isomers; and the pharmaceutically acceptable salts thereof; but excluding compounds selected from the group consisting of ((S)-1-{(S)-1-[(S)-1-(1-benzooxazol-2-yl-methanoyl)-3-methyl-butylcarbamoyl]-3-methyl-butyl}-carbamic acid benzyl ester, {1-[1-(1-1H-imidazol-2-yl-methanoyl)-3-methyl-butylcarbamoyl]-3-methyl-butyl}-carbamic acid tert-butyl ester, [(S)-3-methyl-1-((S)-3-methyl-1-{1-[1-(2-trimethylsilanyl-ethoxymethyl)-1H-imidazol-2-yl]-methanoyl}-butylcarbamoyl)-butyl]-carbamic acid benzyl ester; {(S)-1-[(S)-1-(1-1H-imidazol-2-yl-methanoyl)-3-methyl-butylcarbamoyl]-3-methyl-butyl}-carbamic acid benzyl ester, ((S)-1-{(S)-1-[1-(1-benzyl-1H-imidazol-2-yl)-methanoyl]-3-methyl-butylcarbamoyl}-3-methyl-butyl)-carbamic acid benzyl ester, {(S)-1-[(S)-1-(1-1H-imidazol-2-yl-methanoyl)-3-methyl-butylcarbamoyl]-3-methyl-butyl}-carbamic acid tert-butyl ester, 3-{[1-(4-chloro-phenyl)-methanoyl]-amino}-4-oxo-4-pyridin-3-yl-butyric acid ethyl ester, 4-furan-2-yl-4-oxo-3-{[1-(4-trifluoromethyl-phenyl)-methanoyl]-amino}-butyric acid ethyl ester, 3-(2-methyl-propanoylamino)-4-oxo-4-thiophen-2-yl-butyric acid ethyl ester, 4-oxo-4-thiophen-2-yl-3-[(1-p-tolyl-methanoyl)-amino]-butyric acid ethyl ester, 4-(5-bromo-thiophen-2-yl)-3-{[1-(4-chloro-phenyl)-methanoyl]-amino}-4-oxo-butyric acid ethyl ester, 3-{[1-(4-chloro-phenyl)-methanoyl]-amino}-4-(5-methyl-thiophen-2-yl)-4-oxo-butyric acid ethyl ester, 4-oxo-4-thiophen-3-yl-3-[(1-p-tolyl-methanoyl)-amino]-butyric acid ethyl ester, 3-{[1-(4-methoxy-phenyl)-methanoyl]-amino}-4-oxo-4-thiophen-3-yl-butyric acid ethyl ester, 3-{[1-(3,4-dichloro-phenyl)-methanoyl]-amino}-4-oxo-4-thiophen-3-yl-butyric acid ethyl ester, 4-fluoro-N-[1-(1-thiophen-3-yl-methanoyl)-propyl]-benzamide, 4-{[1-(4-fluoro-phenyl)-methanoyl]-amino}-5-oxo-5-thiophen-3-yl-pentanoic acid ethyl ester and 3-{[1-(4-fluoro-phenyl)-methanoyl]-amino}-2-methyl-4-oxo-4-thiophen-3-yl-butyric acid ethyl ester.

In another particular embodiment, the present invention relates to protease inhibitors of Formula I:

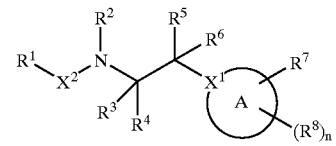

I in which:

A comprises a heteromonocyclic ring containing 5 to 6 ring member atoms or a fused heteropolycyclic ring system containing 8 to 14 ring member atoms, wherein each ring contains 5 to 7 ring member atoms, $X^1$ is a ring member carbon atom and each ring member atom other than $X^1$ is a carbon atom or a heteroatom, with the proviso that (i) at least one ring member atom is a heteroatom and (ii) when A is a heteromonocyclic radical containing 5 ring member atoms, no more than two of the ring member atoms comprising A are heteroatoms;

n is 0, 1, 2 or 3;

$X^1$ is $=C—$ or $—CH—$;

$X^2$ is a bond or a divalent group of Formula (a) or (b):

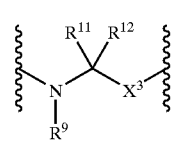

(a)

-continued

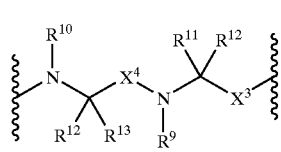

(b)

wherein:

$X^3$ and $X^4$ independently are —C(O)— or —CH$_2$S(O)$_2$—;

$R^9$ and $R^{10}$ independently are hydrogen, (C$_{1-6}$)alkyl or as defined below;

$R^{11}$ at each occurrence independently is hydrogen or (C$_{1-6}$)alkyl;

$R^{12}$ and $R^{13}$ independently are (i) (C$_{1-6}$)alkyl optionally substituted with cyano, halo, nitro, —NR$^{14}$R$^{14}$, —NR$^{14}$C(O)OR$^{14}$, —NR$^{14}$C(O)NR$^{14}$R$^{14}$, —NR$^{14}$C(NR$^{14}$)NR$^{14}$R$^{14}$, —OR$^{14}$, —SR$^{14}$, —C(O)OR$^{14}$, —C(O)NR$^{14}$R$^{14}$, —S(O)$_2$NR$^{14}$R$^{14}$, —P(O)(OR$^{14}$)OR$^{14}$, —OP(O)(OR$^{14}$)OR$^{14}$, —NR$^{14}$C(O)R$^{15}$, —S(O)R$^{15}$, —S(O)$_2$R$^{15}$, —C(O)R$^{15}$, —OR$^{16}$, —SR$^{16}$, —S(O)R$^{16}$, —S(O)$_2$R$^{16}$, —C(O)R$^{16}$, —C(O)OR$^{16}$, —OC(O)R$^{16}$, —NR$^{16}$R$^{17}$, —NR$^{17}$C(O)R$^{16}$, —NR$^{17}$C(O)OR$^{16}$, —C(O)NR$^{16}$R$^{17}$, —S(O)$_2$NR$^{16}$R$^{17}$, —NR$^{17}$C(O)NR$^{16}$R$^{17}$ or —NR$^{17}$C(NR$^{17}$)NR$^{16}$R$^{17}$, wherein $R^{14}$ at each occurrence independently is hydrogen, (C$_{1-6}$)alkyl or halo-substituted (C$_{1-3}$)alkyl, $R^{15}$ (C$_{1-6}$)alkyl or halo-substituted (C$_{1-3}$)alkyl, $R^{16}$ is (C$_{3-12}$)cycloalkyl (C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)polycycloaryl(C$_{0-6}$)alkyl or hetero(C$_{8-12}$)polycycloaryl(C$_{0-6}$)alkyl and $R^{17}$ is hydrogen or (C$_{1-6}$)alkyl, and wherein within $R^{16}$ said cycloalkyl, heterocycloalkyl, aryl, heteroaryl, polycycloaryl or heterpolycycloaryl ring optionally is substituted by a group selected from —R$^{18}$, —X$^5$OR$^{18}$, —X$^5$SR$^{18}$, —X$^5$S(O)R$^{18}$, —X$^5$S(O)$_2$R$^{18}$, —X$^5$C(O)R$^{18}$, —X$^5$C(O)OR$^{18}$, —X$^5$OC(O)R$^{18}$, —X$^5$NR$^{18}$R$^{19}$, —X$^5$NR$^{19}$C(O)R$^{18}$, —X$^5$NR$^{19}$C(O)OR$^{18}$, —X$^5$C(O)NR$^{18}$R$^{19}$, —X$^5$S(O)$_2$NR$^{18}$R$^{19}$, —X$^5$NR$^{19}$C(O)NR$^{18}$R$^{19}$ or —X$^5$NR$^{19}$C(NR$^{19}$)NR$^{18}$R$^{19}$, wherein $X^5$ is a bond or (C$_{1-6}$)alkylene, $R^{18}$ is hydrogen or (C$_{1-6}$)alkyl and $R^{19}$ is (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)polycycloaryl(C$_{0-6}$)alkyl or hetero(C$_{8-12}$)polycycloaryl(C$_{0-6}$)alkyl, or (ii) a group selected from (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)polycycloaryl(C$_{0-6}$)alkyl and hetero(C$_{8-12}$)polycycloaryl(C$_{0-6}$)alkyl, wherein said cycloalkyl, heterocycloalkyl, aryl, heteroaryl, polycycloaryl or heterpolycycloaryl ring optionally is substituted by a group selected from —R$^{18}$, —X$^5$OR$^{18}$, —X$^5$SR$^{18}$, —X$^5$S(O)R$^{18}$, —X$^5$S(O)$_2$R$^{18}$, —X$^5$C(O)R$^{18}$, —X$^5$C(O)OR$^{18}$, —X$^5$OC(O)R$^{18}$, —X$^5$NR$^{18}$R$^{19}$, —X$^5$NR$^{19}$C(O)R$^{18}$, —X$^5$NR$^{19}$C(O)OR$^{18}$, —X$^5$C(O)NR$^{18}$R$^{19}$, —X$^5$S(O)$_2$NR$^{18}$R$^{19}$, —X$^5$NR$^{19}$C(O)NR$^{18}$R$^{19}$ or —X$^5$NR$^{19}$C(NR$^{19}$)NR$^{18}$R$^{19}$, wherein $X^5$, $R^{18}$ and $R^{19}$ are as defined above; wherein within $R^{12}$ and/or $R^{13}$ any alicyclic or aromatic ring system present may be substituted further by 1 to 5 radicals independently selected from (C$_{1-6}$)alkyl, (C$_{1-6}$)alkylidene, cyano, halo, halo-substituted (C$_{1-4}$)alkyl, nitro, —X$^5$NR$^{14}$R$^{14}$, —X$^5$NR$^{14}$C(O)OR$^{14}$, —X$^5$NR$^{14}$C(O)NR$^{14}$R$^{14}$, —X$^5$NR$^{14}$C(NR$^{14}$)NR$^{14}$R$^{14}$, —X$^5$OR$^{14}$, —X$^5$SR$^{14}$, —X$^5$C(O)OR$^{14}$, —X$^5$C(O)NR$^{14}$R$^{14}$, —X$^5$S(O)$_2$NR$^{14}$R$^{14}$, —X$^5$P(O)(OR$^{14}$)OR$^{14}$, —X$^5$OP(O)(OR$^{14}$)OR$^{14}$, —X$^5$NR$^{14}$C(O)R$^{15}$, —X$^5$S(O)R$^{15}$, —X$^5$S(O)$_2$R$^{15}$ and —X$^5$C(O)R$^{15}$, wherein $X^5$, $R^{14}$ and $R^{15}$ are as defined above; or $R^{12}$ together with $R^9$ and/or $R^{13}$ together with $R^{10}$ form trimethylene, tetramethylene or phenylene-1,2-dimethylene, optionally substituted with 1 to 3 radicals independently selected from (C$_{1-6}$)alkyl, (C$_{1-6}$)alkylidene, cyano, halo, halo-substituted (C$_{1-4}$)alkyl, nitro, oxo, —X$^5$NR$^{14}$C(O)OR$^{14}$, —X$^5$NR$^{14}$C(O)NR$^{14}$R$^{14}$, —X$^5$NR$^{14}$C(NR$^{14}$)NR$^{14}$R$^{14}$, —X$^5$OR$^{14}$, —X$^5$SR$^{14}$, —X$^5$C(O)OR$^{14}$, —X$^5$C(O)NR$^{14}$R$^{14}$, —X$^5$S(O)$_2$NR$^{14}$R$^{14}$, —X$^5$P(O)(OR$^{14}$)OR$^{14}$, —X$^5$OP(O)(OR$^{14}$)OR$^{14}$, —X$^5$NR$^{14}$C(O)R$^{15}$, —X$^5$S(O)R$^{15}$, —X$^5$S(O)$_2$R$^{15}$ and —X$^5$C(O)R$^{15}$, wherein $X^5$, $R^{14}$ and $R^{15}$ are defined above; and $R^1$ is —X$^6$X$^7$R$^{20}$, wherein $X^6$ is —C(O)—, —C(O)C(O)— or —S(O)$_2$—, $X^7$ is a bond, —O— or —NR$^{21}$—, wherein $R^{21}$ is hydrogen or (C$_{1-6}$)alkyl, and $R^{20}$ is (i) (C$_{1-6}$)alkyl optionally substituted by cyano, halo, nitro, —NR$^{14}$R$^{14}$, —NR$^{14}$C(O)OR$^{14}$, —NR$^{14}$C(O)NR$^{14}$R$^{14}$, —NR$^{14}$C(NR$^{14}$)NR$^{14}$R$^{14}$, —OR$^{14}$, —SR$^{14}$, —C(O)OR$^{14}$, —C(O)NR$^{14}$R$^{14}$, —S(O)$_2$NR$^{14}$R$^{14}$, —P(O)(OR$^{14}$)OR$^{14}$, —OP(O)(OR$^{14}$)OR$^{14}$, —NR$^{14}$C(O)R$^{15}$, —S(O)R$^{15}$, —S(O)$_2$R$^{15}$, —C(O)R$^{15}$, —OR$^{22}$, —SR$^{22}$, —S(O)R$^{22}$, —S(O)$_2$R$^{22}$, —C(O)R$^{22}$, —C(O)OR$^{22}$, —C(O)NR$^{22}$R$^{23}$, —NR$^{22}$R$^{23}$, —NR$^{23}$C(O)R$^{22}$, —NR$^{23}$C(O)OR$^{22}$, —NR$^{23}$C(O)NR$^{22}$R$^{23}$ or —NR$^{23}$C(NR$^{23}$)NR$^{22}$R$^{23}$, wherein $R^{14}$ and $R^{15}$ are as defined above, $R^{22}$ is (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)bicycloaryl(C$_{0-6}$)alkyl or hetero(C$_{8-12}$)bicycloaryl(C$_{0-6}$)alkyl and $R^{23}$ at each occurrence independently is hydrogen or (C$_{1-6}$)alkyl, or (ii) (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, diphenyl(C$_{0-6}$)alkyl, hetero(C$_{5-12}$)aryl(C$_{0-6}$)alkyl, dihetero(C$_{5-6}$)aryl(C$_{0-6}$)alkyl, (C$_{9-12}$)bicycloaryl(C$_{0-6}$)alkyl or hetero(C$_{8-12}$)bicycloaryl(C$_{0-6}$)alkyl wherein said cycloalkyl, heterocycloalkyl, aryl or heteroaryl may be substituted by —R$^{24}$, —X$^5$OR$^{24}$, —X$^5$SR$^{24}$, —X$^5$S(O)R$^{24}$, —X$^5$S(O)$_2$R$^{24}$, —X$^5$C(O)R$^{24}$, —X$^5$C(O)OR$^{24}$, —X$^5$C(O)NR$^{24}$R$^{25}$, —X$^5$NR$^{24}$R$^{25}$, —X$^5$NR$^{25}$C(O)R$^{24}$, —X$^5$NR$^{25}$C(O)OR$^{24}$, —X$^5$NR$^{25}$C(O)NR$^{24}$R$^{25}$ or —X$^5$NR$^{25}$C(NR$^{25}$)NR$^{24}$R$^{25}$, wherein $X^5$ is as defined above, $R^{24}$ is (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)bicycloaryl(C$_{0-6}$)alkyl or hetero(C$_{8-12}$)bicycloaryl(C$_{0-6}$)alkyl and $R^{25}$ at each occurrence independently is hydrogen or (C$_{1-6}$)alkyl; wherein within $R^1$ any alicyclic or aromatic ring system present may be substituted further by 1 to 5 radicals independently selected from (C$_{1-6}$)alkyl, (C$_{1-6}$)alkylidene, cyano, halo, halo-substituted (C$_{1-4}$)alkyl, nitro, —X$^5$NR$^{14}$R$^{14}$, —X$^5$NR$^{14}$C(O)OR$^{14}$, —X$^5$NR$^{14}$C(O)NR$^{14}$R$^{14}$, —X$^5$NR$^{14}$C(NR$^{14}$)NR$^{14}$R$^{14}$, —X$^5$OR$^{14}$, —X$^5$SR$^{14}$, —X$^5$C(O)OR$^{14}$, —X$^5$C(O)NR$^{14}$R$^{14}$, —X$^5$S(O)$_2$NR$^{14}$R$^{14}$, —X$^5$P(O)(OR$^{14}$)OR$^{14}$, —X$^5$OP(O)(OR$^{14}$)OR$^{14}$, —X$^5$NR$^{14}$C(O)R$^{15}$, —X$^5$S(O)R$^{15}$, —X$^5$S(O)$_2$R$^{15}$ and —X$^5$C(O)R$^{15}$, wherein $X^5$, $R^{14}$ and $R^{15}$ are as defined above; or when $X^2$ is a divalent group of formula (a) or (b) then $R^1$ may also represent hydrogen, carboxy, oxalo or carbamoyl;

$R^2$ is hydrogen or $(C_{1-6})$alkyl;

$R^3$ is (i) $(C_{1-6})$alkyl optionally substituted with cyano, halo, nitro, $-SR^{24}$, $-C(O)OR^{24}$, $-C(O)NR^{24}R^{24}$, $-P(O)(OR^{24})OR^{24}$, $-OP(O)(OR^{24})OR^{24}$, $S(O)R^{25}$, $S(O)_2R^{25}$ or $-C(O)R^{25}$, wherein $R^{24}$ at each occurrence independently is hydrogen, $(C_{1-6})$alkyl or halo-substituted $(C_{1-3})$alkyl and $R^{25}$ $(C_{1-6})$alkyl or halo-substituted $(C_{1-3})$alkyl, or (ii) $(C_{5-6})$cycloalkyl$(C_{2-3})$alkyl, hetero$(C_{3-6})$cycloalkyl$(C_{2-3})$alkyl, $(C_{6-12})$aryl$(C_{2-3})$alkyl or hetero$(C_{5-6})$aryl$(C_{2-3})$alkyl, wherein said cycloalkyl, heterocycloalkyl, aryl or heteroaryl optionally is substituted further with 1 to 5 radicals independently selected from $(C_{1-6})$alkyl, $(C_{1-6})$alkylidene, cyano, halo, halo-substituted $(C_{1-4})$alkyl, nitro, $-X^5NR^{14}C(O)OR^{14}$, $-X^5NR^{14}C(O)NR^{14}R^{14}$, $-X^5NR^{14}C(NR^{14})NR^{14}R^{14}$, $-X^5OR^{14}$, $-X^5SR^{14}$, $-X^5C(O)OR^{14}$, $-X^5C(O)NR^{14}R^{14}$, $-X^5S(O)_2NR^{14}R^{14}$, $-X^5P(O)(OR^{14})OR^{14}$, $-X^5OP(O)(OR^{14})OR^{14}$, $-X^5NR^{14}C(O)R^{15}$, $-X^5S(O)R^{15}$, $-X^5S(O)_2R^{15}$ and $-X^5C(O)R^{15}$, wherein $X^5$, $R^{14}$ and $R^{15}$ are as defined above, provided that when $R^3$ is unsubstituted $(C_{1-5})$alkyl and $R^4$ is hydrogen or unsubstituted $(C_{1-5})$alkyl, then $X^2$ may not represent (i) a bond when $R^1$ is $-C(O)R^{20}$, $-C(O)_2R^{20}$ or $-S(O)_2R^{20}$ in which $R^{20}$ is $(C_{1-6})$alkyl, phenyl$(C_{1-4})$alkyl, phenyl, $(C_{3-7})$cycloalkyl, camphan-10-yl, naphth-1-yl, naphth-2-yl, phenyl substituted by one or more of $(C_{1-4})$alkyl, perfluoro$(C_{1-4})$alkyl, $(C_{1-4})$alkoxy, hydroxy, halo, amido, nitro, amino, $(C_{1-4})$alkylamino, $(C_{1-4})$dialkylamino, carboxy or $(C_{1-4})$alkoxycarbonyl, or naphth-1-yl or naphth-2-yl substituted by one or more of $(C_{1-4})$alkyl, perfluoro$(C_{1-4})$alkyl, $(C_{1-4})$alkoxy, hydroxy, halo, amido, nitro, amino, carboxy or $(C_{1-4})$alkoxycarbonyl or (ii) a divalent group of formula (a) or (b) in which the moiety $R^{12}$ is methyl, isopropyl, n-butyl, sec-butyl, tert-butyl, 1-methylpropyl, benzyl, naphth-1-ylmethyl, naphth-2-ylmethyl, thien-2-ylmethyl, thien-3-ylmethyl, or wherein $R^9$ and $R^{12}$ form ethylene, trimethylene, hydroxy-substituted trimethylene, tetramethylene or phenylene-1,2-dimethylene; or $R^3$ and $R^4$ taken together with the carbon atom to which both $R^3$ and $R^4$ are attached form $(C_{3-8})$cycloalkylene or $(C_{3-8})$heterocycloalkylene, wherein said cycloalkylene or heterocycloalkylene is optionally substituted with 1 to 3 radicals independently selected from $(C_{1-6})$alkyl, $(C_{1-6})$alkylidene, cyano, halo, halo-substituted $(C_{1-4})$alkyl, nitro, $-X^5NR^{14}C(O)OR^{14}$, $-X^5NR^{14}C(O)NR^{14}R^{14}$, $-X^5NR^{14}C(NR^{14})NR^{14}R^{14}$, $-X^5OR^{14}$, $-X^5SR^{14}$, $-X^5C(O)OR^{14}$, $-X^5C(O)NR^{14}R^{14}$, $-X^5S(O)_2NR^{14}R^{14}$, $-X^5P(O)(OR^{14})OR^{14}$, $-X^5OP(O)(OR^{14})OR^{14}$, $-X^5NR^{14}C(O)R^{15}$, $-X^5S(O)R^{15}$, $-X^5S(O)_2R^{15}$ and $-X^5C(O)R^{15}$, wherein $X^5$, $R^{14}$ and $R^{15}$ are as defined above;

$R^3$ and $R^4$ taken together with the carbon atom to which both $R^3$ and $R^4$ are attached form $(C_{3-8})$cycloalkylene or $(C_{3-8})$heterocycloalkylene, wherein said cycloalkylene or heterocycloalkylene is optionally substituted with 1 to 3 radicals independently selected from $(C_{1-6})$alkyl, $(C_{1-6})$alkylidene, cyano, halo, halo-substituted $(C_{1-4})$alkyl, nitro, $-X^5NR^{14}C(O)OR^{14}$, $-X^5NR^{14}C(O)NR^{14}R^{14}$, $-X^5NR^{14}C(NR^{14})NR^{14}R^{14}$, $-X^5OR^{14}$, $-X^5SR^{14}$, $-X^5C(O)OR^{14}$, $-X^5C(O)NR^{14}R^{14}$, $-X^5S(O)_2NR^{14}R^{14}$, $-X^5P(O)(OR^{14})OR^{14}$, $-X^5OP(O)(OR^{14})OR^{14}$, $-X^5NR^{14}C(O)R^5$, $-X^5S(O)R^{15}$, $-X^5S(O)_2R^{15}$ and $-X^5C(O)R^{15}$, wherein $X^5$, $R^{14}$ and $R^{15}$ are as defined above;

$R^4$ is hydrogen, $(C_{1-6})$alkyl or as defined above;

$R^5$ is hydrogen and $R^6$ is hydroxy or $R^5$ and $R^6$ together form oxo;

$R^7$ is a group selected from cyano, halo, nitro, $-R^{29}$, $-X^5NR^{29}R^{30}$, $-X^5NR^{30}C(O)OR^{29}$, $-X^5NR^{30}C(O)NR^{29}R^{30}$, $-X^5NR^{30}C(NR^{30})NR^{29}R^{30}$, $-X^5OR^{29}$, $-X^5SR^{29}$, $-X^5C(O)OR^{29}$, $-X^5C(O)NR^{29}R^{30}$, $-X^5S(O)_2NR^{29}R^{30}$, $-X^5P(O)(OR^{30})OR^{29}$, $-X^5OP(O)(OR^{29})OR^{29}$, $-X^5NR^{30}C(O)R^{20}$, $-X^5S(O)R^{20}$, $-X^5S(O)_2R^{20}$, $-X^5C(O)R^{20}$ and $-C(O)NR^{42}CHR^{43}C(O)OR^{29}$, wherein $X^5$ and $R^{20}$ are as defined as above, $R^{29}$ is hydrogen or $-R^{20}$, wherein $R^{20}$ is defined as above, $R^{30}$ at each occurrence is hydrogen or $(C_{1-6})$alkyl, $R^{42}$ is hydrogen, $(C_{1-6})$alkyl or together with $R^{43}$ forms trimethylene, tetramethylene or phenylene-1,2-dimethylene, optionally substituted with hydroxy or oxo, and $R^{43}$ is as defined above or is (i) $(C_{1-6})$alkyl optionally substituted with cyano, halo, nitro, $-NR^{14}R^{14}$, $-NR^{14}C(O)OR^{14}$, $-NR^{14}C(O)NR^{14}R^{14}$, $-NR^{14}C(NR^{14})NR^{14}R^{14}$, $-OR^{14}$, $-SR^{14}$, $-C(O)OR^{14}$, $-C(O)NR^{14}R^{14}$, $-S(O)_2NR^{14}R^{14}$, $-P(O)(OR^{14})OR^{14}$, $-OP(O)(OR^{14})OR^{14}$, $-NR^{14}C(O)R^{15}$, $-S(O)R^{15}$, $-S(O)_2R^{15}$, $-C(O)R^{15}$, $-OR^{16}$, $-SR^{16}$, $-S(O)R^{16}$, $-S(O)_2R^{16}$, $C(O)R^{16}$, $-C(O)OR^{16}$, $-OC(O)R^{16}$, $-NR^{16}R^{17}$, $-NR^{17}C(O)R^{16}$, $-NR^{17}C(O)OR^{16}$, $-C(O)NR^{16}R^{17}$, $-S(O)_2NR^{16}R^{17}$, $-NR^{17}C(O)NR^{16}R^{17}$ or $-NR^{17}C(NR^{17})NR^{16}R^{17}$ or (ii) a group selected from $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl and hetero$(C_{8-12})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from $-R^{18}$, $-X^5OR^{18}$, $-X^5SR^{18}$, $-X^5S(O)R^{18}$, $-X^5S(O)_2R^{18}$, $-X^5C(O)R^{18}$, $-X^5C(O)OR^{18}$, $-X^5OC(O)R^{18}$, $-X^5NR^{18}R^{19}$, $-X^5NR^{19}C(O)R^{18}$, $-X^5NR^{19}C(O)OR^{18}$, $-X^5C(O)NR^{18}R^{19}$, $-X^5S(O)_2NR^{18}R^{19}$, $-X^5NR^{19}C(O)NR^{18}R^{19}$ or $-X^5NR^{19}C(NR^{19})NR^{18}R^{19}$, wherein $X^5$, $R^{14}$, $R^{15}$, $R^{16}$, $R^{17}$, $R^{18}$ and $R^{19}$ are as defined above; wherein within $R^7$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, $-X^5NR^{14}R^{14}$, $-X^5NR^{14}C(O)OR^{14}$, $-X^5NR^{14}C(O)NR^{14}R^{14}$, $-X^5NR^{14}C(NR^{14})NR^{14}R^{14}$, $-X^5OR^{14}$, $-X^5SR^{14}$, $-X^5C(O)OR^{14}$, $-X^5C(O)NR^{14}R^{14}$, $-X^5S(O)_2NR^{14}R^{14}$, $-X^5P(O)(OR^{14})OR^{14}$, $-X^5OP(O)(OR^{14})OR^{14}$, $-X^5NR^{14}C(O)R^{15}$, $-X^5S(O)R^{15}$, $-X^5S(O)_2R^{15}$ and $-X^5C(O)R^{15}$, wherein $X^5$, $R^{14}$ and $R^{15}$ are as defined above; and $R^8$ at each occurrence independently is selected from $(C_{1-6})$alkyl, halo-substituted $(C_{1-4})$alkyl, $(C_{1-6})$alkylidene, cyano, halo, halo-substituted $(C_{1-4})$alkyl, nitro, $-X^5NR^{14}R^{14}$, $-X^5NR^{14}C(O)OR^{14}$, $-X^5NR^{14}C(O)NR^{14}R^{14}$, $-X^5NR^{14}C(NR^{14})NR^{14}R^{14}$, $-X^5OR^{14}$, $-X^5SR^{14}$, $-X^5C(O)OR^{14}$, $-X^5C(O)NR^{14}R^{14}$, $-X^5S(O)_2NR^{14}R^{14}$, $-X^5P(O)(OR^{14})OR^{14}$, $-X^5OP(O)(OR^{14})OR^{14}$, $-X^5NR^{14}C(O)R^{15}$, $-X^5S(O)R^{15}$, $-X^5S(O)_2R^{15}$ and $-X^5C(O)R^{15}$, wherein $X^5$ is a bond or $(C_{1-6})$alkylene, $R^{14}$ at each occurrence independently is hydrogen, $(C_{1-6})$alkyl or halo-substituted $(C_{1-3})$alkyl and $R^{15}$ $(C_{1-6})$alkyl or halo-substituted $(C_{1-3})$alkyl; and the N-oxide derivatives, prodrug derivatives, protected derivatives, individual isomers and mixtures of isomers; and the pharmaceutically acceptable salts thereof.

In another particular embodiment, the present invention relates to a compound of Formula II:

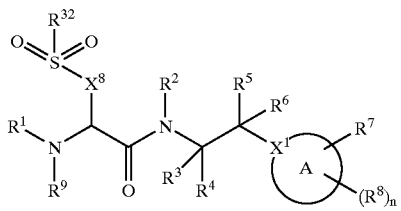

II in which:
  A comprises a heteromonocyclic ring containing 5 to 6 ring member atoms or a fused heteropolycyclic ring system containing 8 to 14 ring member atoms, wherein each ring contains 5 to 7 ring member atoms, $X^1$ is a ring member carbon atom and each ring member atom other than $X^1$ is a carbon atom or a heteroatom, with the proviso that at least one ring member atom is a heteroatom;
  n is 0, 1, 2 or 3;
  $X^1$ is =C— or —CH—;
  $X^8$ is $(C_{1-2})$alkylene;
  $R^1$ is hydrogen, carboxy, oxalo, carbamoyl or —$X^6X^7R^{20}$, wherein $X^6$ is —C(O)—, —C(O)C(O)— or —S(O)$_2$—, $X^7$ is a bond, —O— or —$NR^{21}$—, wherein $R^{21}$ is hydrogen or $(C_{1-6})$alkyl, and $R^{20}$ is (i) $(C_{1-6})$alkyl optionally substituted by cyano, halo, nitro, —$NR^{14}R^{14}$, —$NR^{14}C(O)OR^{14}$, —$NR^{14}C(O)NR^{14}R^{14}$, —$NR^{14}C(NR^{14})NR^{14}R^{14}$, —$OR^{14}$, —$SR^{14}$, —C(O)OR$^{14}$, —C(O)NR$^{14}R^{14}$, —S(O)$_2$NR$^{14}R^{14}$, —P(O)(OR$^{14}$)OR$^{14}$, —OP(O)(OR$^{14}$)OR$^{14}$, —NR$^{14}$C(O)R$^{15}$, —S(O)R$^{15}$, —S(O)$_2$R$^{15}$, —C(O)R$^{15}$, —OR$^{22}$, —SR$^{22}$, —S(O)R$^{22}$, —S(O)$_2$R$^{22}$, —C(O)R$^{22}$, —C(O)OR$^{22}$, —C(O)NR$^{22}R^{23}$, —NR$^{22}R^{23}$, —NR$^{23}$C(O)R$^{22}$, —NR$^{23}$C(O)OR$^{22}$, —NR$^{23}$C(O)NR$^{22}R^{23}$ or —NR$^{23}$C(NR$^{23}$)NR$^{22}R^{23}$, wherein $R^{14}$ at each occurrence independently is hydrogen, $(C_{1-6})$alkyl or halo-substituted $(C_{1-3})$alkyl, $R^{15}$ is $(C_{1-6})$alkyl or halo-substituted $(C_{1-3})$alkyl, $R^{22}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-6})$alkyl or hetero$(C_{8-12})$bicycloaryl$(C_{0-6})$alkyl and $R^{23}$ at each occurrence independently is hydrogen or $(C_{1-6})$alkyl, or (ii) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-6})$alkyl or hetero$(C_{8-12})$bicycloaryl$(C_{0-6})$alkyl or (ii) $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl substituted by —$X^5OR^{24}$, —$X^5SR^{24}$, —$X^5S(O)R^{24}$, —$X^5S(O)_2R^{24}$, —$X^5C(O)R^{24}$, —$X^5C(O)OR^{24}$, —$X^5C(O)NR^{24}R^{25}$, —$X^5NR^{24}R^{25}$, —$X^5NR^{25}C(O)R^{24}$, —$X^5NR^{25}C(O)OR^{24}$, —$X^5NR^{25}C(O)NR^{24}R^{25}$ or —$X^5NR^{25}C(NR^{25})NR^{24}R^{25}$, wherein $X^5$ is a bond or $(C_{1-6})$alkylene, $R^{24}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl and $R^{25}$ at each occurrence independently is hydrogen or $(C_{1-6})$alkyl; wherein within $R^1$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)$ NR$^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above;
  $R^2$ is hydrogen or $(C_{1-6})$alkyl;
  $R^3$ is (i) $(C_{1-6})$alkyl optionally substituted with cyano, halo, nitro, —$NR^{14}R^{14}$, —$NR^{14}C(O)OR^{14}$, —$NR^{14}C(O)NR^{14}R^{14}$, —$NR^{14}C(NR^{14})NR^{14}R^{14}$, —$OR^{14}$, —$SR^{14}$, —C(O)OR$^{14}$, —C(O)NR$^{14}R^{14}$, —S(O)$_2$NR$^{14}R^{14}$, —P(O)(OR$^{14}$)OR$^{14}$, —OP(O)(OR$^{14}$)OR$^{14}$, —NR$^{14}$C(O)R$^{15}$, —S(O)R$^{15}$, —S(O)$_2$R$^{15}$, —C(O)R$^{15}$, —OR$^{16}$, —SR$^{16}$, —S(O)R$^{16}$, —S(O)$_2$R$^{16}$, —C(O)R$^{16}$, —C(O)OR$^{16}$, —OC(O)R$^{16}$, —NR$^{16}R^{17}$, —NR$^{17}$C(O)R$^{16}$, —NR$^{17}$C(O)OR$^{16}$, —C(O)NR$^{16}R^{17}$, —S(O)$_2$NR$^{16}R^{17}$, —NR$^{17}$C(O)NR$^{16}R^{17}$ or —NR$^{17}$C(NR$^{17}$)NR$^{16}R^{17}$, wherein $R^{14}$ at each occurrence independently is hydrogen, $(C_{1-6})$alkyl or halo-substituted $(C_{1-3})$alkyl, $R^{15}$ is $(C_{1-6})$alkyl or halo-substituted $(C_{1-3})$alkyl, $R^{16}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl and $R^{17}$ is hydrogen or $(C_{1-6})$alkyl, and wherein within $R^{16}$ said cycloalkyl, heterocycloalkyl, aryl, heteroaryl, polycycloaryl or heterpolycycloaryl ring optionally is substituted by a group selected from —$R^{18}$, —$X^5OR^{18}$, —$X^5SR^{18}$, —$X^5S(O)R^{18}$, —$X^5S(O)_2R^{18}$, —$X^5C(O)R^{18}$, —$X^5C(O)OR^{18}$, —$X^5OC(O)R^{18}$, —$X^5NR^{18}R^{19}$, —$X^5NR^{19}C(O)R^{18}$, —$X^5NR^{19}C(O)OR^{18}$, —$X^5C(O)NR^{18}R^{19}$, —$X^5S(O)_2NR^{18}R^{19}$, —$X^5NR^{19}C(O)NR^{15}R^{19}$ or —$X^5NR^{19}C(NR^{19})NR^{18}R^{19}$, wherein $X^5$ is as defined above, $R^{18}$ is hydrogen or $(C_{1-6})$alkyl and $R^{19}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl, or (ii) a group selected from $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl and hetero$(C_{8-12})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from —$R^{18}$, —$X^5OR^{18}$, —$X^5SR^{18}$, —$X^5S(O)R^{18}$, —$X^5S(O)_2R^{18}$, —$X^5C(O)R^{18}$, —$X^5C(O)OR^{18}$, —$X^5OC(O)R^{18}$, —$X^5NR^{18}R^{19}$, —$X^5NR^{19}C(O)R^{18}$, —$X^5NR^{19}C(O)OR^{18}$, —$X^5C(O)NR^{18}R^{19}$, —$X^5S(O)_2NR^{18}R^{19}$, —$X^5NR^{19}C(O)NR^{18}R^{19}$ or —$X^5NR^{19}C(NR^{19})NR^{18}R^{19}$, wherein $X^5$, $R^{18}$ and $R^{19}$ are as defined above; wherein within $R^{12}$ and/or $R^{13}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above, or
  $R^3$ and $R^4$ taken together with the carbon atom to which both $R^3$ and $R^4$ are attached form $(C_{3-8})$cycloalkylene or $(C_{3-8})$heterocycloalkylene, wherein said cycloalkylene or heterocycloalkylene is optionally substituted with 1 to 3 radicals independently selected from $(C_{1-6})$alkyl, $(C_{1-6})$alkylidene, cyano, halo, halo-substituted $(C_{1-4})$alkyl, nitro, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above;

$R^4$ is hydrogen, $(C_{1-6})$alkyl or as defined above;

$R^5$ is hydrogen and $R^6$ is hydroxy or $R^5$ and $R^6$ together form oxo;

$R^7$ is a group selected from cyano, halo, nitro, —$R^{29}$, —$X^5NR^{29}R^{30}$, —$X^5NR^{30}C(O)OR^{29}$, —$X^5NR^{30}C(O)NR^{29}R^{30}$, —$X^5NR^{30}C(NR^{30})NR^{29}R^{30}$, —$X^5OR^{29}$, —$X^5SR^{29}$, —$X^5C(O)OR^{29}$, —$X^5C(O)NR^{29}R^{30}$, —$X^5S(O)_2NR^{29}R^{30}$, —$X^5P(O)(OR^{30})OR^{29}$, —$X^5OP(O)(OR^{29})OR^{29}$, —$X^5NR^{30}C(O)R^{31}$, —$X^5S(O)R^{31}$, —$X^5S(O)_2R^{31}$ and —$X^5C(O)R^{31}$, wherein $X^5$ is as defined above, $R^{29}$ is hydrogen or —$R^{31}$, $R^{30}$ at each occurrence is hydrogen or $(C_{1-6})$alkyl and $R^{31}$ is $(C_{1-6})$alkyl, $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl or hetero$(C_{5-12})$aryl$(C_{0-6})$alkyl, wherein within $R^7$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above; and $R^8$ at each occurrence independently is selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above;

$R^9$ is hydrogen or $(C_{1-6})$alkyl; and $R^{32}$ is $(C_{1-8})$alkyl, $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl, wherein within $R^{30}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$x^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above; and the N-oxide derivatives, prodrug derivatives, protected derivatives, individual isomers and mixtures of isomers; and the pharmaceutically acceptable salts thereof.

In another particular embodiment, the present invention relates to a pharmaceutical composition which contains a compound of Formula I or II, or a N-oxide derivative, prodrug derivative, individual isomer or mixture of isomers, or a pharmaceutically acceptable salt thereof in admixture with one or more suitable excipients.

In another particular embodiment, the present invention relates to method of treating a disease in an animal in which inhibition of a cysteine protease can prevent, inhibit or ameliorate the pathology and/or symptomatology of the disease, which method comprises administering to the animal a therapeutically effective amount of compound of Formula I or II or a N-oxide derivative, prodrug derivative, individual isomer or mixture of isomers or a pharmaceutically acceptable salt thereof.

In another particular embodiment, the present invention relates to processes for preparing compounds of Formula I and II and the N-oxide derivatives, prodrug derivative, protected derivatives, individual isomers and mixtures of isomers, and the pharmaceutically acceptable salts thereof as set forth in "Detailed Description of the Invention".

In another particular embodiment, the present invention relates to protease inhibitors of Formula III:

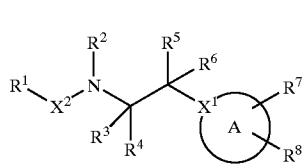

III in which:

A comprises a heteromonocyclic radical containing 5 to 6 annular atoms or a fused heteropolycyclic radical containing 8 to 14 annular atoms, wherein each ring contains 5 to 7 annular atoms, $X^1$ is an annular carbon atom and each annular atom other than $X^1$ optionally is a heteroatom, with the proviso that when A is a heteromonocychc radical containing 5 annular atoms, no more than two of the annular atoms comprising the ring are heteroatoms;

$X^1$ is selected from =C— and —CH—;

$X^2$ is a bond or a divalent group of Formula (a) or (b):

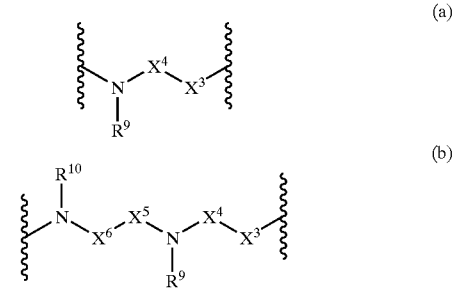

wherein:

$X^3$ and $X^5$ independently are —C(O)— or —S(O)$_2$—, $X^4$ is —CHR$^{11}$—, —CH$_2$CHR$^{11}$— or —CHR$^{11}$CH$_2$— and $X^6$ is —CHR$^{12}$—, —CH$_2$CHR$^{12}$— or —CHR$^{12}$CH$_2$— wherein:

$R^{11}$ and $R^{12}$ are independently (i) $(C_{1-6})$alkyl or halo-substituted$(C_{1-6})$alkyl optionally substituted with —OR$^{13}$, —SR$^{13}$, —S(O)R$^{13}$, —S(O)$_2$R$^{13}$, —C(O)R$^{13}$, —C(O)OR$^{13}$, —NR$^{13}$R$^{14}$, —NR$^{14}$C(O)OR$^{13}$, —C(O)NR$^{13}$R$^{14}$, S(O)$_2$NR$^{13}$R$^{14}$, —NR$^{14}$C(O)NR$^{13}$R$^{14}$ or —NR$^{14}$C(NR$^{14}$)NR$^{13}$R$^{14}$, wherein R$^{13}$ is hydrogen, $(C_{1-6})$alkyl, $(C_{3-12})$cycloalkyl$(C_{0-5})$alkyl, hetero$(C_{3-12})$ cycloalkyl$(C_{0-3})$alkyl, $(C_{6-12})$aryl$(C_{0-3})$alkyl or hetero$(C_{5-12})$aryl$(C_{0-3})$alkyl and $R^{14}$ is hydrogen or $(C_{1-4})$alkyl, or (ii) $(C_{3-12})$cycloalkyl$(C_{0-3})$alkyl, hetero$(C_{3-12})$cycloalkyl$(C_{0-3})$alkyl, $(C_{6-12})$aryl $(C_{0-3})$alkyl, hetero$(C_{5-12})$aryl$(C_{0-3})$alkyl, $(C_{9-12})$ polycycloaryl$(C_{0-3})$alkyl or hetero$(C_{8-12})$ polycycloaryl$(C_{0-3})$alkyl optionally substituted with —$R^{15}$, —$X^{7}OR^{15}$, —$X^{7}SR^{15}$, —$S(O)R^{15}$, —$S(O)_{2}R^{15}$, —$C(O)R^{15}$, —$C(O)OR^{15}$, —$X^{7}NR^{15}R^{16}$, —$X^{7}NR^{16}C(O)OR^{15}$, —$C(O)NR^{15}R^{16}$, —$S(O)_{2}NR^{15}R^{16}$, —$NR^{16}C(O)NR^{15}R^{16}$ or —$NR^{16}C(NR^{16})NR^{15}R^{16}$, wherein $X^{7}$ is a bond or methylene, $R^{15}$ is $(C_{3-12})$ cycloalkyl$(C_{0-3})$alkyl, hetero$(C_{3-12})$cycloalkyl $(C_{0-3})$alkyl, $(C_{6-12})$aryl$(CO_{0-3})$alkyl, hetero$(C_{5-12})$ aryl$(C_{0-3})$alkyl, $(C_{9-12})$polycycloaryl$(C_{0-3})$alkyl or hetero$(C_{8-12})$polycycloaryl$(C_{0-3})$alkyl and $R^{16}$ is hydrogen or $(C_{1-6})$alkyl, or (iii) together with $R^{9}$ or $R^{10}$, respectively, when $X^{4}$ is —$CHR^{11}$— and/ or $X^{6}$ is —$CHR^{12}$—, forms trimethylene, tetramethylene or phenylene-1,2-dimethylene, optionally substituted with hydroxy or oxo; wherein any 1 to 3 annular atoms of any aromatic ring with available valences comprising $R^{11}$ and/or $R^{12}$ are optionally independently substituted with halo, nitro, cyano, $(C_{1-6})$alkyl, halo-substituted$(C_{1-6})$ alkyl, —$OR^{17}$, —$C(O)R^{17}$, —$C(O)OR^{17}$, —$C(O)NR^{17}R^{17}$, —$S(O)_{2}NR^{17}R^{17}$, —$X^{7}NR^{17}R^{17}$, —$X^{7}NR^{17}C(O)OR^{17}$, —$X^{7}NR^{17}C(O)NR^{17}R^{17}$ or —$X^{7}NR^{17}C(NR^{17})NR^{17}R^{17}$, wherein $X^{7}$ is as defined above and each $R^{17}$ independently is hydrogen or $(C_{1-6})$alkyl; and $R^{9}$ and $R^{10}$ are independently hydrogen, $(C_{1-6})$alkyl or as defined above;

$R^{1}$ is hydrogen or —$X^{8}X^{9}R^{18}$, wherein $X^{8}$ is —$C(O)$— or —$S(O)_{2}$—, $X^{9}$ is a bond, —O— or —$NR^{19}$—, wherein $R^{19}$ is hydrogen or $(C_{1-6})$alkyl, and $R^{18}$ is (i) $(C_{1-6})$ alkyl or halo-substituted$(C_{1-6})$alkyl optionally substituted with —$OR^{13}$, —$SR^{13}$, —$S(O)R^{13}$, —$S(O)_{2}R^{13}$, —$C(O)R^{13}$, —$C(O)OR^{13}$, —$NR^{13}R^{14}$, —$NR^{14}C(O)$ $OR^{13}$, —$C(O)NR^{13}R^{14}$, —$S(O)_{2}NR^{13}R^{14}$, —$NR^{14}C$ $(O)NR^{13}R^{14}$ or —$NR^{14}C(NR^{14})NR^{13}R^{14}$, wherein $R^{13}$ and $R^{14}$ are as defined above, or (ii) $(C_{3-12})$cycloalkyl $(C_{0-6})$alkyl, hetero$(C_{3-12})$cycloalkyl$(C_{0-6})$alkyl, $(C_{6-12})$ aryl$(C_{0-6})$alkyl, diphenyl$(C_{0-6})$alkyl, hetero$(C_{5-12})$aryl $(C_{0-6})$alkyl, dihetero$(C_{5-6})$aryl$(C_{0-6})$alkyl, $(C_{9-12})$ polycycloaryl$(C_{0-6})$alkyl or hetero$(C_{8-12})$polycycloaryl $(C_{0-6})$alkyl optionally substituted with —$R^{15}$, —$X^{7}OR^{15}$, —$X^{7}SR^{15}$, —$S(O)R^{15}$, —$S(O)_{2}R^{15}$, —$C(O)R^{15}$, —$C(O)OR^{15}$, —$X^{7}NR^{15}R^{16}$, —$X^{7}NR^{16}C$ $(O)OR^{15}$, —$C(O)NR^{15}R^{16}$, —$S(O)_{2}NR^{15}R^{16}$, —$NR^{16}C(O)NR^{15}R^{16}$ or —$NR^{16}C(NR^{16})NR^{15}R^{16}$, wherein $X^{7}$, $R^{15}$ and $R^{16}$ are as defined above; wherein any 1 to 3 annular atoms of any aromatic ring with available valences comprising $R^{1}$ optionally independently are substituted with halo, nitro, cyano, $(C_{1-6})$ alkyl, halo-substituted$(C_{1-6})$alkyl, —$OR^{17}$, —$C(O)$ $R^{17}$, —$C(O)OR^{17}$, —$C(O)NR^{17}R^{17}$, —$S(O)_{2}NR^{17}R^{17}$, —$X^{7}NR^{17}R^{17}$, —$X^{7}NR^{17}C(O)OR^{17}$, —$X^{7}NR^{17}C(O)$ $NR^{17}R^{17}$ or —$X^{7}NR^{17}C(NR^{17})NR^{17}R^{17}$, wherein $X^{7}$ $R^{17}$ are as defined above;

$R^{2}$ is hydrogen or $(C_{1-6})$alkyl;

$R^{3}$ is phenyl$(C_{2-3})$alkyl, hetero$(C_{5-6})$aryl$(C_{2-3})$alkyl, $(C_{5-6})$cycloalkyl$(C_{2-3})$alkyl or hetero$(C_{5-6})$cycloalkyl $(C_{2-3})$alkyl, wherein any 1 to 3 annular atoms of any aromatic ring with available valences comprising $R^{3}$ optionally independently are substituted with halo, nitro, cyano, $(C_{1-6})$alkyl, halo-substituted$(C_{1-6})$alkyl, —$OR^{17}$, —$C(O)R^{17}$, —$C(O)OR^{17}$, —$C(O)NR^{17}R^{17}$, —$S(O)_{2}NR^{17}R^{17}$, —$X^{7}NR^{17}R^{17}$, —$X^{7}NR^{17}C(O)$ $OR^{17}$, —$X^{7}NR^{17}C(O)NR^{17}R^{17}$ —$X^{7}NR^{17}C(NR^{17})$ $NR^{17}R^{17}$, wherein $X^{7}$ and $R^{17}$ are as defined above, and $R^{4}$ is hydrogen or $R^{3}$ and $R^{4}$ are both methyl, ethyl or propyl or together with the carbon atom to which both $R^{3}$ and $R^{4}$ are attached form cyclopropylene, cyclobutylene or cyclopentylene;

$R^{5}$ is hydrogen and $R^{6}$ is hydroxy or $R^{5}$ and $R^{6}$ together form oxo;

$R^{7}$ is halo, nitro, —$R^{20}$, —$OR^{20}$, —$C(O)R^{20}$, —$C(O)$ $OR^{20}$, —$S(O)_{2}NR^{20}OR^{21}$, —$C(O)NR^{20}R^{21}$ or —$C(O)$ $NR^{22}CHR^{23}C(O)OR^{20}$ and bonded to any annular carbon atom with a free valence comprising A, wherein: $R^{20}$ is hydrogen or $R^{18}$, wherein $R^{18}$ is as defined above;

$R^{21}$ is hydrogen or $(C_{1-6})$alkyl;

$R^{22}$ is hydrogen, $(C_{1-6})$alkyl or together with $R^{23}$ forms trimethylene or phenylene-1,2-dimethylene, optionally substituted with hydroxy or oxo; and $R^{23}$ is as defined above or is (i) $(C_{1-6})$alkyl or halo-substituted$(C_{1-6})$alkyl optionally substituted with —$OR^{13}$, —$SR^{13}$, —$S(O)R^{13}$, —$S(O)_{2}R^{13}$, —$C(O)$ $R^{13}$, —$C(O)OR^{13}$, —$NR^{13}R^{14}$, —$NR^{14}C(O)OR^{13}$, —$C(O)NR^{13}R^{14}$, —$S(O)_{2}NR^{13}R^{14}$, —$NR^{14}C(O)$ $NR^{13}R^{14}$ or —$NR^{14}C(NR^{14})NR^{13}R^{14}$, wherein $R^{13}$ and $R^{14}$ are as defined above, or (ii) $(C_{3-10})$ cycloalkyl$(C_{0-3})$alkyl, hetero$(C_{3-10})$cycloalkyl$(C_{0-3})$ alkyl, $(C_{6-12})$aryl$(C_{0-3})$alkyl, hetero$(C_{5-12})$aryl$(C_{0-3})$ alkyl, $(C_{9-12})$polycycloaryl$(C_{0-3})$alkyl or hetero $(C_{8-12})$polycycloaryl$(C_{0-3})$alkyl optionally substituted with —$R^{15}$, —$X^{7}OR^{15}$, —$X^{7}SR^{15}$, —$S(O)R^{15}$, —$S(O)_{2}R^{15}$, —$C(O)R^{15}$, —$C(O)OR^{15}$, —$X^{7}NR^{15}R^{16}$, —$X^{7}NR^{16}C(O)OR^{15}$, —$C(O)$ $NR^{15}R^{16}$, —$S(O)_{2}NR^{15}R^{16}$, —$NR^{16}C(O)NR^{15}R^{16}$ or —$NR^{16}C(NR^{16})NR^{15}R^{16}$, wherein $X^{7}$, $R^{15}$ and $R^{16}$ are as defined above; wherein any 1 to 3 annular atoms of any aromatic ring with available valences comprising $R^{20}$ and/or $R^{21}$ optionally independently are substituted with halo, nitro, cyano, $(C_{1-6})$alkyl, halo-substituted$(C_{1-6})$alkyl, —$OR^{17}$, —$C(O)R^{17}$, —$C(O)OR^{17}$, —$C(O)NR^{17}R^{17}$, —$S(O)_{2}NR^{17}R^{17}$, —$X^{7}NR^{17}R^{17}$, —$X^{7}NR^{17}C(O)OR^{17}$, —$X^{7}NR^{17}C$ $(O)NR^{17}R^{17}$ or —$X^{7}NR^{17}C(NR^{17})NR^{17}R^{17}$, wherein $X^{7}$ and $R^{17}$ are as defined above; and $R^{8}$ is hydrogen, halo, hydroxy, formyl, carboxy, carbamoyl, sulfamoyl or $(C_{1-6})$alkyl and bonded to any annular carbon atom with a free valence comprising A; and the N-oxide derivatives, prodrug derivatives, protected derivatives, individual isomers and mixtures of isomers; and the pharmaceutically acceptable salts thereof.

DETAILED DESCRIPTION OF THE INVENTION

Definitions

Unless otherwise stated, the following terms used in the specification and claims are defined for the purposes of this Application and have the meanings given this Section:

"Alicyclic" means a moiety characterized by arrangement of the carbon atoms in closed non-aromatic ring structures having properties resembling those of aliphatics and may be saturated or partially unsaturated with two or more double or triple bonds.

"Aliphatic" means a moiety characterized by straight or branched chain arrangement of the constituent carbon atoms and may be saturated or partially unsaturated with two or more double or triple bonds.

"Alkenyl" means alkyl, as defined in this Application, provided that the radical is comprised of at least one double bond. Hence, optionally substituted $(C_{2-6})$alkenyl as used in this Application to define $R^{32}$ includes 2-bromovinyl (—CH=CHBr), buta-1,3-dienyl (—CH=CH—CH=CH$_2$), 2-chloro-1-methylpropenyl (—C(CH$_3$)=CCl—CH$_3$), 2-chlorovinyl (—CH=CHCl), 4-isopropenyl (—C(CH$_3$)=CH$_2$), 1-methylpropenyl (—C(CH$_3$)=CH—CH$_3$), 2-methylpropenyl (—CH=C(CH$_3$)$_2$), 2-nitrovinyl (—CH=CHNO$_2$), propenyl (—CH=CH—CH$_3$), 2-trifluoromethylvinyl (—CH=CH—CF$_3$), trifluorovinyl (—CF=CF$_2$), vinyl (—CH=CH$_2$), and the like).

"Alkoxy" means the radical —OR, wherein R is alkyl as defined in this Application, having the number of carbon atoms indicated (e.g., $(C_{1-4})$alkoxy includes the radicals methoxy, ethoxy, propoxy, isopropoxy, butoxy, sec-butoxy, isobutoxy, tert-butoxy, vinyloxy, allyloxy, 1-propenyloxy, isopropenyloxy, 1-butenyloxy, 2-butenyloxy, 3-butenyloxy, 2-methylallyloxy, ethynyloxy, 1-propynyloxy, 2-propynyloxy, and the like).

"Alkyl" represented by itself means a straight or branched, saturated or unsaturated, aliphatic radical having the number of carbon atoms indicated (e.g. $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g. as in arylalkyl) means a straight or branched, saturated or unsaturated aliphatic divalent radical having the number of atoms indicated or when no atoms are indicated means a bond (e.g. $(C_{6-12})$aryl $(C_{0-6})$alkyl includes phenyl, benzyl, phenethyl, 1-phenylethyl 3-phenylpropyl, and the like).

"Alkylene", unless indicated otherwise, means a straight or branched, saturated or unsaturated, aliphatic, divalent radical having the number of carbon atoms indicated (e.g. $(C_{1-6})$alkylene includes methylene (—CH$_2$—), ethylene (—CH$_2$CH$_2$—), trimethylene (—CH$_2$CH$_2$CH$_2$—), 2-methyltrimethylene (—CH$_2$CH(CH$_3$)CH$_2$—), tetramethylene (—CH$_2$CH$_2$CH$_2$CH$_2$—), 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like). For example, a group of Formula (a), wherein $R^{11}$ is hydrogen and $R^{12}$ taken together with $R^9$ forms optionally substituted trimethylene is depicted by the following illustration:

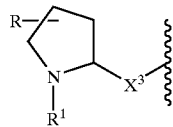

in which R is an optional hydroxy or oxo group and $X^3$ and $R^1$ are as defined in the Summary of the Invention for Formulae I and II.

"Alkylidene" means a straight or branched saturated or unsaturated, aliphatic, divalent radical having the number of carbon atoms indicated (e.g. $(C_{1-6})$alkylidene includes methylene (=CH$_2$), ethylidene (=CHCH$_3$), isopropylidene (=C(CH$_3$)$_2$), propylidene (=CHCH$_2$CH$_3$), allylidene (=CHCH=CH$_2$), and the like).

"Amino" means the radical —NH$_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g. dogs, cats, rabbits, cattle, horses, sheep, goats, swine, deer, or the like) and non-mammals (e.g. birds, or the like).

"Aryl" means a monocyclic or bicyclic ring assembly (fused or linked by a single bond) containing the total number of ring carbon atoms indicated, wherein each ring is comprised of 6 ring carbon atoms and is aromatic or when fused with a second ring forms an aromatic ring assembly. For example,$(C_{6-12})$aryl as used in this Application to define $R^1$ includes phenyl, naphthyl and biphenylyl.

"Aromatic" means a moiety wherein the constituent atoms make up an unsaturated ring system, all atoms in the ring system are sp2 hybridized and the total number of pi electrons is equal to 4n+2.

"Carbamoyl" means the radical —C(O)NH$_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Carboxy" means the radical —C(O)OH. Unless indicated otherwise, the compounds of the invention containing carboxy moieties include protected derivatives thereof. Suitable protecting groups for carboxy moieties include benzyl, tert-butyl, and the like. For example, a compound of Formula I wherein $R^7$ contains a carboxy moiety may exist as either the unprotected or a protected derivative, e.g. wherein $R^7$ is methoxycarbonyl, and both the unprotected and protected derivatives fall within the scope of the invention.

"Cycloalkyl" means a saturated or partially unsaturated, monocyclic ring, bicyclic ring assembly (directly linked by a single bond or fused) or bridged polycyclic ring assembly containing the number of ring member carbon atoms indicated, and any carbocyclic ketone, thioketone or iminoketone derivative thereof (e.g. $(C_{3-12})$cycloalkyl includes cyclopropyl, cyclobutyl, cyclopentyl, cyclohexyl, cyclohexenyl, 2,5-cyclohexadienyl, bicyclohexylyl, cyclopentylcyclohexyl, bicyclo[2.2.2]octyl, adamantan-1-yl, decahydronaphthalenyl, oxocyclohexyl, dioxocyclohexyl, thiocyclohexyl, 2-oxobicyclo[2.2.1]hept-1-yl, and the like).

"Cycloalkylene" means a saturated or partially unsaturated, monocyclic ring or bridged polycyclic ring assembly containing the number of annular carbon atoms indicated, and any carbocyclic ketone, thioketone or iminoketone derivative thereof. For example, the instance wherein $R^3$ and $R^4$ together with the carbon atom to which both $R^3$ and $R^4$ are attached form $(C_{3-8})$cycloalkylene" includes, but is not limited to, the following:

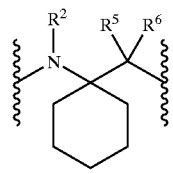 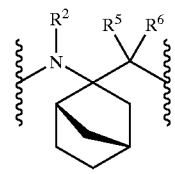

in which $R^2$, $R^5$ and $R^6$ are as defined in the Summary of the Invention, and any substituted derivative thereof.

"Disease" specifically includes any unhealthy condition of an animal or part thereof and includes an unhealthy condition which may be caused by, or incident to, medical or veterinary therapy applied to that animal, i.e., the "side effects" of such therapy.

"Fused heteropolycyclic ring system" means a saturated, partially saturated or aromatic moiety containing two or more rings, wherein at least two ring member atoms of one ring are common to a second ring containing the number of ring member atoms indicated in which at least one of the ring member atoms is a heteroatom and any carbocyclic ketone, thioketone, iminoketone or substituted derivative thereof. For example, the term "a fused heteropolycyclic radical containing 8 to 14 ring member atoms" as used in this Application to define A may include acridinyl, benzofuryl, benzooxazolyl, benzothiazolyl, carbazolyl, carbolinyl, chromanyl, chromenyl, cinnolinyl, indazolyl, indolinyl, indolyl, indolizinyl, isobenzofuryl, isochromenyl, isochromanyl, isoindolinyl, isoquinolyl, naphthyridinyl, perimidinyl, phenanthridinyl, phenanthrolinyl, phenazinyl, phenothiazinyl, phenoxathiinyl, phenoxazinyl, phthalazinyl, pteridinyl, purinyl, pyrrolizinyl, quinazolinyl, quinolizinyl, quinolyl, quinoxalinyl, quinuclidinyl, xanthenyl, and the like.

"Guanidino" means the radical —NHC(NH)NH$_2$. Unless indicated otherwise, the compounds of the invention containing guanidino moieties include protected derivatives thereof. Suitable protecting groups for amino moieties include acetyl, tert-butoxycarbonyl, benzyloxycarbonyl, and the like and both the unprotected and protected derivatives fall within the scope of the invention.

"Halo" means fluoro, chloro, bromo or iodo.

"Halo-substituted alkyl", as a group or part of a group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted (C$_{1-3}$)alkyl includes chloromethyl, dicloromethyl, difluoromethyl, trifluromethyl, 2,2,2-trifluoroethyl, perfluoroethyl, 2,2,2-trifluoro-1,1-dichloroethyl, and the like).

"Heteroaryl" means aryl, as defined herein, provided that one or more of the ring member carbon atoms indicated, is replaced by heteroatom moiety selected from —N=, —NR—, —O— or —S—, wherein R is hydrogen, (C$_{1-6}$) alkyl or a protecting group, and each ring contained therein is comprised of 5 to 6 ring member atoms. For example, hetero(C$_{5-12}$)aryl as used in this Application includes benzofuryl, benzooxazolyl, benzothiazolyl, [2,4'] bipyridinylyl, carbazolyl, carbolinyl, chromenyl, cinnolinyl, furazanyl, furyl, imidazolyl, indazolyl, indolyl, indolizinyl, isobenzofuryl, isochromenyl, isooxazolyl, isoquinolyl, isothiazolyl, naphthyridinyl, oxazolyl, perimidinyl, 2-phenylpyridyl, phthalazinyl, pteridinyl, purinyl, pyrazinyl, pyradazinyl, pyrazolyl, pyridyl, pyrimidinyl, pyrrolizinyl, pyrrolidinyl, pyrrolyl, pyranyl, quinazolinyl, quinolizinyl, quinolyl, quinoxalinyl, tetrazolyl, thiazolyl, 4-thiazol-4-ylphenyl, thienyl, xanthenyl, and the like.

"Heteroatom moiety" includes —N=, —NR—, —O—, —S— or —S(O)$_2$—, wherein R is hydrogen, (C$_{1-6}$)alkyl or a protecting group.

"Heterocycloalkyl" means cycloalkyl, as defined herein, provided that one or more of the ring member carbon atoms indicated is replaced by heteroatom moiety selected from —N=, —NR—, —O— or —S—, wherein R is hydrogen, (C$_{1-6}$)alkyl or a protecting group, and any carbocyclic ketone, thioketone or iminoketone derivative thereof (e.g. the term hetero(C$_{5-12}$)cycloalkyl includes [1,4'] bipiperidinylyl, dihydrooxazolyl, morpholinyl, 1-morpholin-4-ylpiperidinyl, piperazinyl, piperidyl, pirazolidinyl, pirazolinyl, pyrrolinyl, pyrrolidinyl, quinuclidinyl, and the like). Suitable protecting groups include tert-butoxycarbonyl, benzyloxycarbonyl, benzyl, 4-methoxybenzyl, 2-nitrobenzyl, and the like. For example, a compound of Formula I wherein R$^1$ is piperidin-4-ylcarbonyl may exist as either the unprotected or a protected derivative, e.g. wherein R$^1$ is 1-tert-butoxycarbonylpiperidin-4-ylcarbonyl, and both the unprotected and protected derivatives fall within the scope of the invention.

"Heterocycloalkylene" means cycloalkylene, as defined in this Application, provided that one or more of the ring member carbon atoms indicated, is replaced by heteroatom moiety selected from —N=, —NR—, —O—, —S— or —S(O)$_2$—, wherein R is hydrogen or (C$_{1-6}$)alkyl. For example, the instance wherein R$^3$ and R$^4$ together with the carbon atom to which both R$^3$ and R$^4$ are attached form hetero(C$_{3-8}$)cycloalkylene" includes, but is not limited to, the following:

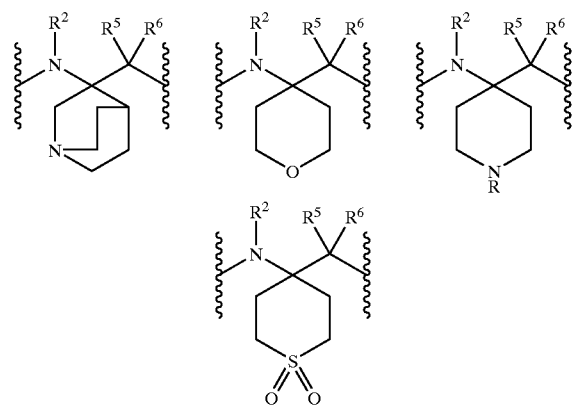

in which R is hydrogen, (C$_{1-6}$)alkyl or a protecting group and R$^2$ is as defined in the Summary of the Invention, and any substituted derivative thereof.

"Heteromonocyclic" means a saturated, partially saturated or aromatic monocyclic radical containing the number of ring member atoms indicated in which at least one of the ring member atoms is a heteroatom and any carbocyclic ketone, thioketone, iminoketone or substituted derivative thereof. For example, the term "a heteromonocyclic containing 5 to 6 ring member atoms" as used in this Application to define A may include dihydrooxazolyl, furazanyl, furyl, imidazolyl, imidazolidinyl, imidazolinyl, isooxazolyl, isothiazolyl, thiazolyl, thienyl, morpholinyl, oxazolyl, piperazinyl, piperidinyl, pirazolidinyl, pirazolinyl, pyranyl, pyrazinyl, pyradazinyl, pyrazolyl, pyridyl, pyrimidinyl, pyrrolidinyl, pyrrolinyl, pyrrolyl, tetrazolyl, and the like.

"Heteropolycycloaryl" means polycycloaryl, as defined herein, except one or more of the ring member carbon atoms indicated are replaced by a heteroatom moiety selected from —N=, —NR—, —O— or —S—, wherein R is hydrogen, (C$_{1-6}$)alkyl or a protecting group, and any carbocyclic ketone, thioketone or iminoketone derivative thereof. For example, hetero(C$_{8-12}$)polycycloaryl includes 1',2'-dihydro-2H-[1,4']bipyridinylyl, chromanyl, imidazolinyl, indolinyl, isochromanyl, isoindolinyl, and the like.

"Hydroxy" means the radical —OH. Unless indicated otherwise, the compounds of the invention containing hydroxy radicals include protected derivatives thereof. Suitable protecting groups for hydroxy moieties include benzyl and the like and both the unprotected and protected derivatives fall within the scope of the invention.

"Iminoketone derivative" means a derivative containing the moiety —C(NR)—, wherein R is hydrogen or (C$_{1-6}$) alkyl.

"Isomers" mean compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g. see "Advanced Organic Chemistry", 3rd edition, March, Jerry, John Wiley & Sons, New York, 1985). It is understood that the names and illustration used in this Application to describe compounds of Formula I are meant to be encompassed all possible stereoisomers and any mixture, racemic or otherwise, thereof.

"Ketone derivative" means a derivative containing the moiety —C(O)—.

"Nitro" means the radical —NO$_2$.

"Optional" or "optionally" means that the subsequently described event or circumstance may or may not occur, and that the description includes instances where the event or circumstance occurs and instances in which it does not. For example, the phrase "(C$_{1-6}$)alkyl optionally substituted with cyano, halo, nitro," means that the alkyl group referred to may or may not be substituted in order to fall within the scope of the invention.

"Oxalo" means the radical —C(O)C(O)OH.

"N-oxide derivatives" means a derivatives of compound of Formula I in which nitrogens are in an oxidized state (i.e., O—N) and which possess the desired pharmacological activity.

"Oxo" means the radical=O.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutaric acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, ammonium hydroxide, aluminum hydroxide and calcium hydroxide. Acceptable organic bases include ethanolamine, diethanolamine, triethanolamine, tromethamine, N-methylglucamine and the like.

"Phenylene-1,2-dimethylene" means the divalent radical —CH$_2$C$_6$H$_4$CH$_2$—, wherein the methylene moieties are attached at the 1- and 2-positions of the phenylene moiety. For example, a group of Formula (a) in which R$^{12}$ together with R$^9$ forms optionally substituted phenylene-1,2-dimethylene is illustrated by the following formula:

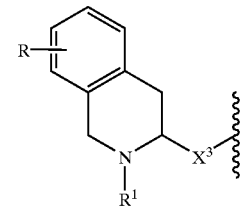

in which R is an optional hydroxy group and X$^3$ and R$^1$ are as defined in the Summary of the Invention for Formulae I and II.

"Polycycloaryl" means a bicyclic ring assembly (directly linked by a single bond or fused) containing the number of ring member carbon atoms indicated, wherein at least one, but not all, of the fused rings comprising the radical is aromatic, and any carbocyclic ketone, thioketone or iminoketone derivative thereof (e.g. (C$_{9-12}$)polycycloaryl includes indanyl, indenyl, 1,2,3,4-tetrahydronaphthalenyl, 1,2-dihydronaphthalenyl, cyclohexylphenyl, phenylcyclohexyl, 2,4-dioxo-1,2,3,4-tetrahydronaphthalenyl, and the like).

"Prodrug" means a compound which is convertible in vivo by metabolic means (e.g. by hydrolysis) to a compound of Formula (I). For example an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulphonates, ethanesulphonates, benzenesulphonates, p-toluenesulphonates, cyclohexylsulphamates and quinates. Suitable esters of compounds of Formula (I) containing a carboxy group, are for example those described by F. J. Leinweber, Drug Metab. Res., 1987, 18, page 379. An especially useful class of esters of compounds of Formula (I) containing a hydroxy group, may be formed from acid moieties selected from those described by Bundgaard et. al., J. Med. Chem., 1989, 32, page 2503–2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates. A prodrug derivative of a compound of Formula I wherein $R^5$ and $R^6$ together are oxo is depicted by the following formula:

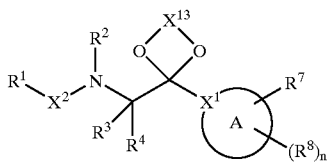

in which $X^{13}$ is a bond, straight, saturated ethylene or (—CH$_2$CR$^{41}$R$^{42}$CH$_2$—), wherein $R^{41}$ and $R^{42}$ independently are hydrogen, halo or $(C_{1-3})$alkyl or taken together form methylene.

"Protected derivatives" means derivatives of compounds of Formula I in which a reactive site or sites are blocked with protecting groups. Protected derivatives of compounds of Formula I are useful in the preparation of compounds of Formula I or in themselves may be active cysteine protease inhibitors. For example, the compound of Formula I which is 2S-amino-N-(2-benzooxazol-2-yl-2-hydroxy-1S-phenethylethyl)-3-cyclohexylpropionamide (i.e., Compound 55, described in Example 6, infra) may be protected with a suitable amino protecting group, e.g. 9H-fluoren-9-ylmethoxycarbonyl, or a suitable hydroxy protecting group, e.g. tert-butyldimethylsilanyl, to provide, respectively, 9H-fluoren-9-ylmethyl 1S-(2-benzooxazol-2-yl-2-hydroxy-1S-phenethylethylcarbamoyl)-2-cyclohexylethylcarbamate (i.e., Compound 51, described in Example 4, infra) and 2S-amino-N-[2-benzooxazol-2-yl-2-(tert-butyldimethylsilanyloxy)-1S-phenethylethyl]-3-cyclohexylpropionamide (i.e., Compound 56, described in Example 7, infra). A comprehensive list of suitable protecting groups can be found in T. W. Greene, Protecting Groups in Organic Synthesis, John Wiley & Sons, Inc. 1981.

"Ring member", as in fused heteropolycyclic ring system containing 8 to 14 ring member atoms, means that the atoms referred to are ring members of the fused heteropolycyclic radical, but not taking into account ring members of any substituents present. Thus, for example, a heteropolycyclic radical containing 8 ring member atoms includes benzooxaxol-2-yl, benzofur-2-yl, 1H-indol-5-yl, benzothiazol-2-yl, and the like.

"Sulfamoyl" means the radical —S(O)$_2$NH$_2$. Unless indicated otherwise, the compounds of the invention containing sulfamoyl radicals include protected derivatives thereof. Suitable protecting groups for sulfamoyl radicals include acetyl, tert-butoxycarbonyl, benzyloxycarbonyl, and the like and both the unprotected and protected derivatives fall within the scope of the invention.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

SPECIFIC EMBODIMENTS OF THE INVENTION

While the broadest definition of the invention is set forth in the Summary of the Invention, certain aspects of the invention are preferred. A preferred aspect of the invention are compounds of Formula I in which $X^1$ is =C—. In particular, the heteromonocyclic ring or fused heteropolycyclic ring system A is selected from 4,5-dihydrooxazol-2-yl, benzooxazol-2-yl, benzothiazol-2-yl and oxazol-2-yl, each substituted by a group $R^7$ and optionally substituted with a group $R^8$, particularly wherein $R^7$ is hydrogen, halo, $(C_{1-4})$alkoxy, $(C_{1-4})$alkoxycarbonyl, nitro or phenyl and $R^8$ at each occurrence independently is halo, $(C_{1-4})$alkoxy, $(C_{1-4})$alkoxycarbonyl, nitro or trifluoromethyl. The ring system A preferably is benzoxazol-2-yl substituted by a group $R^7$ and optionally substituted with a group $R^8$, particularly wherein $R^7$ is hydrogen, halo, $(C_{1-4})$alkoxy, $(C_{1-4})$alkoxycarbonyl or nitro and $R^8$ at each occurrence independently is halo, $(C_{1-4})$alkoxy, $(C_{1-4})$alkoxycarbonyl, nitro or trifluoromethyl.

$X^2$ particularly represents a bond or a divalent group of Formula (a); particularly, wherein within Formula (a) $X^3$ is —C(O)—, $R^9$ represents hydrogen, $R^{11}$ represents hydrogen or methyl, typically hydrogen, and $R^{12}$ particularly represents (i) $(C_{1-6})$alkyl substituted with —SR$^{14}$, —S(O)R$^{14}$ or —S(O)$_2$R$^{14}$, wherein $R^{14}$ is $(C_{6-12})$aryl$(C_{0-6})$alkyl or hetero $(C_{5-12})$aryl$(C_{0-6})$alkyl or (ii) $(C_{3-12})$cycloalkyl$(C_{0-6})$alkyl or $(C_{6-12})$aryl$(C_{0-6})$alkyl; wherein within $R^{12}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —X$^5$NR$^{14}$R$^{14}$, —X$^5$NR$^{14}$C(O)OR$^{14}$, —X$^5$NR$^{14}$C(O) NR$^{14}$R$^{14}$, —X$^5$NR$^{14}$C(NR$^{14}$)NR$^{14}$R$^{14}$, –X$^5$OR$^{14}$, —X$^5$SR$^{14}$, —X$^5$C(O)OR$^{14}$, —X$^5$C(O)NR$^{14}$R$^{14}$, —X$^5$S (O)$_2$ NR$^{14}$R$^{14}$, —X$^5$P(O)(OR$^{14}$)OR$^{14}$, —X$^5$OP(O)(OR$^{14}$)OR$^{14}$, —X$^5$NR$^{14}$C(O)R$^{15}$, —X$^5$S(O)R$^{15}$, —X$^5$S(O)$_2$R$^{15}$ and —X$^5$C(O)R$^{15}$, wherein $X^5$ is a bond or $(C_{1-6})$alkylene, $R^{14}$ at each occurrence independently is hydrogen, $(C_{1-4})$alkyl or halo-substituted $(C_{1-3})$alkyl and $R^{15}$ is $(C_{1-6})$alkyl or halo-substituted $(C_{13})$alkyl.

Further preferred, within Formula (a), $R^{12}$ particularly represents a group having the following formula:

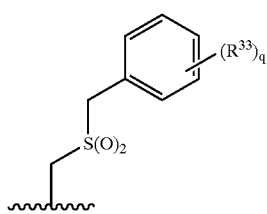

in which q is 0, 1, 2, 4 or 5 and $R^{33}$ at each occurrence independently is selected from a group consisting of $(C_{1-4})$alkyl, cyano, halo, halo-substituted $(C_{1-4})$alkyl, nitro, $—X^5NR^{14}R^{14}$, $—X^5OR^{14}$, $—X^5SR^{14}$, $—X^5C(O)NR^{14}R^{14}$, $—X^5C(O)OR^{14}$, $—X^5S(O)R^{15}$, $—X^5S(O)_2R^{15}$ and $—X^5C(O)R^{15}$, wherein $X^5$ is a bond or $(C_{1-6})$alkylene, $R^{14}$ at each occurrence independently is hydrogen, $(C_{1-3})$alkyl or halo-substituted $(C_{1-3})$alkyl and $R^{15}$ is $(C_{1-3})$alkyl or halo-substituted $(C_{1-3})$alkyl; more particularly in which q is 0, 1 or 2 and $R^{33}$ at each occurrence independently is selected from a group consisting of $(C_{1-4})$alkyl, cyano, halo, halo-substituted $(C_{1-4})$alkyl, nitro, $—OR^{14}$, $—SR^{14}$ and $—C(O)OR^{14}$, wherein $R^{14}$ independently is hydrogen, $(C_{1-3})$alkyl or halo-substituted $(C_{1-3})$alkyl; more particularly in which $R^{33}$ at each occurrence independently is selected from a group consisting of $(C_{1-4})$alkyl, bromo, carboxy, chloro, cyano, difluoromethoxy, fluoro, iodo, methoxy, nitro, trifluoromethoxy, trifluoromethyl and trifluorosulfanyl.

Further preferred, within Formula (a), $R^{12}$ particularly represents benzylsulfonylmethyl, 2-chlorobenzylsulfonylmethyl, 2-cyanobenzylsulfonylmethyl, 2-difluoromethoxybenzylsulfonylmethyl, 3,5-dimethylisooxazol-4-ylmethylsulfonylmethyl, 2-methoxybenzylsulfonylmethyl, 6-methylpyrid-2-ylmethylsulfonylmethyl, 2-nitrobenzylsulfonylmethyl, pyrid-2-ylmethylsulfonylmethyl, o-tolylmethylsulfonylmethyl or 2-trifluoromethylbenzylsulfonylmethyl.

$R^1$ particularly represents $—X^6X^7R^{20}$, wherein $X^6$ is $—C(O)—$ or $—S(O)_2—$, $X^7$ is a bond, $—O—$ or $—NR^{21}—$, wherein $R^{21}$ is hydrogen or $(C_{1-6})$alkyl, and $R^{20}$ is (i) $(C_{1-6})$alkyl optionally substituted by $—C(O)OR^{14}$ or (ii) $(C_{3-12})$cycloalkyl$(C_{0-6})$alkyl, hetero$(C_{3-12})$cycloalkyl$(C_{0-6})$alkyl $(C_{6-12})$aryl$(C_{0-6})$alkyl or hetero$(C_{5-12})$aryl$(C_{0-6})$alkyl or (iii) $(C_{3-6})$cycloalkyl$(C_{0-6})$alkyl, hetero$(C_{3-6})$cycloalkyl $(C_{0-6})$alkyl, phenyl$(C_{0-6})$alkyl or hetero$(C_{5-6})$aryl$(C_{0-6})$alkyl, wherein said cycloalkyl, heterocycloalkyl, phenyl or heteroaryl ring is substituted by $—X^5OR^{24}$, $—X^5C(O)R^{24}$, $—X^5C(O)OR^{24}$, $—X^5C(O)NR^{24}R^{25}$, $—X^5NR^{24}R^{25}$, $—X^5NR^{25}C(O)R^{24}$, $—X^5NR^{25}C(O)OR^{24}$, $—X^5NR^{25}C(O)NR^{24}R^{25}$ or $—X^5NR^{25}C(NR^{25})NR^{24}R^{25}$, wherein $X^5$ is a bond or $(C_{1-6})$alkylene, $R^{24}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl and $R^{25}$ is hydrogen or $(C_{1-6})$ alkyl; wherein within $R^1$ any alicyclic or aromatic ring system present may be substituted further by 1 to 5 substituents independently selected from $(C_{1-6})$alkyl, halo, halo-substituted $(C_{1-4})$alkyl, $—OR^{14}$ and $—C(O)OR^{14}$ wherein $R^{14}$ is hydrogen or $(C_{1-6})$alkyl, or when $X^2$ is a divalent group of formula (a) then $R^1$ may be, but is not limited to, hydrogen or oxalo.

$R^1$ preferably is a group selected from acetyl, azetidin-3-ylcarbonyl, benzyloxycarbonyl, 1-benzyloxycarbonylpiperidin-4-ylcarbonyl, benzylsulfonyl, bicyclo[2.2.2]hept-2-ylcarbonyl, bicyclo[2.2.1]hept-2-ylcarbonyl, tert-butoxycarbonyl, carboxyacetyl, 2-carboxypropionyl, 3-carboxypropionyl, 2-cyclohexylacetyl, 4-cyclohexylbutyryl, 2-cyclohexylethylsulfonyl, cyclohexylmethoxycarbonyl, 3-cyclohexylpropionyl, 2-cyclopentylethylsulfonyl, 3-cyclopentylpropionyl, di(2-methoxyethyl)carbamoyl, dimethylcarbamoyl, 6-hydroxypyrid-3-ylcarbonyl, 1H-imidazol-4-ylcarbonyl, methoxycarbonyl, methylsulfonyl, 4-methylvaleryl, morpholin-4-ylcarbonyl, 2-morpholin-4-ylethylcarbonyl, naphth-1-ylacetyl, naphth-1-ylmethylcarbonyl, oxalo, 3-phenylpropionyl, piperazin-1-ylcarbonyl, piperidin-4-ylcarbonyl, pyrazin-2-ylcarbonyl, pyrid-3-ylcarbonyl, pyrid-4-ylcarbonyl, pyrid-3-ylaminocarbonyl, tetrahydropyran-4-ylcarbonyl and tetrahydropyran-4-yloxycarbonyl.

$R^1$ especially represents morpholin-4-ylcarbonyl, methoxycarbonyl, methylsulfonyl, piperidin-4-ylcarbonyl, pyrazin-2-ylcarbonyl pyrid-3-ylcarbonyl, pyrid-4-ylcarbonyl, tetrahydropyran-4-ylcarbonyl or tetrahydropyran-4-yloxycarbonyl.

$R^2$ typically is hydrogen.

$R^3$ particularly represents hydrogen, $(C_{1-6})$alkyl (optionally substituted with cyano, halo, nitro, $—SR^{26}$, $—C(O)OR^{26}$, $—C(O)NR^{26}R^{26}$, $—P(O)(OR^{26})OR^{26}$, $—OP(O)(OR^{26})OR^{26}$, $—S(O)R^{27}$, $—S(O)_2R^{27}$ or $—C(O)R^{27}$, wherein $R^{26}$ at each occurrence independently is hydrogen, $(C_{1-6})$alkyl, or halo-substituted $(C_{1-3})$alkyl and $R^{27}$ is $(C_{1-6})$alkyl or halo-substituted $(C_{1-3})$alkyl) or $(C_{6-12})$aryl $(C_{2-3})$alkyl, wherein said aryl optionally is substituted further with 1 to 5 radicals independently selected from $(C_{1-6})$alkyl, $(C_{1-6})$alkylidene, cyano, halo, halo-substituted $(C_{1-4})$alkyl, nitro, $—X^5NR^{14}C(O)OR^{14}$, $—X^5NR^{14}C(O)NR^{14}R^{14}$, $—X^5NR^{14}C(NR^{14})NR^{14}R^{14}$, $—X^5OR^{14}$, $—X^5SR^{14}$, $—X^5C(O)OR^{14}$, $—X^5C(O)NR^{14}R^{14}$, $—X^5S(O)_2NR^{14}R^{14}$, $—X^5P(O)(OR^{14})OR^{14}$, $—X^5OP(O)(OR^{14})OR^{14}$, $—X^5NR^{14}C(O)R^{15}$, $—X^5S(O)R^{15}$, $—X^5S(O)_2 R^{15}$ and $—X^5C(O)R^{15}$, wherein $X^5$ is a bond or $(C_{1-6})$alkylene, $R^{14}$ at each occurrence independently is hydrogen, $(C_{1-6})$alkyl or halo-substituted $(C_{1-3})$alkyl and $R^{15}$ is $(C_{1-6})$alkyl or halo-substituted $(C_{1-3})$alkyl, or $R^3$ and $R^4$ taken together with the carbon atom to which both $R^3$ and $R^4$ are attached form $(C_{3-6})$cycloalkylene. In particular, $R^3$ may be selected from hydrogen, $(C_{1-4})$alkyl (e.g. methyl, ethyl, n-propyl, n-butyl), phenyl$(C_{2-3})$alkyl (e.g. phenethyl) or $(C_{1-4})$alkylsulfonyl$(C_{2-4})$alkyl (e.g. 2-methylsulfonylethyl) or $R^3$ and $R^4$ taken together with the carbon atom to which both $R^3$ and $R^4$ are attached form $(C_{3-6})$cycloalkylene (e.g. cyclobutylene or cyclohexylene). $R^3$ preferably is $(C_{1-4})$alkyl.

$R^4$ particularly represents hydrogen or $R^3$ and $R^4$ taken together with the carbon atom to which both $R^3$ and $R^4$ are attached form $(C_{3-6})$cycloalkylene (e.g. cyclobutylene or cyclohexylene).

$R^5$ and $R^6$ preferably together form oxo.

Compounds of Formula II are preferred in which:

n is 0;

$X^1$ is =C— and the ring system A is selected from 4,5-dihydrooxazol-2-yl, benzooxazol-2-yl, benzothiazol-2-yl and oxazol-2-yl, each substituted by a group $R^7$ and optionally substituted with a group $R^8$, particularly wherein $R^7$ is hydrogen, halo, $(C_{1-4})$alkoxy, $(C_{1-4})$alkoxycarbonyl, nitro or phenyl and $R^8$ at each occurrence independently is $(C_{1-4})$alkoxy, $(C_{1-4})$alkoxycarbonyl, nitro or trifluoromethyl.

$X^8$ methylene or ethylene;

$R^1$, $R^3$ and $R^4$ are as defined above;

$R^5$ and $R^6$ together form oxo;

$R^9$ is hydrogen; and $R^{32}$ is —$X^9R^{34}$, wherein $X^9$ is methylene when $X^8$ is methylene and $X^9$ is a bond when $X^8$ is ethylene, $R^{34}$ is —$CR^{35}$=$CHR^{36}$ or —$CR^{37}$=$NR^{38}$, wherein $R^{35}$ and $R^{36}$ together with the atoms to which $R^{35}$ and $R^{36}$ are attached form $(C_{2-6})$alkenyl, $(C_{5-12})$cycloalkenyl, hetero$(C_{5-12})$cycloalkenyl, $(C_{6-12})$aryl, hetero$(C_{6-12})$aryl, $(C_{9-12})$bicycloaryl or hetero$(C_{8-12})$bicycloaryl and $R^{37}$ and $R^{38}$ together with the atoms to which $R^{37}$ and $R^{38}$ are attached form hetero$(C_{5-12})$cycloalkenyl, hetero$(C_{6-12})$aryl or hetero$(C_{8-12})$bicycloaryl, wherein within $R^{34}$ said cycloalkenyl, heterocycloalkenyl, aryl, heteroaryl, bicycloaryl or heterobicycloaryl may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)N^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$ is a bond or $(C_{1-6})$alkylene, $R^{14}$ at each occurrence independently is hydrogen, $(C_{1-6})$alkyl or halo-substituted $(C_{1-3})$alkyl and $R^{15}$ is $(C_{1-6})$alkyl or halo-substituted $(C_{1-3})$alkyl.

$R^{34}$ particularly represents $(C_{6-12})$aryl or hetero$(C_{5-12})$ aryl, each optionally substituted by 1 to 5 radicals selected from a group consisting of $(C_{1-4})$alkyl, cyano, halo, halo-substituted $(C_{1-4})$alkyl, nitro, —$X^5NR^{14}R^{14}$, —$X^5OR^{14}$, —$X^5SR^{14}$, —$X^5C(O)NR^{14}R^{14}$, —$X^5C(O)OR^{14}$, —$X^5S(O)R^{15}$, —$X^5S(O)_2R^{15}$ and —$X^5C(O)R^{15}$, wherein $X^5$ is a bond or $(C_{1-2})$alkylene, $R^{14}$ at each occurrence independently is hydrogen, $(C_{1-3})$alkyl or halo-substituted $(C_{1-3})$alkyl and $R^{15}$ is $(C_{1-3})$alkyl or halo-substituted $(C_{1-3})$alkyl. $R^{34}$ more preferably represents biphenyl, isooxazolyl, naphthyl, phenyl, pyridyl or thienyl, each optionally substituted by 1 to 5 radicals selected from a group consisting of $(C_{1-4})$alkyl, cyano, halo, halo-substituted $(C_{1-4})$alkyl, nitro, —$X^5NR^{14}R^{14}$, —$X^5OR^{14}$, —$X^5SR^{14}$, —$X^5C(O)NR^{14}R^{14}$, —$X^5C(O)OR^{14}$, —$X^5S(O)R^{15}$, —$X^5S(O)_2R^{15}$ and —$X^5C(O)R^{15}$, wherein $X^4$ is a bond or $(C_{1-2})$alkylene, $R^{14}$ at each occurrence independently is hydrogen, $(C_{1-3})$alkyl or halo-substituted $(C_{1-3})$alkyl and $R^{15}$ is $(C_{1-3})$alkyl or halo-substituted $(C_{1-3})$alkyl. $R^{34}$ more preferably represents biphenyl-2-yl, 2,4-bistrifluoromethylphenyl, 2,5-bistrifluoromethylphenyl, 4-tert-butylphenyl, 2-bromophenyl, 3-bromophenyl, 4-bromophenyl, 2-bromo-5-fluorophenyl, 3-chloro-2-fluorophenyl, 2-chlorophenyl, 3-chlorophenyl, 4-chlorophenyl, 5-chlorothien-2-yl, 2-chloro-5-trifluoromethyl, 2-cyanophenyl, 3-cyanophenyl, 4-cyanophenyl, 1,5-dichlorophenyl, 2,6-dichlorophenyl, 3,4-dichlorophenyl, 2,3-difluorophenyl, 2,4-difluorophenyl, 3,4-difluorophenyl, 2-difluoromethoxyphenyl, 3-difluoromethoxyphenyl, 4-difluoromethoxyphenyl, 2,5-difluorophenyl, 2,6-difluorophenyl, 3,5-dimethylisooxazol4-yl, 3,5-dimethylphenyl, 2-fluoro-6-nitrophenyl, 2-fluorophenyl, 4-fluorophenyl, 2-fluoro-3-trifluoromethylphenyl, 2-fluoro-4-trifluoromethylphenyl, 2-fluoro-5-trifluoromethylphenyl, 2-fluoro-6-trifluoromethylphenyl, 4-fluoro-2-trifluoromethylphenyl, 4-fluoro-3-trifluoromethylphenyl, 2-iodophenyl, 3-iodophenyl, 4-iodophenyl, 2-methoxyphenyl, 4-methoxyphenyl, 2-methylphenyl, 3-methylphenyl, 4-methylphenyl, 6-methylpyrid-2-yl, 3-methyl-2-fluorophenyl, naphth-2-yl, 2-nitrophenyl, 3-nitrophenyl, 4-nitrophenyl, 2,3,4,5,6-pentafluorophenyl, phenyl, prop-2-en-1-yl, pyrid-2-yl, pyrid-3-yl, pyrid-4-yl, thien-3-yl, o-tolyl, 2-trifluoromethoxyphenyl, 3-trifluoromethoxyphenyl, 4-trifluoromethoxyphenyl, 3-trifluoromethylphenyl, 4-trifluoromethylphenyl, 2-trifluoromethylsulfanylphenyl, 3-trifluoromethylsulfanylphenyl , 4-trifluoromethylsulfanylphenyl, 2,3,4-trifluoro phenyl, 2,3,5-trifluorophenyl, 2,4,6-trifluorophenyl, 2,4,5-trifluorophenyl or 2,3,6-trifluorophenyl.

A preferred group of compounds of Formula II are those in which —$X^8S(O)_2R^{32}$ represents a group having the following formula:

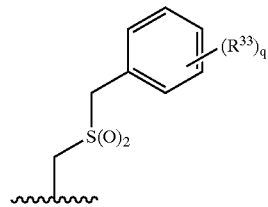

in which q is 0, 1, 2, 4 or 5 and $R^{33}$ at each occurrence independently is selected from a group consisting of $(C_{1-4})$alkyl, cyano, halo, halo-substituted $(C_{1-4})$alkyl, nitro, —$X^5NR^{14}R^{14}$, —$X^5OR^{14}$, —$X^5SR^{14}$, —$X^5C(O)NR^{14}R^{14}$, —$X^5C(O)OR^{14}$, —$X^5S(O)R^{15}$, —$X^5S(O)_2R^{15}$ and —$X^5C(O)R^{15}$, wherein $X^5$ is a bond or $(C_{1-2})$alkylene, $R^{14}$ at each occurrence independently is hydrogen, $(C_{1-3})$alkyl or halo-substituted $(C_{1-3})$alkyl and $R^{15}$ is $(C_{1-3})$alkyl or halo-substituted $(C_{1-3})$alkyl; more particularly in which q is 0, 1 or 2 and $R^{33}$ at each occurrence independently is selected from a group consisting of $(C_{1-4})$alkyl, cyano, halo, halo-subsituted $(C_{1-4})$alkyl, nitro, —$OR^{14}$, —$SR^{14}$ and —$C(O)OR^{14}$, wherein $R^{14}$ at each occurrence independently is hydrogen, $(C_{1-3})$alkyl or halo-substituted $(C_{1-3})$alkyl; more particularly in which $R^{33}$ at each occurrence independently is selected from a group consisting of $(C_{1-4})$alkyl, bromo, carboxy, chloro, cyano, difluoromethoxy, fluoro, iodo, methoxy, nitro, trifluoromethoxy, trifluoromethyl and trifluorosulfanyl. In particular, —$X^8S(O)_2R^{32}$ represents benzylsulfonylmethyl, 2-chlorobenzylsulfonylmethyl, 2-cyanobenzylsulfonylmethyl, 2-difluoromethoxybenzylsulfonylmethyl, 3,5-dimethylisooxazol-4-ylmethylsulfonylmethyl, 2-methoxybenzylsulfonylmethyl, 6-methylpyrid-2-ylmethylsulfonylmethyl, 2-nitrobenzylsulfonylmethyl, pyrid-2-ylmethylsulfonylmethyl, o-tolylmethylsulfonylmethyl or 2-trifluoromethylbenzylsulfonylmethyl.

Reference to the preferred embodiments set forth above is meant to include all combinations of particular and preferred groups.

Further preferred are compounds of Formula I selected from a group consisting of:

2S-acetylamino-N-(1S-benzooxazol-2-ylcarbonyl)-3-phenylpropyl)-3-cyclohexylpropionamide; and N-[1S-(1S-benzooxazol-2-ylcarbonyl-3-phenylpropylcarbamoyl)-2-cyclohexylethylisonicotinamide; and the N-oxide derivatives, prodrug derivatives, protected derivatives, individual isomers and mixtures of isomers; and the pharmaceutically acceptable salts thereof.

Further preferred are compounds of Formula I selected from a group consisting of:

N-[1R-(1S-benzooxazol-2-ylcarbonylbutylcarbamoyl)-2-benzylsulfonylethyl]morpholine-4-carboxamide;
methyl 1R-(1S-benzooxazol-2-ylcarbonylbutylcarbamoyl)-2-benzylsulfonylethylcarbamate;
N-(1S-benzooxazol-2-ylcarbonylbutyl)-2R-methylsulfonylamino-3-benzylsulfonylpropionamide;
N-(1S-benzooxazol-2-ylcarbonylbutylcarbamoyl)-2R-(3,3-dimethylureido)-3-(2-methoxybenzylsulfonyl)propionamide;
N-[1R-(1S-benzooxazol-2-ylcarbonylbutylcarbamoyl)-2-(2-difluoromethoxybenzylsulfonyl)ethyl]morpholine-4-carboxamide;
N-[1R-(1S-benzooxazol-2-ylcarbonylbutylcarbamoyl)-2-(2-methoxybenzylsulfonyl)ethyl]morpholine-4-carboxamide;
N-[1R-(1S-benzooxazol-2-ylcarbonylpentylcarbamoyl)-2-benzylsulfonylethyl]morpholine-4-carboxamide;
N-[1R-(1S-benzooxazol-2-ylcarbonylpentylcarbamoyl)-2-(2-chlorobenzylsulfonyl)ethyl]morpholine-4-carboxamide;
1R-(1S-benzooxazol-2-ylcarbonylpentylcarbamoyl)-2-(2-difluoromethoxybenzylsulfonyl)ethylcarbamate;
N-[1R-(1S-benzooxazol-2-ylcarbonylpentylcarbamoyl)-2-(2-difluoromethoxybenzylsulfonyl)ethyl]morpholine-4-carboxyamide;
N-[1R-(1S-benzooxazol-2-ylcarbonylpentylcarbamoyl)-2-(3,5-dimethylisoxazol-4-ylmethylsulfonylethyl]isonicotinamide;
N-[1R-(1S-benzooxazol-2-ylcarbonylpentylcarbamoyl)-2-(2-nitrobenzylsulfonyl)ethyl]morpholine-4-carboxamide;
N-[1R-(1S-benzooxazol-2-ylcarbonylpentylcarbamoyl)-2-pyridin-2-ylmethylsulfonylethyl]morpholine-4-carboxamide;
N-[1R-(1S-benzooxazol-2-ylcarbonylpentylcarbamoyl)-2-o-tolylmethylsulfonylethyl]morpholine-4-carboxamide;
N-[1R-(1S-benzooxazol-2-ylcarbonylpentylcarbamoyl)-2-(2-trifluoromethylbenzylsulfonyl)ethyl]morpholine-4-carboxamide;
N-[1R-(1S-benzooxazol-2-ylcarbonyl-3-phenylpropylcarbamoyl)-2-benzylsulfonylethyl]nicotinamide;
N-[1R-(1S-benzooxazol-2-ylcarbonyl-3-phenylpropylcarbamoyl)-2-benzylsulfonylethyl]pyrazine-2-carboxamide;
N-[1R-(1S-benzooxazol-2-ylcarbonyl-3-phenylpropylcarbamoyl)-2-(2-chlorobenzylsulfonyl)ethyl]morpholine-4-carboxamide;
N-[1R-(1S-benzooxazol-2-ylcarbonyl-3-phenylpropylcarbamoyl)-2-(2-cyanobenzylsulfonyl)ethyl]isonicotinamide;
N-[1R-(1S-benzooxazol-2-ylcarbonyl-3-methylsulfonylpropylcarbamoyl)-2-(2-difluoromethoxybenzylsulfonyl)ethyl]morpholine-4-carboxamide;
N-[1S-benzooxazol-2-ylcarbonylpentylcarbamoyl)-2-(2-difluoromethoxybenzylsulfonyl)ethyl]isonicotinamide;
N-[1R-(1S-benzooxazol-2-ylcarbonyl)-3-phenylpropylcarbamoyl)-2-benzylsulfonylethyl]morpholine-4-carboxamide;
N-[1R-(1S-benzooxazol-2-ylcarbonyl-3-phenylpropylcarbamoyl)-2-(6-methylpyrid-2-ylmethylsulfonyl)ethyl]isonicotinamide;
N-[1R-(1S-benzooxazol-2-ylcarbonyl-3-phenylpropylcarbamoyl)-2-(2-nitrobenzylsulfonyl)ethyl]morpholine-4-carboxamide;
N-[1R-(1S-benzooxazol-2-ylcarbonyl-3-phenylpropylcarbamoyl)-2-pyrid-2-ylmethylsulfonylethyl]morpholine-4-carboxamide;
N-[1R-(1S-benzooxazol-2-ylcarbonyl-3-phenylpropylcarbamoyl)-2-o-tolylmethylsulfonylethyl]morpholine-4-carboxamide;
N-[1R-(1S-benzooxazol-2-ylcarbonyl-3-phenylpropylcarbamoyl)-2-(2-trifluoromethylbenzylsulfonyl)ethyl]tetrahydropyran-4-carboxamide;
tetrahydropyran-4-yl 1R-(1S-benzooxazol-2-ylcarbonyl-3-phenylpropylcarbamoyl)-2-benzylsulfonylethylcarbamate; and
N-[1R-(1S-benzooxazol-2-ylcarbonyl-3-phenylpropylcarbamoyl)-2-(2-cyanobenzylsulfonyl)ethyl]piperidine-4-carboxamide; and the N-oxide derivatives, prodrug derivatives, protected derivatives, individual isomers and mixtures of isomers; and the pharmaceutically acceptable salts thereof.

A preferred aspect of the invention are compounds of Formula I in which $X^1$ is =C—. In particular, the heteromonocyclic ring or fused heteropolycyclic ring system A is selected from thien-2-yl, oxazol-2-yl, 4,5-dihydrooxazol-2-yl, fur-2-yl, 1H-indol-5-yl, pyrid-2-yl, pyrid-3-yl thiazol-2-yl, 1-methyl-1H-imidazol-2-yl, 1-benzyl-1H-imidazol-2-yl, benzooxazol-2-yl, benzofur-2-yl, benzothiazol-2-yl, 1H-benzoimidazol-2-yl, 1,1-dioxo-1H-1$\lambda^6$-benzo[b]thien-2-yl, quinol-3-yl, [1,3]dioxolan-2-yl, naphtho[2,3-d]oxazol-2-yl, naphtho[1,2-d]oxazol-2-yl and naphtho[2,1-d]oxazol-2-yl, each substituted by a group $R^7$ and optionally substituted with a group $R^8$, particularly wherein $R^7$ is halo, nitro, —$R^{29}$, —$OR^{29}$, —$C(O)R^{20}$, —$C(O)OR^{29}$, —$S(O)_2NR^{29}R^{30}$, —$C(O)NR^{29}R^{30}$ or —$C(O)NHCHR^{43}C(O)OR^{29}$, wherein $R^{20}$ is $(C_{1-6})$alkyl, $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, diphenyl$(C_{0-6})$alkyl, hetero$(C_{5-12})$aryl$(C_{0-6})$alkyl or hetero$(C_{8-12})$polycycloaryl$(C_{0-6})$alkyl and $R^{29}$ is hydrogen or —$R^{20}$, wherein $R^{20}$ is defined as above, wherein said heterocycloalkyl may be substituted with $(C_{6-12})$aryl$(C_{0-3})$alkyl, $R^{30}$ at each occurrence is hydrogen or $(C_{1-6})$alkyl and $R^{43}$ is $(C_{1-6})$alkyl, and $R^8$ at each occurrence independently is hydrogen, $(C_{1-6})$alkyl or halo-substituted $(C_{1-4})$alkyl; wherein within $R^7$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^6NR^{14}R^{14}$, —$X^6NR^{14}C(O)OR^{14}$, —$X^6NR^{14}C(O)NR^{14}R^{14}$, —$X^6NR^{14}C(NR^{14})NR^{14}R^{14}$, —$X^6OR^{14}$, —$X^6SR^{14}$, —$X^6C(O)OR^{14}$, —$X^6C(O)NR^{14}R^{14}$, —$X^6S(O)_2 NR^{14}R^{14}$, —$X^6P(O)(OR^{14})OR^{14}$, —$X^6OP(O)(OR^{14})OR^{14}$, —$X^6NR^{14}C(O)R^{15}$, —$X^6S(O)R^{15}$, —$X^6S(O)_2R^{15}$ and —$X^6C(O)R^{15}$, wherein $X^6$ is a bond or $(C_{1-6})$alkylene, $R^{14}$ at each occurrence independently is hydrogen, $(C_{1-6})$alkyl or halo-substituted $(C_{1-3})$alkyl and $R^{15}$ $(C_{1-6})$alkyl or halo-substituted $(C_{1-3})$alkyl.

The ring system A preferably is oxazol-2-yl, 4,5-dihydrooxazol-2-yl, benzooxazol-2-yl, naphtho[2,3-d]oxazol-2-yl, naphtho[1,2-d]oxazol-2-yl or naphtho[2,1-d]oxazol-2-yl, each substituted by a group $R^7$ and optionally substituted with a group $R^8$, particularly wherein $R^7$ is halo, —$R^{29}$, —$C(O)R^{20}$, —$C(O)OR^{29}$, —$C(O)NR^{29}R^{30}$ or —$S(O)_2NR^{29}R^{30}$, wherein $R^{20}$ is $(C_{1-6})$alkyl, $(C_{3-12})$cycloalkyl$(C_{0-6})$alkyl, $(C_{6-12})$aryl$(C_{0-6})$alkyl, hetero$(C_{5-12})$aryl$(C_{0-6})$alkyl or hetero$(C_{8-12})$polycycloaryl$(C_{0-6})$alkyl.

The ring system A more preferably is oxazol-2-yl, 4,5-dihydrooxazol-2-yl, benzooxazol-2-yl or naphtho[1,2-d]oxazol-2-yl, each substituted by a group $R^7$ and optionally substituted with a group $R^8$, particularly wherein $R^7$ is adamantan-1-ylmethylcarbamoyl, benzyl, benzylcarbamoyl, benzyl(methyl)carbamoyl, 1-benzyloxycarbonyl-3-methylbutylcarbamoyl, 4-benzylpiperidin-1-carbonyl, tert-butyl, chloro, 2,3-dihydroindol-1-ylcarbonyl, 3,4-dihydro-1H-isoquinol-2-ylcarbonyl, 3,4-dihydro-1H-quinol-1-ylcarbonyl, diphenylmethylcarbamoyl, fur-2-ylmethylcarbamoyl, hydrogen, 2-(1H-indol-3-yl)ethylcarbamoyl, methoxy, methoxycarbonyl, methyl, 3-methylbutylcarbamoyl, methylcarbamoyl, 1-methylethylcarbamoyl, naphth-1-ylmethylcarbonyl, nitro, phenyl, phenylcarbamoyl, 2-phenylcyclopropylcarbamoyl, 1-phenylethylcarbamoyl, sulfamoyl, trifluoromethyl, phenethylcarbamoyl, 3-phenylpropylcarbamoyl, piperid-1-ylcarbonyl, pyrid-2-ylmethylcarbamoyl, pyrid-3-ylmethylcarbamoyl, pyrid-4-ylmethylcarbamoyl or pyrrolidin-1-ylcarbonyl and $R^8$ is methyl.

$X^2$ particularly represents a bond or a divalent group of Formula (a), wherein within Formula (a) $X^3$ is —C(O)—, $R^9$ represents hydrogen, $R^{11}$ represents hydrogen or methyl, typically hydrogen, and $R^{12}$ particularly represents $(C_{1-6})$alkyl, preferably isobutyl, sec-butyl or isopropyl.

$R^1$ particularly represents hydrogen or —$X^8X^9R^{20}$, wherein $X^8$ is —C(O)— or —S(O)$_2$—, $X^9$ is a bond or —O— and $R^{20}$ is $(C_{1-6})$alkyl, $(C_{3-12})$cycloalkyl$(C_{3-6})$alkyl, hetero$(C_{3-12})$cycloalkyl$(C_{0-6})$alkyl, $(C_{6-12})$aryl$(C_{0-6})$alkyl or hetero$(C_{5-12})$aryl$(C_{0-6})$alkyl; wherein within $R^1$ any alicyclic or aromatic ring system present may be substituted further by 1 to 5 radicals independently selected from $(C_{1-6})$alkyl, —C(O)OR$^{14}$, —X$^6$NR$^{14}$R$^{14}$ and —X$^6$NR$^{14}$C(O)OR$^{14}$, wherein $X^6$ is a bond or $(C_{1-6})$alkylene, $R^{14}$ at each occurrence independently is hydrogen, $(C_{1-6})$alkyl or halo-substituted $(C_{1-3})$alkyl and $R^{15}$ $(C_{1-6})$alkyl or halo-substituted $(C_{1-3})$alkyl.

$R^1$ particularly represents acetyl, benzoyl, benzyloxycarbonyl, benzylsulfonyl, bicyclo[2.2.2]hept-2-ylcarbonyl, tert-butoxycarbonyl, tert-butyryl, 4-tert-butoxycarbonylpiperazin-1-ylcarbonyl, 1-tert-butoxycarbonylpiperidin-4-ylcarbonyl, 2-cyclohexylacetyl, 4-cyclohexylbutyryl, 2-cyclohexylethylsulfonyl, 3-cyclohexylpropionyl, 2-cyclopentylethylsulfonyl, hydrogen, 4-methylpiperazin-1-ylcarbonyl, methylsulfonyl, 4-methylvaleryl, 3-morpholin-4-ylpropionyl, naphth-2-ylmethyl, 3-phenylpropionyl, piperazin-1-ylcarbonyl, piperidin-4-ylcarbonyl or pyrid-3-ylcarbonyl, wherein within $R^1$ any alicyclic or aromatic ring system present may be substituted further by 1 to 3 radicals independently selected from 3-aminomethyl and 3-tert-butoxycarbonylaminomethyl.

$R^2$ particularly represents hydrogen.

$R^3$ preferably represents $(C_{1-6})$alkyl or $(C_{6-10})$aryl$(C_{1-3})$alkyl, more preferably phenethyl, or $R^3$ and $R^4$ taken together with the carbon atom to which both $R^3$ and $R^4$ are attached form $(C_{3-6})$cycloalkylene, more preferably cyclopropylene.

$R^4$ preferably represents hydrogen or $(C_{1-6})$alkyl, preferably hydrogen or methyl or $R^3$ and $R^4$ or $R^3$ and $R^4$ taken together with the carbon atom to which both $R^3$ and $R^4$ are attached form $(C_{3-6})$cycloalkylene, more preferably cyclopropylene.

$R^5$ and $R^6$ preferably together form oxo.

Reference to the preferred embodiments set forth above is meant to include all combinations of particular and preferred groups.

Pharmacology and Utility

The compounds of the invention are cysteine protease inhibitors, in particular the compounds of the invention inhibit the activity of cathepsins B, L, K and/or S and, as such, are useful for treating diseases in which cathepsin B, L, K and/or S activity contributes to the pathology and/or symptomatology of the disease. For example, the compounds of the invention are useful in treating tumor invasion and metastasis, in particular as anti-angiogenic agents, rheumatoid arthritis, osteo arthritis, pneumocystis carinii, acute pancreatitis, inflammatory airway disease and bone and joint disorders. Furthermore, the compounds of the invention are useful in treating bone resorption disorders, e.g. osteoporosis.

The compounds of the invention are inhibitors of cathepsin S and, as such, are useful for treating diseases in which cathepsin S activity contributes to the pathology and/or symptomatology of the disease. For example, the compounds of the invention are useful in treating autoimmune disorders, including, but not limited to, juvenile onset diabetes, multiple sclerosis, pemphigus vulgaris, Graves' disease, myasthenia gravis, systemic lupus erythemotasus, rheumatoid arthritis and Hashimoto's thyroiditis, allergic disorders, including, but not limited to, asthma, and allogeneic immune responses, including, but not limited to, organ transplants or tissue grafts.

Cathepsin S also is implicated in disorders involving excessive elastolysis, such as chronic obstructive pulmonary disease (e.g. emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsins S are of use in treatment of systemic amyloidosis.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease induced hydrolysis of a peptide based substrate.

Furthermore, the compounds of the invention are useful as intermediates in the preparation of other compounds of Formula I. For example, compounds of Formula I in which $R^5$ is hydroxy can be used to prepare compounds of Formula I in which $R^5$ and $R^6$ taken together form oxo.

Nomenclature

The compounds of Formula I and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 4.0 (Beilstein Information Systems, Inc.). For example, a compound of Formula I in which A is benzooxazol-2-yl; $X^2$ is a group of Formula (a), wherein $R^9$ is hydrogen and $R^{12}$ is cyclohexylmethyl; $R^1$ is acetyl; $R^2$ is hydrogen; $R^3$ is phenethyl; $R^4$ is hydrogen; and $R^5$ and $R^6$ together form oxo; that is, a compound having the following structure:

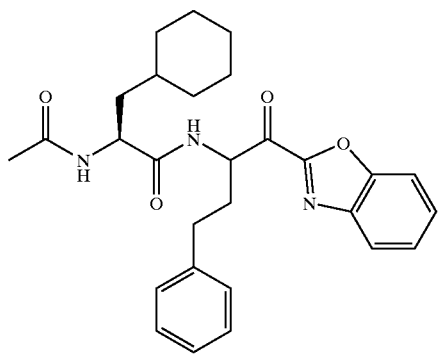

is named 2S-acetylamino-N-(1-benzooxazol-2-ylcarbonyl-3-phenylpropyl)-3-cyclohexylpropionamide; and a compound of Formula I in which A is benzooxazol-2-yl; $X^2$ is a group of Formula (a), wherein $R^9$ is hydrogen and $R^{12}$ is benzylsulfonylmethyl; $R^1$ is morpholin-4-ylcarbonyl; $R^2$ is hydrogen; $R^3$ is phenethyl; $R^4$ is hydrogen; $R^5$ is hydrogen; and $R^6$ is hydroxy; that is, a compound having the following structure:

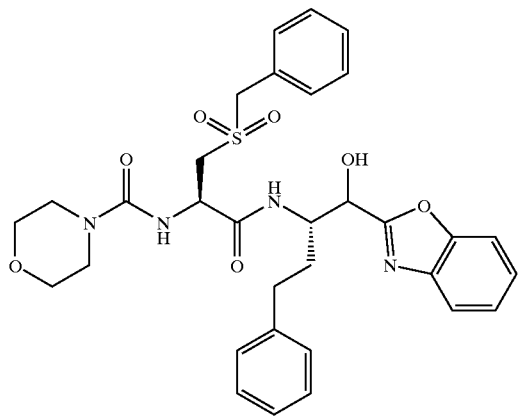

is named N-[1S-(2-benzooxazol-2-yl-2-hydroxy-1S-phenethylethylcarbamoyl)-2-benzylsulfonylethyl]-morpholine-4-carboxamide or morpholine-4-carboxylic acid {(R)-1-[(S)-1-(1-benzooxazol-2-yl-1-hydroxy-methyl)-3-phenyl-propylcarbamoyl]-2-phenylmethanesulfonyl-ethyl}-amide; and a compound of Formula I in which A is benzooxazol-2-yl; $X^2$ is a group of Formula (a), wherein $R^9$ is hydrogen and $R^{12}$ is cyclohexymethyl; $R^1$ is carboxyacetyl; $R^2$ is hydrogen; $R^3$ is phenethyl; $R^4$ is hydrogen; and $R^5$ and $R^6$ together form oxo; that is, a compound having the following structure:

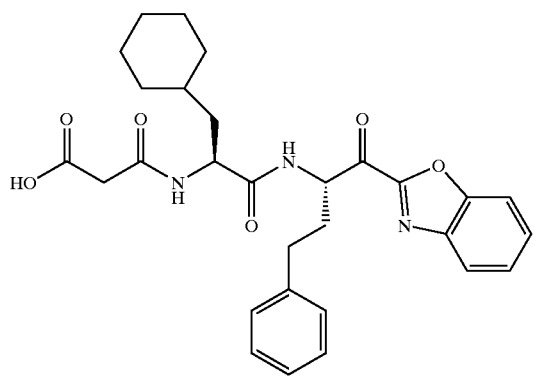

is named N-[1S-(1S-benzooxazol-2-ylcarbonyl-3-phenylpropylcarbamoyl)-2-cyclohexylethyl]malonamic acid or N-{(S)-1-[(S)-1-(1-benzooxazol-2-yl-methanoyl)-3-phenyl-propylcarbamoyl]-2-cyclohexyl-ethyl}-malonamic acid; and a compound of Formula I in which A is benzooxazol-2-yl; $X^2$ is a group of Formula (a), wherein $R^9$ is hydrogen and $R^{12}$ is 2-nitrobenzylsulfonylmethyl; $R^1$ is morpholin-2-ylcarbonyl; $R^2$ is hydrogen; $R^3$ is phenethyl; $R^4$ is hydrogen; and $R^5$ and $R^6$ together form oxo; that is, a compound having the following structure:

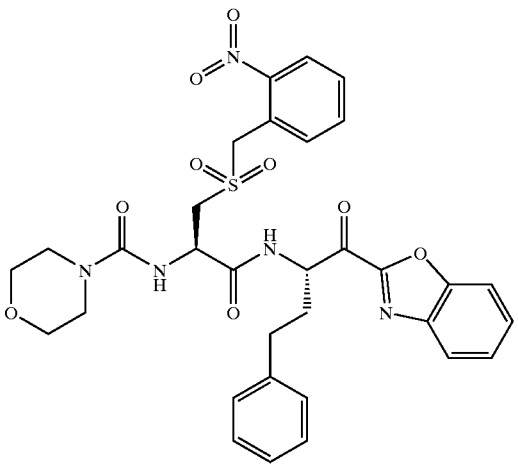

is named N-[1R-(1S-benzooxazol-2-ylcarbonyl-3-phenylpropylcarbamoyl)-2-(2-nitrobenzylsulfonyl)ethyl] morpholine-4-carboxamide or morpholine-4-carboxylic acid [(R)-1-[(S)-1-(-benzooxazol-2-yl-methanoyl)-3-phenyl-propylcarbamoyl]-2-(2-nitrophenylmethanesulfonyl)-ethyl]-amide; and a compound of Formula I in which A is benzooxazol-2-yl; $X^2$ is a group of Formula (a), wherein $R^9$ is hydrogen and $R^{12}$ is benzylsulfonylmethyl; $R^1$ is tetrahydropyran-4-yloxycarbonyl; $R^2$ is hydrogen; $R^3$ is phenethyl; $R^4$ is hydrogen; and $R^5$ and $R^6$ together form oxo; that is, a compound having the following structure:

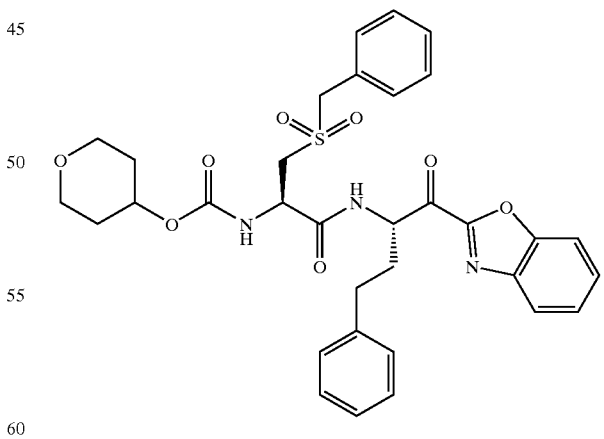

is named tetrahydropyran-4-yl 1R-(1S-benzooxazol-2-ylcarbonyl-3-phenylpropylcarbamoyl)-2-benzylsulfonylethylcarbamate or {(R)-1-[(S)-1-(1-benzooxazol-2-yl-methanoyl)-3-phenyl-propylcarbamoyl]-2-phenylmethanesulfonyl-ethyl}-carbamic acid tetrahydropyran-4-yl ester.

A compound of Formula I in which A is pyrid-2-yl; $X^2$ is a group of Formula (a), wherein $R^9$ is hydrogen and $R^{11}$ is 2-methylpropyl; $R^1$ is benzyloxycarbonyl; $R^2$, $R^4$ and $R^5$ each are hydrogen; $R^3$ is phenethyl; and $R^6$ is hydroxy; that is, a compound having the following structure:

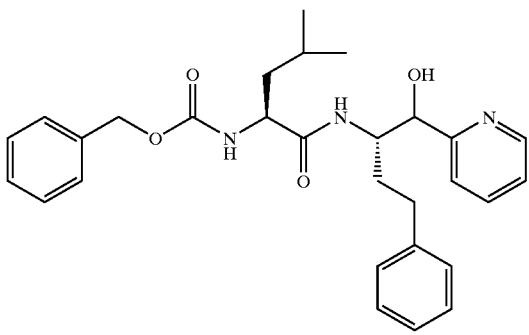

is named benzyl 1S-(1S-pyrid-2-ylcarbonyl-3-phenylpropylcarbamoyl)-3-methylbutylcarbamate or {(S)-1-[(S)-1-(1-hydroxy-1-pyridin-2-yl-methyl)-3-phenyl-propylcarbamoyl]-3-methyl-butyl}-carbamic acid benzyl ester; and a compound of Formula I in which A is thiazol-2-yl; $X^2$ is a group of Formula (a), wherein $R^9$ is hydrogen and $R^{11}$ is 2-methylpropyl; $R^1$ is 4-methylpiperazin-1-ylcarbonyl; $R^2$ and $R^4$ each are hydrogen; $R^3$ is phenethyl; and $R^5$ and $R^6$ together form oxo; that is, a compound having the following structure:

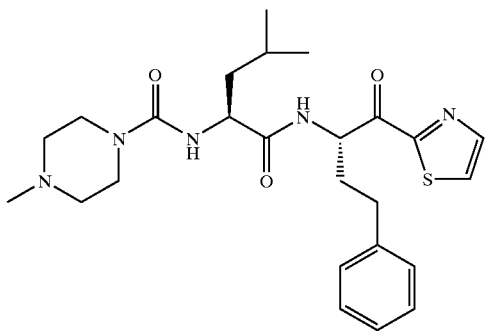

is named N-[3-methyl-1S-(3-phenyl-1-thiazol-2-ylcarbonylpropylcarbamoyl)butyl]-4-methylpiperazine-1-carboxanide or 4-methyl-piperazine-1-carboxylic acid or {(S)-3-methyl-1-[(S)-3-phenyl-1-(1-thiazol-2-yl-methanoyl)-propylcarbamoyl]-butyl}-amide; and a compound of Formula I in which A is 4,5-tetrahydro-4-methoxycarbonyloxazol-2-yl; $X^2$ is a group of Formula (a), wherein $R^9$ is hydrogen and $R^1$ is 2-methylpropyl; $R^1$ is benzyloxycarbonyl; $R^2$ and $R^4$ each are hydrogen; $R^3$ is phenethyl; and $R^5$ and $R^6$ together form oxo; that is, a compound having the following structure:

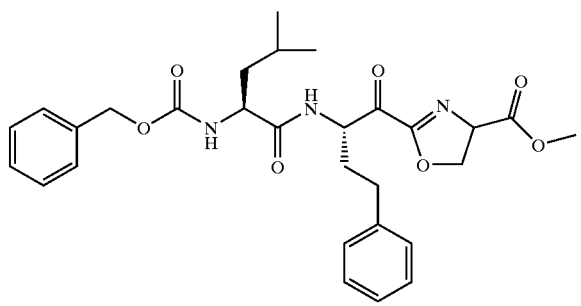

is named methyl 2S-(2S-benzyloxycarbonylamino-4-methylvalerylamino)-4-phenylbutyryl-4,5-dihydrooxazole-4-carboxylate or 2-[(S)-2-((S)-2-benzyloxycarbonylamino-4-methyl-pentanoylamino)-4-phenyl-butanoyl]-4,5-dihydro-oxazole-4-carboxylic acid methyl ester.

Certain compounds of Formula I exist in tautomeric equilibrium. Compounds of Formula I which exist as tautomers are named, illustrated or otherwise described in this application as one possible tautomer. However, it is to be understood that the all possible tautomers are meant to be encompassed by such names, illustrations and descriptions.

Certain compounds of Formulae I and II exist in tautomeric equilibrium. Compounds of Formulae I and II which exist as tautomers are named, illustrated or otherwise described in this application as one possible tautomer. However, it is to be understood that the all possible tautomers are meant to be encompassed by such names, illustrations and descriptions.

Administration and Pharmaceutical Compositions

In general, compounds of Formula I will be administered in therapeutically effective amounts via any of the usual and acceptable modes known in the art, either singly or in combination with another therapeutic agent. A therapeutically effective amount may vary widely depending on the severity of the disease, the age and relative health of the subject, the potency of the compound used and other factors. For example, therapeutically effective amounts of a compound of Formula I may range from 0.1 micrograms per kilogram body weight (μg/kg) per day to 10 milligram per kilogram body weight (mg/kg) per day, typically 1 μg/kg/day to 1 mg/kg/day. Therefore, a therapeutically effective amount for a 80 kg human patient may range from 10 μg/day to 100 mg/day, typically 0.1 mg/day to 10 mg/day. In general, one of ordinary skill in the art, acting in reliance upon personal knowledge and the disclosure of this Application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, or the like). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required.

The compounds of Formula I can be administered alone or in combination with other compounds of Formula I or in combination with one or more other active ingredient(s). For example, the compounds of Formula I can be administered in combination with a therapeutically active amount of a bisphosphonic acid or acid ester derivative or any pharmaceutically acceptable salt thereof. Suitable bisphosphonic acids and acid ester derivatives include compounds corresponding to the following formula:

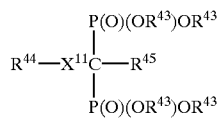

wherein $X^{11}$ is a bond or $(C_{1-7})$alkylene, each $R^{43}$ independently is hydrogen or $(C_{1-30})$alkyl, $R^{44}$ and $R^{45}$ are selected independently from a group consisting of hydrogen, halo, optionally substituted $(C_{1-30})$alkyl, $(C_{3-30})$cycloalkyl, hetero$(C_{5-30})$cycloalkyl, optionally substituted $(C_{6-10})$aryl, hetero$(C_{6-10})$aryl, $-NR^{46}R^{46}$, $-OR^{46}$, $-SR^{46}$, wherein each $R^{46}$ independently is hydrogen, $(C_{1-10})$alkyl, $(C_{3-10})$cycloalkyl, optionally substituted $(C_{6-10})$aryl, provided that both $R^{44}$ and $R^{45}$ are not selected from hydrogen or hydroxy when $X^{11}$ is a bond; or $R^{44}$ and $R^{45}$ taken together form $(C_{2-9})$alkylene; wherein $(C_{3-10})$cycloalkyl includes adamantyl and the like, hetero$(C_{5-10})$cycloalkyl includes pyrrolidinyl and the like, $(C_{6-10})$aryl includes phenyl and naphthyl, and hetero$(C_{6-10})$aryl includes quinolyl, isoquinolyl, pyridyl, furyl, imidazolyl, imidazopyridyl and the like.

Instances wherein $R^{44}$ and/or $R^{45}$ are substituted $(C_{1-30})$alkyl may include, but are not limited to, $(C_{1-30})$alkyl substituted by hetero$(C_{5-10})$cycloalkyl, $(C_{6-10})$aryl, hetero$(C_{6-10})$aryl, $-NR^{47}R^{47}$, $-OR^{147}$ and $-SR^{47}$, wherein each $R^{47}$ is independently hydrogen or $(C_{1-10})$alkyl; wherein hetero$(C_{5-10})$cycloalkyl includes pyrrolidinyl and the like, $(C_{6-10})$aryl includes phenyl and naphthyl, and hetero$(C_{6-10})$aryl includes quinolyl, isoquinolyl, pyridyl, furyl, imidazolyl, imidazopyridyl and the like. Suitable optionally substituted aryl groups include, but are not limited to, halo-substituted phenyl.

A non-limiting class of bisphosphonic acids and acid ester derivatives thereof suitable for administration in combination with compounds of Formula I include those in which $R^{44}$ is selected from the group consisting of hydrogen, hydroxy or halo, and $R^{45}$ is selected from the group consisting of optionally substituted $(C_{1-30})$alkyl, halo and $-SR^{46}$, wherein $R^{46}$ is $(C_{1-10})$alkyl or phenyl.

A non-limiting subclass of bisphosphonic acids and acid ester derivatives thereof suitable for administration in combination with compounds of Formula I include those in which $R^{44}$ is selected from the group consisting of hydrogen, hydroxy and chloro and $R^{45}$ is selected from the group consisting of optionally substituted $(C_{1-30})$alkyl, chloro and chlorophenylthio.

A non-limiting example of a bisphosphonic acid suitable for administration in combination with compounds of Formula I include that in which $X^{11}$ is a bond, each $R^{43}$ is hydrogen, $R^{44}$ is hydroxy and $R^{45}$ is 3-aminopropyl, namely 4-amino-1-hydroxybutylidene-1,1-bisphosphonic acid (aka alendronic acid), or the monosodium trihydrate salt thereof, namely 4-amino-1-hydroxybutylidene-1,1-bisphosphonate monosodium trihydrate (aka alendronate monosodium trihydrate), described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which patents are incorporated by reference herein in their entirety.

Further non-limiting examples of bisphosphonic acids suitable for administration in combination with compounds of Formula I include the following:

cycloheptylaminomethylene-1,1-bisphosphonic acid (aka cimadronic acid), described in U.S. Pat. No. 4,970,335, to Isomura et al., issued Nov. 13, 1990;

1,1-dichloromethylene-1,1-diphosphonic acid (aka clodronic acid) and the disodium salt thereof, namely clodronate disodium, described in Belgium Patent 672,205 (1966) and J. Org. Chem 32, 4111 (1967);

1-hydroxy-3-pyrrolidin-1-ylpropylidene-1,1-bisphosphonic acid (aka EB-1053);

1-hydroxyethylidene-1,1-diphosphonic acid (aka etidronic acid);

1-hydroxy-3-(N-methyl-N-pentylamino)propylidene-1,1-bisphosphonic acid (aka ibandronic acid), described in U.S. Pat. No. 4,927,814, issued May 22, 1990;

6-amino-1-hydroxyhexylidene-1,1-bisphosphonic acid (aka neridronic acid);

3-(dimethylamino)-1-hydroxypropylidene-1,1-bisphosphonic acid (aka olpadronic acid);

3-amino-1-hydroxypropylidene-1,1-bisphosphonic acid (aka pamidronic acid);

2-pyrid-2-ylethylidene-1,1-bisphosphonic acid (aka piridronic acid), described in U.S. Pat. No. 4,761,406;

1-hydroxy-2-pyrid-3-ylethylidene-1,1-bisphosphonic acid (aka risedronic acid);

4-chlorophenylthiomethylenebisphosphonic acid (aka tiludronic acid), described in U.S. Pat. No. 4,876,248, to Breliere et al., Oct. 24, 1989; and 1-hydroxy-2-(1H-imidazol-1-yl)ethylidene-1,1-bisphosphonic acid (aka zoledronic acid);

all of which patents and other documents referred to above are incorporated by reference herein in their entirety.

A non-limiting subclass of bisphosphonic acids suitable for administration in combination with compounds of Formula I include those selected from the group consisting of alendronic acid, cimadronic acid, clodronic acid, tiludronic acid, etidronic acid, ibandronic acid, risedronic acid, piridronic acid, pamidronic acid, zolendronic acid, pharmaceutically acceptable salts thereof, and mixtures thereof. A further example of a bisphosphonic acid suitable for administration in combination with compounds of Formula I is alendronic acid or a pharmaceutically acceptable salt thereof, and mixtures thereof. A further non-limiting example is alendronate monosodium trihydrate.

Compounds of Formula I can be administered in combination with a therapeutically active amount of an estrogen receptor agonist. Non-limiting examples of estrogen receptor agonists suitable for administration in combination with the compounds of Formula I include naturally occurring estrogens such as estradiol, estrone and estroil, or synthetic estrogen receptor agonists such as [6-hydroxy-2-(4-hydroxyphenyl)benzo[b]thien-3-yl][4-(2-piperidin-1- ylethoxy)phenyl]methanone (aka raloxifene) and {2-[4-(1,2-diphenylbut-1-enyl)phenoxy]ethyl}dimethylamine (aka tamoxifen). A non-limiting subclass of estrogen receptor agonists suitable for administration in combination with the compounds of Formula I include estrogen receptor partial agonists (i.e., estrogen receptor agonists with mixed agonist/antagonist properties), sometimes referred to as estrogen receptor modulators. Estrogen receptor partial agonists can exert tissue-selective estrogen agonist effects. Tamoxifen, for example, selectively exerts an estrogen agonist effect on the bone, in humans. Additional suitable estrogen receptor partial agonists are described in Tissue-Selective Actions Of Estrogen Analogs, Bone Vol. 17, No. 4, October 1995, 181S–190S. Certain 3-[4-(2-phenylindol-1-ylmethyl) phenyl]acrylamides, described in U.S. Pat. No. 5,985,910 to Miller et al., Nov. 16, 1999; benzothiphene compounds, described in U.S. Pat. No. 5,985,897 to Meuhl et al., Nov. 16, 1999; naphthyl compounds, described in U.S. Pat. No. 5,952,350 to Cullinan et al., Sep. 14, 1999; substituted benzothiophene compounds, described in U.S. Pat. No. 5,962,475 to Schmid et al., Oct. 4, 1999, are suitable estrogen receptor partial agonists for administration with the compounds of Formula I; all of which patents and other documents referred to above are incorporated by reference herein in their entirety.

More particularly a pharmaceutical composition of this invention may comprise a therapeutically effect amount of a compound of Formula I in combination with one or more active ingredient(s) selected from the group consisting of (i) a therapeutically effect amount of a bisphosphonic acid or acid ester thereof or a pharmaceutically acceptable salt thereof and (ii) a therapeutically effect amount of an estrogen receptor agonist or a pharmaceutically acceptable salt thereof; and one or more pharmaceutically acceptable excipient(s). Non-limiting examples of such bisphosphonic acids include 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiometbylenebisphosphonic acid and 1-hydroxy-2-(1H-imidazol-1-yl)ethylidene-1,1-bisphosphonic acid or acid ester thereof or a pharmaceutically acceptable salt thereof; particularly 1,1-dichloromethylene-1,1-diphosphonic acid or a pharmaceutically acceptable salt thereof and preferably 1,1-dichloromethylene-1,1-diphosphonate monosodium trihydrate.

Chemistry

Processes for Making Compounds of Formula I

Compounds of Formula I in which $R^5$ and $R^6$ together form oxo can be prepared by proceeding as in the following Scheme 1:

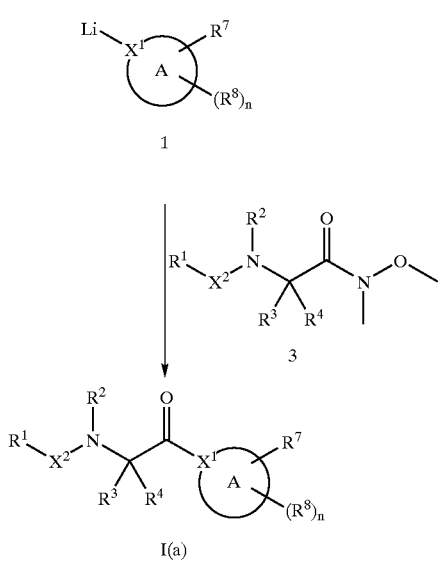

in which n, A, $X^1$, $X^2$, $R^1$, $R^2$, $R^3$, $R^4$, $R^7$ and $R^8$ are as defined in the Summary of the Invention for Formulae I and II.

Compounds of Formula I in which $R^5$ and $R^6$ together form oxo (Formula I(a)) can be prepared by reacting an organometallic compound of Formula 2 with a compound of Formula 3. The reaction is carried out in a suitable solvent (e.g. tetrahydrofuran (THF), ether, or the like) at −80 to −70° C., preferably at about −78° C., and requires 30 minutes to an hour to complete. The organometallic compound of Formula 2 is generated by treating a corresponding organo compound, or a brominated derivative thereof, with n-butyllithium or tert-butyllithium in a suitable solvent (e.g. THF, ether, or the like) at −80 to −70° C., preferably at about −78° C., for approximately 30 minutes to an hour.

Compounds of Formula I in which the ring comprised by $X^1$ is a 4,5-tetrahydrooxazol-2-yl or oxazol-2-yl or moiety, $R^5$ is hydrogen and $R^6$ is hydroxy can be prepared by proceeding as in the following Scheme 2:

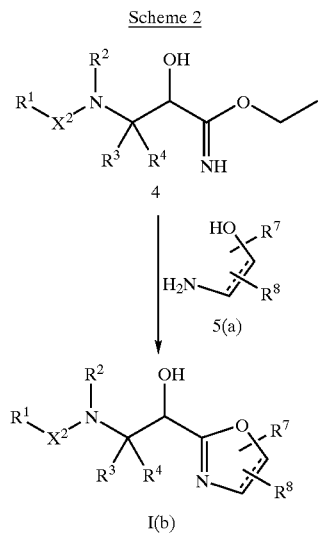

in which $X^2$, $R^1$, $R^2$, $R^3$, $R^4$, $R^7$ and $R^8$ are as defined in the Summary of the Invention for Formulae I and II.

Compounds of Formula I can be prepared by reacting a compound Formula 4 with a compound of the Formula 5(a). The reaction is carried out in a suitable solvent (e.g. chloroform, ethanol, or the like) at reflux temperatures and requires 3 to 24 hours to complete. In a similar fashion, using analogous reaction conditions to those described in Scheme 1, compounds of Formula I in which A is a heteropolycyclic radical wherein $X^1$ is a ring member atom of an oxazole ring, $R^5$ is hydrogen and $R^6$ is hydroxy can be prepared by reacting a compound of Formula 4 with a compound of Formula 5(b):

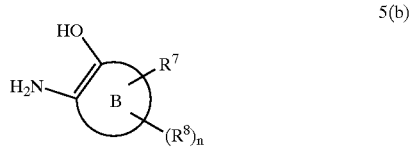

5(b)

in which n is 0, 1, 2 or 3 and B is a heteromonocyclic radical containing 5 to 6 ring member atoms or a fused heteropolycyclic radical containing 8 to 11 ring member atoms, wherein each ring contains 5 to 7 ring member atoms and each ring member atom is a carbon atom or a heteroatom, and $R^7$ and $R^8$ is as defined in the Summary of the Invention for Formulae I and II.

Compounds of Formula I can be prepared by proceeding as in the following Scheme 3:

Scheme 3

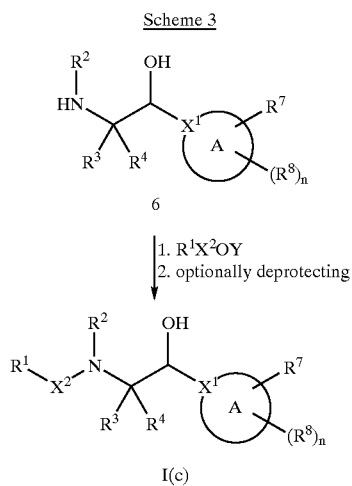

in which Y is hydrogen or an activating group (e.g. 2,5-dioxopyrrolidin-1-yl (NBS), or the like) and n, A, $X^1$, $X^2$, $R^1$, $R^2$, $R^3$, $R^4$, $R^7$ and $R^8$ are as defined in the Summary of the Invention for Formulae I and II.

Compounds of Formula I can be prepared by reacting a compound of Formula 6, or a protected derivative thereof, with a compound of the formula $R^1X^2OY$, or a protected derivative thereof, and then optionally deprotecting. The reaction is carried out in the presence of a suitable base (e.g. triethylamine, diisopropylethylamine, or the like) and in a suitable solvent (e.g. acetonitrile, N,N-dimethylformamide (DMF), dichloromethane, or any suitable combination thereof, or the like) at 10 to 30° C., preferably at about 25° C., and requires 24 to 30 hours to complete. When Y is hydrogen a suitable coupling agent (e.g. benzotriazole-1-yloxytrispyrrolidinophosphonium hexafluorophosphate (PyBOP®), 1-(3-dimethylaminopropyl)-3-ethylcarbodiimide hydrochloride (EDC), O-benzotriazol-1-yl-N,N,N',N'-tetramethyluronium hexafluorophosphate (HBTU), O-(7-azabenzotriazol-1-yl)-1,1,3,3-tetramethyluronium hexafluorophosphate (HATU), 1,3-dicyclohexylcarbodiimide (DCC), or the like) and base (e.g. N,N-diisopropylethylamine, triethylamine, or the like) is required and the reaction requires 2 to 3 hours to complete. Deprotection can be effected by any means which removes the protecting group and gives the desired product in reasonable yield. A detailed description of the techniques applicable to the creation of protecting groups and their removal can be found in T. W. Greene, *Protecting Groups in Organic Synthesis*, John Wiley & Sons, Inc. 1981. Detailed descriptions of the preparation of a compound of Formula I in accordance with Scheme 3 are set forth in Examples 8, 9, 10 and 12, infra.

Compounds of Formula I can be prepared by proceeding as in the following Scheme 4:

Scheme 4

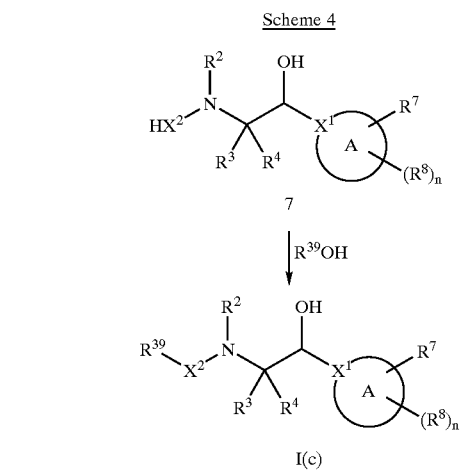

in which $R^{39}$ is $—X^7X^8R^{20}$ and n, $X^1$, $X^2$, $X^7$, $X^8$, $R^1$, $R^2$, $R^3$, $R^4$, $R^7$, $R^8$ and $R^{20}$ are as defined in the Summary of the Invention for Formulae I and II.

Additional Processes for Preparing Compounds of Formula I

Compounds of Formula I in which A is optionally substituted oxazol-2-yl can be prepared by oxidizing a corresponding compound of Formula I in which A is 4,5-dihydrooxazol-2-yl. The reduction is carried out in the presence of base (e.g. 1,8-diazabicyclo[5.4.0]undec-7-ene (DBU), 1,5-diazabicyclo[3.4.0]non-5-ene (DBN), or the like) in a suitable solvent (e.g. dichloromethane, or the like) at 20 to 25° C. and requires 6 to 12 hours to complete.

Compounds of Formula I in which $R^7$ is —C(O)OH can be prepared from a corresponding compound of Formula I in which $R^7$ is methoxycarbonyl. The conversion can be effected by treating the methyl ester with sodium hydroxide in a suitable solvent (e.g, ethanol, or the like) at 20 to 25° C. and requires 6 to 12 hours to complete.

Compounds of Formula I in which $R^7$ is —C(O)NR$^{29}$R$^{30}$ or —C(O)NR$^{42}$CHR$^{43}$C(O)OR$^{29}$, can be prepared by reacting a corresponding compound of Formula I in which $R^7$ is —C(O)OH with a compound of the formula NHR$^{20}$R$^{21}$ or NHR$^{42}$CHR$^{43}$C(O)OR$^{29}$, respectively. The reaction is carried out in the presence of a suitable coupling agent (PyBOP®, EDC, HBTU, DCC, or the like) and base (e.g, N,N-diisopropylethylamine, triethylamine, or the like) in a suitable solvent (e.g., DMF, or the like) at 20 to 25° C. and requires 2 to 4 hours to complete.

Compounds of Formula I in $R^1$ is —X$^6$X$^7$R$^{20}$ can be prepared by reacting a compound of Formula I in which $R^1$ is hydrogen with a compound of the formula $R^{20}X^7X^6OH$. The reaction is carried out by procedures analogous to those described above for carrying out Reaction Scheme 3.

Compounds of Formula I in which $R^5$ and $R^6$ together form oxo can be prepared by oxidizing a compound of Formula I in which $R^5$ is hydrogen and $R^6$ is hydroxy. The oxidation can be carried out with a suitable oxidizing agent (e.g. Dess-Martin periodinate, or the like) in a suitable solvent (e.g. dichloromethane, or the like) at 15 to 25° C. and requires 10 to 20 hours to complete.

Compounds of Formula I in which $R^{12}$ contains a sulfonyl moiety can be prepared by oxidizing a corresponding compound of Formula I containing a sulfanyl moiety. The oxidation is carried out with a suitable oxidizing agent (e.g. potassium peroxymonosulfate (OXONE®, or the like) in a suitable solvent (e.g. methanol, water, or the like, or any suitable combination thereof) at ambient temperature and requires 16 to 24 hours to complete.

A compound of Formula I in which A is 1,1-dioxo-1H-1$\lambda^6$-benzo[b]thien-2-yl can be prepared by oxidizing a corresponding compound of Formula I in which A is benzo[b]thien-2-yl. Proceeding in this fashion benzyl 1-[1-(1,1-dioxo-1H-1$\lambda^6$-benzo[b]thien-2-ylcarbonyl)-3-phenylyropylcarbamoyl]-3-methylbutylcarbamate (Compound 209) was prepared. $^1$H NMR (CDCl$_3$): $\delta$ 0.83–0.95 (m, 6H), $\delta$ 1.35–1.52 (m, 1H), $\delta$ 1.61–1.69 (m, 2H), $\delta$ 2.07–2.20 (m, 1H, $\delta$ 2.36–2.71 (m, 3H), $\delta$ 4.57 (m, 1H), $\delta$ 4.76 (m, 1H), $\delta$ 4.98–5.26 (m, 3H), $\delta$ 5.35 (bs, 1H), $\delta$ 7.06–7.62 (m, 14H);

A compound of Formula I can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I can be prepared by reacting the free acid form of the compound with a pharmaceutically acceptable inorganic or organic base. Inorganic and organic acids and bases suitable for the preparation of the pharmaceutically acceptable salts of compounds of Formula I are set forth in the definitions section of this application. Alternatively, the salt forms of the compounds of Formula I can be prepared using salts of the starting materials or intermediates.

The free acid or free base forms of the compounds of Formula I can be prepared from the corresponding base addition salt or acid addition salt form. For example, a compound of Formula I in an acid addition salt form can be converted to the corresponding free base by treating with a suitable base (e.g. ammonium hydroxide solution, sodium hydroxide, or the like). A compound of Formula I in a base addition salt form can be converted to the corresponding free acid by treating with a suitable acid (e.g. hydrochloric acid, etc).

The N-oxides of compounds of Formula I can be prepared by methods known to those of ordinary skill in the art. For example, N-oxides can be prepared by treating an unoxidized form of the compound of Formula I with an oxidizing agent (e.g. trifluoroperacetic acid, permaleic acid, perbenzoic acid, peracetic acid, meta-chloroperoxybenzoic acid, or the like) in a suitable inert organic solvent (e.g. a halogenated hydrocarbon such as dichloromethane) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g. sulfur, sulfur dioxide, triphenyl phosphine, lithium borohydride, sodium borohydride, phosphorus trichloride, tribromide, or the like) in an suitable inert organic solvent (e.g. acetonitrile, ethanol, aqueous dioxane, or the like) at 0 to 80° C.

Prodrug derivatives of the compounds of Formula I can be prepared by methods known to those of ordinary skill in the art (e.g. for further details see Saulnier et al.(1994), *Bioorganic and Medicinal Chemistry Letters.* 4:1985). For example, appropriate prodrugs can be prepared by reacting a non-derivatized compound of Formula I with a suitable carbamylating agent (e.g. 1,1-acyloxyalkylcarbonochloridate, para-nitrophenyl carbonate, or the like).

Protected derivatives of the compounds of Formula I can be made by means known to those of ordinary skill in the art. A detailed description of the techniques applicable to the creation of protecting groups and their removal can be found in T. W. Greene, *Protecting Groups in Organic Synthesis,* John Wiley & Sons, Inc. 1981.

Compounds of Formula I can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula I, dissociable complexes are preferred (e.g. crystalline diastereoisomeric salts). Diastereomers have distinct physical properties (e.g. melting points, boiling points, solubilities, reactivity, and the like) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, Honh Wiley & Sons, Inc. (1981).

In summary, an aspect of the invention is a process for preparing a compound of Formula I, which process comprises:

(A) reacting an organometallic compound of Formula 2:

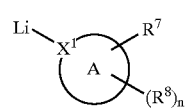

2 with a compound of Formula 3:

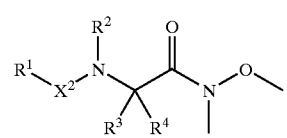

3 wherein n, A, $X^1$, $X^2$, $R^1$, $R^2$, $R^3$, $R^4$, $R^7$ and $R^8$ are as defined in the Summary of the Invention for Formulae I and II, to give a compound of Formula I in which $R^5$ and $R^6$ together form oxo; or (B) reacting a compound of Formula 4:

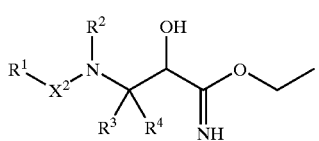

4 with a compound of Formula 5(a) or 5(b):

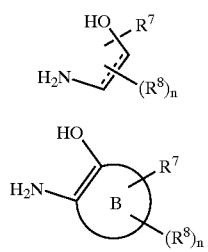

5(a)

5(b)

wherein the dashed line represents an optional bond and B is a monocyclic radical containing 5 to 6 ring member atoms or a fused polycyclic radical containing 8 to 11 ring member atoms, wherein each ring contains 5 to 7 ring member atoms and each ring member atom is a carbon atom or a heteroatom and n, $R^1$, $R^2$, $R^3$, $R^4$, $R^7$ and $R^8$ are as defined in the Summary of the Invention for Formulae I and II, to give a compound of Formula I in which the ring comprised by $X^1$ is a 4,5-tetrahydrooxazol-2-yl or oxazol-2-yl or moiety, respectively, $R^5$ is hydrogen and $R^6$ is hydroxy or (C) reacting a compound of Formula 6:

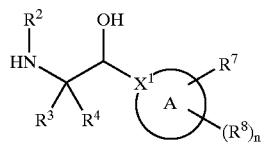

6 with a compound of the formula $R^1X^2OY$, wherein Y is hydrogen or an activating group and n, A, $X^1$, $X^2$, $R^1$, $R^2$, $R^3$, $R^4$, $R^7$ and $R^8$ are as defined in the Summary of the Invention for Formulae I and II, to give a compound of Formula I in which $R^5$ is hydrogen and $R^6$ is hydroxy; or (D) reacting a compound of Formula 7:

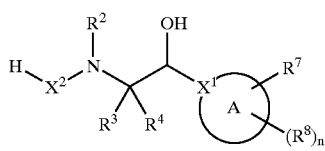

7 or a protected derivative thereof, with $R^{39}OH$, wherein $R^{39}$ is $-X^7X^8R^{20}$ and n, A, $X^1$, $X^2$, $X^7$, $X^8$, $R^2$, $R^3$, $R^4$, $R^7$, $R^8$ and $R^{20}$ are as defined in the Summary of the Invention for Formulae I and II, and deprotecting if necessary to give a compound of Formula I in which $R^1$ is $-X^7X^8R^{20}$, (E) optionally oxidizing a compound of Formula I in which $R^5$ is hydrogen and $R^6$ is hydroxy to give a compound of Formula I in which $R^5$ and $R^6$ together form oxo;

(F) optionally oxidizing a compound of Formula I in which A is optionally substituted 4,5-dihydroxyoxazol-2-yl to give a compound of Formula I in which A is optionally substituted oxazol-2-yl;

(G) optionally converting a compound of Formula I in which $R^7$ is $-C(O)OH$ to a compound of Formula I in which $R^7$ is methoxycarbonyl;

(H) optionally converting a compound of Formula I into a pharmaceutically acceptable salt;

(I) optionally converting a salt form of a compound of Formula I to non-salt form;

(J) optionally converting an unoxidized form of a compound of Formula I into a pharmaceutically acceptable N-oxide;

(K) optionally converting an N-oxide form of a compound of Formula I its unoxidized form;

(L) optionally converting a non-derivatized compound of Formula I into a pharmaceutically prodrug derivative; and (M) optionally converting a prodrug derivative of a compound of Formula I to its non-derivatized form.

Processes for Preparing Intermediates

Compounds of Formula 3 can be prepared by reacting a compound of the Formula 8:

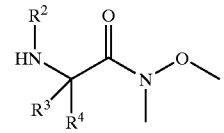

8 with a compound of the formula $R^1X^2OY$, in which Y is hydrogen or an activating group (NBS, or the like). The reaction is carried out under conditions analogous to those set for Reaction Scheme 3.

Compounds Formula 8 can be prepared by reacting a corresponding amino protected carboxylic acid with N,O-dimethylhydroxylamine hydrochloride and then deprotecting. The reaction with the amine is carried out in the presence of a suitable coupling agent (PyBOP®, EDC, HBTU, DCC, or the like) and base (e.g. N,N-diisopropylethylamine, triethylamine, or the like) in a suitable solvent (e.g. dichloromethane, DMF, or the like) at 20 to 30° C., preferably at about 25° C., and requires 2 to 4 hours to complete (e.g. see Reference 1, infra.). Deprotection can be effected by any means which removes the protecting group and gives the desired product in reasonable yield (e.g. see Example 2, infra.). A detailed description of the preparation of a compound of Formula 8 is set forth in References 1 and 6, infra.

Compounds of Formula 4 can be prepared by reacting a nitrile of Formula 9:

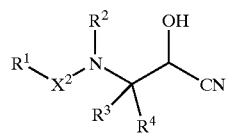

9 with ethanol. The reaction is carried out by adding the nitrile to a mixture comprising a catalytic amount of dry hydrogen chloride in a suitable solvent (e.g. chloroform, ethanol, or the like) and then allowing the reaction to proceed at 0 to 25° C. for 4 to 6 hours. Dry hydrogen chloride is conveniently generated by combining a slightly excessive amount of ethanol with acetyl chloride prior to adding the imidate to the reaction mixture. Alternatively, the hydrogen chloride is introduced to the reaction medium as a gas.

Compounds of Formula 6 can be prepared by methods known to those of ordinary skill in the art. For example, compounds of Formula 6 in which A is optionally substituted benzooxazol-2-yl can be prepared by reacting a compound of Formula 10:

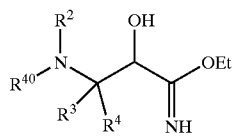

in which $R^{40}$ is a protecting group, with 2-aminophenol and deprotecting. The reaction with the phenol is carried out in the presence of a suitable base (e.g. diisopropylethylamine, triethylamine, or the like) and in a suitable solvent (e.g. chloroform, or the like) at reflux temperatures to 25° C. and requires 10 to 12 hours to complete. Deprotection can be effected by any means which removes the protecting group and gives the desired product in reasonable yield. A detailed description of the preparation of a compound of Formula 6 is set forth in Reference, infra.

Compounds of Formula 7 can be prepared by condensing a compound of Formula 6 with a compound of the formula $R^{40}X^2OY$, wherein $R^{40}$ is a protecting group, and then deprotecting. The condensation is carried out in the presence of a suitable base (e.g. triethylamine, diisopropylethylamine, or the like) and in a suitable solvent (e.g. acetonitrile, DMF, dichloromethane, or any suitable combination thereof, or the like) at 10 to 30° C., preferably at about 25° C., and requires 24 to 30 hours to complete. When Y is hydrogen a suitable coupling agent (e.g. PyBOP®, EDC, HBTU, HATU, DCC, or the like) and base (e.g. N,N-diisopropylethylamine, triethylamine, or the like) is required and the reaction requires 2 to 3 hours to complete. Deprotection can be effected by any means which removes the protecting group and gives the desired product in reasonable yield.

EXAMPLES

The following abbreviations used in this Application area defined as follows:

PyBOP®=benzotriazole-1-yloxytrispyrrolidinophosphonium hexafluorophosphate;
TBF=tetrahydrofuran;
OXONE®=potassium peroxymonosulfate;
EDC=1-(3-dimethylaminopropyl)-3-ethylcarbodiimide hydrochloride;
DMF=N,N-dimethylformamide;
HATU=O-(7-azabenzotriazol-1-yl)-1,1,3,3-tetramethyluronium hexafluorophosphate;
HOBT=1-hydroxybenzotriazole hydrate.

Reference 1

Benzyl 1S-(N-methoxy-N-methylcarbamoyl)-3-phenylpropylcarbamate

A solution of 2-benzyloxycarbonylamino-4-phenylbutyric acid (5.05 g, 16.1 mmol) in dichloromethane (70 mL) was cooled to 0° C. and treated with diisopropylethylamine (2.82 mL, 16.2 mmol) added dropwise and then PyBOP® (8.53 g, 16.4 mmol) added in one portion. The mixture was stirred for 5 minutes and then treated with N,O-dimethylhydroxylamine hydrochloride (1.73 g, 17.71 mmol) added in one portion. The mixture was neutralized with diisopropylethylamine (4.6 mL, 26.44 mmol) added dropwise, stirred for 2 hours at room temperature and then diluted with dichloromethane (70 mL). The dilution was washed sequentially with 1N aqueous hydrochloric acid (3×40 mL), saturated sodium bicarbonate (3×40 mL) and brine (40 mL) and then concentrated. The product was purified from the residue by column chromatography eluting with 2:3 ethyl acetate/hexane to provide benzyl 1S-(N-methoxy-N-methylcarbamoyl)-3-phenylpropylcarbamate (5.48 g, 15.4 mmol) as an oil. MS(PCI) m/z=357 (M+1).

Proceeding as in Reference 1 provided tert-butyl 1S-(N-methoxy-N-methylcarbamoyl)-3-phenylpropylcarbamate; $^1$H NMR (CDCl$_3$): δ 1.35 (s, 9H), δ 1.64–1.72 (m, 2H), δ 2.40–2.54 (m, 1H), δ 2.60–2.77 (m, 1H), δ 3.00 (s, 3H) 3.52 (s, 3H), δ 4.23 (m, 1H), δ 7.10–7.37 (m, 5H).

Reference 2

3-(2-Cyanobenzylsulfanyl)-2R-pyrid-4-ylcarbonylaminopropionic acid

A mixture of isonicotinic acid (3 g), N-hydroxysuccinimide (2.79 g) and N,N-dicyclohexylcarbodiimide (5.52 g) was stirred in THF (200 mL) for 16 hours. The solid was filtered off and the solvent evaporated under reduced pressure. The residue was triturated with ethyl acetate and more solid filtered off. The filtrates were concentrated under reduced pressure gave 2,5-dioxopyrrolidin-1-yl isonicotinate (5.27 g). MS: 221 [MH]$^+$.

A solution of L-cysteine (6 g) in ethanol (57 mL) was treated sequentially with aqueous 2N sodium hydroxide solution (30 mL) and 2-bromomethylbenzonitrile (9.71 g). The reaction mixture was stirred 2 hours at room temperature then neutralized by addition of concentrated hydrochloric acid. A resulting solid was collected by filtration and wash sequentially with water, ethanol and diethylether to provide 2R-amino-3-(2-cyanobenzylsulfanyl)propionic acid as a white solid. MS: 237 [MH]$^+$. MS: 235 [M]$^+$.

A solution of 2R-amino-3-(2-cyanobenzylsulfanyl) propionic acid (590 mg) in dichloromethane was treated with 2,5-dioxopyrrolidin-1-yl isonicotinate (1.41 g) and diisopropylethyamine (0.435 mL). The reaction mixture was stirred for 6 hours and then concentrated. The residue was treated with water and a resulting insoluble solid was filtered off. The aqueous filtrate was extracted twice with ethyl acetate and the combined extracts were dried over magnesium sulfate and then concentrated to provide 3-(2-cyanobenzylsulfanyl)-2R-pyrid-3-carbonylaminopropionic acid (340 mg) as a gum. MS: 342 [MH]$^+$. HPLC:R$_T$=10.63 minutes.

Reference 3

3-Benzylsulfanyl-2R-tetrahydropyran-4-yloxycarbonylaminopropionic acid

A solution of tetrahydropyran-4-ol (200 mg) in acetonitrile (5 mL) was treated with bis(2,5-dioxocyclopentyl) carbonate (0.753 g) and triethylamine (0.81 mL). The reaction mixture was stirred for 4 hours at room temperature and then concentrated. The residue was dissolved in ethyl acetate and the solution was washed with a saturated sodium bicarbonate solution, dried over magnesium sulfate and then concentrated to provide 2,5-dioxo-pyrrolidin-1-yl tetrahydropyran-4-yl carbonate.

A solution of 2R-amino-3-benzylsulfanylpropionic acid (1 g) and triethylamine (0.8 mL) in dichloromethane (40 mL) was treated with 2,5-dioxo-pyrrolidin-1-yl tetrahydropyran-4-yl carbonate (1.15 g). The mixture was stirred for 16 hours at room temperature and then concentrated. The residue was dissolved in ethyl acetate and the solution was washed sequentially with hydrochloric acid and brine, dried over magnesium sulfate and then concentrated. The residue was subjected to flash column chromatography on silica eluting with a mixture of ethyl acetate and pentane (1:1, v/v) to provide 3-benzylsulfanyl-2R-tetrahydropyran-4-yloxycarbonylaminopropionic acid (800 mg) as an oil.

Reference 4

3-Benzylsulfanyl-2R-morpholin-4-ylcarbonylaminopropionic acid

A solution of 3-benzylsulfanyl-2R-aminopropionic acid hydrochloride (25 g, 0.118 mol) in 2N sodium hydroxide (59 mL, 0.118 mol) was cooled in an ice bath and then treated simultaneously with morpholine-4-carbonyl chloride (13.8 mL, 0.118 mol) and 1N sodium hydroxide (118 mL, 0.118 mol). The mixture was stirred at 0° C. for 30 minutes and then filtered. The filtrate was acidified with 5N hydrochloric acid and extracted with ethyl acetate (5×100 mL). The combined extracts were dried ($MgSO_4$), filtered and concentrated to provide 3-benzylsulfanyl-2R-morpholin-4-ylcarbonylaminopropionic acid (19.65 g, 60.6 mmol) as a white solid.

Reference 5

3-Benzylsulfonyl-2R-morpholin-4-ylcarbonylaminopropionic acid

A solution of 3-benzylsulfanyl-2R-morpholin-4-ylcarbonylaminopropionic acid (17.58 g, 54.2 mmol), provided as in Reference 4, in methanol (550 mL) was treated with a solution of OXONE® (50 g, 81.4 mL) in water (550 mL). The mixture was stirred at room temperature for 2 hours and then concentrated to dryness. The residue was taken up into water (90 mL) and ethyl acetate (600 mL). The mixture was stirred vigorously and the aqueous layer was separated and extracted with ethyl acetate (2×100 mL). The combined ethyl acetate layers were dried ($MgSO_4$) and concentrated. The residue was triturated with diethyl ether and the solid material was collected by filtration to provide 3-benzylsulfonyl-2R-morpholin-4-ylcarbonylaminopropionic acid.

Reference 6

2-Amino-N-methoxy-N-methyl-4-phenylbutyramide trifluoroacetic acid salt

A solution of tert-butyl 1-(N-methoxy-N-methylcarbamoyl)-3-phenylpropylcarbamate (9.32 g, 29 mmol), provided as in Reference 1, in dichloromethane (100 mL) was cooled to 0° C. and then treated with anisole (5 mL, 46.5 mmol) and trifluoroacetic acid (50 mL, 296 mmol). The mixture was stirred for 30 minutes, while allowing it to warm to room temperature, and then concentrated. The residue was dissolved in toluene (100 mL) and the solution was concentrated. The residue was again dissolved in toluene (100 mL) and concentrated to provide 2-amino-N-methoxy-N-methyl-4-phenylbutyramide trifluoroacetic acid salt (9.74 g 29 mmol) as a crude product. MS(PCI) m/z=223 (M+1).

Reference 7

Ethyl 3S-benzyloxycarbonylamino-2-hydroxy-5-phenylpentanimidate

A suspension comprised of lithium aluminum hydride (0.885 g, 23.3 mmol) in anhydrous diethyl ether was cooled to −45° C. under nitrogen and then treated with a solution of benzyl 1S-(N-methoxy-N-methylcarbamoyl)-3-phenylpropylcarbamate (5.53 g, 15.53 mmol), provided as in Reference 1, in ether (75 mL) and TEF (25 mL) added dropwise over a period of 30 minutes such that the temperature of the mixture was maintained at −40 to −45° C. The mixture was allowed to warm to 5° C. and then recooled to −35° C. A saturated solution of sodium bicarbonate (7 mL, 0.5 M) was added dropwise and the mixture was allowed to warm to 0° C. The mixture was allowed to warm to room temperature and stirred for 1 hour to provide a precipitate. The precipitate was collected by filtration and washed with ether (100 mL). The filtrate and washings were combined and washed sequentially with ice cold 1N hydrochloric acid (2×50 mL), saturated sodium bicarbonate (2×50 mL) and brine (50 mL), dried ($Na_2SO_4$) and concentrated in vacuo to provide benzyl 1S-formyl-3-phenylpropylcarbamate (4.01 g, 13.5 mmol) as a colorless oil. MS (PCI) m/z=298 (M+1).

A solution of benzyl 1S-formyl-3-phenylpropylcarbamate (4.557 g, 15.3 mmol) in anhydrous dichloromethane (50 mL) was stirred while sequentially treated with 2-hydroxy-2-methylpropionitrile (4.25 mL, 46.2 mmol) and triethylamine (1.28 mL, 9.20 mmol). The mixture was stirred for 4 hours at room temperature and concentrated in vacuo. The residue was dissolved in ether (100 mL) and the solution was washed sequentially with water (5×20 mL) and brine (20 mL), dried ($MgSO_4$) and concentrated to provide benzyl 2-cyano-2-hydroxy-1S-phenethylethylcarbamate (4.957 g, 15.3 mmol) as a yellow oil. $^1$H NMR ($CDCl_3$): δ 1.75–2.01 (m, 2H), δ 2.08–2.24 (m, 1H), δ 2.51–2.80 (m, 2H), δ 3.70–4.02 (m, 1H), δ 5.07, δ5.33 (m, 3H), δ 7.10–7.47 (m, 10H).

A mixture of chloroform (30 mL) and anhydrous ethanol (30 mL, 510 mmol) was cooled to 0° C. and then treated with acetyl chloride (32.6 mL, 459 mmol) added dropwise over a period of 30 minutes. The mixture was cooled by adding a solution of crude benzyl 2-cyano-2-hydroxy-1S-phenethylethylcarbamate (4.957 g, 15.3 mmol) in chloroform (30 mL). The mixture was stirred for 2 hours at 0° C. and then 6 hours at room temperature and concentrated in vacuo to provide ethyl 3S-benzyloxycarbonylamino-2-hydroxy-5-phenylpentanimidate (6.212 g 15.3 mmol) as a crude yellow oil. MS (PCI) m/z=371 (M+1).

Reference 8

2S-Amino-4-phenyl-1-(4S-phenyl-4,5-dihydrooxazol-2-yl)butan-1-ol (a) A mixture comprised of ethyl 3S-benzyloxycarbonylamino-2-hydroxy-5-phenylpentanimidate (0.78 g, 1.92 mmol), provided as in Reference 7, diisopropylethylamine (0.218 μL, 1.26 mmol) and 2S-amino-2-phenylethanol (0.260 g, 1.9 mmol) in chloroform (25 mL) was heated at reflux for 3 hours and then was stirred for approximately 12 hours, while allowing to cool to room temperature. The mixture was concentrated and the residue was dissolved in ethyl acetate (50 mL). The solution was washed sequentially with 0.5N sodium hydroxide (40 mL) and brine (40 mL), dried ($MgSO_4$) and then concentrated. Product was purified from the residue by flash chromatography eluting with 1:3 hexanes/ethyl acetate to provide benzyl 2-hydroxy-2-(4,5-dihydro-4S-phenyloxazol-2-yl)-1S-phenyethylethylcarbamate (0.475 g, 1.1 mmol) as an oily mixture of diastereomers. MS (PCI) m/z=445 (M+1). ($C_{27}H_{28}N_2O_4$).

(b) A solution comprised of benzyl 2-hydroxy-2-(4,5-dihydro4S-phenyloxazol-2-yl)-1S-phenyethylethylcarbamate (100 mg, 0.22 mmol) in methanol (10 mL) was placed under a nitrogen atmosphere and stirred while Pearlman's catalyst (20 mg) was added. The mixture was stirred vigorously under a hydrogen atmosphere until the reaction was complete and then filtered. The filter was washed with methanol (2×25 mL). The combined filtrates were concentrated to provided 2S-amino-4-phenyl-1-(4S-phenyl-4,5-dihyrooxazol-2-yl)butan-1-ol (51 mg, 0.16 mmol) as a clear oil. MS (PCI) m/z=311(M+1). ($C_{19}H_{22}N_2O_2$).

Proceeding as in Reference 8 provided methyl 2-(2S-benzyloxycarbonylamino-1-hydroxy-4-phenylbutyl)-4,5-dihydrooxazole-4-carboxylate.

Reference 9

2S-Amino-1-oxazol-2-yl-4-phenylbutan-1-ol trifluoroacetic acid salt

A solution comprised of oxazole (0.25 g, 3.62 mmol) in THF (20 mL) was treated with borane tetrahydrofuran complex (3.62 mL, 3.62 mmol) under nitrogen and the mixture was stirred for 30 minutes and then cooled to −78° C. A solution comprised of sec-butyl lithium (2.78 mL, 3.62 mmol) in cyclohexane was added dropwise and the mixture was stirred for 30 minutes. A solution comprised of tert-butyl (S)-1-formyl-3-phenylpropylcarbamate (0.476 g, 1.81 mmol) in THF (25 mL) was added and the mixture was stirred and allowed to warm while the reaction proceeded to completion. The mixture then was cooled to −78 ° C., quenched by slowly adding 5% acetic acid in ethanol (20 mL), allowed to warm to ambient temperature and stirred for 18 hours. The mixture was concentrated to dryness and the residue was extracted with ether (2×25 mL). The combined extracts were washed with brine, dried (MgSO$_4$) and concentrated to dryness to provide tert-butyl 2-hydroxy-2-oxazol-2-yl-1S-phenethylethylcarbamate (0.125 g, 0.376 mmol) as a yellow oil. MS (PCI) m/z=333 (M+1).

A mixture comprised of tert-butyl 2-hydroxy-2-oxazol-2-yl-1S-phenethylethylcarbamate (0.125 g, 0.376 mmol), anisole (0.2 mL) and trifluoroacetic acid (0.6 mL) in dichloromethane (20 mL) was stirred at room temperature for 2 hours and then concentrated to provide 2S-amino-1-oxazol-2-yl-4-phenylbutan-1-ol trifluoroacetic acid salt (0.08 g, 0.229 mmol) as a yellow oil. MS (PCI) m/z=233 (M+1).

Reference 10

Methyl 2-(2S-amino-1-hydroxy-4-phenylbutyl) oxazole-4-carboxylate

A solution comprised of methyl 2-(2S-benzyloxycarbonylamino-1-hydroxy-4-phenylbutyl)-4,5-dihydrooxazole-4-carboxylate (0.100 g, 0.235 mmol), provided as in Reference 10, in dichloromethane (3 mL) was cooled to 0° C. and then treated with DBU (39 mL, 0.26 mmol) and bromotrichloromethane (26 mL, 0.26 mmol). The mixture was stirred for 6 hours at 0° C., washed with ammonium chloride (10 mL) and concentrated. The residue was dried (MgSO$_4$) to provide methyl 2-(2S-benzyloxycarbonylamino-1-hydroxy-4-phenylbutyl)oxazole-4-carboxylate. MS(PCI) m/z=425 (M+1).

Deprotecting provided methyl 2-(2S-amino-1-hydroxy-4-phenylbutyl)oxazole-4-carboxylate.

Reference 11

2-Benzooxazol-2-yl-2-(tert-butyl-dimethyl-silanyloxy)-1S-phenethylethylamine

A solution of 2S-amino-1-benzooxazol-2-yl-4-phenylbutan-1-ol (600 mg), provided as in Reference 12, in dichloromethane (15 mL) was cooled to 0° C. and then treated with 2,6-lutidine (0.57 mL) followed by tert-butyldimethylsilyl trifluoromethanesulfonate (1.08 mL). The solution was stirred for 3 hours and then additional dichloromethane was added (50 mL). The mixture was washed sequentially with a saturated sodium bicarbonate solution (50 mL) and brine (50 mL×2), dried over magnesium sulphate and concentrated under reduced pressure to provide 2-benzooxazol-2-yl-2-(tert-butyl-dimethyl-silanyloxy)-1S-phenethylethylamine as an orange oil.

Reference 12

2S-Amino-1-benzooxazol-2-yl-4-phenylbutan-1-ol

A solution of (S)-2-tert-butoxycarbonylamino-4-phenylbutyric acid (500 g, 179 mmol), EDC (37.8 g, 197 mmol), HOBT (41.1 g, 269 mmol) and N,O-dimethylhydroxylamine hydrochloride (19.2 g, 197 mmol) in, dichloromethane (500 mL) was cooled in an ice bath and then treated with a solution of triethylamine (27.5 mL, 197 mmol) in dichloromethane (150 mL). The ice bath was removed and the reaction mixture was stir at room temperature for approximately 12 hours. The mixture was concentrated by rotary evaporation and the residue was treated with ethyl acetate (450 mL), water (300 mL) and saturated sodium bicarbonate until all solids were dissolved. The ethyl acetate layer was separated and washed sequentially with saturated sodium bicarbonate (100 mL), water (100 mL), 1N hydrochloric acid (100 mL), water (100 mL) and brine (50 mL). The solution was dried over anhydrous magnesium sulfate and concentrated to provide tert-butyl (S)-1-(N-methoxy-N-methylcarbamoyl)-3-phenylpropylcarbamate (53.41 g, 93% yield) as a clear, colorless oil.

The tert-butyl (S)-1-(N-methoxy-N-methylcarbamoyl)-3-phenylpropylcarbamate provided above was divided into three portions (5.0 g 15.5 mmol; 4.88 g, 15.1 mmol; and 4.54 g, 14.1 mmol). Each portion was azeotroped with toluene by rotary evaporation and dried under reduced pressure to remove residual ethyl acetate and water. Each portion of the ester was taken up into anhydrous diethyl ether (75 mL) and the mixtures were cooled in an ice bath under nitrogen. Each of the mixtures were treated with lithium aluminum hydride (1M in diethyl ether, 23.3 mL, 22.7 mL, and 21.1 mL, respectively) added by syringe and the mixtures were stirred at 0° C. for 90 minutes. The mixtures were treated with ethyl acetate (5 mL), stirred for 15 minutes, further treated with saturated KH$_2$PO$_4$ (5 mL), 1N hydrochloric acid (1 mL) and then additional 1N hydrochloric acid until the solid mass dissolved. The resulting solutions were combined and extracted with ethyl acetate (3×200 mL). The extracts were dried over anhydrous magnesium sulfate and concentrated. The residue was dried under reduced pressure to provide tert-butyl (S)-1-formyl-3-phenylpropylcarbamate (11.61 g, 99% yield).

A solution of tert-butyl (S)-1-formyl-3-phenylpropylcarbamate (11.15 g, 42.3 mmol) in dichloromethane (25 mL) was cooled in an ice bath under nitrogen and then treated sequentially with acetone cyanohydrin (10.8 mL, 119 mmol) and triethylamine (3.5 mL, 25.4 mmol). The reaction was stirred for approximately 12 hours at room temperature and then concentrated by rotary evaporation. The residue was dissolved in 1:1 hexanes:ethyl acetate (250 mL) and the solution was washed sequentially with water (3×100 mL) and brine (50 mL), dried over anhydrous magnesium sulfate and concentrated. Product was purified from the residue by silica gel chromatography using 2:1 hexanes:ethyl acetate eluent to provide tert-butyl 2-cyano-2-hydroxy-1S-phenethylethylcarbamate (12.05 g, 98% yield).

A mixture of chloroform (12.8 mL) and absolute ethanol (9 mL, 153 mmol), under a nitrogen stream with an attached Firestone valve bubbler, was cooled in an ice bath and then treated with acetyl chloride (9.2 mL, 129 mmol) added by syringe. The mixture was allowed to stand for 5 minutes and then a solution of tert-butyl 2-cyano-2-hydroxy-1S-phenethylethylcarbamate (2.34 g, 8 mmol) in chloroform (19.2 mL) was added. The nitrogen inlet was removed and the mixture was stirred and slowly warm to room temperature over approximately 12 hours. The mixture then was concentrated by rotary evaporation and the residue was treated with absolute ethanol (40 mL) and o-aminophenol (873 mg, 8 mmol). The mixture was heated at 95° C. under nitrogen for 5 hours and then stirred at room temperature for approximately 12 hours. The mixture was treated with diethyl ether (150 mL) and the resulting solution was washed repeatedly with 1N KOH until the aqueous wash layer was colorless. The organic phase was separated, dried over anhydrous magnesium sulfate and concentrated. The residue was recrystallized from hot hexane and a minimum amount of ethyl acetate to give a tan powder (335 mg). The mother liquor was combined with the mixed fractions from a similarly performed reaction run and purified by silica gel dochromatography using 5% methanol in dichloromethane to provide 2S-amino-1-benzooxazol-2-yl-4-phenylbutan-1-ol (1.27 g, 52% average yield) as an orange semi-solid mass.

Proceeding as in Reference 12 provided the following compounds:

2-amino-1-benzooxazol-2-yl-ethanol;
2-amino-1-benzooxazol-2-yl-2-methyl-propan-1-ol;
(S)-2-amino-1-benzooxazol-2-yl-hexan-1-ol;
1-(1-amino-cyclopropyl)-1-benzooxazol-2-yl-methanol;
(S)-2-amino-1-benzooxazol-2-yl-propan-1-ol;
(S)-2-amino-1-benzooxazol-2-yl-4-methanesulfonyl-butan-1-ol;
(S)-2-amino-1-benzooxazol-2-yl-pentan-1-ol;
(S)-2-amino-1-benzooxazol-2-yl-butan-1-ol; and
2-Amino-1-benzooxazol-2-yl-3-methoxy-propan-1-ol;
$^1$H NMR (CDCl$_3$): 7.70 (m, 1H), 7.53 (m, 1H), 7.34 (m, 2H), 4.88–5.0 (m, 1H), 3.60 (m, 1H), 3.53 (m, 3H), 3.37 (s, 1H), 3.30 (s, 1H).

Example 1

N-[1R-(2-Benzooxazol-2-yl-2-hydroxy-1S-phenethylethylcarbamoyl)-2-benzylsulfonylethyl]-morpholine-4-carboxamide (Compound 1)

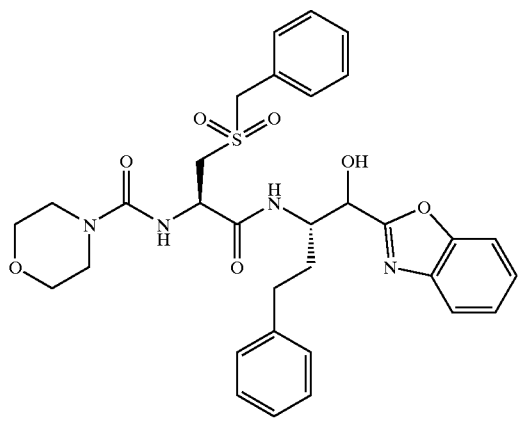

A mixture of 2S-amino-1-benzooxazol-2-yl-4-phenylbutan-1-ol (2.2 g, 7.8 mmol), provided as in Reference 12, 2-morpholin-4-ylcarbonylamino-3-benzylsulfonylpropionic acid (2.78 g, 7.8 mmol), EDC (1.64 g, 8.57 mmol), 1-hydroxybenzotriazole hydrate (1.58 g, 11.7 mmol) and N-methylmorpholine (2.4 mL, 17.1 mmol) in dichloromethane was stirred for 1 hour. The mixture was treated with additional amounts of EDC (0.1 eq) and 1-hydroxybenzotriazole hydrate (0.1 eq) and stirred for 30 minutes. The mixture was treated with an additional amount of EDC (0.1 eq) and stirred for 15 minutes. The mixture was treated with an additional amount of EDC (0.1 eq) and stirred for 30 minutes. The mixture was concentrated and the residue was taken up into ethyl acetate. The mixture was washed sequentially with 1N hydrochloric acid (3×50 mL), saturated sodium bicarbonate solution (2×50 mL) and brine (50 mL), dried (MgSO$_4$) and concentrated to provide N-[1R-(2-benzooxazol-2-yl-2-hydroxy-1S-phenethylethylcarbamoyl)-2-benzylsulfonylethyl] morpholine-4-carboxamide (4 g, 6.44 mmol); $^1$H NMR (CDCl$_3$): 7.68 (m, 1H), 7.52 (m, 1H), 7.10–7.45 (m, 12H), 6.0–6.25 (m, 1H), 4.95–5.1 (m, 1H), 4.52–4.80 (m, 1H), 4.15–4.5 (m, 3H), 3.1–3.75 (m, 10H), 2.69 (m, 2H), 2.06 (m, 1H), 1.80 (m, 1H); MS: m/e 621.0;

Example 2

2S-Acetylamino-N-(2-oxazol-2-yl-2-hydroxy-1S-phenethylethyl)-3-cyclohexylpropionamide (Compound 2)

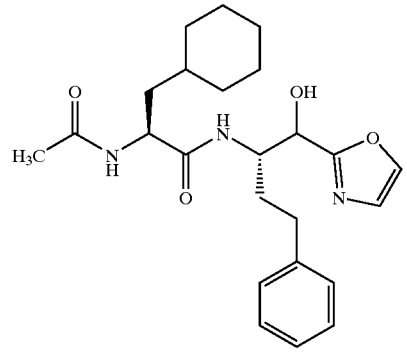

A mixture comprised of 2-acetylamino-3-cyclohexylpropionic acid (0.45 g, 0.211 mmol), PyBOP® (0.11 g, 0.21 mmol) and diisopropylethylamine (0.037 g, 0.211 mmol) in DMF (10 mL) was stirred for 15 minutes at room temperature and a solution comprised of 2S-amino-1-oxazol-2-yl-4-phenylbutan-1-ol trifluoroacetic acid salt, provided as in Reference 9, in DMF and neutralized with diisopropylethylamine was added. Additional diisopropylethylamine (0.037 g, 0.211 mmol) was added and the mixture was stirred for 2 hours at room temperature and then poured into 100 mL of ice cold water. The aqueous phase was extracted with ethyl acetate (3×25 mL) and the combined organic layers were washed sequentially with 1 N hydrochloric acid (2×25 mL), water (2×25 mL) and brine (2×25 mL), dried (MgSO$_4$) and concentrated. Product was purified from the residue by flash chromatography eluting with 1:3 hexanes/ethyl acetate to provide 2S-acetylamino-N-(2-oxazol-2-yl-2-hydroxy-1S-phenethylethyl)-3-cyclohexylpropionamide (0.036 g, 0.084 mmol) as an oil. MS (ESI) m/z=428 (M+1); $^1$H-NMR (300 MHz, CD$_3$OD): δ 0.80 (m, 2H), δ 1.12 (m, 4H), δ 1.40 (m, 2H), δ 1.65 (m, 6H), δ 1.80 (m, 1H), δ 2.00 (m, 4H), δ 2.70 (m, 1H), δ 2.80 (m, 1H), δ 4.44 (m, 1H), δ 4.51 (m, 1H), δ 7.11–7.47 (m, 6H), δ 7.99 (s, 1H), (C$_{24}$H$_{33}$N$_3$O$_4$).

Proceeding as in Example 2 provided the following compounds of Formula I:

3-cyclohexyl-N-{2-hydroxy-2-(5-phenyloxazol-2-yl)-1S-phenethylethyl}propionamide (Compound 3); MS (ESI) m/z=448 (M+1); $^1$H-NMR (300 MHz, CDCl$_3$): δ 0.89 (m, 2H), δ 1.20 (m, 4H), δ 1.45 (m, 1H), δ 1.65 (m, 6H), δ 1.80 (m, 1H), δ 2.09 (m, 4H), δ 2.73 (t, J=4 Hz, 2H), δ 4.51 (m, 1H), δ 4.96 (m, 2H), δ 6.00 (m, 1H), δ 7.11–7.47 (m, 9H), δ 7.60 (m, 2H), (C$_{28}$H$_{35}$N$_2$O$_3$);

2S-acetylamino-N-[2-hydroxy-1S-phenethyl-2-(5-phenyloxazol-2-yl)ethyl]-3-cyclohexylpropionamide (Compound 4); MS (ESI) m/z=505 (M+1); $^1$H-NMR (300 MHz, CDCl$_3$): δ 0.80 (m, 2H), δ 1.12 (m, 4H), δ 1.40 (m, 2H), δ 1.65 (m, 6H), δ 1.80 (m, 1H), δ 2.00 (m, 5H), δ 2.70 (m, 2H), δ 4.51 (m, 1H), δ 4.96 (m, 2H), δ 6.19 (m, 1H), δ 6.98 (m, 1H), δ 7.11–7.47 (m, 9H), δ 7.62 (m, 2H), (C$_{30}$H$_{38}$N$_3$O$_4$); and N-(1S-benzothiazol-2-ylcarbonyl-3-phenylpropyl)-3-cyclohexylpropionamide (Compound 5); $^1$H NMR: δ 0.83 (m, 2H), δ 1.20 (m, 5H), δ 1.48 (q, 2H, J=9 Hz), δ 1.67 (m, 4H), δ 2.20 (m, 3H), δ 2.48 (m, 1H), δ 2.75 (m, 2H), δ 5.95 (m, 1H), δ 6.35 (d, 1H, J=9 Hz), δ 7.25 (m, 5H), δ 7.57 (m, 2H), δ 7.93 (d, 1H, J=9 Hz), δ 8.18 (d, 1H, J=9 Hz); ES-MS m/z 435 (MH+); and 2S-acetylamino-N-(S-benzothiazol-2-ylcarbonyl-3-phenylpropyl)-3-cyclohexylpropionamide (Compound 6); $^1$H NMR: δ 0.87 (m, 8H), δ 1.22 (m, 6H), δ 1.92 (m, 1H), δ 2.12 (m, 1H), δ 2.48 (m, 1H), δ 2.78 (m, 2H), δ 3.87 (d, 1H, J=7 Hz), δ 5.62 (m, 1H), δ 7.20 (m, 6H), δ 7.53 (m, 2H), δ 7.98 (d, 1H, J=7 Hz), δ 8.18 (d, 1H, J=7 Hz); ES-MS m/z 492 (MH+).

N-[1S-(1S-phenethyl-2-benzooxazol-2-yl-1-oxoethylcarbamoyl)-2-naphth-2-ylethyl]piperidine-4-carboxamide (Compound 7), $^1$H NMR (DMSO-d$_6$): δ 1.32–1.76 (m, 4H), δ 1.90–2.09 (m, 2H), δ 2.22–2.60 (m, 2H), δ 2.65–3.26 (m, 6H), δ 4.72–4.86 (m, 1H), δ 5.26 (m, 1H), δ 7.06–7.31 (m, 5H), δ 7.45 (m, 4H), δ 7.55 (dt, J=1.26, 7.84 Hz, 1H), δ 7.65 (dt, J=1.18, 8.00 Hz, 1H), δ 7.72–7.88 (m, 3H), δ 7.90 (d, J=8.06 Hz, 1H), δ 7.99 (d, J=7.86 Hz, 1H), δ 8.14 (bs, 1H), δ 8.24 (d, J=8.04 Hz, 1H), δ 8.46 (bs, 1H), δ 8.94 (d, J=6.43 Hz, 1H);

2S-acetylamino-N-(1S-benzooxazol-2-ylcarbonyl-3-phenylpropyl)-3-cyclohexylproaionamide (Compound 8); MS (ESI) m/z=476 (M+1); $^1$H-NMR (300 MHz, CDCl$_3$): δ 0.85 (m, 2H), δ 1.26 (m, 4H), δ 1.47 (m, 2H), δ 1.64 (m, 6H), δ 1.99 (s, 3H), δ 2.15 (m, 2H), δ 2.41 (m, 1H), δ 2.72 (t, J=6 Hz, 2H), δ 4.59 (q, J=4 Hz, 1H), δ 5.65 (q, J=2 Hz, 1H), δ 6.26 (d, J=6 Hz, 1H), δ 7.10–7.26 (m, 6H), δ 7.41–7.65 (m, 3H), δ 7.86 (d, J=6 Hz 1H), (C$_{28}$H$_{33}$N$_3$O$_4$);

tert-butyl 1S-(1S-benzooxazol-2-ylcarbonyl-3-phenelnropylcarbamoyl)-2-cyclohexylethylcarbamate (Compound 9);

N-[1-(benzooxazol-2-ylcarbonyl)-3-phenylpropyl]-3-cyclohexylpropionamide (Compound 10);

3-cyclohexyl-N-[3S-phenyl-1-(5-phenyloxazol-2-ylcarbonyl)propyl-propionamide (Compound 11); MS (ESI) m/z=445 (M+1); $^1$H-NMR (300 MHz, CDCl$_3$): δ 0.89 (m, 2H), δ 1.20 (m, 4H), δ 1.55 (m, 2H), δ 1.68 (m, 6H), δ 2.12 (m, 1H), δ 2.27 (t, J=4 Hz, 2H), δ 2.48 (m, 2H), δ 2.76 (m, 2H), δ 5.70 (m, 1H), δ 6.35 (d, 1H, J=4 Hz), δ 7.19–7.30 (m, 5H), δ 7.48 (m, 3H), δ 7.57 (s, 1H), δ 7.79 (d, J=4 Hz, 2H), (C$_{28}$H$_{32}$N$_2$O$_3$);

2S-acetylamino-N-[1S-(5-phenyloxazol-2-ylcarbonyl)-3-phenylpropyl]-3-cyclohexylpropionamide (Compound 12); MS (ESI) m/z=502 (M+1); $^1$H-NMR (300 MHz, CDCl$_3$): δ 0.80 (m, 2H), δ 1.12 (m, 4H), δ 1.50 (m, 1H), δ 1.65 (m, 6H), δ 1.80 (m, 1H), δ 2.05 (s, 3H), δ 2.12 (m, 1H), δ 2.48 (m, 1H), δ 2.70 (t, J=6 Hz, 2H), δ 4.52 (q, J=2 Hz, 1H), δ 5.60 (q, J=2 Hz, 1H), δ 5.98 (d, J=6 Hz, 1H), δ 6.92 (d, J=6 Hz, 1H), δ 7.19–7.30 (m, 5H), δ 7.48 (m, 3H), δ 7.57 (s, 1H), δ 7.79 (d, J=4 Hz, 2H), (C$_{30}$H$_{35}$N$_3$O$_4$);

benzyl 1S-(benzooxazol-2-ylcarbonylmethylcarbamoyl)-3-methylbutylcarbamate (Compound 13);

benzyl 1S-(5-phenylbenzooxazol-2-ylcarbonylmethylcarbamoyl)-3-methylbutylcarbamate (Compound 14);

2S-acetylamino-N-(1S-oxazol-2-ylcarbonyl-3-phenylpropyl)-3-cyclohexylpropionamide (Compound 15); MS (ESI) m/z=426 (M+1); $^1$H-NMR (300 MHz, CDCl$_3$): δ 0.85 (m, 2H), δ 1.20 (m, 4H), δ 1.50 (m, 2H), δ 1.65 (m, 6H), δ 2.05 (s, 3H), δ 2.48 (m, 1H), 2.70 (t, J=6 Hz, 2H), δ 4.52 (q, J=2 Hz, 1H), δ 5.60 (q, J=2 Hz, 1H), δ 5.93 (d, J=6 Hz, 1H), δ 6.89 (d, J=6 Hz, 1H), δ 7.19–7.38 (m, 5H), δ 7.47 (s, 1H), δ 7.79 (s, 1H), (C$_{24}$H$_{31}$N$_3$O$_4$);

benzyl 1S-benzooxazol-2-ylcarbonyl-3-phenylpropylcarbamate (Compound 16);

2-acetylamino-N-(1S-benzooxazol-2-ylcarbonyl-3-phenylpropyl)-3-phenylpropionamide (Compound 17);

N-(1S-benzooxazol-2-ylcarbonyl-3-phenylpropyl)benzylsulfonamide (Compound 18); $^1$H NMR (CDCl$_3$): 7.88 (d, J=6.2 Hz, 1H), 7.67 (d, J=6.2 Hz, 1H), 7.60 (t, J=6.2 Hz, 1H), 7.51 (t, J=6.2 Hz, 1H), 7.35 (d, J=6.2 Hz, 2H), 7.08–7.29 (m, 7H), 6.96 (t, J=6.2 Hz, 1H), 5.52 (d, JK=9.4 Hz, 1H), 4.90 (td, J=9.4, 3.1 Hz, 1H), 4.31 (dd, J=10.9, 10.9 Hz, 2H), 2.80 (m, 1H), 2.27 (m, 1H), 2.04 (m, 1H); MS: m/e=435.0;

N-(1S-benzooxazol-2-ylcarbonyl-3-phepylpropyl)-2-cyclohexylethanesulfonamide (Compound 19); $^1$H NMR (CDCl$_3$): 7.94 (d, J=6.3 Hz, 1H), 7.70 (d, J=6.3 Hz, 1H) 7.62 (t, J=6.3 Hz, 1H), 7.52 (t, J=6.3 Hz, 1H), 7.17–7.34 (m, 5H), 5.42 (d, J=9.5 Hz, 1H), 5.17–5.25 (m, 1H), 2.79–3.09 (m, 4H), 2.38–2.55 (m, 1H), 2.08–2.21 (m, 1H), 1.52–1.79 (m, 7H), 1.08–1.34 (m, 4H), 0.77–1.01 (m, 2H); MS m/e=455.1;

N-(1-benzooxazol-2-ylcarbonyl-3-phenylpropyl)-3-cyclopentylpropionamide (Compound 20);

N-(1S-benzooxazol-2-ylcarbonyl-3-phenylpropyl)-2-cyclohexylacetamide (Compound 21);

N-(1S-benzooxazol-2-ylcarbonyl-3-phenylpropyl)-2-bicyclo[2.2.1]hept-2-ylacetamide (Compound 22);

N-(1S-benzooxazol-2-ylcarbonyl-3-phenylpropyl)-4-methylpentanamide (Compound 23);

N-(1S-benzooxazol-2-ylcarbonyl-3-phenylpropyl)-2-naphthalen-1-ylacetamide (Compound 24); $^1$H NMR (CDCl$_3$): 7.96 (m, 1H), 7.84 (m, 2H), 7.82 (m, 1H), 7.42–7.75 (m, 6H), 7.14 (m, 4H), 6.86 (m, 2H), 6.25 (m, 1H), 5.64 (m, 2H), 4.08 (m, 1H), 2.45 (m, 2H), 2.42 (m, 1H), 1.90 (m, 1H);

N-(1-benzooxazol-2-ylcarbonyl)-3-phenylpropyl]-3-phenylpropionamide (Compound 25); $^1$H NMR (CDCl$_3$): 7.90 (d,J=8.0 Hz, 11H), 7.65 (d,J=8.0 Hz, 11H), 7.59 (m, 1H), 7.56 (m, 1H), 7.05–7.35 (m, 11H), 6.20 (d, J=7.0 Hz, 1H), 5.76 (m, 1H), 2.97 (m, 2H), 2.5–2.7 (m, 4H), 2.4 (m, 1H), 2.1 (m, 1H);

methyl 2-[2-(3S-cyclohexylpropionylamino)-4-phenylbutyryl]-4,5-dihydrooxazole-4S-carboxylate (Compound 26); MS (ESI) m/z=429 (M+1); $^1$H-NMR (300 MHz, CDCl$_3$): δ 0.89 (m, 2H), δ 1.22 (m, 4H), δ 1.51 (m, 1H), δ 1.65 (m, 6H), δ 2.05 (m, 1H), δ 2.20 (t, J=4 Hz, 2H), δ 2.46 (m, 1H), δ 2.73 (m, 2H), δ 3.80 (s, 3H), δ 4.55 (m, 1H), δ 4.60 (m, 1H), δ 5.00 (m, 1H), δ 5.45 (m, 1H), δ 6.15 (m, 1H), δ 7.13–7.35 (m, 5H), (C$_{24}$H$_{32}$N$_2$O$_5$);

methyl 2-[2-(3S-cyclohexylpropionylamino)-4-phenylbutyryl]oxazole-4-carboxylate (Compound 27); MS (ESI) m/z=427 (M+1); ¹H-NMR (300 MHz, CDCl₃): δ 0.89 (m, 2H), δ 1.22 (m, 4H), δ 1.49 (m, 1H), δ 1.65 (m, 6H), δ 2.20 (m, 3H), δ 2.46 (m, 1H), ι2.74 (m, 2H), δ 3.99 (s, 3H), δ 5.62 (m, 1H), δ 6.20 (d, J=4 Hz, 1H), δ 7.15–7.35 (m, 5H), δ 8.40 (s, 1H), ($C_{24}H_{30}N_2O_5$);

benzyl 1S-(1S-benzooxazol-2-ylcarbonyl)-3-phenylpropylcarbamoyl)-2-naphthalen-2-ylethylcarbamate (Compound 28);

2-acetylamino-N-(1S-benzooxazol-2-ylcarbonyl-3-phenylpropyl]-3-(2-fluorophenyl)propionamide (Compound 29);

2S-acetylamino-N-(1S-benzooxazol-2-ylcarbonyl-3-phenylpropyl)-2-methyl-3-phenylpropionamide (Compound 30);

tert-butyl 1S-(1S-benzooxazol-2-ylcarbonyl-3-phenylpropylcarbamoyl)-3-phenylpropylcarbamate (Compound 31);

N-(1-benzooxazol-2-ylcarbonyl)-3-phenylpropyl)-4-cyclohexylbutyramide (Compound 32); ¹H NMR (CDCl₃): 7.94 (d, J=7.9 Hz, 1H), 7.68 (d, 7.9 Hz, 1H), 7.58 (t,J=7.9 Hz, 1H), 7.50 (t, J=7.9 Hz, 1H), 7.10–7.32 (m, 5H), 6.27 (d, J=11.8 Hz, 1H), 5.76–5.89 (m, 1H), 2.74–2.89 (m, 2H), 2.42–2.61 (m, 1H), 2.11–2.32 (m, 3H), 1.53–1.79 (m, 9H), 1.05–1.32 (m, 4H), 0.79–1.0 (m, 2H); MS: m/e=433;

methyl 2-[2S-(3-cyclohexylpropionylamino)-4-phenylbutyryl]-4,5-dihydrooxazol-4S-ylcarboxylate (Compound 33); MS (ESI) m/z=429 (M+1); ¹H-NMR (300 MHz, CDCl₃): δ 0.89 (m, 2H), δ 1.22 (m, 4H), δ 1.51 (m, 1H), 1.65 (m, 6H), δ 2.05 (m, 1H), δ 2.20 (t, J=4 Hz, 2H), δ 2.46 (m, 1H), δ 2.73 (m, 2H), δ 3.80 (s, 3H), δ 4.58 (m, 2H), δ 5.00 (m, 1H), δ 5.45 (m, 1H), δ 6.15 (m, 1H), δ 7.13–7.35 (m, 5H), ($C_{24}H_{32}N_2O_5$);

3-cyclohexyl-N-[1-(5-methoxybenzooxazol-2-ylcarbonyl)-3-phenylpropyl]propionamide (Compound 34); MS (ESI) m/z=449 (M+1); ¹H-NMR (300 MHz, CDCl₃): δ 0.95 (m, 2H), δ 1.22 (m, 4H), δ 1.51 (m, 2H), δ 1.65 (m, 6H), δ 2.15 (m, 1H), δ 2.20 (t, J=4 Hz, 2H), δ 2.50 (m, 1H), δ 2.77 (q, J=2 Hz, 2H), δ 3.92 (s, 3H), δ 5.78 (m, 1H), δ 6.37 (m, 1H), δ 7.13–7.35 (m, 5H), δ 7.53 (d, J=6 Hz, 1H), ($C_{27}H_{32}N_2O_4$);

2-acetyl-N-(1S-benzooxazol-2-ylcarbonyl-3-phenylpropyl)-1,2,3,4-tetrahydroisoqiuinoline-3S-carboxamide (Compound 35);

2S-acetylamino-N-(1S-benzooxazol-2-ylcarbonyl-3-phenylpropyl)-3-(2-chlorophenyl)propionamide (Compound 36);

3-cyclohexyl-N-[1S-(6-methoxybenzooxazol-2-ylcarbonyl)-3-phenylpropyl]propionamide (Compound 37); MS (ESI) m/z=449 (M+1); ¹H-NMR (300 MHz, CDCl₃): δ 0.95 (m, 2H), δ 1.22 (m, 4H), δ 1.51 (m, 2H), δ 1.65 (m, 6H), δ 2.15 (m, 1H), δ 2.20 (t, J=4 Hz 2H), δ 2.50 (m, 1H), δ 2.77 (q, J=2 Hz, 2H), δ 3.95 (s, 3H), δ 5.78 (m, 1H), δ 6.37 (d, J=6 Hz, 1H), δ 7.10–7.35 (m, 5H), δ 7.77 (d, J=6 Hz, 1H), ($C_{27}H_{32}N_2O_4$);

3-cyclohexyl-N-[1S-(5-trifluoromethylbenzooxazol-2-ylcarbonyl)-3-phenylpropyl]propionamide (Compound 38); MS (ESI) m/z=487 (M+1); ¹H-NMR (300 MHz, CDCl₃): δ 0.95 (m, 2H), δ 1.22 (m, 4H), δ 1.51 (m, 1H), δ 1.65 (m, 6H), δ 2.20 (m, 3H), δ 2.51 (m, 1H), δ 2.80 (q, J=2 Hz, 2H), δ 5.76 (m, 1H), δ 6.22 (d, J=6 Hz, 1H), δ 7.15–7.35 (m, 5H), δ 7.77 (m, 2H), δ 8.25(s, 1H), ($C_{27}H_{29}F_3N_2O_3$);

2-acetylamino-N-(1-benzooxazol-2-ylcarbonyl-3-phenylpropyl)-3-(2-trifluoromethylphenyl)propionamide (Compound 39);

N-(1-benzooxazol-2-ylcarbonyl-3-phenylpropyl)-3-morpholin-4-ylpropionamide (Compound 40);; ¹H NMR (CDCl₃): 7.90 (m, 1H), 7.76 (m, 1H), 7.06–7.36 (m, 7H), 4.00 (m, 1H), 3.12 (m, 4H), 2.50–3.5 (m, 2H), 2.0–2.5 (m, 2H), 1.83 (m, 4H); MS: m/e=421.9.

3-cyclohexyl-N-[1S-(5-nitrobenzooxazol-2ylcarbonyl)-33-phenylpropyl]propionamide (Compound 41); MS (ESI) m/z=464 (M+1); ¹H-NMR (300 MHz, CDCl₃): δ 0.95 (m, 2H), δ 1.22 (m, 4H), δ 1.51 (m, 1H), δ 1.65 (m, 6H), δ 2.20 (m, 3H), δ 2.51 (m, 1H), δ 2.80 (m, 2H), δ 5.67 (m, 1H), δ 6.17 (d, J=6 Hz, 1H), δ 7.09–7.35 (m, 5H), δ 7.77 (d, J=6 Hz, 1H), δ 8.50 (d, J=6 Hz, 1H), δ 8.77 (s, 1H), ($C_{26}H_{29}N_3O_5$);

methyl 2-[2S-(3-cyclohexylpropionylamino)-4-phenylbutyryl]benzooxazole-6-carboxylate (Compound 42); MS (ESI) m/z=477 (M+1); ¹H-NMR (300 MHz, CDCl₃): δ 0.95 (m, 2H), δ 1.22 (m, 4H), δ 1.51 (m, 1H), δ 1.65 (m, 6H), δ 2.23 (m, 3H), δ 2.50 (m, 1H), δ 2.77 (m, 2H), δ 4.00 (s, 3H), δ 5.78 (m, 1H), δ 6.27 (d, J=6 Hz, 1H), 7.15–7.35 (m, 5H), δ 7.98 (d, J=6 Hz, 1H), δ 8.22 (d, J=6 Hz, 1H), δ 8.39 (s, 1H), ($C_{28}H_{32}N_2O_5$);

N-[1-(5-chlorobenzooxazol-2-ylcarbonyl)-3-phenylproyl]-3-cyclohexylproionamine (Compound 43); MS (ESI) m/z=453 (M+1); ¹H-NMR (300 MHz, CDCl₃): δ 0.95 (m, 2H), δ 1.22 (m, 4H), δ 1.53 (m, 2H), δ 1.65 (m, 5H), δ 2.20 (m, 3H), δ 2.50 (m, 1H), δ 2.77 (m, 2H), δ 5.74 (m, 1H), δ 6.20 (d, J=6 Hz, 1H), δ 7.09–7.35 (m, 5H), δ 7.60 (m, 2H), δ 7.90 (s, 1H), ($C_{26}H_{29}ClN_2O_3$);

benzyl 1S-(1S-benzooxazol-2-ylcarbonyl-3-phenylpropylsulfamoylmethyl)-3-methylbutylcarbamate (Compound 44); ¹H NMR (CDCl₃): 7.92 (d, J=7.7 Hz, 1H), 7.64 (m, 1H), 7.57 (m, 1H), 7.50 (m, 1H), 7.21–7.34 (m, 10H), 6.30 (d,j=9.2 Hz, 1H), 5.34 ((m, 1H), 5.11 (m, 1H), 4.91 (d,J=9.6 Hz, 1H), 4.51 (m, 1H), 3.11 (m, 2H), 2.89 (m, 2H), 2.50 (m, 1H), 2.20 (m, 1H), 1.70 (m, 1H), 1.5 (m, 1H), 1.23–1.46 (m, 1H), 0.;92 (t,J=7.4 Hz, H); MS: m/e=578.1;

N-{1S-[1S-(benzooxazol-2-ylcarbonyl)-3-phenylpropylsulfamoylmethyl]-3-methylbutyl}acetamide (Compound 45); ¹H NMR (CDCl₃): 7.89 (d,J=7.7 Hz, 1H), 7.62 (m, 1H), 7.55 (m, 1H), 7.49 (m, 1H), 7.18–7.30 (m, 5H), 6.7 (d, J=8.9 Hz, 1H), 5.61 (d, J=9.4 Hz, 1H), 5.34 (m, 1H), 4.86 (m, 1H), 3.06 (m, 2H), 2.90 (t, J=7.7 Hz,. 2H), 2.24 (m, 1H), 2.22 (m, 1H), 2.04 (s, 3H), 1.66 (m, 1H), 1.48 (m, 1H), 1.38 (m, 1H), 0.91 (t, J=6.2 Hz, 6H); MS m/e= 486.1;

benzyl 1R-(1S-benzooxazol-2-ylcarbonyl-3-phenylpropylsulfamoylmethyl)-3-methylbutylcarbamate (Compound 46) ¹H NMR (CDCl₃): 7.9 (m, 1H), 7.60 (m, 1H), 7.58 (m, 1H), 7.5 (m, 1H), 7.75–7.4 (m, 10H), 5.85 (m, 1H), 5.0–5.4 (m, 3H), 4.2 (m, 1H), 3.15–3.35 (m, 2H), 2.65–2.85 (m, 2H), 2.45 (m, 1H), 2.15 (m, 1H), 1.9 (m, 1H), 1.4–1.7 (m, 3H), 0.9 (m, 6H); MS: m/e=578.1; and N-[1-(1-benzooxazol-2-ylcarbonyl-3-phenylpropylsulfamoylmethyl)-3-methylbutyl]acetamide (Compound 47) ¹H NMR (CDCl₃): 7.9 (m, 1H), 7.65 (m, 1H), 7.61 (m, 1H), 7.60 (m, 1H), 7.18–7.30 (m, 5H), 6.0 (m, 1H), 5.85 (m, 1H), 5.28 (m, 1H), 4.50 (m, 1H), 3.20 (m, 1H), 2.85 (m, 1H), 2.70 (m, 1H), 1.8–2.2 (m, 2H), 1.95 (S, 3H), 1.35–1.70 (m, 2H), 0.9 (m, 6H); MS: m/e=486.0.

Example 3 tert-Butyl 1R-(2-benzooxazol-2-yl-2-hydroxy-1S-phenethylethylcarbamoyl)-2-(2-cyanobenzylsulfanyl)ethylcarbamate (Compound 48)

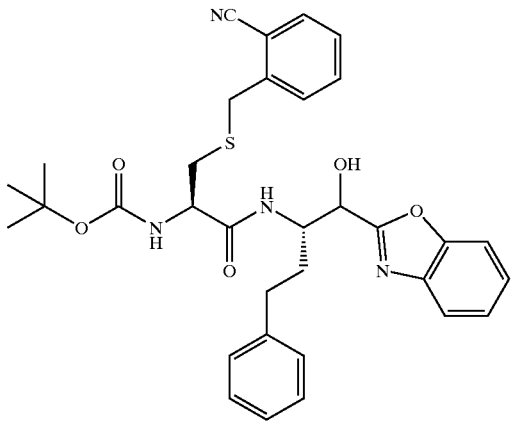

A solution of 2R-tert-butoxycarbonylamino-3-(2-cyanobenzylsulfanyl)propionic acid (336 mg), 2S-amino-1-benzooxazol-2-yl-4-phenylbutan-1-ol (282 mg), 1-(3-dimethylaminopropyl)-3-ethylcarbodiimide hydrochloride (211 mg) and 1-hydroxybenzotriazole (197 mg) in dichloromethane (20 mL) was treated with N-methylmorpholine (2.2 mL). The reaction mixture was stirred 0.5 hour and then concentrated by evaporation. The residue was dissolved in ethyl acetate (40 mL) and the solution was washed sequentially with water (20 mL), 1N hydrochloric acid (30 mL), a saturated sodium bicarbonate solution (30 mL) and then brine (3 mL), dried over magnesium sulfate and concentrated by evaporation. The residue was subjected to flash column chromatography on silica eluting with diethyl ether to provide tert-butyl 1R-(2-benzooxazol-2-yl-2-hydroxy-1-phenethylethylcarbamoyl)-2-(2-cyanobenzylsulfanyl)ethylcarbamate as an off white solid. MS: 601 [MH]$^+$.

Proceeding as in Example 3 provided tert-butyl 1R-(2-benzooxazol-2-yl-2-hydroxy-1S-phenethylethylcarbamoyl)-2-benzylsulfanylethylcarbamate (Compound 49), MS: 576 [MH]$^+$.

Example 4

N-[1R-(2-Benzooxazol-2-yl-2-hydroxy-1S-phenethylethylcarbamoyl)-2-(2-cyanobenzylsulfanyl)ethyl]isonicotinamide (Compound 50)

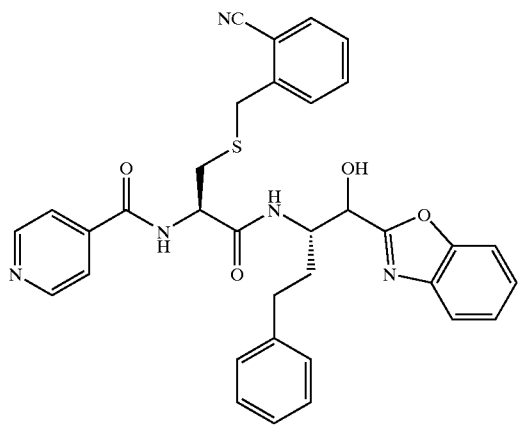

A solution of 3-(2-cyanobenzylsulfanyl)-2R-(pyrid-4-ylcarbonyl)aminopropionic acid (425 mg), provided as in Reference 2, 2S-amino-1-benzooxazol-2-yl-4-phenylbutan-1-ol (356 mg) and HATU (356 mg) in dimethylformamide (40 mL) was treated with diisopropylamine (0.239 mL). The reaction mixture was stirred for 16 hours at room temperature then concentrated by evaporation. The residue was dissolved in ethyl acetate and the solution was washed with saturated sodium bicarbonate solution, dried over magnesium sulfate and then concentrated by evaporation. The residue was subjected to flash column chromatography on silica eluting with ethyl acetate to provide N-[1R-(2-benzooxazol-2-yl-2-hydroxy-1S-phenethylethylcarbamyl)-2-(2-cyanobenzylsulfanyl)ethyl]isonicotinamide (216 mg) as a gum. MS: 606 [MH]$^+$. HPLC: $R_T$=13.20 minutes.

Proceeding as in Example 4 provided 9H-fluoren-9-ylmethyl 1S-(2-benzooxazol-2-yl-2-hydroxy-1S-phenethylethylcarbamoyl)-2-cyclohexylethylcarbamate (Compound 51);

9H-fluoren-9-ylmethyl 1S-[2-benzooxazol-2-yl-2-(tert-butyldimethylsilanyloxy)-1S-phenethylethylcarbamoyl]-2-cyclohexylethylcarbamate (Compound 52), MS: 772 [MH]$^+$.

Example 5

2R-Amino-N-(2-benzooxazol-2-yl-2-hydroxy-1S-phenethylethyl)-3-(2-cyanobenzylsulfanyl)-propionamide hydrochloride (Compound 53)

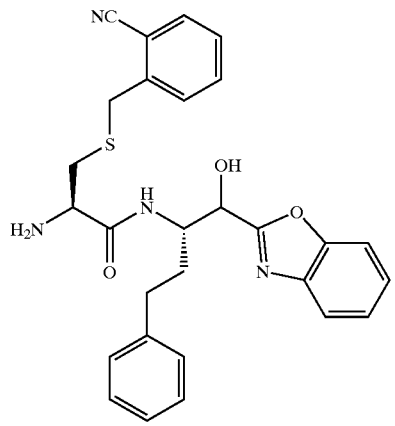

A solution tert-butyl 1R-(2-benzooxazol-2-yl-2-hydroxy-1S-phenethylethylcarbamoyl)-2-(2-cyanobenzylsulfanyl)ethylcarbamate (145 mg), provided as in Example 3, in dioxane (20 mL) was treated with hydrogen chloride, bubbling the gas through the solution for 30 minutes. The reaction mixture was concentrated by evaporation and the residue was triturated with diethyl ether to provide 2R-amino-N-(2-benzooxazol-2-yl-2-hydroxy-1S-phenethylethyl)-3-(2-cyanobenzylsulfanyl)propionamide hydrochloride (117 mg) as a an off-white solid. MS: 537 [MH]$^+$.

Proceeding as in Example 5 provided 2R-amino-N-[2-benzooxazol-2-yl-2-hydroxy-1S-phenethylethyl)-3-benzylsulfonylpropionamide hydrochloride (Compound 54), MS: 508 [MH]$^+$.

Example 6

2S-Amino-N-(2-benzooxazol-2-yl-2-hydroxy-1S-phenethylethyl)-3-cyclohexylpropionamide (Compound 55)

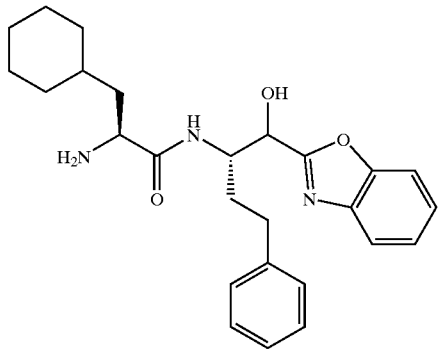

A solution of 9H-fluoren-9-ylmethyl 1S-(2-benzooxazol-2-yl-2-hydroxy-1S-phenethylethylcarbamoyl)-2-cyclohexylethylcarbamate (165 mg), provided as in Example 4, in dichloromethane (30 mL) was treated with tris(2-aminoethyl)amine bound to polysterene beads (4.48 g). The mixture was stirred at room temperature for 48 hours and then filtered. The resin was washed four times with dichloromethane (20 mL) and the combined filtrates were concentrated under reduced pressure to provide 2S-amino-N-(2-benzooxazol-2-yl-2-hydroxy-1S-phenethylethyl)-3-cyclohexylproionamide (147 mg) as a colourless oil.

Example 7

2S-Amino-N-[2-benzooxazol-2-yl-2-(tert-butyldimethylsilanyloxy)-1S-phenethylethyl]-3-cyclohexylpropionamide (Compound 56), a protected compound of Formula I

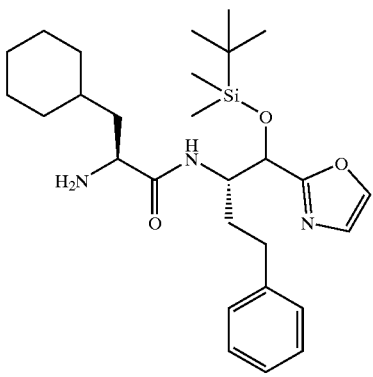

A solution of 9H-fluoren-9-ylmethyl 1S-[2-benzooxazol-2-yl-2-(tert-butyldimethylsilanyloxy)-1S-phenethylethylcarbamoyl]-2-cyclohexylethylcarbamate (1.48 g), provided as in Example 4, in dichloromethane (50 mL) was treated with tris-(2-aminoethyl)amine (14.4 mL). The reaction mixture was stirred for 75 minutes and then additional dichloromethane was added (50 mL). The mixture was washed sequentially with brine (50 mL×4) and a pH 5.3 buffer (50 mL×3), dried over magnesium sulphate and concentrated to provide 2S-amino-N-[2-benzooxazol-2-yl-2-(tert-butyldimethylsilanyloxy)-1S-phenethylethyl]-3-cyclohexylproionamide as an orange oil.

Example 8 tert-Butyl 4-[1R-(2-benzooxazol-2-yl-2-hydroxy-1S-phenethylethylcarbamoyl]-2-(2-cyanobenzylsulfanyl)ethylcarbamoylpiperidine-1-carboxylate (Compound 57)

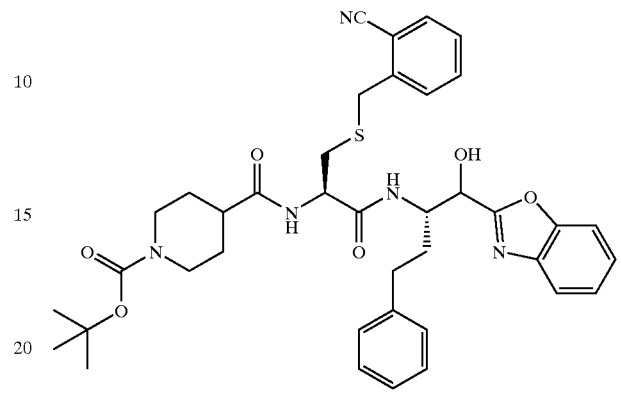

A solution of 2R-amino-N-(2-benzooxazol-2-yl-2-hydroxy-1S-phenethylethyl)-3-(2-cyanobenzylsulfanyl)propionamide hydrochloride (170 mg), provided as in Example 5, in dimethylformamide (7 mL) was treated with 1-tert-butoxycarbonylpiperidine-4-carboxylic acid tetrafluorophenyl ester tert-butyl ester on resin (excess), prepared according to the procedure described in International Patent Application No. WO99/67228, and triethylamine (0.053 mL). The suspension was agitated for 16 hours, then filtered, and the filtrate was washed with dimethylformamide and then concentrated by evaporation. The residue was subjected to flash column chromatography on silica eluting with ethyl acetate to give tert-butyl 4-[1R-(2-benzooxazol-2-yl-2-hydroxy-1S-phenethylethylcarbamoyl]-2-(2-cyanobenzylsulfanyl)ethylcarbamoylpiperidine-1-carboxylate (95 mg) as a gum. MS: 712 [MH]$^+$.

Proceeding as in Example 8 provided benzyl 4-[1S-(2-benzooxazol-2-yl-2-hydroxy-1S-phenethylethylcarbamoyl)-2-cyclohexylethylcarbamoyl]piperidine-1-carboxylate (Compound 58), MS: 681 [M]$^+$.

Example 9

N-[1R-(2-Benzooxazol-2-yl-2-hydroxy-1S-phenethylethylcarbamoyl)-2-benzylsulfonylethyl]-tetrahydropyran-4-carboxamide (Compound 59)

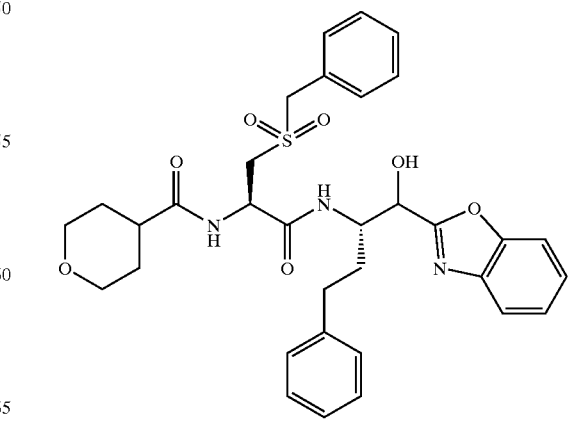

A mixture of 2R-amino-N-(2-benzooxazol-2-yl-2-hydroxy-1S-phenethylethyl)-3-benzylsulfonylpropionamide hydrochloride (0.3 g), prepared as in Example 5, tetrahydropyran-4-carboxylic acid (0.072 g), 1-(3-dimethylaminopropyl)-3-ethylcarbodiimide hydrochloride (0.116 g) and 1-hydroxybenzotriazole (0.112 g) in dichloromethane (20 mL) was treated with 4-N-methylmorpholine (0.12 mL). After stirring at room temperature for 4 hours the reaction mixture was left to stand 16 hours and then concentrated by evaporation. The residue was treated with dichloromethane (50 mL) and the mixture was washed sequentially with 1N hydrochloric acid solution (5 mL), saturated sodium bicarbonate solution (5 mL) and brine (5 mL), dried over magnesium sulfate and then concentrated by evaporation. The residue was subjected to flash column chromatography on silica eluting with ethylacetate to provide N-[1R-(2-benzooxazol-2-yl-2-hydroxy-1S-phenethylethylcarbamoyl)-2-benzylsulfonylethyl]-tetrahydropyran-4-carboxamide (66 mg) as a cream solid. MS: 618 [MH]$^+$.

Proceeding as in Example 9 provided the following compounds of Formula I:

N-[1R-(2-benzooxazol-2-yl-2-hydroxy-1S-phenethylethylcarbamoyl)-2-benzylsulfonylethyl]-nicotinamide (Compound 60), MS: 613 [MH]$^+$;

N-[1R-(2-benzooxazol-2-yl-2-hydroxy-1S-phenethylethylcarbamoyl)-2-benzylsulfonyl-ethyl] pyrazine-2-carboxamide (Compound 61), MS: 614 [MH]$^+$;

4-[1S-(2-benzooxazol-2-yl-2-hydroxy-1S-phenethylethylcarbamoyl)-2-cyclohexyl-ethylcarbamoyl]piperidine-1-carboxylate (Compound 62); and N-[1S-(2-benzooxazol-2-yl-2-hydroxy-1S-phenethylethylcarbamoyl)-2-cyclohexylethyl]-isonicotinamide (Compound 63).

Example 10 tert-Butyl 4-[1R-(2-benzooxazol-2-yl-2-hydroxy-1S-phenethylethylcarbamoyl]-2-(3-methylpyrid-2-ylmethylsulfonyl)ethylcarbamoyl]piperidine-1-carboxylate (Compound 64)

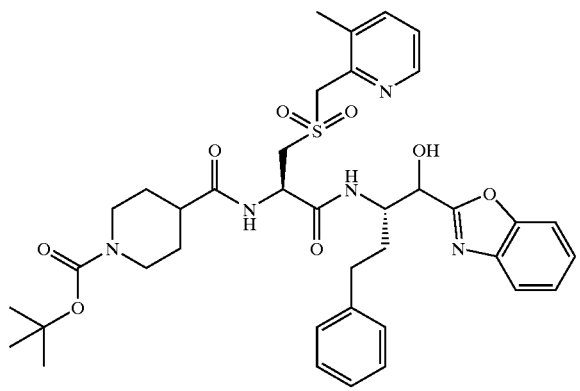

A solution of 2R-amino-N-(2-benzooxazol-2-yl-2-hydroxy-1S-phenethylethyl)-3-(3-methylpyrid-2-ylmethylsulfonyl)propionamide (178 mg), HATU (137 mg) and 1-tert-butoxycarbonylpiperidine-4-carboxylic acid (69 mg) in dimethylformamide (10 mL) was treated with N,N-diisopropylethylamine (0.174 mL). The reaction mixture was stirred for 9 hours and then concentrated by evaporation. The residue was dissolved in ethyl acetate and the solution was washed with saturated sodium bicarbonate solution, dried over magnesium sulfate and then concentrated by evaporation. The residue was subjected to flash column chromatography on silica eluting with ethyl acetate to provide tert-butyl 4-[1R-(2-benzooxazol-2-yl-2-hydroxy-1S-phenethylethylcarbamoyl]-2-(3-methylpyrid-2-ylmethylsulfonyl)ethylcarbamoyl]piperidine-1-carboxylate (81 mg). MS: 734 [MH]$^+$.

Proceeding as in Example 10 provided the following compounds of Formula I:

tetrahydropyran-4-yl 1R-(2-benzooxazol-2-yl-2-hydroxy-1S-phenethylethylcarbamoyl)-2-benzylsulfanylethylcarbamate (Compound 65);

N-[1S-(2-benzooxazol-2-yl-2-hydroxy-1S-pbenethylethylcarbamoyl)-2-cyclohexylethyl] tetrahydropyran-4-carboxamide (Compound 66), MS: 548 [M]$^+$; and N-[1S-(2-benzooxazol-2-yl-2-hydroxy-1S-phenethylethylcarbamoyl)-2-cyclohexylethyl]-6-hydroxynicotinamide (Compound 67).

Example 11

N-[2-Benzooxazol-2-yl-2-(tert-butyldimethylsilanyloxy)-1S-phenethylethyl]-3-cyclohexyl-2S-(3-pyrid-3-ylureido)propionamide (Compound 68), a protected compound of Formula I

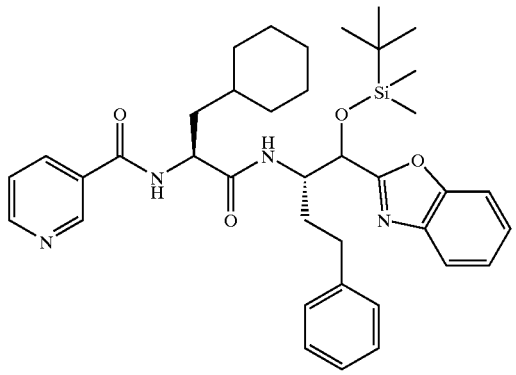

A solution of 2S-amino-N-[2-benzooxazol-2-yl-2-(tert-butyldimethylsilanyloxy)-1S-phenethylethyl]-3-cyclohexylpropionamide (200.1 mg), provided as in Example 7, in dichloromethane (10 mL) was treated with 3-pyridyl isocyanate (48 mg). The mixture was stirred at room temperature for 16 hours and the solvent evaporated under reduced pressure. The residue was subjected to flash column chromatography on silica eluting with a mixture of pentane and ethylacetate (2:1, v/v) to provide N-[2-benzooxazol-2-yl-2-(tert-butyldimethylsilanyloxy)-1S-phenethylethyl]-3-cyclohexyl-2S-(3-pyrid-3-ylureido) propionamide (172 mg) as a colorless oil.

Example 12

N-{1S-[2-Benzooxazol-2-yl-2-(tert-butyldimethylsilanyloxy)-1S-phenethylethylcarbamoyl]-2-cyclohexylethyl}morpholine-4-carboxamide (Compound 69), a protected compound of Formula I

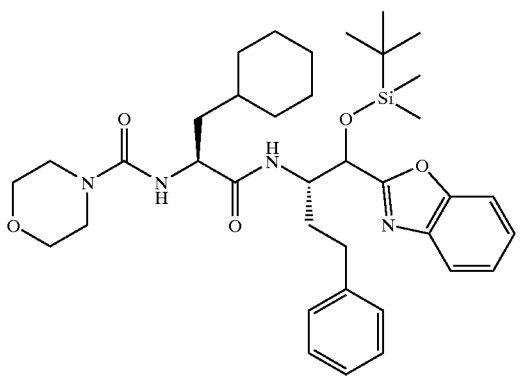

A solution of 2S-amino-N-[2-benzooxazol-2-yl-2-(tert-butyldimethylsilanyloxy)-1S-phenethylethyl]-3-cyclohexylpropionamide (200 mg), provided as in Example 7, in dichloromethane (8 mL) was treated with 4-morpholinecarbonyl chloride (0.094 mL) and triethylamine (0.112 mL). The solution was stirred at room temperature for 20 hours. The solvent was evaporated under reduced pressure and the residue was purified by flash chromatography on silica eluting with a mixture of pentane and ethylacetate (2:1, v/v) to provide N-{1S-[2-benzooxazol-2-yl-2-(tert-butyldimethylsilanyloxy)-1S-phenethylethylcarbamoyl]-2-cyclohexylethyl}morpholine-4-carboxamide (143 mg) as a white solid. MH$^+$663.

Example 13 tert-butyl 4-[1R-(2-benzooxazol-2-yl-2-hydroxy-1S-phenethylethylcarbamoyl]-2-(2-cyanobenzylsulfonyl)ethylcarbamoylpiperidine-1-carboxylate (Compound 70)

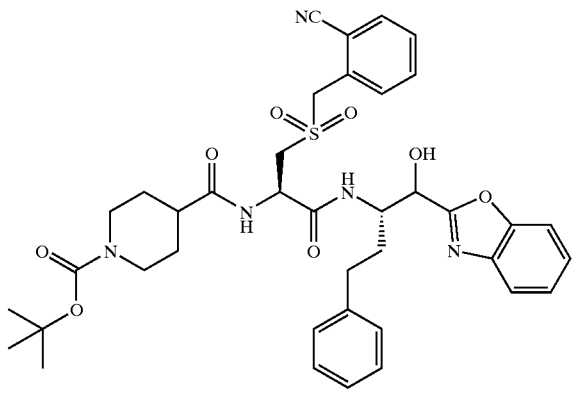

A solution of tert-butyl 4-[1R-(2-benzooxazol-2-yl-2-hydroxy-1S-phenethylethylcarbamoyl]-2-(2-cyanobenzylsulfanyl)ethylcarbamoylpiperidine-1-carboxylate (95 mg), provided as in Example 8, in methanol (8 mL) was treated with a solution of OXONE® (246 mg) in water (8 mL). After stirring at room temperature for 10 hours the methanol was distilled under reduced pressure and the remaining aqueous phase was extracted four times with ethyl acetate (2 mL). The combined extracts were dried over magnesium sulfate and then concentrated by evaporation. The residue was subjected to flash column chromatography on silica eluting with ethyl acetate to give the tert-butyl 4-[1R-(2-benzooxazol-2-yl-2-hydroxy-1S-phenethylethylcarbamamoyl]-2-(2-cyanobenzylsulfonyl)ethylcarbamoylpiperidine-1-carboxylate (35 mg) as a gum. MS: 744 [MH]$^+$.

Proceeding as in Example 13 provided N-[1R-(2-benzooxazol-2-1-2-hydroxy-1S-phenethylethylcarbamoyl)-2-(2-cyanobenzylsulfonyl)ethyl]isonicotinamide (Compound 71), HPLC: R$_f$=12.89 minutes.

Example 14 tert-Butyl 1R-(2-benzooxazol-2-yl-2-hydroxy-1S-phenethylethylcarbamoyl)-2-benzylsulfonylethylcarbamate (Compound 72)

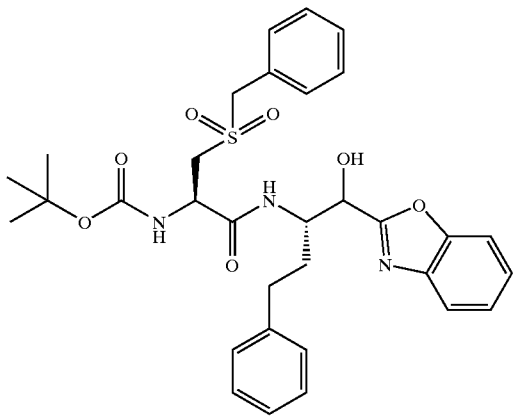

A solution of tert-butyl 1R-(2-benzooxazol-2-yl-2-hydroxy-1S-phenethylethylcarbamoyl)-2-benzylsulfanylethylcarbamate (3.62 g), provided as in Example 3, in dichloromethane (174 mL) was treated with meta-chloroperbenzoic acid (6.9 g). After stirring at room temperature for 5 hours the reaction mixture was diluted with dichloromethane (100 mL), washed sequentially with a saturated sodium bicarbonate solution (100 mL) and brine (100 mL), dried over magnesium sulfate and then concentrated by evaporation. The residue was subjected to flash column chromatography on silica eluting with a mixture of pentane and ethylacetate (1:1, v/v) to provide tert-butyl 1R-(2-benzooxazol-2-yl-2-hydroxy-1S-phenethylethylcarbamoyl)-2-benzylsulfonylethylcarbamate (0.95 g) as a yellow solid. MS: 608 [MH]$^+$.

Proceeding as in Example 14 provided N-[1R-(2-benzooxazol-2-yl-2-hydroxy-1S-phenethylethylcarbamoyl)-2-pyrid-3-ylmethylsulfonylethyl]pyrazine-2-carboxamide (Compound 73).

Example 15

N-(2-Benzooxazol-2-yl-2-hydroxy-1S-phenethylethyl)-3-cyclohexyl-2S-(3-pyrid-3-ylureido)propionamide (Compound 74)

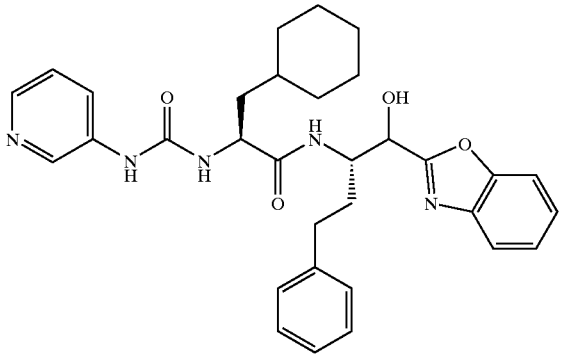

A solution of N-[2-benzooxazol-2-yl-2-(tert-butyldimethylsilanyloxy)-1S-phenethylethyl]-3-cyclohexyl-2S-(3-pyrid-3-ylureido)propionamide (172 mg) in tetrahydrofuran (5 mL), provided as in Example 11, under an inert atmosphere at room temperature was treated with a solution of tetrabutylammoniumfluoride in 1M tetrahydrofuran (0.4 mL). After stirring at room temperature for 90 minutes, the solvent was distilled under reduced pressure. The residue was subjected to flash column chromatography on silica eluting with a mixture of ethylacetate and pentane (5:1, v/v) to provide N-(2-benzooxazol-2-yl-2-hydroxy-1S-phenethylethyl)-3-cyclohexyl-2S-(3-pyrid-3-ylureido)propionamide (108 mg) as a white solid.

Proceeding as in Example 15 provided N-[1S-(2-benzooxazol-2-yl-2-hydroxy-1S-phenethylethylcarbamoyl)-2-cyclohexylethyl]morpholine-4-carboxamide (Compound 75).

Example 16 tert-Butyl 4-[1R-(1S-benzooxazol-2-ylcarbonyl-3-phenylpropylcarbamoyl)-2-(2-cyanobenzylsulfonyl)ethylcarbamoyl]piperidine-1-carboxylate (Compound 76)

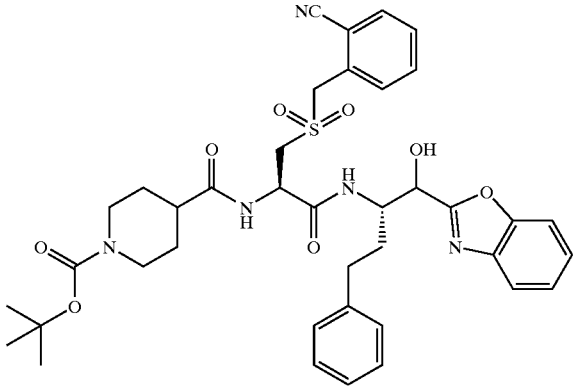

A solution tert-butyl 4-[1R-(2-benzooxazol-2-yl-2-hydroxy-1S-phenethylethylcarbamoyl)-2-(2-cyanobenzylsulfonyl)ethylcarbamoylpiperidine-1-carboxylate (35 mg, prepared as in Example 13, in dichloromethane (10 mL) was treated with Dess-Martin reagent (60 mg). The reaction mixture was stirred at room temperature for 5 hours, then washed with sodium thiosulfate in saturated sodium bi-carbonate solution, dried over magnesium sulfate and then concentrated by evaporation. The residue was subjected to flash column chromatography on silica eluting with a mixture of ethyl acetate and pentane (1:1, v/v) to give tert-butyl 4-[1R-(1S-benzooxazol-2-ylcarbonyl-3-phenylpropylcarbamoyl)-2-(2-cyanobenzylsulfonyl)ethylcarbamoyl]piperidine-1-carboxylate (26 mg) as a gum. MS: 742 [MH]$^+$.

Proceeding as in Example 16 provided the following compounds of Formula I:

N-[1R-(1S-benzooxazol-2-ylcarbonyl)-3-phenylpropylcarbamoyl)-2-benzylsulfonylethyl] tetrahydropyran-4-carboxamide (Compound 77), m.p. 178–180° C., MS: 618 [MH]$^+$;

N-[1R-(1S-benzooxazol-2-ylcarbonyl-3-phenylpropylcarbamoyl)-2-benzylsulfonylethyl] nicotinamide (Compound 78), m.p. 193–195° C., MS: 611 [MH]$^+$;

N-[1R-(1S-benzooxazol-2-ylcarbonyl-3-phenylpropylcarbamoyl)-2-benzylsulfonylethyl]pyrazine-2-carboxamide (Compound 79), m.p. 194–196° C. MS: 612 [MH]$^+$;

tert-butyl 4-[1S-(1S-benzooxazol-2-ylcarbonyl-3-phenylpropylcarbamoyl)-2-cyclohexylethylcarbamoyl] piperidine-1-carboxylate (Compound 80);

tert-butyl 4-[1S-(1-benzooxazol-2-ylcarbonyl-3-phenylpropylcarbamoyl)-2-(6-methylpyrid-2-ylmethylsulfonyl)ethylcarbamoyl]piperidine-1-carboxylate (Compound 81), MS: 732 [MH]$^+$, HPLC: R$_t$=15.18 minutes;

N-[1R-(1S-benzooxazol-2-ylcarbonyl-3-phenylpropylcarbamoyl)-2-(2-cyanobenzylsulfonyl)ethyl] isonicotinamide (Compound 82), m.p. 204–206° C., MS: 636 [MH]$^+$;

tetrahydropyran-4-yl 1R-(1S-benzooxazol-2-ylcarbonyl-3-phenylpropylcarbamoyl)-2-benzylsulfonylethylcarbamate (Compound 83), m.p. 93° C. (with decomposition), MS: 634 [MH]$^+$;

benzyl 4-[1S-(1S-benzooxazol-2-ylcarbonyl-3-phenylpropylcarbamoyl)-2-cyclohexylethylcarbamoyl] piperidine-1-carboxylate (Compound 84), MS: 677 [M]$^+$;

N-(1S-benzooxazol-2-ylcarbonyl-3-phenylpropyl)-3-cyclohexyl-2S-(3-pyrid-3-ylureido)propionamide (Compound 85), MS: 554 [M]$^+$;

N-[1S-(1S-benzooxazol-2-ylcarbonyl-3-phenylpropylcarbamoyl)-2-cyclohexylethyl]morpholine-4-carboxamide (Compound 86), MS: 547 [MH]$^+$;

N-[1S-(1S-benzooxazol-2-ylcarbonyl-3-phenylpropylcarbamoyl)-2-cyclohexylethylisonicotinamide (Compound 87), MS: 537 [M]$^+$;

N-[1S-(1S-benzooxazol-2-ylcarbonyl-3-phenylpropylcarbamoyl)-2-cyclohexylethyl] tetrahydropyran-4-carboxamide (Compound 88), MS: 546 [M]$^+$; and N-[1S-(1S-benzooxazol-2-ylcarbonyl-3-phenylpropylcarbamoyl)-2-cyclohexylethyl]-6-hydroxynicotinamide (Compound 89), MS: 555 [M]$^+$.

Example 17

N-[1R-(1S-Benzooxazol-2-ylcarbonyl)-3-phenylpropylcarbamoyl)-2-benzylsulfonylethyl] morholine-4-carboxamide (Compound 90)

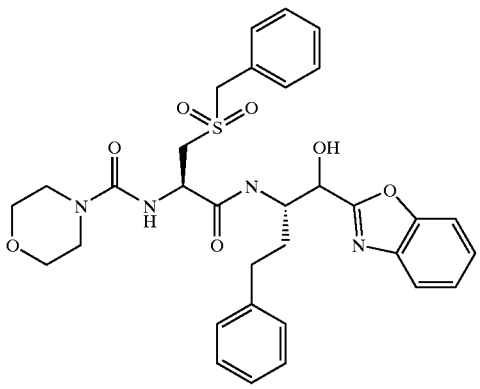

A mixture of N-[1S-(2-benzooxazol-2-yl-2-hydroxy-1S-phenethylethylcarbamoyl)-2-benzylsulfonylethyl]morpholine-4-carboxamide (7.2 g, 11.6 mmol), prepared as in Example 1, and Dess-Martin periodinane (9.87 g, 23.3 mmol) in dichloromethane (57 mL) was stirred at room temperature for 1 hour and then diluted with a solution of 0.26 M sodium thiosulfate in saturated sodium bicarbonate. The dilution was extracted with ethyl acetate and the extract was filtered. The filtrate was concentrated to provide N-[1S-(1S-benzooxazol-2-ylcarbonyl)-3-phenylpropylcarbamoyl)-2-benzylsulfonylethyl]morpholine-4-carboxamide (2.33 g) as an orange/tan oil. The solids collected from the filtration were taken up into dichloromethane (700 mL) and the mixture was washed sequentially with water and saturated sodium bicarbonate solution, dried and concentrated to provide N-[1R-(1S-benzooxazol-2-ylcarbonyl)-3-phenylpropylcarbamoyl)-2-benzylsulfonylethyl]morpholine-4-carboxamide (4.2 g) as a white powder. $^1$H NMR (DMSO-d6) 8.024 (d, J=6.68 Hz, 1H), 7.9787 (d, J=7.92 Hz, 1H), 7.8857 (d, J=8.16 Hz, 1H), 7.6471 (td, J=8.41, 0.99 Hz, 1H), 7.5455 (td, J=8.16, 1.24 Hz, 1H), 7.3806 (s, 5H), 7.2479 (m, 5H), 7.1210 (d, J=4.53 Hz), 1H), 5.2578 (m, 1H), 4.7395 (m, 1H), 4.5059 (s, 2H), 3.5342 (m, 4H), 3.4082 (m, 2H), 3.30 (m, 4H (+water)), 2.6963 (m, 2H), 2.2768 (m, 1H), 2.0497 (m, 1H). MS (M+1) 619.2.

Proceeding as in Example 17 provided the following compounds of Formula I:

N-[1R-(2-benzooxazol-2-yl-1,1-dimethyl-2-oxoethylcarbamoyl)-2-benzylsulfonylethyl]morpholine-4-carboxamide (Compound 91); $^1$H NMR: (DMSO) 9.26 (s, 1H), 7.79 (d, J=8 Hz, 1H), 7.73 (d, J=8 Hz, 1H), 7.56 (t, J=8 Hz, 1H), 7.47 (t, J=8 Hz, 1H), 7.36–7.25 (m, 5H), 6.70 (d, J=8 Hz, 1H), 4.67 (m, 1H), 4.39 (d, J=14 Hz, 1H), 4.32 (d, J=14 Hz, 1H), 3.49–3.00 (m, 10H), 1.56 (s, 3H), 1.51 (s, 3H); MS: (M$^+$+1) 543;

N-[1R-(1S-benzooxazol-2-ylcarbonylpentylcarbamoyl)-2-(3,5-dimethylisoxazol-4-ylmethylsulfonyl)ethyl] morpholin-4-carboxamide (Compound 92); $^1$H NMR: (DMSO) 8.66 (d, J=6.6 Hz, 1H), 7.99 (d, J=8 Hz, 1H), 7.88 (d, J=8 Hz, 1H), 7.62 (t, J=8 Hz, 1H), 7.52 (t, J=8 Hz, 1H), 7.02 (d, J=7.7 Hz, 1H), 5.24 (m, 1H), 4.39 (d, J=14 Hz, 1H), 4.27 (d, J=14 Hz, 1H), 3.63–3.20 (m, 10H), 2.33 (s, 3H), 2.15 (s, 3H), 1.94 (m, 1H), 1.69 (m, 1H), 1.40–1.22 (m, 4H), 0.84 (t, J=6.7 Hz, 3H); MS: (M$^+$+1) 590; and N-[1R-(1S-benzooxazol-2-ylcarbonylpentylcarbamoyl)-2-(3,5-dimethylisoxazol-4-ylmethylsulfonylethyl] isonicotinamide (Compound 93); $^1$H NMR: (DMSO) 9.23 (d, J=8 Hz, 1H), 8.87 (d, J=7 Hz, 1H), 8.71 (m, 2H), 7.98 (d, J=8 Hz, 1H), 7.87 (d, J=8 Hz, 1H), 7.70 (m, 2H), 7.62 (t, J=8 Hz, 1H), 7.51 (t, J=8 Hz, 1H), 5.28 (m, 1H), 5.10 (m, 1H), 4.44 (d, J=14 Hz, 1H), 4.37 (d, J=14 Hz, 1H), 3.80–3.52 (m, 2H), 2.33 (s, 3H), 2.14 (s, 3H), 1.95 (m, 1H), 1.69 (m, 1H), 1.40–1.22 (m, 4H), 0.82 (t, J=6.7 Hz, 3H); MS: (M$^+$+1) 582.

Example 18

N-[1R-(1S-Benzooxazol-2-ylcarbonyl-3-phenylpropylcarbamoyl)-2-(2-cyanobenzylsulfonyl)ethyl]piperidine-4-carboxamide (Compound 94)

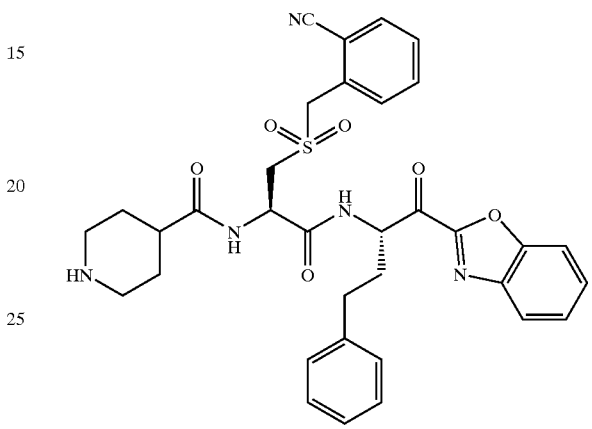

A solution of tert-butyl 4-[1R-(1S-benzooxazol-2-ylcarbonyl-3-phenylpropylcarbamoyl)-2-(2-cyanobenzylsulfonyl)ethylcarbamoyl]piperidine-1-carboxylate (26 mg), provided as in Example 16, in ethyl acetate (10 mL) was treated with hydrogen chloride, bubbling the gas through the solution for 3 minutes. A white solid formed which was filtered and dried under reduced pressure to provide N-[R-(1S-benzooxazol-2-ylcarbonyl-3-phenylpropylcarbamoyl)-2-(2-cyanobenzylsulfonyl)ethyl] piperidine-4-carboxamide (19 mg) as a solid, m.p.= 155–157° C. MS: 678 [MH]$^+$.

Proceeding as in Example 18 provided N-[1S-(1S-benzooxazol-2-ylcarbonyl-3-phenylpropylcarbamoyl)-2-cyclohexylethyl]piperidine-4-carboxamide hydrochloride (Compound 95), MS: 634 [MH]$^+$; and N-[1R-(1S-benzooxazol-2-ylcarbonyl-3-phenylpropylcarbamoyl)-2-(6-methylpyrid-2-ylmethylsulfonyl)ethyl]piperidine-4-carboxamide (Compound 96), MS: 632 [MH]$^+$, HPLC: R$_T$=12.05 minutes.

Example 19

N-(1S-Benzooxazol-2-ylcarbonylbutyl)-2R-methylsulfonylamino-3-benzylsulfonylpropionamide (Compound 159)

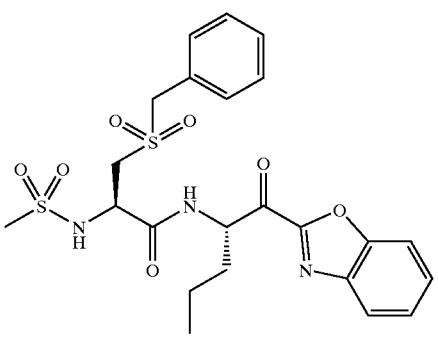

A solution of (R)-2-(2-methylsulfonylacetylamino)-3-benzylsulfonylpropionic acid (212 mg, 0.66 mmol), (S)-2-amino-1-benzooxazol-2-ylpentan-1-ol (150 mg, 0.66 mmol), EDCI (165 mg, 0.858 mmol) and HOBT (110 mg, 0.726 mmol) in methylene chloride (3 mL) was stirred at room temperature for 2 hours, sequentially washed with hydrochloric acid, sodium bicarbonate solution and brine and then concentrated. The residue was dissolved in dichloromethane and the solution was treated with Dess-Martin reagent (340 mg, 0.8 mmol) for 1 hour. The mixture was stirred with a sodium thiosulfate/sodium bicarbonate solution and the mixture was extracted with ethyl acetate. The extract was washed sequentially with dilute hydrochloric acid, sodium bicarbonate and brine, dried (MgSO$_4$) and then concentrated to provide N-(1S-benzooxazol-2-ylcarbonylbutyl)-2R-methylsulfonylamino-3benzylsulfonylpropionamide (49 mg, 0.09 mmol). $^1$H NMR (DMSO): 9.0 (d,J=7 Hz, 1H), 8.0 (d,J=8 Hz, 1H), 7.90 (d,J=9 Hz, 1H), 7.66 (t,J=8 Hz, 1H), 7.55 (t,J=9 Hz, 1H), 7.39 (s, 5H), 5.32 (m, 1H), 4.55 (m, 3H), 3.35 (m, 3H), 2.95 (s, 3H), 1.94 (m, 1H), 1.71 (m, 1H), 1.45(m, 2H), 0.92 (t, J=8 Hz, 3H); MS: m/e=522.03.

Example 20

Methyl 1R-(1S-benzooxazol-2-ylcarbonylbutylcarbamoyl)-2-benzylsulfonylethylcarbamate (Compound 158)

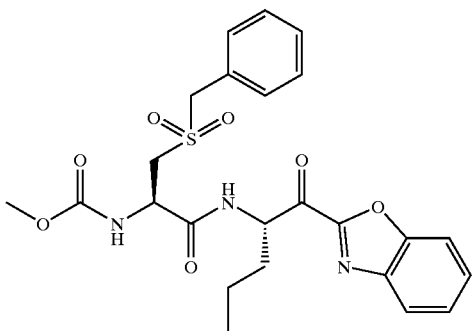

A solution of (R)-2-(2-methoxycarbonylamino)-3-benzylsulfonylpropionic acid (200 mg, 0.66 mmol), (S)-2-amino-1-benzooxazol-2-ylpentan-1-ol (150 mg, 0.66 mmol), EDCI (165 mg, 0.858 mmol) and HOBT (110 mg, 0.726 mmol) in methylene chloride (3 mL) was stirred at room temperature for 2 hours, sequentially washed with hydrochloric acid, sodium bicarbonate solution and brine and then concentrated. The residue was treated with Dess-Martin reagent (340 mg, 0.8 mmol) in dichloromethane (4 mL) for 1 hour. The mixture was stirred with a sodium thiosulfate/sodium bicarbonate solution and the mixture was extracted with ethyl acetate. The extract was washed sequentially with dilute hydrochloric acid, sodium bicarbonate and brine, dried (MgSO$_4$) and then concentrated. The residue was heated with ethyl acetate and then treated with tert-butyloxymethyl. The mixture was let stand for approximately 12 hours and then cooled in an ice bath. Resulting solids were collected by filtration and washed with cold ethyl acetate to provide methyl 1R-(1S-benzooxazol-2-ylcarbonylbutylcarbamoyl)-2-benzylsulfonylethylcarbamate (133 mg, 0.26 mmol). $^1$H NMR (DMSO): 8.77 (d,J=7 Hz, 1H), 8.01 (d,J=9 Hz, 1H), 7.90 (d,J=9 Hz, 1H), 7.6 (m, 2H), 7.55 (t,J=9 Hz, 1H), 7.39 (s, 5H), 5.3 (m, 1H), 4.68 (m, 1H), 4.48 (s, 2H), 3.55 (s, 3H), 3.52–3.4 (m, 1H), 3.3 (m, 1H), 1.92 (m, 1H), 1.73 (m, 1H), 1.42 (m, 2H), 0.91 (t, J=8 Hz, 3H); MS: m/e=502.05.

Example 21

N-[1R-(1S-Benzooxazol-2-ylcarbonylbulylcarbamoyl)-2-benzylsulfonylethyl]morpholine-4-carboxamide (Compound 158)

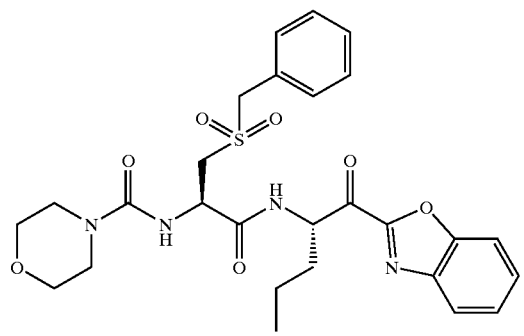

A solution of (R)-2-(2-morpholin-4-ylcarbonylamino)-3-benzylsulfonylpropionic acid (356 mg, 1 mmol), EDCI (240 mg, mmol) and HOBT (178 mg, mmol) in methylene chloride (8 mL) was (S)-2-amino-1-benzooxazol-2-ylpentan-1-ol (220 mg, mmol). The mixture was stirred at room temperature for 1.5 hours and then treated with additional EDCI (80 mg). The mixture was stirred for an additional 0.5 hours and then poured into cold, dilute hydrochloric acid. The mixture was extracted with ethyl acetate (2×) and the extract washed sequentially with aqueous sodium bicarbonate and brine, dried (MgSO$_4$) and concentrated. The residue was dissolved in methylene chloride (8 mL) and the solution was treated with Dess-Martin reagent (544 mg). The mixture was stirred for 1.5 hours and then stirred a sodium thiosulfate/sodium bicarbonate solution for 15 minutes. The mixture was extracted with ethyl acetate (2×) and the extract was washed with brine, dried (MgSO$_4$) and then concentrated. The residue was triturated with ethyl acetate and then hexanes. The mixture cooled in an ice bath and resulting solids were collected and dried to provide N-[1R-(1S-benzooxazol-2-ylcarbonylbutylcarbamoyl)-2-benzylsulfonylethyl]morpholine-4-carboxamide (408 mg, 73% yield). $^1$H NMR 300 mHz: 8.65 (d,J=7.1H$_3$, 1H), 8.01 (d, J=8.8H$_3$, 1H), 7.91 (d, J=9.1H$_3$, 1H), 7.65 (t, J=8.2H$_3$, 1H), 7.55 (t, J=9.1H$_3$, 1H), 7.38 (s, 5H), 7.05 (d, J=9.4H$_3$, 1H), 5.29 (m, 1H), 4.73 (m, 1H), 4.48 (s, 2H), 3.53 (m, 4H), 3.4–3.2 (m, 6H), 1.94 (m, 1H), 1.73 (m, 1H), 1.42 (m, 2H), 0.91 (t, J=8H$_3$, 3H), MS=557.21 M+=556.20.

Proceeding by methods analogous to those described in this Application provided the following compounds of Formula I:

2S-acetylamino-N-(2-benzooxazol-2-yl-1S-butyl-2-hydroxyethyl)-3-cyclohexylpropionamide (Compound 97); $^1$H NMR (CDCl$_3$): 7.67 (d, J=8.0 Hz, 1H), 7.53 (d, J=6.0 Hz, 1H), 7.34 (m, 2H), 6.64 (d, J=8.1 Hz, 1H), 5.99 (d, J=8.1 Hz, 1H), 4.39 (m, 2H), 2.02–0.70 (m, 22 Hz); MS ESI: MH$^+$ 430;

2S-acetylamino-N-(1S-benzooxazol-2-ylcarbonylpentyl)-3-cyclohexylpropionamide (Compound 98); $^1$H NMR (CDCl$_3$): 7.93 (d, J=7.5 Hz, 1H), 7.67 (d, J=8.1 Hz, 1H), 7.54 (t, J=7.2 Hz, 1H), 7.46 (t, J=7.8 Hz, 1H), 6.78 (d, J=7.2 Hz, 1H), 5.91 (d, J=8.4 Hz, 1H), 5.63 (m, 1H), 4.59 (m, 1H), 2.09–0.85 (m, 24 Hz); MS ESI: MH$^+$ 428;

tert-butyl 1S-[1-benzooxazol-2-ylcarbonyl)-3-phenylpropylcarbamoyl)-2-cyclohexylethyl]carbamate (Compound 99);

2S-acetylamino-N-(1-benzooxazol-2-ylcarbonyl)-3-phenylpropyl)-3-cyclohexylpropionamide (Compound 100);

2S-acetylamino-N-(1-benzooxazol-2-ylcarbonylcyclobutyl)-3-cyclohexylpropionamide (Compound 101);

2S-acetylamino-N-(1R-benzooxazol-2-ylcarbonyl-3-phenylpropyl)-3-cyclohexylpropionamide (Compound 102);

2S-acetylamino-N-(2-benzooxazol-2-yl-2-hydroxy-1R-phenylpropyl)-3-cyclohexylpropionamide (Compound 103);

N-[1S-(1S-benzooxazol-2-ylcarbonyl)-3-phenylpropylcarbamolyl]-2-cyclohexylethyl]succinamic acid (Compound 104); $^1$H NMR (CDCl$_3$): 7.87 (m, 1H), 7.62 (m, 1H), 7.52 (m, 1H), 7.43 (m, 1H), 7.15 (m, 6H), 6.89 (m, 1H), 5.62 (m, 1H), 4.56 (m, 1H), 2.75 (m, 2H), 2.70 (m, 1H), 2.48 (m, 2H), 2.16 (m, 1H), 1.6 (m, 7H), 0.7–1.4 (m, 7H); MS: m/e 534;

N-[1S-(2-benzooxazol-2-yl-2-hydroxy-1S-phenethylethylcarbamoyl)-2-cyclohexylethyl]succinamic acid (Compound 105); $^1$H NMR (CDCl$_3$): 12.04 (s, 1H), 7.89 (m, 1H), 7.80 (m, 1H), 7.65 (m, 2H), 7.36 (m, 2H), 7.13–7.29 (m, 4H), 6.08–6.23 (m, 1H), 4.62–4.93 (m, 1H), 4.15 (m, 1H), 2.64 (m, 1H), 2.50 (m, 1H), 2.34 (m, 6H), 1.78 (m, 1H), 1.45–1.68 (m, 4H), 1.37 (m, 1H), 0.95–1.3 (m, 3H), 0.87 (m, 2H); MS: m/e=535.8;

N-{1S-[1S-benzooxazol-2-ylcarbonyl)-3-phenylpropylcarbamoyl]-2-cyclohexylethyl}oxalamic acid (Compound 106); $^1$H NMR (CDCl$_3$): 6.6–7.9 (m,10H), 5.6 (m, 1H), 4.5 (m, 1H), 2.72 (m, 1H), 2.45 (m, 1H), 0.8–2.1 (m, 15H); MS: m/e 506.2;

N-[1S-(1S-benzooxazol-2-ylcarbonyl-3-phenylpropylcarbamoyl)-2-cyclohexylethyl]-3H-imidazole-4-carboxamide (Compound 107); $^1$H NMR (CDCl$_3$): 8.1 (m,1H), 7.3–7.6 (m, 3H), 6.95–7.2 (m, 8H), 5.62 (m, 1H), 4.74 (m, 1H), 2.77 (m, 2H), 2.38 (m, 1H), 2.25 (m, 1H), 0.8–1.9 (m, 13H); MS: m/e 528.2;

N-[1S-(2-benzooxazol-2-yl-2-hydroxy-1S-phenylethylethylcarbamoyl)-2-cyclohexylethyl]-3H-imidazole-4-carboxamide (Compound 108); $^1$H NMR (CDCl$_3$): 7.0–7.6 (m, 12H), 5.05 (m, 1H), 4.5 (m, 1H), 2.75 (m, 2H), 0.6–2.2 (m, 15H); MS: m/e 529.6;

tert-butyl 1R-(1-benzooxazol-2-ylcarbonylcyclobutylcarbamoyl)-2-benzylsulfonylethylcarbamate (Compound 109), m.p.= 70–85° C., MH$^+$ 542;

N-[1S-(1S-benzooxazol-2-ylcarbonyl-3-phenylpropylcarbamoyl)-2-cyclohexylethyl]malonamic acid (Compound 110); $^1$H NMR (CDCl$_3$): 6.8–7.9 (m, 9H), 5.63 (m, 1H), 4.56 (m, 1H), 2.6–2.8 (m, 4H), 2.0–2.4 (m, 2H), 0.7–2.0 (m, 13H); MS: m/e 520.4;

N-[1R-(1S-benzooxazol-2-ylcarbonyl-3-phenylpropylcarbamoyl)-2-o-tolylmethylsulfonylethyl] morpholine-4-carboxamide (Compound 111); $^1$H NMR 300 mHz (DMSO-d$_6$) PPM, 8.841 (d, J=6.2 Hz, 1H), 7.942 (d, J=5.2 Hz, 1H), 7.860 (d, J=8.4 Hz, 1H), 7.618 (t, J=8.1 Hz, 1H), 7.516 (t, J=8.1 Hz, 1H), 7.16 (m, 10H), 5.22 (m, 1H), 4.78 (m, 1H), 4.516 (s, 2H), 3.567 (m, 2H), 3.500 (m, 6H), 3.3 (s, 3H), 2.75 (m, 1H), 2.65 (m, 1H), 2.44 (m, 1H), 2.26 (m, 2H), 2.01 (m, 1H); MS: M$^+$=633.4 M$^-$=631.4;

N-[1R-(1S-benzooxazol-2-ylcarbonyl-3-phenylpropylcarbamoal)-2-(2-nitrobenzylsulfonyl)ethyl] morpholine-4-carboxamide (Compound 112); $^1$H NMR 300 mHz (DMSO-d$_6$) PPM, 8.840 (d, J=7.0 Hz, 1H), 8.025 (d, J=8.0 Hz, 1H), 7.950 (d, J=8.4 Hz, 1H), 7.858 (d, J=7.7 Hz, 1H), 7.730 (d, J=8.8 Hz, 1H), 7.646 (t, J=8.4 Hz, 1H), 7.515 (t, J=7.7 Hz, 1H), 5.223 (m, 1H), 5.004 (s, 2H), 4.694 (m, 1H), 3.561 (m, 2H), 3.510 (m, 6H), 2.756 (m, 1H), 2.652 (m, 1H), 2.429 (m, 2H), 2.243 (m, 1H), 1.983 (m, 1H); MS: M$^+$=664.2 M$^-$=662.4;

N-[1R-(1S-benzooxazol-2-ylcarbonyl-3-phenylpropylcarbamoyl)-2-(2-chlorobenzylsulfonyl)ethyl] morpholine-4-carboxamide (Compound 113); $^1$H NMR 300 mHz (DMSO-d$_6$) PPM, 8.851 (d, J=6.2 Hz, 1H), 7.953 (d, J=8.8 Hz, 1H), 7.855 (d, J=8.4 Hz, 1H), 7.627 (t, J=6.6 Hz, 1H), 7.498 (m, 3H), 7.365 (m, 2H), 7.211 (m, 6H), 5.220 (m, 1H), 4.774 (m, 1H), 4.659 (m, 2H), 3.578 (m, 2H), 3.499 (m, 6H), 2.752 (m, 1H), 2.648 (m, 1H), 2.472 (m, 2H), 2.243 (m, 1H), 1.992 (m, 1H); MS: M$^+$=653.2;

N-[1R-(1S-benzooxazol-2-ylcarbonylpentylcarbamoyl)-2-benzylsulfonylethyl]morpholine-4-carboxamide (Compound 114); NMR 300 mHz (DMSO-d$_6$), 8.64 (d, J=7.4H$_3$, 1H), 8.01 (d, J=8.8H$_3$, 1H), 7.91 (d, J=9.1H$_3$, 1H), 7.68 (t, J=6H$_3$, 1H), 7.55 (t, J=8.2H$_3$, 1H), 7.38 (s, 5H), 7.05 (d, J=9.6H, 1H), 5.26 (m, 1H), 4.72 (m, 1H), 4.49 (s, 2H), 3.55 (m, 4H), 3.5–3.2(m, 6H), 1.96 (m, 1H), 1.76 (m, 1H), 1.38 (m, 4H), 0.87 (t, J=7.4H$_3$, 3H); MS: 571.24 M$^+$=570.20;

N-[1R-(1S-benzooxazol-2-ylcarbonylpentylcarbarnoyl)-2-o-tolylmethylsulfonylethyl]morpholine-4-carboxamide (Compound 115); NMR 300 mHz (DMSO-d$_6$), 8.70 (d, J=6.9H$_3$, 1H), 8.01(d, J=9.1H$_3$, 1H), 7.91 (d, J=8.8H$_3$, 1H), 7.67 (t, J=8H$_3$, 1H), 7.55 (t, J=8.5H, 3H), 7.3–7.1 (m, 4H), 7.05 (d, J=9.6H$_3$ H), 5.26 (m, 1H), 4.80 (m, 1H), 4.53 (s, 2H), 3.58 (m, 4H), 3.33 (m, 6H), 2.33 (s, 3H), 1.96 (m, 1H), 1.72 (m, 1H), 1.35 (m, 4H), 0.87 (t, J=7.7H$_3$); MS=585.30, M$^+$=584.23;

N-[1R-(1S-benzooxazol-2-ylcarbonylpentylcarbamoyl)-2-(2-nitrobenzylsulfonyl)ethyl]morpholine-4-carboxamide (Compound 116); NMR 300 mHz (DMSO-d$_6$), 8.70 (d, J=7.2H$_3$, 1H), 8.1–7.5 (m, 8H), 7.05 (d, J=9.3H$_3$, 1H), 5.26 (m, 1H), 5.01 (s, 2H), 4.70 (m, 1H), 3.57 (m, 5H), 3.30 (m, 5H), 1.96 (m, 1H), 1.72 (m, 1H), 1.34 (m, 4H), 0.87 (t, J=7.7H$_3$, 3H); MS: 616.09 M$^+$=615.20;

N-[1R-(1S-benzooxazol-2-ylcarbonylpentylcarbamoyl)-2-(2-chlorobenzylsulfonyl)ethyl]morpholine-4-carboxamide (Compound 117); NMR 300 mHz DMSO-d$_6$), 8.71 (d, J=7.1H$_3$, 1H), 8.1–73 (m, 8H), 7.06 (d,J=9.6H$_3$, 1H), 5.26 (m, 1H), 4.79 (m, 1H), 4.72 (d, J=15H$_3$, 1H), 4.65 (d, J=15H$_3$, 1H), 3.56 (m, 4H), 3.30 (m, 6H), 1.96 (m, 1H), 1.73 (m, 1H), 1.35 (m, 4H), 0.87 (t, J=7.7H$_3$, 3H); MS: 605.24 M+=605.10;

N-[1R-(2-benzooxazol-2-yl-1,1-dimethyl-2-oxoethylcarbamoyl)-2-o-toylymethylsulfonylethyl] morpholine-4-carboxamide (Compound 118); MS: (M$^+$+1) 557;

N-[1R-(2-benzooxazol-2-yl-1,1-dimethyl-2-oxoethylcarbamoyl)-2-(2-chlorobenzylsulfonyl)ethyl] morpholine-4-carboxamide (Compound 119); MS: (M$^+$+1) 578;

N-[1R-(2-benzooxazol-2-yl-1,1-dimethyl-2-oxoethylcarbamoyl)-2-(2-nitrobenzylsulfonyl)ethyl] morpholine-4-carboxamide (Compound 120); $^1$H NMR (DMSO) 9.34 (s, 1H), 8.02 (d, J=7.7 Hz, 1H), 7.82–7.45 (m, 7H), 6.74 (d, J=8.8 Hz, 1H), 4.87 (m, 2H), 4.64 (m, 1H), 3.44–3.11 (m, 10H), 1.56 (s, 3H), 1.50 (s, 3H); MS: (M$^+$+1) 588;

N-[1R-(1S-benzooxazol-2-ylcarbonyl-3-phenylpropylcarbamoyl)-2-pyrid-2-ylmethylsulfonylethyl] piperidine-4-carboxamide (Compound 121); MS:m/e+1= 616.2;

N-[1R-(1S-benzooxazol-2-ylcarbonylpentylcarbamoyl)-2-pyrid-2-ylmethylsulfonylethyl]morpholine-4-carboxamide (Compound 122); ¹H NMR: 8.62 (d, 6.9 Hz, 1 H), 8.55 (d, 3.2 Hz, 1H), 8.00 (d, 7.0 Hz, 1H), 7.86 (m, 2H), 7.65 (t, 6.2 Hz, 1H), 7.48–7.58 (m, 2H), 7.40 (m, 1H), 7.06–7.25 (m, 3H), 5.28 (m, 1H), 4.74 (m, 1H), 4.67 (d, 1.1 Hz, 2H), 3.53 (m, 4H), 3.31 (m, 4H), 1.99 (m, 1H), 1.75 (m,1H), 1.32 (m, 4H), 0.87 (t, 6.7 Hz, 3H); MS: M+1=571.8;

N-[1R-(1R-benzooxazol-2-ylcarbonyl-3-phenylpropylcarbamoyl)-2-benzylsulfonylethyl]morpholine-4-carboxamide (Compound 123);

N-[1R-(1-benzooxazol-2-ylcarbonylcyclobutylcarbamoyl)-2-benzylsulfonylethyl]morpholine-4-carboxamide (Compound 124), MH⁺ 555;

benzyl 1S-(2-benzooxazol-2-yl-2-hydroxyethylcarbamoyl)-3-methylbutylcarbamate (Compound 125);

2S-acetylamino-N-(2-benzooxazol-2-yl-1S-methyl-2-oxoethyl)-3-cyclohexylpropionamide (Compound 126); ¹H NMR (CDCl₃): 7.92 (d, J=8.4 Hz, 1H), 7.73–7.67 (m, 1H), 7.60–7.48 (m, 2H), 5.94 (d, J=8.7 Hz, 1H), 6.65 (m, 1H), 2.03 (d, J=7.2 Hz, 2H), 1.64 (m, 6H), 1.56–0.92 (m, 10 Hz); MS ESI: MH⁺ 386;

tert-butyl 1R-(1-benzooxazol-2-ylcarbonylcyclobutylcarbamoyl)-2-benzylsulfanylethylcarbamate (Compound 127);

N-[1R-(1S-benzooxazol-2-ylcarbonyl-3-methylsulfonylpropylcarbamoyl)-2-benzylsulfonylethyl]morpholine-4-carboxamide (Compound 128); ¹H NMR (CDCl₃): 7.89 (d, J=7.4 Hz, 1H), 7.65 (m, 1H), 7.57 (m, 1H), 7.48 (m, 1H), 7.4 (m, 5H), 6.0 (m, 1H), 5.7 (m, 1H), 4.93 (m, 1H), 4.33 (m, 3H), 3.70 (m, 5H), 3.25–3.4 (m, 7H), 2.93 (m, 3H), 2.8 (m, 1H), 2.35 (m, 1H); MS: m/e 653.2;

N-[1-(1S-benzooxazol-2-ylcarbonylpentylcarbamoyl)-3-phenylsulfanylpropyl]morpholine-4-carboxamide (Compound 129); ¹H NMR (DMSO): 8.52 (d,J=8 Hz, 1H), 8.98 (d,J=8 Hz, 1H), 8.88 (d,J=9 Hz, 1H), 7.64 (t,J=8 Hz, 1H), 7.53 (t,J=9 Hz, 1H), 7.30 (m, 4H), 7.19 (m, 1H), 5.25 (m, 1H), 4.35 (m, 1H); 3.51 (m, 4H), 3.26 (m, 4H), 2.94 (t, J=8 Hz, 2H), 1.9 (m, 3H), 1.7 (m, 1H), 1.31 (m, 4H), 0.86 (t,J=8 Hz, 3H), 6.43 (d,J=9 Hz, 1H); MS: m/e=539.24;

N-[1R-(1S-benzooxazol-2-ylcarbonlpentylcarbamoyl)-2-(2-trifluoromethylbenzylsulfonyl)ethyl]morpholine-4-carboxamide (Compound 131); ¹H NMR: (DMSO) 8.78 (d, J=8 Hz, 1H), 8.06–7.50 (m, 8H), 7.04 (d, J=8 Hz, 1H), 5.27 (m, 1H), 4.82–4.64 (m, 3H), 3.65–3.25 (m, 10H), 1.96 (m, 1H), 1.71 (m, 1H), 1.41–1.22 (m, 4H),), 0.84 (t,J=7 Hz, 3H). MS: (M⁺+1) 639;

N[1R-(1S-benzooxazol-2-ylcarbonyl-3-phenylpropylcarbamoyl)-2-pyrid-2-ylmethylsulfonylethyl]morpholine-4-carboxamide (Compound 132);¹H NMR (DMSO): 8.78 (d,J=7.2 Hz, 1H), 8.56 (d,J=5.41H, 1H), 7.98 (d,J=8.4 Hz, 1H), 7.85 (m, 2H), 7.64 (t,J=12.1 Hz, 1H), 7.52 (m, 2H), 7.38 (m, 1H), 7.10–7.34 (m, 8H), 5.25 (m, 1H), 4.70 (m, 3H), 3.55–3.70 (m, 4H), 3.35 (s, 4H), 2.80 (m, 2H), 2.25 (m, 1H), 2.0 (m, 1H); MS: m/e (+1)=620.0;

N-[1R-(1S-benzooxazol-2-ylcarbonyl-3-methylsulfonylpropylcarbamoyl)-2-pyrid-2-ylmethylsulfonylethyl]morpholine-4-carboxamide (Compound 133); ¹H NMR (DMSO): 8.83 (d,J=7.6 Hz, 1H), 8.55 (d,J=4.0 Hz, 1H), 7.97 (d,J=7.6 Hz, 1H), 7.88 (m, 3H), 7.64 (t,J=7.2 Hz, 1H), 7.39–7.54 (m, 4H), 7.15 (d, J=7.6 Hz, 1H), 5.36 (m, 1H), 4.70 (m, 3H), 3.56 (m, 6H), 3.24 (m, 4H), 2.40 (m, 1H), 2.15 (m, 1H), 2.99 (s, 3H); MS: m/e (+1)= 622.2;

2-[2-(1-benzooxazol-2-ylcarbonylpentylcarbamoyl)-2-morpholin-4-ylcarbonylamino)ethanesulfonylmethyl]pyridine 1-oxide (Compound 134); ¹H NMR (DMSO): 8.75 (d, J=6.5 Hz, 1H), 8.38 (m, 2H), 7.96 (d, J=7.7 Hz, 1H), 7.89 (d,J=7.7 Hz, 1H), 7.48–7.69 (m, 6H), 7.05 (d, J=6.8 Hz, 1H), 5.22 (m, 1H), 4.95 (d, J=2.7 Hz, 2H), 5.85 (m, 1H), 5.53 (m, 4H), 3.30 (s, 4H), 1.95 (m, 1H), 1.70 (m, 1H), 1.30 (m, 4H), 0.88 (t, J=5.4 Hz, 3H); MS: MW=587.65 M+1=588.2;

N-[1R-(1S-benzooxazol-2-ylcarbonylbutylcarbamoyl)-2-(2-difluoromethoxybenzylsulfonyl)ethyl]morpholine-4-carboxamide (Compound 135); NMR 300 mHz (DMSO-d₆), 8.70 (d, J=7.1H₃, 1H), 8.01 (d, J=8.8H₃, 1H), 7.91 (d, J=9.1H₃, 1H), 7.65 (t, J=8H₃, 1H), 7.55 (t, J=8.2H₃, 1H), 7.11 (t, J=8.2H₃, 1H), 7.4–6.8 (m, 5H), 5.28 (m, 1H), 4.76 (m, 1H), 4.5 (s, 2H), 3.55 (m, 4H), 3.3 (m, 6H), 1.93 (m, 1H), 1.71 (m, 1H), 1.42 (m, 2H), 0.91 (t, J=8H₃, 3H); MS: 623.38 M+=622.19;

N-[3-phenylsulfonyl-1-(1S-benzooxazol-2-ylcarbonylpentylcarbamoyl)propyl]morpholine-4-carboxamide (Compound 136); ¹H NMR (DMSO): 8.5 (m, 2H), 8.00 (d,J=9 Hz, 1H), 7.9–7.5 (m, 8H), 6.54 (t,J=9 Hz, 1H), 4.28 (m, 1H), 3.49 (m, 4H), 3.24 (m, 6H), 1.90 (m, 3H), 1.65 (m, 1H), 1.31 (m, 4H), 0.85 (t,J=7 Hz, 3H); MS: m/e=571.39;

N-[1R-(1S-benzooxazol-2-ylcarbonylpentylcarbamoyl)-2-(2-difluoromethoxybenzylsulfonyl)ethyl]morpholine-4-carboxyamide (Compound 137); ¹H NMR: (DMSO) 8.66 (d, J=6.6 Hz, 1H), 7.99 (d, J=8 Hz, 1H), 7.87 (d, J=8 Hz, 1H), 7.67–6.83 (m, 8H), 5.25 (m, 1H), 4.73 (m, 1H), 4.54 (s, 2H), 3.60–3.23 (m, 10H), 1.93 (m, 1H), 1.68 (m, 1H), 1.40–1.22 (m, 4H), 0.84 (t, J=6.7 Hz, 3H); MS: (M⁺+1) 637;

N-[1R-(1S-benzooxazol-2-ylcarbonylpentylcarbamoyl)-2-(2-difluoromethoxybenzylsulfonyl)ethyl]isonicotinamide (Compound 138); ¹H NMR: (DMSO) 9.22 (d, J=8 Hz, 1H), 8.87 (d, J=6 Hz, 1H), 8.70 (m, 2H), 7.97–7.19 (m, 10H), 7.08 (t, J_{H,F}=74 Hz, 1H), 5.30–5.09 (m, 2H), 4.58 (s, 2H), 3.73–3.59 (m, 2H), 1.94 (m, 1H), 1.71 (m, 1H), 1.41–1.22 (m, 4H), ), 0.82 (t, J=6.7 Hz, 3H); MS: (M⁺+1) 629;

N-[1R-(1S-benzooxazol-2-ylcarbonylbutylcarbamoyl)-2-pyrid-2-ylmethylsulfonyl)ethyl]morpholine-4-carboxamide (Compound 139);¹H NMR (DMSO): 8.6 (m, 2H), 8.05 (d,J=5.1 Hz, 1H), 7.85 (m, 2H), 7.3–7.8 (m, 4H), 7.2 (m, 3H), 5.32 (m, 1H), 4.72 (m, 1H), 4.65 (d,J=3.1 Hz, 2H), 3.21–3.75 (m, 8H), 1.90 (m, 1H), 1.75 (m, 1H), 1.45 (m, 2H), 0.90 (t,J=4.5 Hz, 3H); MS:m/e+1=558.2;MS: m/e (+1) 558.2;

2-[2R-(1S-benzooxazol-2-ylcarbonylbutylcarbamoyl)-2-morpholin-4-ylcarbonylaminoethylsulfonylmethyl]pyridine 1-oxide (Compound 140); ¹H NMR (DMSO): 8.57 (m, 3H), 7.97 (m, 1H), 7.63–7.82 (m, 3H), 7.35–7.45 (m, 4H), 6.93 (m, 1H), 4.50–4.95 (m, 2H), 4.18 (m, 2H), 3.10–3.80 (m, 8H), 1.10–1.70 (m, 4H), 0.82 (t,J=5.4 Hz, 3H); MS:m/e (+1)=574.2;

1R-(1S-benzooxazol-2-ylcarbonylpentylcarbamoyl)-2-(2-difluoromethoxybenzylsulfonyl)ethylcarbamate (Compound 141); MS: (M⁺+1) 582;

N[1R-(1S-benzooxazol-2-ylcarbonylpentylcarbamoyl)-2-benzylsulfonylethyl]succinamic acid (Compound 142); ¹H NMR: (DMSO) 12.09 (s, 1H), 8.63 (d, J=6 Hz, 1H), 8.51 (d, J=8 Hz, 1H), 7.98 (d, J=8 Hz, 1H), 7.87 (d, J=8 Hz, 1H), 7.62 (t, J=8 Hz, 1H), 7.52 (t, J=8 Hz, 1H), 7.38–7.30 (m, 5H), 5.25 (m, 1H), 4.84 (m, 1H), 4.46 (s, 2H), 3.53–3.21 (m, 2H), 5.28–5.25 (m, 4H), 1.93 (m, 1H), 1.68 (m, 1H), 1.40–1.22 (m, 4H), 0.84 (t, J=6.2 Hz, 3H); MS: (M⁺+1) 558;

2R-[3,3-bis(2-metboxyethyl)ureido]-N-(1S-benzooxazol-2-ylcarbonylpentyl)-3-benzylsulfonylpropionamide (Compound 143); ¹H NMR: (DMSO) 8.50 (d, J=6.6 Hz, 1H), 7.98 (d, J=8 Hz, 1H), 7.88 (d, J=8 Hz, 1H), 7.62 (t, J=8 Hz, 1H), 7.52 (t, J=8 Hz, 1H), 7.38–7.30 (m, 5H), 6.82 (d, J=8 Hz, 1H), 5.26 (m, 1H), 4.70 (m, 1H), 4.46 (s, 2H), 3.52–3.22 (m, 10H), 3.31 (s, 6H), 1.94 (m, 1H), 1.69 (m, 1H), 1.40–1.22 (m, 4H), 0.85 (t, J=6.6 Hz, 3H); MS: (M⁺+1) 617;

N[1R-(1S-benzooxazol-2-ylcarbonyl-3-phenylpropylcarbamoyl)-2-(6-methylpyrid-2-ylmethylsulfonyl)ethyl]isonicotinamide (Compound 144); ¹H NMR (DMSO): 8069 (t,J=6 Hz, 1H), 8.55 (d,J=9 Hz, 1H), 7.91 (m, 2H), 7.51 (m, 3H), 4.51 (m, 1H), 4.11 (d,J=6 Hz, 2H), 1.5 (m, 15H); MS: m/e=328.05;

N-[1R-(1S-benzooxazol-2-ylcarbonyl-3-phenylpropylcarbamoyl)-2-benzylsulfonylethyl]succinamic acid (Compound 145); MS (ESI) MH+478.2;

N-[1R-(1S-benzooxazol-2-ylcarbonyl-3-phenylpropylcarbamoyl)-2-(2-trifluoromethylbenzylsulfonyl)ethyl]tetrahydropyran-4-carboxamide (Compound 146);

N-[1R-(1S-benzooxazol-2-ylcarbonyl-3-phenylpropylcarbamoyl)-2-thien-3-ylmethylsulfonylethyl]isonicotinamide (Compound 147);

N-[1R-(1S-benzooxazol-2-ylcarbonyl-3-phenylpropylcarbamoyl)-2-(6-methylpyrid-2-ylmethylsulfonyl)ethyl]tetrahydropyran-4-carboxamide (Compound 148);

N-[1R-(1-benzooxazol-2-ylcarbonylcyclobutylcarbamoyl)-2-(2-trifluoromethylbenzylsulfonyl)ethyl]tetrahydropyran-4-carboxamide (Compound 149);

N-[1R-(1S-benzooxazol-2-ylcarbonyl-3-phenylpropylcarbamoyl)-2-pyrid-3-ylmethylsulfonylethyl]pyrazine-2-carboxamide (Compound 150);

N-[1-(1-benzooxazol-2-ylcarbonyl-3-phenylpropylcarbamoyl)-2-thien-3-ylmethylsulfonylethyl]piperidine-4-carboxamide (Compound 151);

N-[1S-(1S-benzooxazol-2-ylcarbonyl-3-phenylpropylcarbamoyl)-2-thien-3-ylmethylsulfonylethyl]azetidine-3-carboxamide (Compound 152);

N[1R-(1S-benzooxazol-2-ylcarbonyl)butylcarbamoyl)-2-pyrid-3-ylmethylsulfonylethyl]morpholine-4-carboxamide (Compound 153); ¹H NMR (DMSO): 8.66 (d, J=6.7 Hz, 1H), 8.56 (m, 3H), 8.01 (d, J=7.9 Hz, 1H), 7.90 (d,J=8.1 Hz, 1H), 7.79 (m, 1H), 7.65 (t, J=7.1 Hz, 1H), 7.55 (t, J=7.1 Hz, 1H), 7.43 (dd, J=4.9,7.9 Hz, 2H), 6.93 (d, J=8.40 Hz, 1H), 5.30 (m, J=1 Hz, 1H), 4.76 (m, 1H), 4.57 (d, J=3.7 Hz, 2H), 3.24–3.70 (m, 8H), 1.91 (m, 1H), 1.73 (m, 1H), 1.40 (m, 2H), 0.82 (t, J=5.4 Hz, 3H); MS:m/e (+1)=555.8;

N-1R-(1S-benzooxazol-2-ylcarbonyl-3-phenylopylcarbamoyl)-2-benzylsulfonylethyl]piperazine-1-carboxamide (Compound 154);

N-[1R-(1S-benzooxazol-2-ylcarbonyl-3-methylsulfonylpropylcarbamoyl)-2-(2-difluoromethoxybenzylsulfonyl)ethyl]morpholine-4-carboxamide (Compound 155); ¹H NMR (CDCL₃, 300 MHz) 7.8944 (d, J=7.92 Hz, 1H), 7.67 (m, 1H), 7.58 (m, 1H), 4.49 (m, 2H), 7.415 (m, 1H), 7.24 (m, 3H), 6.5811 (t, J=73.24 Hz, 1H), 5.7633 (m, 1H), 4.9199 (m, 1H), 4.4871 (dd, J=13.61, 23.75 Hz, 2H), 3.7101 (m, 4H), 3.4189 (m, 4H), 3.27 (m, 2H), 2.9289 (s, 3H), 2.77 (m, 1H), 2.37 (m, 1H); MS: (M⁺) 687.3 (M⁻) 685.6;

N-[1R-(1S-benzooxazol-2-ylcarbonyl-3-methylesulfonylpropylcarbamoyl)-2-(2-methoxybenzylsulfonyl)ethyl]morpholine-4-carboxamide (Compound 156); ¹H NMR (CDCl₃): 7.89 (m, 1H), 7.45–7.8 (m, 3H), 7.35 (m, 2H), 6.9–7.05 (m, 2H), 5.83–5.9 (m, 1H), 5.62–5.8 (m, 1H), 4.82 (m, 1H), 4.40 (m, 2H), 3.89 (s, 3H), 3.70 (m, 5H), 3.25–3.42 (m, 7H), 2.95 (s, 3H), 2.75 (m, 1H), 2.35 (m, 1H); MS: m/e 651.4;

N-[1R-(1S-benzooxazol-2-ylcarbonylpentylcarbamoyl)-2-benzylsulfonylethyl]piperazine-1-carboxamide (Compound 157); ¹H NMR: (DMSO) 9.20–9.11 (m, 2H), 8.73 (m, 1H), 7.98 (d, J=8 Hz, 1H), 7.88 (d, J=8 Hz, 1H), 7.63 (t, J=8 Hz, 1H), 7.52 (t, J=8 Hz, 1H), 7.39–7.30 (m, 5H), 5.24 (m, 1H), 4.74 (m, 1H), 4.50 (s, 2H), 3.62–3.30 (m, 6H), 3.05–2.95 (m, 4H), 1.94 (m, 1H), 1.69 (m, 1H), 1.40–1.22 (m, 4H), 0.84 (t, J=6.6 Hz, 3H); MS: (M⁺+1) 570;

N-(1S5-benzooxazole-2-ylcarbonyl-3-methylsulfonylpropyl)-2R-methylsulfonylamino-3-benzylsulfonylpropionamide (Compound 160); ¹H NMR (DMSO-d₆) 7.9498 (m, 2H), 7.6577 (m, 1H), 7.5556 (m, 1H), 7.3870 (m, 5H), 5.4016 (m, 1H), 4.5444 (m, 3H), 3.32 (m, 2H), 2.9784 (s, 1H), 2.9326 (s, 1H), 2.49 (m, 1H), 2.20 (m, 1H); MS: (M⁺) 586.0, (M⁻) 584.0;

methyl 1R-(1S-benzooxazol-2-ylcarbonyl-3-phenylpropylcarbamoyl)-2-pyrid-2-ylmethylsulfonylethylcarbamate (Compound 161); MS: m/e (+1)=564.6;

methyl 1R-(1S-benzooxazol-2-ylcarbonyl-3-methylsulfonylpropylcarbamoyl)-2-benzylsulfonylethylcarbamate (Compound 162); ¹H NMR (DMSO): 9.03 (d, J=7.2 Hz, 1H), 7.97 (d, J=7.9 Hz, 1H), 7.90 (d, J=8.2 Hz, 1H), 7.65 (td, J=7.2, 1.2 Hz, 1H), 7.55 (t, J=7.9 Hz, 1H), 7.37 (m, 5H), 5.32 (m, 1H), 4.65 (m, 1H), 4.50 (m, 2H), 3.53 (m, 1H), 3.49 (s, 3H), 3.33 (s, 2H), 3.24 (m, 1H), 2.98 (s, 3H), 2.41 (m, 1H), 2.18 (m, 1H); MS: m/e 653.2;

N-(1S-benzooxazol-2-ylcarbonylpentyl)-2R-[3,3-di(2-methoxyethyl)ureido]-3pyrid-2-ylmethylsulfonylpropionamide (Compound 163); MS:m/e +1=615.6;

N-[1R-(1S-benzooxazol-2-ylcarbonylbutylcarbamoyl)-2-(2-methoxybenzylsulfonyl)ethyl]morpholine-4-carboxamide (Compound 164); ¹H NMR (DMSO): 8.66 (d,J=6 Hz, 1H), 8.03 (d,J=9 Hz, 1H), 7.93 (d,J=9 Hz, 1H), 7.68 (t,J=8 Hz, 1H), 7.58 (t,J=9 Hz, 1H), 7.36 (m, 2H), 7.0 (m, 3H), 5.29 (m, 1H), 4.77 (m, 1H), 4.54 (d,J=14 Hz, 1H), 4.43 (d,J=14 Hz, 1H), 3.84 (s, 3H), 3.5–3.3 (m, 10H), 1.95 (m, 1H), 1.74 (m, 1H), 1.46 (m, 2H), 0.93 (t, J=8 Hz, 3H); MS: m/e=587.31;

N-(1S-benzooxazol-2-ylcarbonylbutylcarbamoyl)-2R-(3,3-dimethylureido)-3-(2-methoxybenzylsulfonyl)propionamide (Compound 165); NMR 300 mHz (DMSO-d₆), 8.63 (d, J=6.9H₃, 1H), 8.03 (d, J=8.8H₃, 1H), 7.92 (d, J=9.1, 1H), 7.70 (t, J=8.8H₃, 1H), 7.58 (t, J=8.2H₃, 1H), 7.37 (m, 2H), 7.08 (d, J=9.1H₃, 1H), 6.98 (t, J=8.2H₃, 1H), 6.71 (d, J=9.1H₃, 1H), 5.27 (m, 1H), 4.77 (m, 1H), 4.55 (d, J=15.1H₃, 1H), 4.43 (d, J=15.1H₃, 1H, 3.79 (s, 3H), 3.47 (d, J=6.9H₃, 2H), 2.83 (s, 6H), 1.93 (m, 1H), 1.75 (m, 1H), 1.43 (m, 2H), 0.93 (t, J=8H₃, 3H);

N-(1S-benzooxazol-2-ylcarbonylbutyl)-2-methylsulfonylamino-3-(2-methoxybenzylsulfonyl)propionamide (Compound 166); ¹H NMR (DMSO): 9.0 (d,J=6 Hz, 1H), 8.01 (d,J=8 Hz, 1H), 7.91 (d,J=8 Hz, 1H), 7.67 (t,J=7 Hz, 1H), 7.36 (t, J=8 Hz, 2H), 7.07 (d, J=8 Hz, 1H), 6.97 (dt, J=2,7 Hz, 1H), 7.85 (m, 1H); 5.33 (m, 4H), 4.5 (m, 3H), 3.8 (s, 3H), 3.35 (m, 2H), 2.92 (s, 3H), 1.93 (m, 1H), 1.72 (m, 1H), 1.44 (m, 2H), 0.91 (t, J=7 Hz, 3H); MS: m/e=552.19;

3-cyclohexyl-N-[2-hydroxy-2-(5-nitrobenzooxazol-2-yl)-1S-phenethylethyl]propionamide (Compound 167); MS (ESI) m/z=466 (M+1); $^1$H-NMR (300 MHz, CDCl$_3$): δ 0.95 (m, 2H), δ 1.22 (m, 4H), δ 1.51 (m, 2H), δ 1.65 (m, 6H), δ 2.15 (m, 2H), δ 2.65 (m, 2H), δ 4.15 (m, 1H) δ 4.50 (m, 1H), δ 5.08 (m, 1H), δ 5.80 (d, J=6 Hz, 1H), δ 6.09 (m, 1H), δ 7.00–7.35 (m, 5H), δ 7.60 (m, 1H), δ 8.40 (m, 1H), δ 8.55 (m, 1H), (C$_{26}$H$_{31}$N$_3$O$_5$);

methyl 2-[2S-(3-cyclohexylpropionylamino)-1-hydroxy-4-phenylbutyl]benzooxazole-6-carboxylate (Compound 168); MS (ESI) m/z=478 (M+1); $^1$H-NMR (300 MHz, CDCl$_3$): δ 0.84 (m, 2H), δ 1.22 (m, 4H), δ 1.51 (m, 7H), δ 1.90 (m, 1H), δ 2.11 (m, 2H), δ 2.65 (m, 2H), δ 3.95 (s, 3H), δ 4.19 (m, 1H), δ 4.50 (m, 1H), δ 5.09 (s, 1H), δ 6.09 (m, 1H), δ 6.49 (m, 1H), δ 7.01–7.35 (m, 5H), δ 7.65 (m, 1H), δ 8.01 (m, 1H), δ 6.09 (m, 1H), δ 6.49 (m, 1H), δ 7.01–7.35 (m, 5H), δ 7.65 (m, 1H), δ 8.01 (m, 1H), δ 8.17 (m, 1H), (C$_{28}$H$_{34}$N$_2$O$_5$);

N-[2-(5-chlorobenzooxazol-2-yl)-2-hydroxy-1S-phenethylethyl]-3-cyclohexylpropionamide (Compound 169); MS (ESI) m/z=455 M+1); $^1$H-NMR (300 MHz, CDCl$_3$): δ 0.84 (m, 2H), δ 1.12 (m, 4H), δ 1.20 (m, 2H), δ 1.51 (m, 6H), δ 2.00 (m, 3H), δ 2.65 (m, 2H), δ 4.21 (m, 1H), δ 4.50 (m, 1H), δ 5.02 (s, 1H), δ 6.44 (m, 1 H), δ 7.01–7.47 (m, 7H), δ 7.65 (s, 1 H), (C$_{26}$H$_{31}$ClN$_2$O$_3$);

benzyl 1S-(2-benzooxazol-2-yl-2-hydroxy-1S-phenethylethylsulfamoylmethyl)-3-methylbutylcarbamate (Compound 170); $^1$H NMR (CDCl$_3$): 7.71 (m, 1H), 7.52 m, 1H), 7.20–7.40 (m, 12H), 5.9 (m, 0.5H), 5.6 (m, 0.5H), 4.80–5.20 (m, 5H), 4.1–4.3 (m, 2H), 2.7–2.9 (m, 4H), 1.7–2.0 (m, 2H), 0.90 (m, 3H), 0.79 (m, 3H), 3.30 (m, 1H);

N-[1S-(2-benzooxazol-2-yl-2-hydroxy-1S-phenethylethylsulfamoylmethyl)-3-methylbutyl]acetamide (Compound 171);

benzyl 1S(2-benzooxazol-2-yl-2-hydroxy-1Sphenethylethylsulfamoylmethyl)-3-methylbutylcarbamate (Compound 172); $^1$H NMR (DMSO): 7.71 (m, 1H), 7.5 (m, 1H), 7.0–7.4 (m, 12H), 4.9–6.2 (m, 6H), 4.0–4.35 (m, 2H), 3.75 (m, 1H), 3.20–3.60 (m, 2H), 2.5–3.0 (m, 2H), 1.15–2.15 (m, 3H), 0.6–1.05 (m, 6H); MS: m/e 580.1;

N-[1R-(2-benzooxazol-2-yl-2-hydroxy-1S-phenethylethylsulfamoylmethyl)-3-methylbutyl]acetamide (Compound 173);

2S-acetylamino-N-(2-benzooxazol-2-yl-2-hydroxy-1S-phenethylethyl)-3-cyclohexylpropionamide (Compound 174);

tert-butyl 1S-(2-benzooxazol-2-yl-2-hydroxy-1S-phenethylethyl]-2-cyclohexylethyl)carbamate (Compound 175);

2-acetylamino-N-2-benzooxazol-2-yl-1,1-dimethyl-2-oxoethyl)-3-cyclohexylpropionamide (Compound 176);

benzyl 1S-[2-(5-phenylbenzooxazol-2-yl)-2-hydroxyethylcarbamoyl]-3-methylbutylcarbamate (Compound 177);

N-(2-benzooxazol-2-yl-2-hydroxy-1S-phenethylethyl)-3-cyclopentylpropionamide (Compound 178); $^1$H NMR (CDCl$_3$): 7.72 (m, 1H), 7.53 (m, 1H), 7.08–7.19 (m, 8H), 5.98 (m, 1H), 5.05 (m, 2H), 4.51 (m, 1H), 2.6–2.8 (m, 4H), 2.17–2.29 (m, 1H), 1.95–2.15 (m, 2H), 1.8–1.95 (m, 1H), 1.68–1.78 (m, 1H), 1.3–1.7 (m, 6H), 1.0–1.12 (m, 1H), 0.85–1.0 (m, 1H);

N-(2-benzooxazol-2-yl-2-hydroxy-1S-phenyethylethyl)-2-bicyclo[2.2.1]hept-2-ylacetamide (Compound 179);

N-(2-benzooxazol-2-yl-2-hydroxy-1S-phenethylethyl)-2-naphthalen-1-ylacetamide (Compound 180);

N-(2-benzooxazol-2-yl-2-hydroxy-1S-phenethylethyl)-3-phenylpropionamide (Compound 181); $^1$H NMR (CDCl$_3$): 7.69 (m, 1H), 7.53 (m, 1H), 7.37 (m, 2H), 7.03–7.35 (m, 10H), 5.9 (m, 1H), 4.98 (m, 1H), 4.40–4.55 (m, 1H), 3.0 (m, 1H), 2.80 (t, J=7.7 Hz, 2H), 2.55 (m, 2H), 2.38 (t, J=7.5 Hz, 2H);

methyl 2-[2S-(3-cyclohexylpropionylamino)-1-hydroxy-4-phenylbutyl]-4,5-dihydrooxazole-4S-carboxylate (Compound 182); MS (ESI) m/z=431 (M+1); $^1$H-NMR (300 MHz, CDCl$_3$): δ 0.89 (m, 2H), δ 1.20 (m, 4H), δ 1.48 (m, 2H), δ 1.65 (m, 6H), δ 2.00 (m, 2H), δ 2.15 (m, 2H), δ 2.73 (t, J=4 Hz, 2H), δ 3.76 (s, 3H), δ 4.30–4.65 (m, 5H), δ 6.00 (d, J=6 Hz, 1H), δ 7.13–7.35 (m, 5H), (C$_{24}$H$_{34}$N$_2$O$_5$);

methyl 2-[2S-(3-cyclohexylpropionylamino)-1-hydroxy-4-phenylbutyl]oxazole-4-carboxylate (Compound 183);

N-(2-benzooxazol-2-yl-2-hydroxy-1S-phenethyl)-4-cyclohexylbutyramide (Compound 184); $^1$H NMR (CDCl$_3$): 7.62–7.73 (m, 1H), 7.46–7.59 (m, 1H), 7.05–7.43 (m, 2H), 6.22–6.38 (m, 1H), 5.11 (s, 1H), 4.50–4.69 (m, 1H), 2.58–2.82 (m, 2H), 2.14–2.24 (m, 1H), 2.0, 2.14 (m, 1H), 1.50–1.76 (m, 6H), 1.31–1.50 (m, 1H), 0.94–1.31 (m, 7H), 0.63–0.93 (m, 2H); MS: m/e=435.1;

methyl 2-[2S-(3-cyclohexylpropionylamino)-1-hydroxy-4-phenylbutyl]-4,5-dihydrooxazole-4R-carboxylate (Compound 185); MS (ESI) m/z=431 (M+1); $^1$H-NMR (300 MHz, CDCl$_3$): δ 0.89 (m, 2H), δ 1.20 (m, 4H), δ 1.48 (m, 2H), δ 1.65 (m, 6H), δ 2.00 (m, 2H), δ 2.15 (m, 2H), δ 2.73 (t, J=4 Hz, 2H), δ 3.76 (s, 3H), δ 4.35–4.72 (m, 5H), δ 5.75 (m, 1H), δ 7.13–7.35 (m, 5H), (C$_{24}$H$_{34}$N$_2$O$_5$);

3-cyclohexyl-N-[2-hydroxy-2-(5-trifluoromethylbenzooxazol-2-yl)-1S-phenethylethyl]propionamide (Compound 186); MS (ESI) m/z=489 (M+1); $^1$H-NMR (300 MHz, CDCl$_3$): δ 0.77 (m, 2H), δ 1.22 (m, 4H), δ 1.51 (m, 2H), δ 1.60 (m, 6H), δ 2.15 (m, 4H), δ 2.70 (m, 2H), δ 4.51 (m, 1H), δ 5.11 (s, 1H), δ 6.10 (d, J=6 Hz, 1H), δ 7.00–7.35 (m, 5H), δ 7.56 (s, 2H), δ 7.99 (s, 1H), (C$_{27}$H$_{31}$F$_3$N$_2$O$_3$);

2S-acetylamino-N-(2-benzooxazol-2-yl-2-hydroxy-1S-phenethylethyl)-3-(2-trifluoromethylphenyl)propionamide (Compound 187);

methyl 1-(1-benzooxazol-2-ylcarbonyl-3-phenylpropylcarbamoyl)-2-cyclohexylethylcarbamate (Compound 188); $^1$H NMR (CDCl$_3$): 7.89 (d,J=7.4 Hz, 1H), 7.62 (M, 1H0, 7.54 (m, 1H), 7.46 (m, 1H), 7.13–7.30 (m, 1H), 6.87 (d, J=7.9 Hz, 1H), 5.68 (m, 1H), 5.04 (d, J=9.6 Hz, 1H), 4.24 (m, 1H), 3.66 (s, 3H), 2.75 (5,J=8.3 Hz, 2H), 2.45 (m, 1H), 2.19 (m, 1H), 2.00 (M, 1H), 1.52–1.80 (m=5H), 1.44 (m, 1H), 1.12–1.27 (m, 4H), 0.89 (m, 2H); MS: m/e=492.04;

N-(1-benzooxazol-2-ylcarbonyl-3-phenylpropyl)-3-cyclohexyl-2-methylsulfonylaminopropionamide (Compound 189); $^1$H NMR (CDCl$_3$): 7.87 (m, 1H), 7.62 (m, 1H), 7.55 (m, 1H), 7.46 (m, 1H), 7.13–7.28 (m, 5H), 6.79 (d, J=7.9 Hz, 1H), 5.71 (m, 1H), 4.92 (m, 1H), 4.00 (m, 1H), 2.95 (2, 3H), 2.75 (m, 2H), 2.48 (m, 1H), 2.21 (m, 1H), 1.78 (m, 1H), 1.61 (m, 5H), 1.45 (m, 1H), 1.16 (m, 4H), 0.89 (m, 2H);

cyclohexylmethyl 1-benzooxazol-2-ylcarbonyl-3-phenylpropylcarbamate (Compound 190); $^1$H NMR (CDCl$_3$): 7.88 (m, 1H), 7.62 (m, 1H), 7.52 (m, 1H), 7.49 (m, 1H), 7.13–7.23 (m, 5H), 5.57 (m, 1H), 3.89 (d, J=6.5 Hz, 2H), 2.79 (m, 2H), 2.42 (m, 1H), 2.12 (m, 1H), 1.50–1.73 (m, 6H), 1.24 (m, 6H), 0.89 (m, 2H); MS: m/e=421.0;

benzyl 1-(1-benzooxazol-2-ylcarbonyl-3-phenylpropylsulfamoylmethyl)-2-methylbutylcarbamate (Compound 191); $^1$H NMR (CDCl$_3$): 7.88 (d,J=7.7 Hz, 1H), 7.62 (m, 1H), 7.55 (m, 1H), 7.47 (m, 1H), 7.33 (m, 5H), 7.19

(m, 5H), 6.35 (d, J=7.7 Hz, 1H), 5.45 (m, 1H), 5.13 (s, 2H), 5.0 (m, 1H), 4.43 (m, 1H), 3.06 (m, 1H), 2.87 (m, 1H), 2.45 (m, 1H), 2.15 (m, 1H), 1.41 (m, 1H), 1.07 (m, 1H), 0.88 (m, 6H); MS: m/e=5.78.1;

N-[1R-(1S-benzooxazol-2-ylcarbonyl-3-phenylpropylcarbamoyl)-2-(6-methylpyrid-2-ylmethylsulfonyl)ethyl]thiophene-3-carboxamide (Compound 192);

N-[1R-(1S-benzooxazol-2-ylcarbonyl)-3-phenylpioylcarbamoyl)-2-(2-methylpyrid-3-ylmethylsulfonyl)ethyl]nicotinamide (Compound 193);

N[1R-(1S-benzooxazol-2-ylcarbonyl-3-phenylpropylcarbamoyl)-2-(2-cyanobenzylsulfonyl)ethyl]azetidine-3-carboxamide (Compound 194);

tert-butyl 1R-(1-benzooxazol-2-ylcarbonylcyclobutylcarbamoyl)-2-(2-difluoromethoxybenzylsulfonyl)ethylcarbamate (Compound 195);

tert-butyl 1R-(1S-benzooxazol-2-ylcarbonyl-3-phenylpropylcarbamoyl)-2-(4-trifluoromethylpyrid-3-ylmethylsulfonyl)ethylcarbamate (Compound 196);

N-[1R-(1-benzooxazol-2-ylcarbonylcyclobutylcarbamoyl)-2-(2-difluoromethoxybenzylsulfonyl)ethylmorpholine-4-carboxamide (Compound 197);

N-[1R-(1S-benzooxazol-2-ylcarbonylpentylcarbamoyl)-2-pyrid-3-ylmethylsulfonylethyl]isonicotinamide (Compound 198);

methyl 1R-(1S-benzooxazol-2-ylcarbonylbutylcarbamoyl)-2-(2-methoxybenzylsulfonyl)ethylcarbamate (Compound 199);

N[1R-(1S-benzooxazol-2-ylcarbonylpropylcarbamoyl)-2-benzylsulfonylethl]morpholine4-carboxamide (Compound 200); NMR 300 mHz (DMSO-$d_6$), 8.65 (d, J=7.1$H_3$, 1H), 8.01 (d, J=8.2$H_3$, 1H), 7.91 (d, J=8.8$H_3$, 1H), 7.66 (t, J=8$H_3$, 1H), 7.55 (t, J=7.7$H_3$, 1H), 7.38 (s, 5H), 7.05 (d, J=9.4$H_3$, 1H), 5.21 (m, 1H), 4.75 (m, 1H), 4.49 (s, 2H), 3.53 (m, 4H), 3.45 (m, 2H), 3.32 (m, 4H), 2.02 (m, 1H), 1.77 (m, 1H), 0.96 (t, J=8$H_3$, 3H); M=543.24 M$^+$=542.61;

N-(1R-benzooxazol-2-ylcarbonylpropyl)-2-(3,3-dimethylureido)-3-(2-methoxybenzolsulfonyl)propionamide (Compound 201); NMR 300 mHz (DMSO-$d_6$), 8.61 (d, J=7.4$H_3$, 1H), 8.01 (d, J=8.5$H_3$, 1H), 7.90 (d, J=7.1$H_3$, 1H), 7.65 (t, J=8$H_3$, 1H), 7.55 (t, J=8H3, 1H), 7.33 (m, 2H), 7.05 (d, J=8.8$H_3$, 1H), 6.96 (t, J=8.2$H_3$, 1H), 6.70 (d, J=9.1$H_3$, 1H), 5.20 (m, 1H), 4.53 (d, J=15.4$H_3$, 1H), 4.41 (d, J=15.4$H_3$, 1H), 3.77 (s, 3H), 3.45 (d, J=7.1$H_3$, 2H), 2.81 (s, 6H), 2.0 (m, 1H), 1.7 (m, 1H), 0.96 (t, J=8$H_3$, 3H); MS=651.33 M$^+$=650.59;

methyl 1R-(1S-benzooxazol-2-ylcarbonylpropylcarbamoyl)-2-(2-methoxybenzylsulfonylethyl)carbamate (Compound 202);

N-(1-benzooxazol-2-ylcarbonylpentyl)-2R-[3.3-bis(2-methoxyethyl)ureido]-3-pyrid-3-ylmethylsulfonylpropionamide (Compound 203);

N-(1S-benzooxazol-2-ylcarbonylpentyl)-2R-[3,3-bis(2-medioxyethyl)ureido]-3-(3,5-dimethylisoxazol-4-ylmethylsulfonyl)propionamide (Compound 204);

N-(1S-benzooxazol-2-ylcarbopylpropyl)-3-(3,5-dimethylisoxazol-4-ylmethylsulfonyl)-2R-methylsulfonylaminopropionanide (Compound 205); $^1$H NMR: (DMSO) 9.04 (d, J=6.6 Hz, 1H), 8.00–7.87 (m, 3H), 7.63 (t, J=8 Hz, 1H), 7.53 (t, J=8 Hz, 1H), 5.25 (m, 1H), 4.61–4.36 (m, 3H), 3.56–3.31 (m, 2H), 2.91 (s, 3H), 2.36 (s, 3H), 2.17 (s, 3H), 2.02 (m, 1H), 1.74 (m, 1H), 0.96 (t, J=7 Hz, 3H); MS: (M$^+$+1) 527;

methyl 1R-(1S-benzooxazol-2-ylcarbonylpropylcarbamoyl)-2-(3,5-dimethylisoxazol-4-ylmethylsulfonyl)ethylcarbamate (Compound 206); $^1$H NMR: (DMSO) 8.78 (d, J=5.8 Hz, 1H), 7.99 (d, J=8 Hz, 1H), 7.87 (d, J=8 Hz, 1H), 7.69 (d, J=8.5 Hz, 1H), 7.62 (t, J=8 Hz, 1H), 7.52 (t, J=8 Hz, 1H), 5.20 (m, 1H), 4.68 (m, 1H), 4.39 (d, J=14 Hz, 1H), 4.29 (d, J=14 Hz, 1H), 3.52 (s, 3H), 3.60–3.28 (m, 2H), 2.37 (s, 3H), 2.15 (s, 3H), 2.02 (m, 1H), 1.74 (m, 1H), 0.95 (t, J=7 Hz, 3H); MS: (M$^+$+1) 507;

N-[1R-(1-benzooxazol-2-ylcarbonylpentylcarbamoyl)-2-pyrid-2-ylmethylsulfonylethyl]isonicotinamide (Compound 207); NMR 1H: 9.15–9.30 (m, 1H), 8.4–8.9 (m, 4 H), 7.32–8.05 (m, 9H), 5.28 (m, 1H), 5.10 (m, 1H), 4.75 (m, 2H), 3.75 (m, 1H), 3.62 (m, 1H), 1.95 (m, 1H), 1.75 (m, 1H), 1.05–1.45 (m, 4H), 0.87 (m, 3H); MS: M+1=564.0; and 4-[1R-(1S-benzooxazol-2-ylcarbonylpentylcarbamoyl)-2-pyrid-2-ylmethylsulfonylethylcarbamoyl]pyridine 1-oxide (Compound 208).

Reference 13

Benzyl 1S-(N-methoxy-N-methylcarbamoyl)-3-phenylpropylcarbamate

A solution of 2-benzyloxycarbonylamino-4-phenylbutyric acid (5.05 g, 16.1 mmol) in methylene chloride (70 mL) was cooled to 0° C. and treated with diisopropylethylamine (2.82 mL, 16.2 mmol) added dropwise and then PyBOP® (8.53 g, 16.4 mmol) added in one portion. The mixture was stirred for 5 minutes and then treated with N,O-dimethylhydroxylamine hydrochloride (1.73 g, 17.71 mmol) was added in one portion. The mixture was neutralized with diisopropylethylamine (4.6 mL, 26.44 mmol) added dropwise, stirred for 2 hours at room temperature and then diluted with methylene chloride (70 mL). The dilution was washed with 1N aqueous hydrochloric acid (3×40 mL), saturated sodium bicarbonate (3×40 mL) and brine (40 mL) and then concentrated. The product was purified from the residue by column chromatography eluting with 2:3 ethyl acetatelhexane to provide benzyl 1S-(N-methoxy-N-methylcarbamoyl)-3-phenylpropylcarbamate (5.48 g, 15.4 mmol) as an oil. MS(PCI) m/z=357 (M+1).

Proceeding as in Reference 13 provided tert-butyl 1S-(N-methoxy-N-methylcarbamoyl)-3-phenylpropylcarbamate; $^1$H NMR (CDCl$_3$): δ 1.35 (s, 9H), δ 1.64–1.72 (m, 2H), δ 2.40–2.54 (m, 1H), δ 2.60–2.77 (m, 1H), δ 3.00 (s, 3H) 3.52 (s, 3H), δ 4.23 (m, 1H), δ 7.10–7.37 (m, 5H).

Reference 14

2S-Amino-N-methoxy-N-methyl-4-phenylbutyramide trifluoroacetic acid salt

A solution of tert-butyl 1-(N-methoxy-N-methylcarbamoyl)-3-phenylpropylcarbamate (9.32 g, 29 mmol), provided as in Reference 13, in methylene chloride (100 mL) was cooled to 0° C. and then treated with anisole (5 mL, 46.5 mmol) and trifluoroacetic acid (50 mL, 296 mmol). The mixture was stiffed for 30 minutes, while allowing it to warm to room temperature, and then concentrated. The residue was dissolved in toluene (100 mL) and the solution was concentrated. The residue was again dissolved in toluene (100 mL) and concentrated to provide 2S-amino-N-methoxy-N-methyl-4-phenylbutyramide trifluoroacetic acid salt (9.74 g 29 mmol) as a crude product. MS(PCI) m/z=223 (M+1).

Reference 15

Benzyl 1-[1-(N-methoxy-N-methylcarbamoyl)-3S-phenylpropyycarbamoyl]-3-methylbutylcarbamate A solution comprised of 2S-amino-N-methoxy-N-methyl-4-phenylbutyramide trifluoroacetic acid salt (9.74 g, 29 mmol), provided as in Reference 2, in DMF (75 mL) was cooled to 0° C. and then neutralized with diisopropylety-lamine added dropwise. A solution comprised of 2,5-dioxopyrrolidin-1-yl 2-benzyloxycarbonylamino-4-methylvalerate (10.50 g, 29 mmol) in DMF (75 mL) and an additional amount of duisopropylethylamine (10.10 mL, 58 mmol) were added to the cooled butyramide solution. The mixture was stirred for 2 hours, while allowing it to warm to room temperature, and then poured into ice water (300 mL). The mixture was let stand for 1 hour to provide a white precipitate. The precipitate was collected by filtration and dried ($P_2O_5$) under vacuum to provide benzyl 1-[1-(N-methoxy-N-methylcarbamoyl)-3-phenylpropylcarbamoyl]-3-methylbutylcarbamate (12.24 g, 26.1 mmol). $^1$H NMR (CDCl$_3$): δ 0.91 (d, J=5.88 Hz, 6H), δ 1.45–1.55 (m, 1H), δ 1.45–1.55 (m, 2H), δ 1.77–2.00 (m, 1H), δ 2.11–2.22 (m, 1H), δ 2.70 (m, 2H), δ 3.20 (s, 3H), 3.60 (s, 3H) 4.25 (m, 1H), δ 5.00 (m, 1H), δ 5.15 (s, 2H), δ 6.6 (d, J=8.15 Hz, 1H), δ 7.15–7.45 (m, 10H).

Reference 16

Ethyl 3S-benzyloxycarbonylamino-2-hydroxy-5-phenylpentanimidate

A suspension comprised of lithium aluminum hydride (0.885 g, 23.3 mmol) in anydrous diethyl ether was cooled to −45° C. under nitrogen and then treated with a solution of benzyl 1S-(N-methoxy-N-methylcarbamoyl)-3-phenylpropylcarbamate (5.53 g, 15.53 mmol), provided as in Reference 13, in ether (75 mL) and THF (25 mL) was added dropwise over a period of 30 minutes such that the temperature of the mixture was maintained at −40 to −45° C. The mixture was allowed to warm to 5° C. and then recooled to −35° C. A saturated solution of sodium bicarbaonate (7 mL, 0.5 M) was added dropwise and the mixture was allowed to warm to 0° C. The mixture was allowed to warm to room temperature and stirred for 1 hour to provide a precipitate. The precipitate was collected by filtration and washed with ether (100 mL). The filtrate and washings were combined and washed with ice cold 1N hydrochloric acid (2×50 mL), saturated sodium bicarbonate (2×50 mL) and brine (50 mL), dried (Na$_2$SO$_4$) and concentrated in vacuo to provide benzyl 1S-formyl-3-phenylpropylcarbamate (4.01 g, 13.5 mmol) as a colorless oil. MS (PCI) m/z=298 (M+1).

A solution of benzyl 1S-formyl-3-phenylpropylcarbamate (4.557 g, 15.3 mmol) in anhydrous methylene chloride (50 mL) was stirred while sequentially treating with 2-hydroxy-2-methylpropionitrile (4.25 mL, 46.2 mmol) and triethylamine (1.28 mL, 9.20 mmol). The mixture was stirred for 4 hours at room temperature and concentrated in vacuo. The residue was dissolved in ether (100 mL) and the solution was washed with water (5×20 mL) and brine (20 mL), dried (MgSO$_4$) and concentrated to provide benzyl 2-cyano-2-hydroxy-1S-phenethylethylcarbamate (4.957 g, 15.3 mmol) as a yellow oil. $^1$H NMR (CDCl$_3$): δ 1.75–2.01 (m, 2H), δ 2.08–2.24 (m, 1H), δ 2.51–2.80 (m, 2H), δ 3.70–4.02 (m, 1H), δ 5.07, δ5.33 (m, 3H), δ 7.10–7.47 (m, 10H).

A comprised of chloroform (30 mL) and anhydrous ethanol (30 mL, 510 mmol) was cooled to 0° C. and then treated with acetyl chloride (32.6 mL, 459 mmol) added dropwise over a period of 30 minutes. The mixture was cooled with solution of crude benzyl 2-cyano-2-hydroxy-1-phenethylethylcarbamate (4.957 g, 15.3 mmol) in chloroform (30 mL). The mixture was stirred for 2 hours at 0° C. and then 6 hours at room temperature and concentrated in vacuo to provide ethyl 3S-benzyloxycarbonylamino-2-hydroxy-5-phenylpentanimidate (6.212 g 15.3 mmol) as a crude yellow oil. MS (PCI) m/z=371 (M+1).

Reference 17

2S-Amino-4-phenyl-1-(4S-phenyl-4,5-dihydrooxazol-2-yl)butan-1-ol

A mixture comprised of ethyl 3S-benzyloxycarbonylamino-2-hydroxy-5-phenylpentanimidate (0.78 g, 1.92 mmol), provided as in Reference 16, diisopropylethylamine (0.218 µL, 1.26 mmol) and 2S-amino-2-phenylethanol (0.260 g, 1.9 mmol) in chloroform (25 mL) was heated at reflux for 3 hours and then was stirred for approximately 12 hours, while allowing to cool to room temperature. The mixture was concentrated and the residue was dissolved in ethyl acetate (50 mL). The solution was washed with 0.5N sodium hydroxide (40 mL) and brine (40 mL), dried (MgSO$_4$) and then concentrated. Product was purified from the residue by flash chromatography eluting with 1:3 hexanes/ethyl acetate to provide benzyl 2-hydroxy-2-(4,5-dihydro-4S-phenyloxazol-2-yl)-1S-phenyethylethylcarbamate (0.475 g, 1.1 mmol) as an oily mixture of diastereomers. MS (PCI) m/z=445 (M+1). ($C_{27}H_{28}N_2O_4$).

A solution comprised of benzyl 2-hydroxy-2-(4,5-dihydro-4S-phenyloxazol-2-yl)-1S-phenyethylethylcarbamate (100 mg, 0.22 mmol) in methanol (10 mL) was placed under a nitrogen atmosphere and stirred while Pearlman's catalyst (20 mg) was added. The mixture was stirred vigorously under a hydrogen atmosphere until the reaction was complete and then filtered. The filter was washed with methanol (2×25 mL). The combined filtrates were concentrated to provided 2S-amino-4-phenyl-1-(4,5-dihydro-4S-phenyloxazol-2-yl)butan-1-ol (51 mg, 0.16 mmol) as a clear oil. MS (PCI) m/z=311(M+1). ($C_{19}H_{22}N_2O_2$).

Reference 18

2S-Amino-1-oxazol-2-yl-4-phenylbutan-1-ol

A solution comprised of oxazole (0.25 g, 3.62 mmol) in THF (20 mL) was treated with borane tetrahydrofuran complex (3.62 mL, 3.62 mmol) under nitrogen and the mixture was stirred for 30 minutes and then cooled to −78° C. A solution comprised of sec-butyl lithium (2.78 mL, 3.62 mmol) in cyclohexane was added dropwise and the mixture was stirred for 30 minutes. A solution comprised of tert-butyl (S)-1-formyl-3-phenylpropylcarbamate (0.476 g, 1.81 mmol) in THF (25 mL) was added and the mixture was stirred and allowed to warm while the reaction proceeded to completion. The mixture then was cooled to −78° C., quenched by slowly adding 5% acetic acid in ethanol (20 mL), allowed to warm to ambient temperature and stirred for 18 hours. The mixture was concentrated to dryness and the residue was extracted with ether (2×25 mL). The combined extracts were washed with brine, dried (MgSO$_4$) and concentrated to dryness to provide tert-butyl 2-hydroxy-2-oxazol-2-yl-1S-phenethylethylcarbamate (0.125 g, 0.376 mmol) as a yellow oil. MS (PCI) m/z=333 (M+1).

A mixture comprised of tert-butyl 2-hydroxy-2-oxazol-2-yl-1S-phenethylethylcarbamate (0.125 g, 0.376 mmol), anisole (0.2 mL) and trifluoroacetic acid (0.6 mL) in methylene chloride (20 mL) was stirred at room temperature for 2 hours and then concentrated to provide 2S-amino-1-oxazol-2-yl-4-phenylbutan-1-ol trifluoroacetic acid salt (0.08 g, 0.229 mmol) as a yellow oil. MS (PCI) m/z=233 (M+1).

Reference 19

Methyl 2-(2S-amino-1-hydroxy-4-phenylbutyl) oxazole-4-carboxmlate

A solution comprised of methyl 2-(2S-benzyloxycarbonylamino-1-hydroxy-4-phenylbutyl)-4,5- dihydrooxazole-4-carboxylate (0.100 g, 0.235 mmol) in methylene chloride (3 mL) was cooled to 0° C. and then treated with DBU (39 mL, 0.26 mmol) and bromotrichloromethane (26 mL, 0.26 mmol). The mixture was stirred for 6 hours at 0° C., washed with ammonium chloride (10 mL) and concentrated. The residue was dried (MgSO$_4$) to provide methyl 2-(2S-benzyloxycarbonylamino-1-hydroxy-4-phenylbutyl)oxazole-4-carboxylate. MS(PCI) m/z=425 (M+1).

Deprotecting provided methyl 2-(2S-amino-1-hydroxy-4-phenylbutyl)oxazole-4-carboxylate.

Example 19
Benzyl 1S-[2-(4,5-dihydrooxazol-2-yl)-2-hydroxy-1S-phenethylethylcarbamoyl]-3-methylbutylcarbamate (Compound 210)

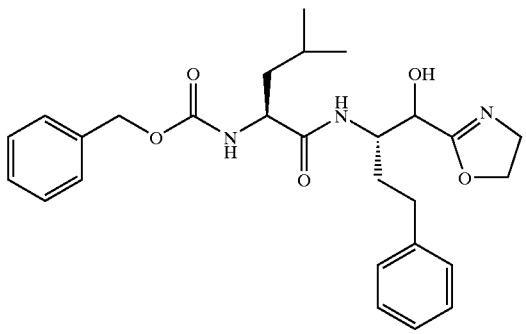

A mixture comprised of ethyl 3-(2-benzyloxycarbonylamino4-methylvalerylamino)-2-hydroxy-5-phenylpentanimidate (0.327 g, 0.63 mmol), diisopropylethylamine (0.218 mL, 1.26 mmol) and ethanolamine (38.4 mg, 0.63 mmol) in chloroform (20 mL) was heated (reflux temperature) for 3 hours and then stirred at room temperature for approximately 12 hours. The mixture was concentrated and the residue was dissolved in ethyl acetate (50 mL). The solution was washed with 0.5 M sodium hydroxide (40 mL) and brine (40 mL), dried (MgSO$_4$) and concentrated in vacuo. Product was purified from the residue by flash chromatography eluting with 3:1 ethyl acetate/hexanes to provide benzyl 1S-[2-(4,5-dihydrooxazol-2-yl)-2-hydroxy-1S-phenethylethylcarbamoyl]-3-methylbutylcarbamate (38 mg, 0.079 mmol) as a white solid. MS (PCI) m/z=482 (M+1). ($C_{27}H_{35}N_3O_5$).

Proceeding as in Example 19 provided benzyl 1S-[2-(1H-benzoimidazol-2-yl)-2-hydroxy-1S-phenyethylethylcarbamoyl]-3-methylbutylcarbamate (Compound 211);

Example 20
Benzyl 1s-[2-(4,5-dihydro-4S-phenyloxazol-2-yl)-2-hydroxy-1S-phenethylethylcarbamoyl]-3-methylbutylcarbamate (Compound 212)

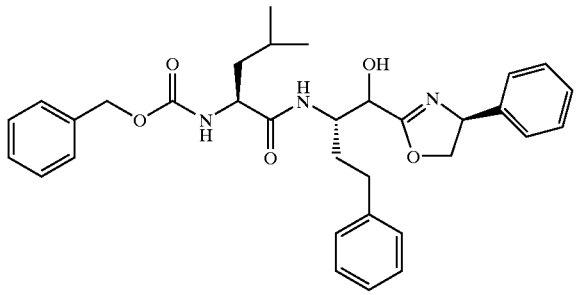

A solution comprised of 2S-amino4-phenyl-1-(4S-phenyl-4,5-dihydrooxazol-2-yl)butan-1-ol (51 mg, 0.165 mmol), provided as in Example 18, in DMF (2 mL) was cooled to 0° C. and a second solution comprised of 2,5-dioxopyrrolidin-1-yl 2S-benzyloxycarbonylamino4-methylvalerate (0.063 g, 0.174 mmol) and diisopropylethylamine (30.3 μL, 0.174 mmol) in DMF (3 mL) was added. The mixture was stirred for 2 hours, while allowing to warm to room temperature, and then concentrated. Product was purified from the residue by column chromatography eluting with ethyl 1:1 acetate/hexane to provide benzyl 1S-[2-(4,5-dihydro-4S-phenyloxazol-2-yl)-2-hydroxy-1S-phenethyletbylcarbamoyl]-3-methylbutylcarbamate (34 mg, 0.061 mmol) as a clear oil. MS (PCI) m/z=558(M+1). ($C_{33}N_{39}N_3O_5$).

Proceeding as in Example 20 provided the following compounds of Formula I:

benzyl 1S-(2-benzooxazol-2-yl-2-hydroxy-1S-phenethylethylcarbamoyl)-3-methylbutylcarbamate (Compound 213); MS (ESI) m/z=530 (M+1); $^1$H-NMR (300 MHz, CDCl$_3$,): δ 0.65–0.7 (dd, 6H), δ 0.98 (d, J=6 Hz 2H), δ 1.10–1.55 (m, 3H), δ 1.65–1.85 (m, 1H), 2.08 (m, 1H), δ 2.70 (m, 2H), δ 3.99–4.13 (m, 1H), δ 4.50(m, 1H), δ 4.90–5.21 (m, 3H), δ 6.40–6.70 (dd, 1H), δ 7.05–7.35 (m, 10H), δ 7.47 (d, J=4 Hz, 2H), δ 7.51 (d, J=2 Hz, 2H), ($C_{31}H_{35}N_3O_5$);

benzyl 1-[2-(4,5-dihydro-5-phenyloxazol-2-yl)-2-hydroxy-1-phenethylethylcarbamoyl]-3-methylbutylcarbamate (Compound 214);

benzyl 1-[2-(4,5-dihydro-4S-methyl-5S-phenyloxazol-2-yl)-2-hydroxy-1-phenyethylcarbamoyl]-3-methylbutylcarbamate (Compound 215);

benzyl 3-methyl-1-(2-hydroxy-2-naphtho[2,3-d]oxazol-2-yl-1-phenethylethylcarbamoyl}butylcarbamate (Compound 216); MS (ESI) m/z=580 (M+1); $^1$H-NMR (300 MHz, CDCl$_3$): δ 0.65–0.95 (m, 6H), δ 1.25 (m, 3H), δ 1.54 (m, 3H), δ 2.20 (m, 1H), δ 2.82 (t, J=4 Hz, 2H), δ 4.00–4.20 (m, 1H), δ 4.35–4.55 (m, 1H), δ 4.90–5.09 (m, 3H), δ 6.60 (m, 1H), δ 7.23 (m, 10H), δ 7.56 (m, 2H), δ 7.96 (m, 3H), δ 8.18 (s, 1H), ($C_{35}H_{37}N_3O_5$);

benzyl 1S-(2-benzooxazol-2-yl-2-hydroxy-1S-phenethylethylcarbamoyl)-2-methylpropylcarbamate (Compound 217);

benzyl 1S-(2-benzooxazol-2-yl-2-hydroxy-1S-phenethylethylcarbamoyl)-3-methylbutylcarbamate (Compound 218);

benzyl 1S-[2-(4,5-dihydro-4,4-dimethyloxazol-2-yl)-2-hydroxy-1S-phenethylethylcarbamoyl]-3-methylbutylcarbamate (Compound 219), MS(PCI) m/z=510 (M+1); $^1$HNMR (CDCl$_3$): δ 0.8–0.99(d, J=6 Hz, 6H), 1.11–1.35 (m, 6H), δ 1.4–1.78 (m, 3H), δ 1.82–2.01 (m, 2H), δ 2.55–2.72 (m, 2H), δ 3.95 (m, 1H), δ 4.0–4.25 (m, 3H), δ 4.30 (s, 1H), δ 5.10 (s, 2H), δ 5.35 (s, 1H), δ 6.58 (m, 1H) 7.1–7.37 (m, 10H); ($C_{29}H_{39}N_3O_5$);

methyl 2-[2-(2-benzyloxycarbonylamino-4-methylvalerylamino)-1-hydroxy-4-phenylbutyl]-4,5-dihydrooxazole-4-carboxylate (Compound 220), MS(PCI) m/z=540 (M+1); $^1$H NMR (CDCl$_3$): δ 0.8–0.99 (d, J=6 Hz, 6H),1.25 (m, 1H), δ 1.47 (m, 1H) 1.65 (m, 2H), δ 1.99 (m, 2H), δ 2.15 (s, 1H), δ 2.65 (t, J=4 Hz, 2H), δ 3.70 (s, 3H) 4.18 (m, 1H), δ 4.25–4.50 (m, 3H), δ 4.51–4.64 (m, 2H), δ 5.17 (m, 2H), δ 5.35 (d, J=5 Hz, 1H) 6.65 (d, J=6 Hz, 1H), δ 7.17–7.45(m, 10H); ($C_{29}H_{37}N_3O_7$);

methyl 2-[2-(2,2-dimethylpropionylamino)-4-phenylbutyryl]oxazole-4-carboxylate (Compound 221); MS (ESI) m/z=373 (M+1); $^1$H-NMR (300 MHz, CDCl$_3$): δ 1.25 (s, 9H), δ 2.20 (m, 1H), δ 2.46 (m, 1H), δ 2.77 (t, J=4 Hz, 2H), δ 3.99 (s, 3H), δ5.55 (m, 1H), δ 6.41 (d, J=4 Hz, 1H), δ 7.20–7.38 (m, 5H), δ 8.41 (s, 1H), (C$_{20}$H$_{24}$N$_2$O$_5$);

tert-butyl 4-{1S-[2-(5-tert-butylbenzooxazol-2-yl)-2-hydroxy-1S-phenethylethylcarbamoyl]-3-methylbutylcarbamoyl}piperidine-1-carboxylate (Compound 222);

tert-butyl 4-{1S-[2-hydroxy-1S-phenethyl-2-(5-sulfamoylbenzooxazol-2-yl)ethylcarbamoyl]-3-methylbutylcarbamoyl}piperidine-1-carboxylate (Compound 223);

tert-butyl 4-[1S-(2-hydroxy-2-naphtho[1,2-d]oxazol-2-yl-1S-phenethylethylcarbamoyl)-3-methylbutylcarbamoyl]piperidine-1-carboxylate (Compound 224);

tert-butyl 4-[1S-(2-hydroxy-2-naphtho[2,1-d]oxazol-2-yl-1S-phenethylethylcarbamoyl)-3-methylbutylcarbamoyl]piperidine-1-carboxylate (Compound 225);

tert-butyl 4-{1S-[2-hydroxy-1S-phenethyl-2-(5-phenylbenzooxazol-2-yl)ethylcarbamoyl]-3-methylbutylcarbamoyl}piperidine-1-carboxylate (Compound 226);

tert-butyl 4-[1S-(2-benzooxazol-2-yl)-2-hydroxy-1S-phenethylethylcarbamoyl)-2-methylbutylcarbamoyl]piperidine-1-carboxylate (Compound 227); MS (ESI) m/z=607 (M+1); $^1$H-NMR (300 MHz, CDCl$_3$): δ 0.50–0.61 (m, 1H), δ 0.75–0.98 (m, 6H), δ 1.22 (m, 1H), δ 1.41 (s, 9H), δ 1.81–1.85 (m, 1H), δ 1.99–2.06 (m, 1H), δ 2.70 (m, 2H), 4.24 (d, J=2 Hz 2H), δ 4.50–4.70 (m, 1H), δ 4.99–5.14 (m, 2H), δ 6.96–7.81 (m, 15H), (C$_{34}$H$_{46}$N$_4$O$_6$);

tert-butyl 3-[1S-(2-benzooxazol-2-yl)-2-hydroxy-1S-phenethylethylcarbamoyl)-2-methylbutylcarbamoyl]benzylcarbamate (Compound 228);

tert-butyl 4-[1S-(2-benzooxazol-2-yl)-2-hydroxy-1S-phenethylethylcarbamoyl)-2cyclohexylethylcarbamoyl]piperidine-1-carboxylate (Compound 229);

benzyl 3-methyl-1S-[2-hydroxy-1S-phenethyl-2-(5-phenyloxazol-2-yl)ethylcarbamoyl]butylcarbamate (Compound 230); MS (ESI) m/z=556 (M+1); $^1$H-NMR (300 MHz, CDCl$_3$): δ 0.75–0.95 (m, 6H), δ 1.25–1.80 (m, 5H), δ 2.00 (m, 2H), δ 2.67 (m, 2H), δ 4.15 (m, 1H), δ 4.55(m, 1H), δ 4.85–5.20 (m, 2H), δ 5.50 (m, 1H), δ 6.80 (d, J=6 Hz, 1H), δ 7.12–7.48 (m, 14H), δ 7.62 (d, J=2 Hz, 2H), (C$_{33}$H$_{37}$N$_3$O$_5$);

pyrid-3-yl 3-methyl-1S-[2-hydroxy-1S-phenethyl-2-(5-phenyloxazol-2-yl)ethylcarbamoyl]butylcarbamate (Compound 231); MS (ESI) m/z=527 (M+1); $^1$H-NMR (300 MHz, CDCl$_3$): δ 0.75–0.95 (m, 6H), δ 1.45–1.75 (m, 5H), δ 2.00 (m, 2H), δ 2.67 (m, 2H), δ 4.40–5.10 (m, 3H), δ 5.60(s, 1H), δ 7.00–7.47 (m, 10H), δ 7.62 (m, 2H), δ 8.15 (m, 1H), δ 8.65 (m, 1H), δ 9.15 (m, 1H), (C$_{31}$H$_{34}$N$_4$O$_4$); and benzyl 1S-[2-hydroxy-1S-phenethyl-2-(5-phenyloxazol-2-yl)ethylsulfamoylmethyl]-2R-methylbutylcarbamate (Compound 232); MS (ESI) m/z=606 (M+1); $^1$H-NMR (300 MHz, CDCl$_3$): δ 0.75–0.95 (m, 6H), δ 1.30–1.50 (m, 5H), δ 1.98 (m, 2H), δ 2.77 (m, 3H), δ 3.55 (m, 2H), δ 4.09 (m, 1H), δ 4.90–5.10 (m, 3H), δ 5.60 (m, 1H), δ 7.02–7.47 (m, 14H), δ 7.62 (m, 2H), (C$_{33}$H$_{39}$N$_3$O$_6$S).

Example 21

Benzyl 3-methyl-1S-(1S-pyrid-2-ylcarbonyl-3-phenylpropylcarbamoyl)butylcarbamate (Compound 233)

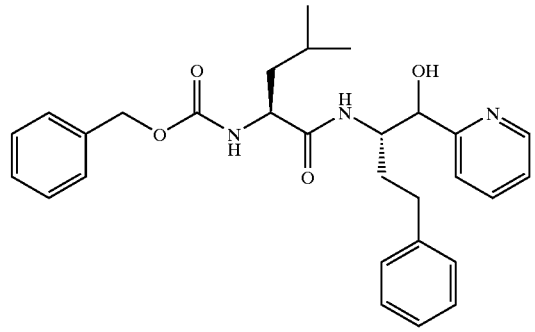

A solution comprised of 2-bromopyridine (0.291 mL, 3.06 mmol) in dry THF (2 mL) was cooled to −78° C. and then a solution of n-butyllithium (1.6 mL, 2.72 mmol) in pentane was added dropwise over 2 minutes. The mixture was stirred at −78° C. for 10 minutes and then a solution of benzyl 1-[1-(N-methoxy-N-methylcarbamoyl)-3-phenylpropylcarbamoyl]-3-methylbutylcarbamate (0.3 g, 0.64 mmol) in THF (2 mL) was added slowly. The mixture was stirred, while allowing to slowly warm to room temperature, and then poured into a solution comprising acetic acid (0.163 mL) in diethyl ether (50 mL). The organic phase was washed with brine (40 mL), dried (MgSO$_4$) and concentrated in vacuo. Product was purified from the residue by flash chromatography on silica gel eluting with 1:2 ethyl acetate/hexanes to provide benzyl 3-methyl-1-(1-pyrid-2-ylcarbonyl-3-phenylpropylcarbamoyl)butylcarbamate (82 mg, 0.17 mmol) as a white solid. MS (ESI) m/z=488 (M+1); $^1$H NMR (CDCl$_3$): δ 0.8–1.05 (d, J=4 Hz, 6H), 1.5 (m, 1H), δ 1.6–1.78 (t, 2H), δ 1.99–2.20 (m, 1H), δ 2.6–2.9 (m, 1H), δ 2.55–2.85 (m, 2H), δ 4.25 (m, 1H), δ 5.17 (s, 2H), δ 5.25 (m, 1H), δ 6.00 (m, 1H), δ 6.85–6.95 (d, J=10 Hz, 1H), δ 7.1–7.4 (m, 10H) 7.50(t, J=4 Hz, 1H), δ 7.85 (t, J=6 Hz, 1H) 8.01 (d, J=8 hz, 1H), δ 8.69 (m, 1H). Anal (C$_{29}$H$_{33}$N$_3$O$_4$).

Proceeding as in Example 21 provided the following compounds of Formula I:

benzyl 1-[1-(pyrid-3-ylcarbonyl)-3-phenylpropylcarbamoyl]-3-methylbutylcarbamate (Compound 234), MS(PCI) m/z=488 (M+1); $^1$H NMR (CDCl$_3$): δ 0.8–1.05 (d, J=4 Hz, 6H)), 1.5 (m, 1H), δ 1.6–1.78 (t, 2H), δ 1.80–2.01 (m, 2H), δ 2.25 (m, 1H) 2.6–2.9 (t, J=3 Hz, 1H), δ 2.55–2.85 (m, 2H), δ 4.30 (m, 1H), δ 5.17 (s, 2H), δ 5.35 (d, J=6 Hz, 1H), δ 5.55 (m, 1H), δ 7.02 (d, J=8 Hz, 1H), δ 7.1–7.4 (m, 10H) 8.05(d, J=5 Hz, 1H), δ 8.78 (d, J=4 Hz, 1H), δ 9.10 (s, 1H); (C$_{29}$H$_{33}$N$_3$O$_4$); and benzyl 1-[1-(quinol-3-ylcarbonyl)-3-phenylpropylcarbamoyl]-3-methylbutylcarbamate (Compound 235), MS(PCI) m/z=538 (M+1); $^1$H NMR (CDCl$_3$): δ 0.8–1.05 (d, J=4 Hz, 6H), 1.5 (m, 1H), δ 1.6–1.78 (m, 2H), δ 1.99–2.20 (m, 1H), δ 2.6–2.9 (m, 1H), δ 2.55–2.85 (m, 2H), δ 4.35 (m, 1H), δ 5.17–5.25 (m, 3H), δ 5.70 (m, 1H), δ 6.75–6.85 (d, J=10 Hz, 1H), δ 7.20–7.45 (m, 10H), δ 7.65 (t, J=6 Hz, 2H), δ 7.77–7.90 (m, 2H), δ 8.22 (d, J=7, 1H), δ 8.46 (s, 1H), δ 9.4 (s, 1H); (C$_{33}$H$_{35}$N$_3$O$_4$).

Example 22

Benzyl 1-[1-(1H-indol-5-ylcarbonyl)-3-phenylpropylcarbamoyl]-3-methylbutylcarbamate (Compound 236)

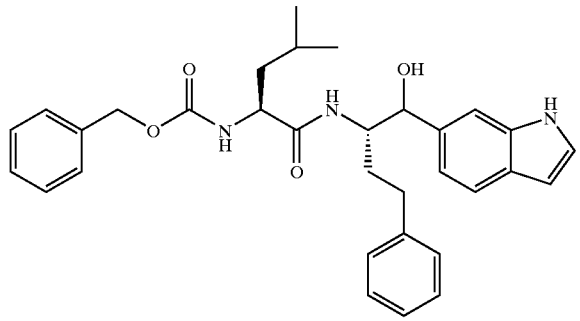

A mixture comprised of potassium hydride (0.29 g, 2.56 mmol, 67% in mineral oil) in anhydrous ether (5 mL) was cooled to 0° C. and then a solution comprised of 5-bromo-1H-indole (0.5 g, 2.56 mmol) in anhydrous ether (5 ml) was added. The mixture was stirred for 15 minutes and then cooled to −78° C. under nitrogen. A solution comprised of tert-butyllithium (3 mL in pentane, 5.08 mmol) in anhydrous ether (5 mL) was cooled to −78° C. and added to the indole mixture over 2 minutes. The mixture was stirred for 10 minutes and then a solution comprised of benzyl 1-[1-(N-methoxy-N-methylcarbamoyl)-3-phenylpropylcarbamoyl]-3-methylbutylcarbamate (0.3 g, 0.64 mM) in ether (10 mL) was added. The mixture was allowed to warm to room temperature and then poured into a cold solution at 0° C. of phosphoric acid (25 mL, 1 M in water). The aqueous layer was separated and extracted with ethyl acetate (25 mL). The organic layers were combined and washed with saturated sodium bicarbonate (25 mL), dried (MgSO$_4$) and concentrated. The product was purified from the residue by flash chromatography on silica gel eluting with 1:2 ethyl acetate/hexanes to provide benzyl 1-[1-(1H-indol-2-ylcarbonyl)-3-phenylpropylcarbamoyl]-3-methylbutylcarbamate (112 mg, 0.21 mmol) as a white solid. MS (ESI) m/z=526(M+1); $^1$H NMR (CDCl$_3$): δ 0.8–1.05 (d, J=4 Hz, 6H), 1.5 (s, 1H), δ 1.5–1.78 (m, 3H), δ 2.00 (m, 1H), δ 2.4 (m, 1H), δ 2.65 (m, 2H), δ 4.35 (m, 1H), δ 5.17 (s, 2H), δ 5.25 (d,J=6 Hz 1H), δ 5.75 (m, 1H), δ 6.55 (s, 1H) 7.05 (d, J=4 Hz, 1H), δ 7.1–7.45 (m, 10H) 7.7(d, J=4 Hz, 1H), δ 8.15 (d, J=4 Hz, 1H) 8.78 (m, 1H). (C$_{32}$H$_{35}$N$_3$O$_4$).

Example 23 benzyl 1-[1-(benzofur-2-ylcarbonyl)-3-phenylpropylcarbamoyl]-3-methylbutylcarbamate (Compound 237)

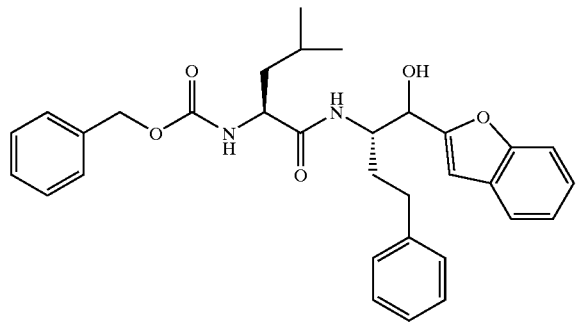

A solution comprised of benzofuran (0.302 g, 2.56 mmol) in anhydrous ether (5 mL) was cooled to −15° C. under a nitrogen atmosphere and then a solution of n-butyllithium (1.6 mL in hexanes) was added dropwise over 2 minutes. The mixture was stirred for 1 hour and then a solution comprised of benzyl 1-[1-(N-methoxy-N-methylcarbamoyl)-3-phenylpropylcarbamoyl]-3-methylbutylcarbamate (0.3 g, 0.64 mmol) in diethyl ether was added. The mixture was stirred at −15° C. until the reaction was complete. The mixture was quenched with a solution of acetic acid (0.153 mL) in diethyl ether (50 mL). The organic phase was washed with brine (40 mL), dried (MgSO$_4$) and concentrated in vacuo. The product was purified from the residue by flash chromatography eluting with 2:3 ethyl acetate/hexanes to provide benzyl 1-[1-(benzofur-2-ylcarbonyl)-3-phenylpropylcarbamoyl]-3-methylbutylcarbamate (70 mg, 0.13 mmol) as a white solid. $^1$H NMR (CDCl$_3$): δ 0.8–0.99 (d, J=4 Hz, 6H), 1.5 (m, 1H), δ 1.6–1.72 (m, 2H), δ 1.99–2.18 (m, 1H), δ 2.22–2.41 (m, 1H), δ 2.6–2.75 (m, 2H), δ 4.21 (m, 1H), δ 5.01 (m, 1H), δ 5.17 (s, 2H), δ 5.50 (m, 1H), δ 6.75–6.81 (d, J=7 Hz, 1H), δ 7.10–7.37 (m, 11H) 7.4–7.59(m, 3H), δ 7.64 (d, J=7 Hz, 1H). (C$_{32}$H$_{34}$N$_2$O$_5$).

Proceeding as in Example 23 provided the following compounds of Formula I:

benzyl 1-[1-(benzothiazol-2-ylcarbonyl)-3-phenylpropylcarbamoyl]-3-methylbutylcarbamate (Compound 238), $^1$H NMR (CDCl$_3$): δ 0.91 (d, J=5.88 Hz, 6H), δ 1.39–1.54 (m, 1H), δ 1.60–1.72 (m, 2H), δ 2.11–2.25 (m, 1H), δ 2.40–2.54 (m, 1H), δ 2.72 (m, 2H), δ 4.21 (m, 1H), δ 5.10 (s, 3H), δ 5.84 (m, 1H), δ 6.87 (d, J=8.15 Hz, 1H), δ 7.10–7.40 (m, 10H), δ 7.54 (dt, J=1.62, 8.10 Hz, 1H), δ 7.58 (dt, J=1.46, 7.80 Hz, 1H), δ 7.97 (dd, J=1.80, 8.15 Hz, 1H), δ 8.17 (dd, J=1.66, 7.67 Hz, 1H);

benzyl 3-methyl-1S-(3-phenyl-1S-thiazol-2-ylcarbonylpropylcarbamoyl)butylcarbamate (Compound 239);

N-[3-methyl-1S-(3-phenyl-1S-thiazol-2-ylcarbonylpropylcarbamoyl)butyl]-4-methylpiperazine-1-carboxamide (Compound 240);

tert-butyl 4-[3-methyl-1S-(3-phenyl-1S-thiazol-2-ylcarbonylpropylcarbamoyl)butylcarbamoyl]piperazine-1-carboxylate (Compound 241);

benzyl 3-methyl-1S-(3-phenyl-1S-thien-2-ylcarbonylpropylcarbamoyl)butylcarbamate (Compound 242);

benzyl 1S-[1S-(1-methyl-1H-imidazol-2-ylcarbonyl-3-phenylpropylcarbamoyl]-methylbutylcarbamate (Compound 243):

benzyl 1S-(1S-thiazol-2-ylcarbonyl)-3-phenylpropylcarbamoyl)-2-methylpropylcarbamate (Compound 244);

N-[3-methyl-1S-(3-phenyl-1S-thiazol-2-ylcarbonylpropylcarbamoyl)butyl]piperazine-1-carboxamide (Compound 245);

benzyl 1S-[1S-(4-methylthiazol-2-ylcarbonyl)-3-phenylpropylcarbamoyl]-3-methylbutylcarbamate (Compound 246);

benzyl 1S-(1S-furyl-2-ylcarbonyl)-3-phenylpropylcarbamoyl)-3-methylbutylcarbamate (Compound 247), $^1$H NMR (CDCl$_3$): δ 0.91 (d, J=6.18 Hz, 6H), δ 1.42–1.70 (m, 3H), δ 1.98–2.13 (m, 1H), δ 2.19–2.37 (m, 1H), δ 2.69 (t, J=7.60 Hz, 2H), δ 4.22 (m, 1H), δ 5.10 (d, J=7.76 Hz, 1H), δ 5.12 (s, 2H), δ 5.54 (m, 1H), δ 6.76 (d, J=8.15 Hz, 1H), δ 7.16–7.36 (m, 10H), δ 7.39 (dt, J=1.82, 7.86 Hz, 1H), δ 7.47 (dt, J=1.63, 7.79 Hz, 1H), δ 7.69 (s, 1H), δ 7.80 (d, J=7.15 Hz, 1H), δ 7.85 (d, J=8.18 Hz, 1H);

benzyl 1S-[1S-(1-benzyl-1H-imidazol-2-ylcarbonyl-3-phenylpropylcarbamoyl]-3-methylbutylcarbamate (Compound 248);

benzyl 3-phenyl-1-(4,5-dihydro-4S-phenyloxazol-2-ylcarboyl)propyl]carbamate (Compound 249);

benzyl 3-phenyl-1-(4,5-dihydro-5-phenyloxazol-2-ylcarbonylpropyl]carbamate (Compound 250);

benzyl [1-(4,5-dihydro-4S-methyl-5S-phenyloxazol-2-ylcarbonyl)-3-phenylpropyl]carbamate (Compound 251); and ethyl 2-[2-(2-benzyloxycarbonylamino-4-methylvalerylamino)-4-phenylbutyryl]thiazole-4-carboxylate (Compound 252).

Example 24

Methyl 2-[2-(2-benzyloxycarbonylamino-4-methylvalerylamino)-1-hydroxy-4-phenylbutyl]oxazole-4-carboxylate (Compound 253)

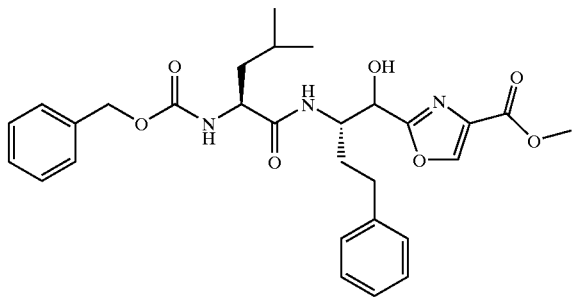

A solution comprised of methyl 2-[2-(2-benzyloxycarbonylamino-4-methylvalerylamino)-1-hydroxy-4-phenylbutyl]-4,5-dihydrooxazole-4-carboxylate (0.036 g, 0.067 mmol) in methylene chloride (3 mL) was cooled to 0° C. and then DBU (11.2 mg, 72.7 µmol) and bromotrichloromethane (14.6 mg, 73.7 µmol) were added. The mixture was stirred for 6 hours at room temperature and concentrated. The residue was dissolved in ethyl acetate (20 mL) and the solution was dried (MgSO$_4$) and concentrated. The product was purified from the residue by flash chromatography eluting with 1:3 hexanes/ethyl acetate to provide methyl 2-[2-(2-benzyloxycarbonylamino-4-methylvalerylamino)-1-hydroxy-4-phenylbutyl]oxazole-4-carboxylate (12 mg, 0.022 mmol) as a white solid. MS(PCI) m/z=538 (M+1) $^1$H NMR (CDCl$_3$): δ 0.8–1.05 (d, J=4 Hz, 6H), δ 1.55–1.70 (m, 3H), δ 2.00 (m, 1H), δ 2.40 (m, 1H), δ 2.69 (m, 2H), δ 3.99 (m, 3H) 4.45 (m, 1H), δ 5.17 (s, 2H), δ 5.78 (m, 1H), δ 7.01 (d, J=4 Hz 1H), δ 7.14–7.47 (m, 10H) 7.72(d, J=4 Hz, 1H), δ 8.40 (s, 1H). (C$_{29}$H$_{35}$N$_3$O$_7$).

Example 25

2-[2-(2-Benzyloxycarbonylamino-4-methylvalerylamino)-1-hydroxy-4-phenylbutyl]oxazole-4-carboxylic acid (Compound 254)

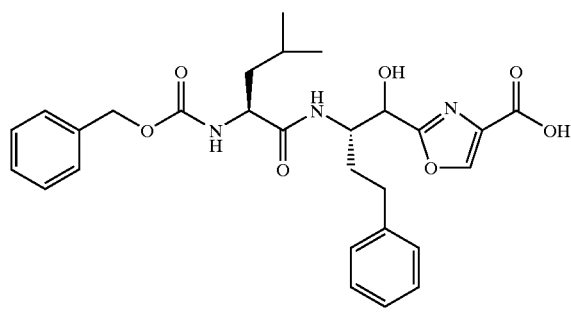

A mixture comprised of methyl 2-[2-(2-benzyloxycarbonylamino-4-methylvalerylamino)-1-hydroxy-4-phenylbutyl]oxazole-4-carboxylate (2.16 g, 4.02 mmol), provided as in Example 18, and sodium hydroxide (0.815 mL, 1.63 M in water) in methanol (10 mL) was stirred for approximately 12 hours at room temperature, acidified with 1 M hydrochloric acid and concentrated. The residue was dissolved in ethyl acetate (50 mL) and the solution dried (MgSO$_4$). The product was recrystallized from methanol and ether to provide 2-[2-(2-benzyloxycarbonylamino-4-methylvalerylamino)-1-hydroxy-4-phenylbutyl]oxazole-4-carboxylic acid (1.77 g, 3.38 mmol) as an off white solid.

Example 26

Benzyl 3-methyl-1-[2-hydroxy-1-phenethyl-2-(4-phenylcarbamoyloxazol-2-yl)ethylcarbamoyl]butylcarbamate (Compound 255)

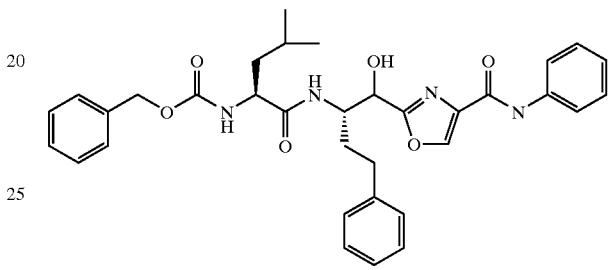

A solution comprised of 2-[2-(2-benzyloxycarbonylamino-4-methylvalerylamino)-1-hydroxy-4-phenylbutyl]oxazole-4-carboxylic acid (0.05 g, 0.096 mmol), provided as in Example 7, in DMF (5 mL) was stirred while PyBOP® (0.05 g, 0.096 mmol) and aniline (9 mg, 0.096 mmol) were added. The mixture was stirred for an additional 2 minutes and diisopropylethylamine (12.4 mg, 0.096 mmol) was added. The mixture was stirred for 2 hours at room temperature, poured into cold water 0° C. at and extracted with ethyl acetate (4×30 mL). The extracts were combined, dried (MgSO$_4$) and then concentrated. The product was purified from the residue by flash chromatography eluting with 1:2 hexanes/ethyl acetate to provide benzyl 3-methyl-1-[2-hydroxy-1-phenethyl-2-(4-phenylcarbamoyloxazol-2-yl)ethylcarbamoyl]butylcarbamate (30 mg, 0.05 mmol) as a white solid. MS (ESI)) m/z=599 (M+1); $^1$H NMR (CDCl$_3$): δ 0.8–1.05 (d, J=4 Hz, 6H), 1.35 (m, 1H), δ 1.55 (m, 1H), δ 2.00–2.15 (m, 2H), δ 2.62 (m, 2H), δ 2.80 (m, 2H), δ 3.65 (m, 2H), δ 4.11 (m, 1H1), δ 4.30 (m, 1H), δ 4.45 (m, 1H), δ 4.95 (s, 1H) 5.17 (s, 2H), δ 5.2 (d, J=4 Hz, 1H), δ 6.70 (d, J=5 Hz 1H), δ 7.1–7.45 (m, 15H) 7.7(d, J=4 Hz, 1H), δ 8.19 (s, 1H), δ 8.99 (s, 1H), (C$_{34}$H$_{38}$N$_4$O$_6$).

Proceeding as in Example 26 provided the following compounds of Formula I:

benzyl 1-[2-(4-benzylcarbamoyloxazol-2-yl)-2-hydroxy-1-phenethylethylcarbamoyl]-3-methylbutylcarbamate (Compound 256), MS (ESI)) m/z=613 (M+1); $^1$H NMR (CDCl$_3$): δ 0.8–1.05 (d, J=4 Hz, 6H), δ 1.25–1.75 (m, 3H), δ 2.00–2.20 (m, 2H), δ 2.69 (m, 2H), δ 3.85 (m, 1H), δ 3.95 (m, 1H), δ 4.25 (m, 1H), δ 4.60 (m, 2H), δ 4.80 (s, 1H), δ 5.17 (s, 2H), δ 5.59 (m, 1H), δ 6.59 (d, J=4 Hz 1H), δ 7.05–7.47 (m, 15H), δ 8.20 (s, 1H); (C$_{35}$H$_{40}$N$_4$O$_6$); and benzyl 3-methyl-1-[2-hydroxy-1-phenethyl-2-(4-phenyethylcarbamoyloxazol-2-yl)ethylcarbamoyl]butylcarbamate (Compound 257), MS (ESI)) m/z=627 (M+1); $^1$H NMR (CDCl$_3$): δ 0.8–1.05 (d, J=4 Hz, 6H), δ 1.25–1.75 (m, 4H), δ 2.00 (m, 2H), δ 2.59 (m, 2H) 2.88 (m, 2H), δ 3.65 (m, 2H), δ 4.02 (m, 1H), δ 4.25 (m,1 H), δ 4.80 (s, 1H), δ 5.17 (s, 2H), δ 6.59 (d, J=4 Hz, 1H), δ 7.00–7.42 (m, 15H), δ 8.20 (s, 1H); (C$_{36}$H$_{42}$N$_4$O$_6$).

Example 27 benzyl 1-[1-(4,5-dihydro-4S-phenyloxazol-2-ylcarbonyl)-3-phenylpropylcarbamoyl]-3-methylbutylcarbamate (Compound 258)

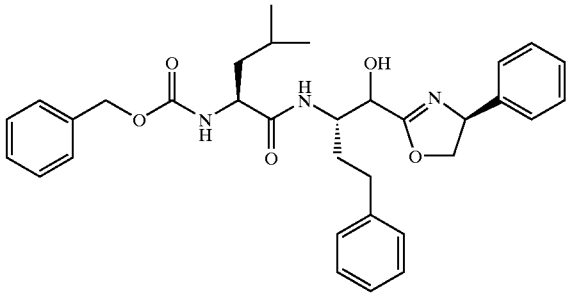

A solution comprised of benzyl 1S-[2-(4,5-dihydro-4S-phenyloxazol-2-yl)-2-hydroxy-1S-phenethylethylcarbamoyl]-3-methylbutylcarbamate (0.038 g, 0.078 mmol), provided as in Example 14, and Dess-Martin Periodinane (0.031 g, 0.072 mmol) in methylene chloride (5 mL) was stirred while a mixture of 0.001:1 methylene chloride/water (2 mL) was slowly added. The mixture was stirred until the reaction was complete and then concentrated. The residue was dissolved in ethyl acetate (50 mL) and the solution was washed with saturated sodium bicarbonate (40 mL), sodium thiosulfate (40 mL, 10% wt/wt), water (40 mL) and brine (40 mL), dried (MgSO$_4$) and then concentrated. Product was purified from the residue by flash chromatography eluting with 3:1 ethyl acetate/hexanes to provide benzyl 1-[1-(4,5-dihydro-4S-phenyloxazol-2-ylcarbonyl)-3-phenylpropylcarbamoyl]-3-methylbutylcarbamate (0.014 g, 37.5%) as a white solid. MS (PCI) m/z=556 (M+1) $^1$H NMR (CDCl$_3$): δ 0.8–1.05 (d, J=6 Hz, 6H), δ 1.4–1.78 (m, 3H), δ 1.87–2.12 (m, 1H), δ 2.40 (m, 1H), δ 2.65(t, J=4 Hz, 2H), δ 4.25 (t, J=3 Hz, 2H), δ 4.75 (t, J=4 Hz, 1H), δ 5.10 (s, 2H), δ 5.40(d J=3 Hz, 1H), δ 5.50 (t, J=4 Hz, 1H), δ 6.97 (d, J=3 Hz, 1H) 7.1–7.49(m, 15H). (C$_{33}$H$_{37}$N$_3$O$_5$).

Proceeding as in Example 27 provided the following compounds of Formula I:

benzyl 1S-(1S-benzooxazol-2-ylcarbonyl-3-penylcarbamoyl)-3-methylbutylcarbamate (Compound 259);

benzyl 1S-[1S-(4,5-dihydrooxazol-2-ylcarbonyl)-3-phenylpropylcarbamoyl]-3-methylbutylcarbamate (Compound 260), MS (PCI) m/z=480 (M+1) $^1$H NMR (CDCl$_3$): δ 0.8–1.05 (d, J=6 Hz, 6H), δ 1.4–1.78 (m, 3H), δ 1.82–2.01 (m, 2H), δ 2.65 (t, J=5 Hz 2H), δ 2.99 (t, J=4 Hz, 1H), δ 3.75 (d, J=3 Hz,1H), δ 4.10–4.35 (m, 3H), δ 4.50 (m, 1H), δ 5.17 (s, 3H), δ 6.85 (s, 1H), δ 7.1–7.49(m, 10H), (C$_{27}$H$_{33}$N$_3$O$_5$);

N-[3-methyl-1S-(3-phenyl-1S-benzooxazol-2-ylcarbonylpropylcarbamoyl)bulyl]piperidine-4-carboxamide (Compound 261), $^1$H NMR (DMSO-d$_6$): δ 0.83 (d, J=6.91 Hz, 6H), δ 1.34–1.87 (m, 7H), δ 1.92–2.07 (m, 1H), δ 2.20–2.33 (m, 1H), δ 2.41–2.54 (m, 1H), δ 2.62–2.92 (m, 4H), δ 3.26 (bd, J=12.12 2H), δ 4.39 (m, 1H), δ 5.18 (m, 1H), δ 7.16–7.33 (m, 5H), δ 7.54 (t, J=7.64 Hz, 1H), δ 7.64 (t, 7.82 Hz, 1H), δ 7.87 (d, J=8.40 Hz, 1H), δ 7.96 (d, J=7.67 Hz, 1H), δ 8.07 (d, J=8.15 Hz, 1H), δ 8.29 (bs, 1H), δ 8.60 (bs, 1H), δ 8.76 (d, J=6.45 Hz, 1H);

benzyl 1-[1-(4,5-dihydro-5-phenyloxazol-2-ylcarbonyl)-3-phenylpropylcarbamoyl]3-methylbutylcarbamate (Compound 262);

benzyl 1-[1-(4,5-dihydro-5S-phenyl-4S-methyloxazol-2-ylcarbonyl)-3-phenylpropylcarbamoyl)-3-methylbutylcarbamate (Compound 263);

benzyl 1S-(1S-phenethyl-2-benzimidazol-2-yl-1-oxoethylcarbamoyl)-3-methylbutylcarbamate (Compound 264), $^1$H NMR (CDCl$_3$): δ 0.82–0.96 (m, 6H), δ 1.44–1.75 (m, 3H), δ 2.17–2.32 (m, 1H), δ 2.43–2.56 (m, 1H), δ 2.61–2.80(m, 2H), δ 4.55 (m, 1H), δ 5.13 (m, 2H), δ 5.35 (d, J=8.67 Hz, 1H), δ 5.70–5.88 (m, 1H), δ 7.00–7.42 (m, 14H), δ 7.50–7.83 (m, 2H);

benzyl 1-[1-(naphtho[2,3-d]oxazol-2-ylcarbonyl)-3-phenylpropylcarbamoyl]-3-methylbutylcarbamate (Compound 265);

methyl 2-[2-(2-benzyloxycarbonylamino-4-methylvalerylamino)-4-phenylbutyryl]-4,5-dihydrooxazole-4-carboxylate (Compound 266), MS(PCI) m/z=538 (M+1); $^1$H NMR (CDCl$_3$): δ 0.8–0.99 (d, J=6 Hz, 6H),1.25 (m, 1H), δ 1.47 (m, 1H) 1.65 (m, 3H), δ 1.99 (m, 1H), δ 2.35 (m, 1H), δ 2.65 (m, 2H), δ 3.70 (m, 3H) 4.18 (m, 2H), δ 4.55 (m, 1H), δ 5.17 (s, 2H), δ 5.35 (m, 1H) 6.75 (m, 1H), δ 7.17–7.45(m, 10H), (C$_{29}$H$_{35}$N$_3$O$_7$);

benzyl 1S-[1S-(4,5-dihydro-4,4-dimediyloxazol-2-ylcarbonyl)-3-phenylpropylcarbamoyl]-3-methylbutylcarbamate (Compound 267), MS(PCI) m/z=508 (M+1); $^1$H NMR (CDCl$_3$): δ 0.8–0.99 (d, J=6 Hz, 6H), δ 1.36 (s, 6H), δ 1.5 (m, 1H), δ 1.65 (m, 2H) 1.82–2.01 (m, 1H), δ 2.35 (m, 1H), δ 2.6 (t, J=6 Hz, 2H), δ 4.05 (s, 2H), δ 4.25 (m, 2H), δ 5.10 (s, 2H), δ 5.4 (m, 1H), δ 6.75 (d J=8 Hz, 1H) 7.1–7.38(m, 10H); (C$_{29}$H$_{37}$N$_3$O$_5$);

benzyl 1S-(1S-benzooxazol-2-ylcarbonyl-3-phenylpropylcarbamoyl)-2-methylpropylcarbamate (Compound 268), $^1$H NMR (CDCl$_3$): δ 0.90 (d, J=6.91 Hz, 3H), δ 0.97 (d, J=6.94 Hz, 3H), δ 2.06–2.25 (m, 2H), δ 2.38–2.55 (m, 1H), δ 2.74 (m, 2H). δ 4.03 (dd, J=1.73, 6.45 Hz, 1H), δ 5.10 (s, 2H), δ 5.29 (d, J=8.67 Hz, 1H), δ 5.73 (m, 1H), δ 6.66 (d, J=7.42 Hz, 1H), δ 7.09–7.40 (m, 10H), δ 7.46 (dt, J=1.62, 8.10 Hz, 1H), δ 7.55 (dt, J=1.83, 7.76 Hz, 1H), δ 7.64 (d, J=8.06 Hz, 1H), δ 7.89 (d, J=7.46 Hz, 1H);

benzyl 1S-(1S-benzooxazol-2-ylcarbonyl-3-phenylproylcarbamoyl)-2-methylbutylcarbamate (Compound 269), $^1$H NMR (CDCl$_3$): δ 0.88 (t, J=7.43 Hz, 3H), δ 0.91 (d, J=6.67 Hz, 3H), δ 1.04–1.21 (m, 1H), δ 1.40–1.55 (m, 1H), δ 1.78–1.93 (m, 1H), δ 2.10–2.24 (m, 1H), δ 2.40–2.54 (m, 1H), δ 2.74 (t, J=7.60 Hz, 2H), δ 4.06 (t, J=6.21 Hz, 1H), δ 5.09 (s, 2H), δ 5.29 (d, J=8.67 Hz, 1H), δ 5.72 (m, 1H), δ 6.66 (d, J=8.00 Hz, 1H), δ 7.09–7.39 (m, 10H), δ 7.46 (dt, J=1.68, 7.80 Hz, 1H), δ 7.55 (dt, J=1.44, 7.56 Hz, 1H), δ 7.63 (d, J=8.04 Hz, 1H), δ 7.89 (d, J=7.82 Hz, 1H);

benzyl 1S-[1S-(5-chlorobenzooxazol-2-ylcarbonyl)-3-phenylproylcarbamol]-3-methylbutylcarbamate (Compound 270), $^1$H NMR (CDCl$_3$): δ 0.90 (m, 6H), δ 1.39–1.53 (m, 1H), δ 1.59–1.70 (m, 2H), δ 2.07–2.21 (m, 1H), δ 2.37–2.52 (m, 1H), δ 2.73 (t, J=7.91 Hz, 2H), δ 4.20 (m, 1H), δ 5.06 (d, J=7.91 Hz, 1H), δ 5.10 (s, 2H), δ 5.64 (m, 1H), δ 6.77 (d, J=7.67 Hz, 1H), δ 7.09–7.37 (m, 10H), δ 7.53 (dq, J=1.86, 8.91 Hz, 2H), δ 7.89 (d, J=1.73 Hz, 1H);

N-{3-methyl-1S-[3-phenyl-1S-(5-chlorobenzooxazol-2-ylcarbonyl)propylcarbamoyl]butyl}piperidine-4-carboxamide (Compound 271);

N-[2-cyclohexyl-1S-(3-phenyl-1S-benzooxazol-2-ylcarbonylpropylcarbamoyl)ethyl]piperidine-4-carboxamide (Compound 272); MS (ESI) m/z=545 (M+1) $^1$H-NMR (300 MHz, CDCl$_3$, CD$_3$OD): δ 0.85 (m, 2H), δ 1.02–1.58 (m, 4H), δ 1.40–1.71 (m, 7H), δ 1.75–2.21 (m, 5H), δ 2.38 (m, 1H), δ 2.51 (m, 1H), δ 2.69 (t, J=4 Hz, 2H), δ 3.32 (m, 2H), δ 4.39 (q, J=6 Hz 1H), δ 5.53 (q, J=3 Hz, 1H), δ 7.11–7.21 (m, 5H), δ 7.24 (s, 1H), δ 7.38–7.61 (m, 3H), δ 7.73 (d, J=6 Hz, 1H), δ 7.82(d, J=6 Hz, 1H), ($C_{32}H_{40}N_4O_4$);

methyl 2-(2-benzyloxycarbonylamino-4-methylvalerylamino)-4-phenylbutyryloxazole-4-carboxylate (Compound 273);

benzyl 1-[1-(4-phenylcarbamoyloxazol-2-ylcarbonyl)-3-phenylpropylcarbamoyl]-3-methylbutylcarbamate (Compound 274), MS (ESI) ) m/z=597 (M+1); $^1$H NMR (CDCl$_3$): δ 0.8–1.05 (d, J=4 Hz, 6H), δ 1.55 (m, 1H), δ 1.70 (s, 2H), δ 2.00–2.20 (m, 1H), δ 2.40 (m, 1H), δ 2.69 (m, 2H), δ 2.97 (t, J=4 Hz, 2H), δ 3.70(q, J=3 Hz, 2H) 4.25 (m, 1H), δ 5.17 (s, 2H), δ 5.59 (m, 1H), δ 6.99 (d, J=4 Hz 1H), δ 7.14–7.47 (m, 15H) 7.72(d, J=4 Hz, 1H), δ 8.47 (s, 1H), δ 8.65 (s, 1H), ($C_{34}H_{36}N_4O_6$);

benzyl 1-(1-(4-benzylcarbamoyloxazol-2-ylcarbonyl)-3-phenylproylcarbamoyl]-3-methylbutylcarbamate (Compound 275), MS (ESI) ) m/z=611 (M+1); $^1$H NMR (CDCl$_3$): δ 0.8–1.05 (d, J=4 Hz, 6H), δ 1.45–1.70 (m, 4H), δ 2.00–2.20 (m, 1H), δ 2.40 (m, 1H), δ 2.69 (m, 2H), δ 4.25 (m, 1H), δ 4.67 (t, J=3 Hz, 2H), δ 5.17 (m, 3H), δ 5.59 (m, 1H), δ 6.85 (d, J=4 Hz 1H), δ 7.10–7.47 (m, 15H), δ 8.47 (s, 1H), ($C_{35}H_{38}N_4O_6$);

tert-butyl 4{1S-[1S-(5-tert-butylbenzooxazol-2-ylcarbonyl)-3-phenylpropylcarbamoyl]-3-methylbutylcarbamoyl}piperidine-1-carboxylate (Compound 276), $^1$H NMR (CDCl$_3$): δ 0.86–0.97 (m, 6H), δ 1.34–1.85 (m, 7H), δ 1.38 (s, 9H), δ 1.43 (s, 9H), δ 2.09–2.30 (m, 2H), δ 2.37–2.52 (m, 1H), δ 2.72 (m, 4H), δ 4.11 (bd, J=12.85, 2H), δ 4.49 (m, 1H), δ 5.66 (m, 1H), δ 5.97 (d, J=7.91 Hz, 1H), δ 6.89 (d, J=7.67 Hz, 1H), δ 7.11–7.27 (m, 5H), δ 7.50–7.64 (m, 2H), δ 7.86 (d, J=1.56 Hz, 1H);

tert-butyl 4-{1S-[1S-(5-sulfamoylbenzooxazol-2-ylcarbonyl)-3-phenypropylcarbamoyl]-3-methylbutylcarbamoyl}piperidine-1-carboxylate (Compound 277), $^1$H NMR (CDCl$_3$): δ 0.85–0.96 (m, 6H), δ 1.37–1.82 (m, 7H), δ 1.42 (s, 9H), δ 2.08–2.46 (m, 3H), δ 2.71 (m, 4H), δ 4.02 (bs, 2H), δ 4.56 (m, 1H), δ 5.38 (bs, 1H), δ 5.78 (bs, 2H), δ 6.38 (d, J=8.42 Hz, 1H), δ 7.07–7.25 (m, 5H), δ 7.70 (dd, J=3.48, 8.64 Hz, 1H), δ 8.08 (dd, J=1.73, 8.67 Hz, 1H), δ 8.41 (dd, J=1.49, 3.96 Hz, 1H);

N-{3-methyl-1S-[3-phenyl-1S-(5-tert-butylbenzooxazol-2-ylcarbonyl)propylcarbamoyl]butyl}piperidine-4-carboxamide (Compound 278), $^1$H NMR (DMSO-d$_6$): δ 0.82 (t, J=6.18 Hz, 6H), δ 1.36 (s, 9H), δ 1.33–1.88 (m, 7H), δ 1.91–2.06 (m, 1H), δ 2.19–2.34 (m, 1H), δ 2.42–2.54 (m, 1H), δ 2.61–2.92 (m, 4H), δ 3.27 (bd, J=12.02 2H), δ 4.39 (m, 1H), δ 5.19 (m, 1H), δ 7.15–7.33 (m, 5H), δ 7.74 (dq, J=1.97, 7.91 Hz, 2H), δ 7.90 (d, J=1.83 Hz, 1H), δ 8.07 (d, J=8.15 Hz, 1H), δ 8.27 (bs, 1H), δ 8.56 (bs, 1H), δ 8.72 (d, J=6.43 Hz, 1H);

N-{3-methyl-1S-[3-phenyl-1S-(5-sulfamoylbenzooxazol-2-ylcarbonyl)propylcarbamoyl]butyl}piperidine-4-carboxamide (Compound 279), $^1$H NMR (DMSO-d$_6$): δ 0.80–0.88 (m, 6H), δ 1.31–1.86 (m, 7H), δ 1.92–2.05 (m, 1H), δ 2.22–2.33 (m, 1H), δ 2.41–2.52 (m, 1H), δ 2.63–2.89 (m, 4H), δ 3.26 (bd, J=11.88 2H), δ 4.40 (m, 1H), δ 5.13 (m, 1H), δ 7.16–7.31 (m, 5H), δ 7.57 (s, 2H), δ 8.05 (m, 3H), δ 8.25 (bs, 1H), δ 8.32 (s, 1H), δ 8.55 (bs, 1H), δ 8.82 (d, J=6.18 Hz, 1H), δ 8.88 (d, J=6.84 Hz, 1H);

tert-butyl 4-[1S-(1S-naphtho[1,2-d]oxazol-2-ylcarbonyl-3-phenylpropylcarbonyl)-3-methylbutylcarbamoyl] piperidine-1-carboxylate (Compound 280), $^1$H NMR (CDCl$_3$): δ 0.87–0.95 (m, 6H), δ 1.39–1.85 (m, 7H), δ 1.44 (s, 9H), δ 2.13–2.32 (m, 2H), δ 2.45–2.60 (m, 1H), δ 2.65 (m, 4H), δ 4.12 (m, 2H), δ 4.53 (m, 1H), δ 5.79 (m, 1H), δ 6.00 (d, J=7.94 Hz, 1H), δ 6.90 (d, J=7.67 Hz, 1H), δ 7.12–7.26 (m, 5H), δ 7.56–7.80 (m, 3H), δ 7.93–8.00 (m, 2H), δ 8.52 (dd, J=1.97, 8.00 Hz, 1H);

tert-butyl 4-[1S-(1S-naphtho[2,1-d]oxazol-2-ylcarbonyl-3-phenylpropylcarbamoyl)-3-methylbutylcarbamoyl] piperidine-1-carboxylate (Compound 281), $^1$H NMR (CDCl$_3$): δ 0.88–0.97 (m, 6H), δ 1.38–1.86 (m, 7H), δ 1.43 (s, 9H), δ 2.15–2.31 (m, 2H), δ 2.43–2.57 (m, 1H), δ 2.67–2.79 (m, 4H), δ 4.11 (m, 2H), δ 4.52 (m, 1H), δ 5.73 (m, 1H), δ 5.96 (d, J=7.94 Hz, 1H), δ 6.90 (d, J=7.91 Hz, 1H), δ 7.12–7.26 (m, 5H), δ 7.66 (m, 2H), δ 7.85 (s, 1H), δ 7.99 (dd, J=1.85, 7.80 Hz, 1H), δ 8.33 (dd, J=1.97, 7.94 Hz, 1H);

tert-butyl 4-{1S-[1S-(5-phenylbenzooxazol-2-ylcarbonyl)-3-phenylpropylcarbamoyl]-3-methylbutylcarbamoyl}piperidine-1-carboxylate (Compound 282); MS (ESI) m/z=681 (M+1); $^1$H-NMR (300 MHz, CDCl$_3$): δ 0.85–0.98 (m, 6H), δ 1.43 (s, 9H), δ 1.60–1.85 (m, 5H), δ 2.14–2.30 (m, 2H), δ 2.56 (m, 1H), δ 2.75 (m, 4H), δ 4.12 (m, 2H), δ 4.52 (m, 1H), δ 5.69 (m, 1H), δ 5.92 (d, J=6 Hz, 1H), δ 6.85 (d, J=6 Hz, 1H), δ 7.13–7.26 (m, 7H), δ 7.36–7.80 (m, 7H), δ 8.05 (s, 1H), ($C_{40}H_{48}N_4O_6$);

N-{3-methyl-1S-[3-phenyl-1S-(naphtho[1,2-d]oxazol-2-ylcarbonyl)propylcarbamoyl]butyl}piperidine-4-carboxamide (Compound 283), $^1$H NMR (DMSO-d$_6$): δ 0.81 (m, 6H), δ 1.35–1.86 (m, 7H), δ 1.96–2.11 (m, 1H), δ 2.26–2.53 (m, 2H), δ 2.64–2.91 (m, 4H), δ 3.26 (bd, J=11.63 2H), δ 4.42 (m, 1H), δ 5.27 (m, 1H), δ 7.19–7.36 (m, 5H), δ 7.70 (t, J=7.91 Hz, 1H), δ 7.83 (t, J=7.43 Hz, 1H), δ 8.01 (d, J=8.91 Hz, 1H), δ 8.08 (m, 1H), δ 8.18 (d, J=8.91 Hz, 2H), δ 8.27 (bs, 1H), δ 8.39 (d, J=7.91 Hz, 1H), δ 8.56 (bs, 1H), δ 8.75 (d, J=6.45 Hz, 1H);

N-{3-methyl-1S-[3-phenyl-1S-(naphtho[2,1-d]benzooxazol-2-ylcarbonyl)propylcarbamoyl]butyl}piperidine-4-carboxamide (Compound 284), $^1$H NMR (DMSO-d$_6$): δ 0.81 (t, J=6.43 Hz, 6H), δ 1.34–1.87 (m, 7H), δ 1.97–2.12 (m, 1H), δ 2.24–2.38 (m, 1H), δ 2.42–2.53 (m, 1H), δ 2.66–2.93 (m, 4H), δ 3.26 (bd, J=10.12 2H), δ 4.41 (m, 1H), δ 5.26 (m, 1H), δ 7.16–7.34 (m, 5H), δ 7.77 (m, 2H), δ 7.97 (d, J=8.91 Hz, 1H), δ 8.05 (d, J=8.86 Hz, 1H), δ 8.07 (d, J=8.64 Hz, 1H), δ 8.19 (d, J=7.91 Hz, 1H), δ 8.26 (bs, 1H), δ 8.28 (d, J=7.67 Hz, 1H), δ 8.56 (bs, 1H), δ 8.78 (d, J=6.43 Hz, 1H);

N-{3-methyl-1-[3-phenyl-1-(5-phenylbenzooxazol-2-ylcarbonyl)propylcarbamoyl]butyl}piperidine-4-carboxamide (Compound 285);

benzyl 1-[1-(4-phenyethylcarbamoyloxazol-2-ylcarbonyl)-3-phenylpropylcarbamoyl]-3-methylbutylcarbamate (Compound 286), MS (ESI) ) m/z=625 (M+1); $^1$H NMR (CDCl$_3$): δ 0.8–1.05 (d, J=4 Hz, 6H), δ 1.50 (m, 1H), δ 1.65 (m, 3H), δ 2.00–2.20 (m, 1H), δ 2.35 (m, 1H), δ 2.60 (m, 2H), δ 2.99 (t, J=4 Hz, 2H), δ 3.67(q, J=3 Hz, 2H),4.19 (m, 1H), δ 5.17 (s, 2H), δ 5.59 (m, 1H), δ 6.85–6.98 (m, 2H), δ 7.10–7.47 (m, 15H), δ 8.43 (s, 1H); ($C_{36}H_{40}N_4O_6$);

benzyl 1-{1-[4-(3-phenylproylcarbamoyl)oxazol-2-ylcarbonyl]-3-phenylpropylcarbamoyl}-3-methylbutylcarbamate (Compound 287), MS (ESI) m/z=625 (M+1); $^1$H-NMR (300 MHz, CDCl$_3$): δ 0.95 (d, J=6 Hz, 6H), δ 1.50 (m, 1H), δ 1.65 (m, 3H), δ 2.00 (m, 4H), δ 2.35 (m, 1H), δ 2.67 (m, 4H), δ 3.49 (m, 2H), δ 4.20 (m, 1H), δ 5.09 (s, 2H), δ 5.50 (m, 1H), δ 6.85 (m, 1H), δ 7.23(m, 15H), δ 8.35 (s, 1H), δ($C_{37}H_{42}N_4O_6$);

tert-butyl 4-[1S-(1S-benzooxazol-2-ylcarbonyl-3-phenylpropylcarbamoyl)-2-methalbutylcarbamoyl] piperidine-1-carboxylate (Compound 288);

tert-butyl 3-[1S-(1S-benzooxazol-2-ylcarbonyl-3-phenylpropylcarbamoyl)-2-methylbutylcarbamoyl]benzylcarbamate (Compound 289);

N-[2-methyl-1S-(3-phenyl-1S-benzooxazol-2-ylcarbonylpropylcarbamoyl)butyl]piperidine-4-carboxamide (Compound 290);

N-[2-methyl-1S-(3-phenyl-1S-benzooxazol-2-ylcarbonylpropylcarbamoyl)butyl]-3-aminomethylbenzamide (Compound 291);

benzyl 1-{1-[4-(2-indol-3-ylethylcarbamoyl)oxazol-2-ylcarbonyl]-3-phenylpropylcarbamoyl}-3-methylbutylcarbamate (Compound 292); MS (ESI) m/z=664 (M+1); $^1$H-NMR (300 MHz, CDCl$_3$): δ 0.94 (d, J=6 Hz, 6H), δ 1.40–1.70 (m, 6H), δ 2.00 (m, 1H), δ 2.25(m, 1H), δ 2.67 (m, 2H), δ 3.09 (m, 2H), δ 3.52–3.85 (m, 2H), δ 4.20 (m, 1H), δ 5.09 (s, 2H), δ 5.50 (m, 1H), δ 6.80 (d, J=6 Hz, 1H), δ 6.99–7.41(m, 14H), δ 7.65 (d, J=6 Hz, 1H), δ 8.35 (s, 1H), δ 8.39 (s, 1H), (C$_{38}$H$_{41}$N$_5$O$_6$);

benzyl 1-[1-(4-methylcarbamoaloxazol-2-ylcarbonyl)-3-phenylpropylcarbamoyl]-3-methylbutylcarbamate (Compound 293); MS (ESI) m/z=535 (M+1); $^1$H NMR (300 MHz, CDCl$_3$): δ 0.95 (d, J=6 Hz, 6H), δ 1.33–1.70 (m, 5H), δ 2.00 (m, 1H), δ 2.28 (m, 1H), δ 2.67 (m, 2H), δ 2.99 (d, J=2 Hz, 3H), δ 4.15 (m, 1H), δ 5.09 (m, 2H), δ 5.50 (m, 1H), δ 6.88 (m, 1H), δ 7.09–7.38 (m, 10H), δ 8.35 (s, 1H), (C$_{29}$H$_{34}$N$_4$O$_6$);

benzyl 2-{2-[2-(2-benzyloxycarbonylamino-4-methylvalerylamino)-4-phenylbutyryl]oxazol-2-ylcarbonylamino}valerate (Compound 294);

benzyl 1S-{1S-[4-(4-benzylpiperidin-1-ylcarbonyl)oxazol-2-ylcarbonyl]-3-phenylpropylcarbamoyl}-3-methylbutylcarbamate (Compound 295); MS (ESI) m/z=679 (M+1); $^1$H-NMR (300 MHz, CDCl$_3$): δ 0.92 (m, 6H), δ 1.25 (m, 1H), δ 1.48 (q, J=4 Hz, 1H), δ 1.52–1.85 (m, 6H), δ 2.09(m, 1H), δ 2.36 (m, 1H), δ 2.53–2.77 (m, 3H), δ 3.03 (t, J=8 Hz, 4H), δ 4.19 (m, 1H), δ 4.65 (m, 1H), δ 5.02–5.13 (m, 3H), δ 5.53 (m, 1H), δ 6.68 (d, J=6 Hz, 1H), δ 7.08–7.39 (m, 15H), δ 8.28 (s, 1H), (C$_{40}$H$_{46}$N$_4$O$_6$);

benzyl 1S-[1S-(4-fur-2-ylmethylcarbamoyloxazol-2-ylcarbonyl)-3-phenylpropylcarbamoyl]-3-methylbutylcarbamate (Compound 296); MS (ESI) m/z=601 (M+1); $^1$H-NMR (300 MHz, CDCl$_3$): δ 0.98 (d, J=6 Hz 6H), δ 1.58 (q, J=6 Hz 1H), 1.62 (m, 4H), δ 2.00 (m, 1H), δ 2.27 (m, 1H), δ 2.76 (m, 2H), δ 4.20 (m, 1H), δ 4.70 (d, J=4 Hz, 2H), δ 4.98–5.18 (m, 2H), δ 5.56 (m, 1H), δ 6.82 (m, 1H), δ 7.05–7.42 (m, 13H), δ 8.32 (d, J=4 Hz, 1H), (C$_{33}$H$_{36}$N$_4$O$_7$);

benzyl 3-methyl-1S-[1S-(4-pyrid-2-ylmethylcarbamoyloxazol-2-ylcarbonyl)-3-phenylpropylcarbamoyl]butylcarbamate (Compound 297); MS (ESI) m/z=612 (M+1); $^1$H-NMR (300 MHz, CDCl$_3$): δ 0.98 (d, J=6 Hz 6H), δ 1.4–2.15 (m, 5H), δ 2.32 (m, 1H), δ 2.71 (m, 2H), δ 4.21 (m, 1H), δ 4.75 (d, J=2 Hz, 2H), δ 5.09 (m, 2H), δ 5.15–5.5 (m, 1H), δ 7.10–7.38 (m, 13H), δ 7.7 (t, J=4 Hz, 1H), δ 7.95 (m, 1H), δ 8.32 (d, J=4 Hz, 1H), δ 8.59 (s, 1H). (C$_{34}$H$_{37}$N$_5$O$_6$);

benzyl 3-methyl-1S-[1S-(4-pyrid-3-ylmethylcarbamoyloxazol-2-ylcarbonyl)-3-phenylpropylcarbamoyl]butylcarbamate (Compound 298); MS (ESI) m/z=612 (M+1); $^1$H-NMR (300 MHz, CDCl$_3$); δ 0.98 (d, J=6 Hz 6H), δ 1.5 (q, J=4 Hz, 1H), δ 1.65 (m, 2H), δ 1.95 (m, 3H), 2.25 δ(m, 1H), δ 2.68 (m, 2H), δ 4.19 (m, 1H), δ 4.72 (d, J=2 Hz, 2H), δ 5.09 (s, 2H), δ 5.41 (m, 1H), δ 6.90 (t, J=2 Hz, 1H), δ 7.05–7.35 (m, 10H), δ 7.46 (m, 1H), δ 7.72 (d, J=6 Hz, 1H), δ 8.31 (d, J=4 Hz, 1H), δ 8.62 (d, J=4 Hz 1H), δ 8.73 (s, 1H), (C$_{34}$H$_{37}$N$_5$O$_6$);

benzyl 3-methyl-1S-[1S-(4-pyrid-4ylmethylcarbamoyloxazol-2-ylcarbonyl)-3-phenylpropylcarbamoyl]butylcarbamate (Compound 299); MS (ESI) m/z=612 (M+1); $^1$H-NMR (300 MHz, CDCl$_3$): δ 0.98 (d, J=6 Hz, 6H), δ 1.5 (q, J=4 Hz, 1H), 1.65 (m, 2H), 1.95 (m, 3H), 2.25 (m, 1H), 2.68 (m, 2H), 4.19 (m, 1H), 4.72 (t, J=2 Hz, 2H), 5.11 (d, J=4 Hz, 2H), 5.43 (m, 1H), δ 6.92 (d, J=6 Hz, 1H), 7.05–7.35 (m, 11H), 7.46 (m, 1H, 8.33 (d, J=4 Hz, 1H), 8.58 (m, 2H), (C$_{34}$H$_{37}$N$_5$O$_6$);

benzyl 1S-{1S-[4-(2-chlorobenzylcarbamoyl)oxazol-2-ylcarbonyl]-3-phenylpropylcarbamoyl}-3-methylbutylcarbamate (Compound 300); MS (ESI) m/z=646 (M+1); $^1$H-NMR (300 MHz, CDCl$_3$): δ 0.98 (d, J=6 Hz, 6H), δ 1.5 (q, J=4 Hz, 1H), δ 1.62 (m, 4H), 1.95 δ(m, 1H), δ 2.30 (m, 1H), δ 2.65 (m, 2H), δ 4.19 (m, 1H), δ 4.70 (d, J=2 Hz, 2H), δ 5.09 (m, 2H), δ 5.47 (m, 1H), δ 6.82 (m, 1H) δ 7.05–7.45 (m, 14H), δ 8.33 (d, J=4 Hz, 1H), (C$_{35}$H$_{37}$ClN$_4$O$_6$);

benzyl 1S-{1S-[4-(3-chlorobenzylcarbamoyl)oxazol-2-ylcarbonyl]-3-phenylpropylcarbamoyl}-3-methylbutylcarbamate (Compound 301); MS (ESI) m/z=646 (M+1); $^1$H-NMR (300 MHz, CDCl$_3$): δ 0.98 (d, J=6 Hz, 6H), δ 1.5 (q, J=4 Hz, 1H), δ 1.62 (m, 4H), δ 2.00 (m, 1H), δ 2.25 (m, 1H), δ 2.65 (m, 2H), δ 4.20 (m, 1H), δ 4.68 (d, J=2 Hz, 2H), δ 5.09 (m, 2H), δ 5.43 (m, 1H), δ 6.85 (d, J=6 Hz, 1H), δ 7.05–7.45 (m, 14H), δ 8.33 (d, J=4 Hz, 1H), (C$_{35}$H$_{37}$ClN$_4$O$_6$);

benzyl 1S-{1S-[4-(4-chlorobenzylcarbamoyl)oxazol-2-ylcarbonyl]-3-phenylpropylcarbamoyl}-3-methylbutylcarbamate (Compound 302); MS (ESI) m/z=646 (M+1); $^1$H-NMR (300 MHz, CDCl$_3$): δ 0.98 (d, J=6 Hz, 6H), δ 1.5 (q, J=4 Hz, 1H), δ 1.62 (m, 4H), δ 2.00 (m, 1H), δ 2.25 (m, 1H), δ 2.65 (m, 2H), δ 4.20 (m, 1H), δ 4.68 (d, J=2 Hz, 2H), δ 5.09 (m, 2H), δ 5.43 (m, 1H), δ 6.85 (m, 1H), δ 7.05–7.45 (m, 14H), δ 8.33 (d, J=4 Hz, 1H), (C$_{35}$H$_{37}$ClN$_4$O$_6$);

benzyl 3-methyl-1S-{1S-[4-(2S-phenylcyclonrop-1S-ylcarbamoyl)oxazol-2-ylcarbonyl]-3-phenylpropylcarbamoyl}-3-methylbutylcarbamate (Compound 303); MS (ESI) m/z=637 (M+1); $^1$H NMR (300 MHz, CDCl$_3$): δ 0.92 (d, J=6 Hz, 6H), δ 1.46–1.78 (m, 6H), δ 2.00 (m, 3H), δ 2.31 (m, 1H), δ 2.67 (m, 2H), δ 2.99–3.22 (m, 1H), δ 4.20 (m, 1H), δ 5.04 (d, J=6 Hz, 1H), δ 5.11 (s, 2H), δ 5.54 (m, 1H), δ 6.87 (m, 1H), δ 7.08–7.47 (m, 15H), δ 8.30 (d, J=2 Hz, 1H), (C$_{37}$H$_{40}$N$_4$O$_6$);

benzyl 3-methyl-1S-[1S-(4-diphenylmethylmethylcarbamoyloxazol-2-ylcarbonyl)-3-phenylpropylcarbamoyl]-3-methylbutylcarbamate (Compound 304); MS (ESI) m/z=687 (M+1); $^1$H-NMR (300 MHz, CDCl$_3$): δ 0.98 (d, J=6 Hz, 6H), δ 1.48 (q, J=4 Hz, 1H), δ 1.62 (m, 2H), δ 2.00 (m, 1H), δ 2.30 (m, 1H), δ 2.67 (m, 2H), δ 4.18 (m, 1H), δ 5.09 (m, 3H), δ 5.43 (m, 1H), δ 6.42 (d, J=6 Hz, 1H), δ 6.80 (d, J=6 Hz, 1H), δ 7.02–7.72 (m, 20H), δ 7.79 (d, J=6 Hz, 1H), δ 8.33 (d, J=4 Hz, 1H), (C$_{41}$H$_{42}$N$_4$O$_6$);

benzyl 1S-[1S-(4-adamantan-1-ylmethylcarbamoyloxazol-2-ylcarbonyl)-3-phenylpropylcarbamoyl]-3-methylbutylcarbamate (Compound 305); MS (ESI) m/z=670 (M+1); $^1$H-NMR (300 MHz, CDCl$_3$): δ 0.92 (m, 8H), δ 1.18–1.78 (m, 16H), δ 2.00 (m, 1H), δ 2.31 (m, 1H), δ 2.67 (m, 2H), δ 2.99–3.09 (m, 2H), δ 4.21 (m, 1H), δ 5.11 (m, 3H), δ 5.51 (m, 1H), δ 6.87 (m, 1H), δ 7.02 (m, 1H), δ 7.08–7.47 (m, 10H), δ 8.31 (d, J=2 Hz, 1H), (C$_{39}$H$_{48}$N$_4$O$_6$);

benzyl 1-{1-[4-(1-methylethylcarbamoyl)oxazol-2-ylcarbonyl]-3-phenylpropylcarbamoyl}-3-methylbutylcarbamate (Compound 306);

benzyl 1-{1-[4-(1S-phenylethylcarbamoyl)oxazol-2-ylcarbonyl]-3-phenylpropylcarbamoyl}-3-methylbutylcarbamate (Compound 307); MS (ESI) m/z=625 (M+1); ¹H-NMR (300 MHz, CDCl₃): δ 0.92 (d, J=6 Hz, 6H), δ 1.54–1.65 (m, 7H), δ 2.00 (m, 1H), δ 2.25 (m, 1H), δ 2.65 (m, 2H), δ 4.15 (m, 1H), δ 4.99 (d, J=2 Hz, 1H), δ 5.09 (s, 2H), δ 5.32 (m, 1H), δ 5.43 (m, 1H), δ 6.79 (d, J=6 Hz, 1H), δ 7.05–7.45 (m, 15H), δ 8.31 (s, 1H), (C₃₆H₄₀N₄O₆);

benzyl 1-{1-[4-(1R-phenylethylcarbamoyL)oxazol-2-ylcarbonyl]-3-phenylpropylcarbamoyl}-3-methylbutylcarbamate (Compound 308); MS (ESI) m/z=625 (M+1); ¹H-NMR (300 MHz, CDCl₃): δ 0.92 (d, J=6 Hz, 6H), δ 1.45–1.68 (m, 7H), δ 2.00 (m, 1H), δ 2.25 (m, 1H), δ 2.65 (m, 2H), δ 4.15 (m, 1H), δ 4.99 (d, J=2 Hz, 1H), δ 5.09 (s, 2H), δ 5.32 (m, 1H), δ 5.43 (m, 1H), δ 6.79 (d, J=6 Hz, 1H), δ 7.05–7.45 (m, 15H), δ 8.31 (s, 1H), (C₃₆H₄₀N₄O₆);

benzyl 1-{1-[4-(N-benzyl-N-methylcarbamoyl)oxazol-2-ylcarbonyl]-3-phenylpropylcarbamoyl}-3-methylbutylcarbamate (Compound 309); MS (ESI) m/z=625 (M+1); ¹H-NMR (300 MHz, CDCl₃): δ 0.90 (d, J=6 Hz, 6H), δ 1.27–1.68 (m, 4H), δ 2.00 (m, 1H), δ 2.25 (m, 1H), δ 2.65 (m, 2H), δ 3.10 (s, 1H), δ 4.19 (m, 1H), δ 4.71 (s, 2H), δ 5.09 (s, 2H), δ 5.22 (m, 1H), δ 5.43 (m, 1H), δ 6.99 (d, J=6 Hz, 1H), δ 7.05–7.45 (m, 15H), δ 7.60 (m, 1H), δ 8.31 (s, 1H), (C₃₆H₄₀N₄O₆);

benzyl 1-[1-(4-pyrrolidin-1-ylcarbonyloxazol-2-ylcarbonyl)-3-phenylpropylcarbamoyl]-3-methylbutylcarbamate (Compound 310); MS (ESI) m/z=575 (M+1); ¹H-NMR (300 MHz, CDCl₃): δ 0.93 (d, J=6 Hz, 6H), δ 1.45–1.73 (m, 3H), δ 1.85–2.12 (m, 5H), δ 2.34 (m, 1H), δ 2.64 (m, 2H), δ 3.62 (t, J=4 Hz, 2H), δ 3.82 (m, 2H), δ 4.21 (m, 1H), 4.99–5.11 (m, 2H), δ 5.55 (m, 1H), δ 5.43 (m, 1H), δ 6.79 (m, 1H), δ 7.05–7.45 (m, 10H), δ 8.31 (d, J=2 Hz, 1H), (C₃₂H₃₈N₄O₆);

benzyl 1-[1-(4-piperidin-1-ylcarbonyloxazol-2-ylcarbonyl)-3-phenylpropylcarbamoyl]-3-methylbutylcarbamate (Compound 311); MS (ESI) m/z=589 (M+1); ¹H-NMR (300 MHz, CDCl₃): δ 0.90 (d, J=6 Hz, 6H), δ 1.25 (m, 2H), δ 1.49–1.66 (m, 6H), δ 2.12 (m, 1H), δ 2.34 (m, 1H), δ 2.64 (m, 2H), δ 3.65 (m, 2H), δ 3.85 (m, 2H), δ 4.17 (m, 1H), δ 4.99–5.11 (m, 3H), δ 5.55 (m, 1H), δ 6.67 (m, 1H), δ 7.08–7.39 (m, 11H), δ 8.27 (s, 1H), (C₃₃H₄₀O₆);

benzyl 1-{1-[4-(2,3-dihydroindol-1-ylcarbonyl)oxazol-2-ylcarbonyl]-3-phenylpropylcarbamoyl}-3-methylbutylcarbamate (Compound 312);

benzyl 1-{1-[4-(3,4-dihydro-1H-isoquinol-2-ylcarbonyl)oxazol-2-ylcarbonyl]-3-phenylpropylcarbamoyl}-3-methyl (Compound 313); MS (ESI) m/z=637 (M+1); ¹H-NMR (300 MHz, CDCl₃): δ 0.90 (d, J=6 Hz, 6H), δ 1.25 (m, 2H), δ 1.45–1.79 (m, 4H), δ 2.11 (m, 1H), δ 2.40 (m, 1H), δ 2.68 (m, 2H), δ 2.95 (t, J=4 Hz, 2H), δ 3.96 (t, J=4 Hz, 1H), δ 4.15 (m, 2H), δ 4.86 (d, J=6 Hz, 1H), δ 4.99–5.11 (m, 3H), δ 5.59 (m, 1H, δ 6.70 (m, 1H), δ 7.05–7.45 (m, 12H), δ 8.35 (s, 1H), (C₃₇H₄₀N₄O₆);

benzyl 1-{1-[4-(3,4-dihydro-2H-quinol-1-ylcarbonyl)oxazol-2-ylcarbonyl]-3-phenylpropylcarbamoyl}-3-methylbutylcarbamate (Compound 314); MS (ESI) m/z=637 (M+1); ¹H-NMR (300 MHz, CDCl₃): δ 0.90 (d, J=6 Hz, 6H), δ 1.25 (m, 2H), δ 1.40–1.69 (m, 3H), δ 2.05 (m, 2H), δ 2.52 (t, J=6 Hz, 2H), δ 2.82 (t, J=4 Hz, 2H), δ 3.80–4.21 (m, 4H), δ 4.86 (m, 1H), δ 5.09 (s, 2H), δ 5.21 (m, 1H), δ 6.62 (m, 1H), δ 6.85–7.31 (m, 11H), δ 7.51 (m, 1H), δ 7.67 (m, 1H), δ 8.31 (s, 1H), (C₃₇H₄₀N₄O₆);

benzyl 1-[1-(4-naphth-1-ylmethylcarbamoyloxazol-2-ylcarbonyl)-3-phenylpropylcarbamoyl]-3-methylbutylcarbamate (Compound 315); MS (ESI) m/z=661 (M+1); ¹H-NMR (300 MHz, CDCl₃): δ 0.90 (d, J=6 Hz, 6H), δ 1.25 (m, 2H), δ 1.54 (m, 3H), δ 2.05 (m, 1H), δ 2.59 (t, J=6 Hz, 1H), δ 2.82 (t, J=4 Hz, 2H), δ 4.12 (m, 1H), δ 4.90–5.09 (m, 4H), δ 5.34 (m, 1H), δ 6.71 (m, 1H), δ 6.95–7.12 (m, 3H), δ 7.27 (m, 10H), δ 7.51(m, 2H), δ 7.88 (t, J=6 Hz, 1H), δ 8.06 (d, J=6 Hz, 1H), δ 8.35 (s, 1H), (C₃₀H₄₀N₄O₆);

tert-butyl 4-[1S-(1S-benzooxazol-2-ylcarbonyl)-3-phenylpropylcarbamoyl)-2-cyclohexylethylcarbamoyl] piperidine-1-carboxylate (Compound 316);

1S-{1S-[4-(3,4-dihydro-2H-quinol-1-ylcarbonyl)oxazol-2-ylcarbonyl]-ethylcarbamoyl}-3-methylbutylcarbamate (Compound 317);

benzyl 3-methyl-1S-[1S-(5-phenyloxazol-2-ylcarbonyl)-3-phenylpropylcarbamoyl]butylcarbamate (Compound 318); MS (ESI) m/z=554 (M+1); ¹H-NMR (300 MHz, CDCl₃): δ 0.97 (d, J=4 Hz, 6H), δ 1.50 (t, J=4 Hz, 1H), δ 1.65–1.82 (m, 3H), δ 2.20 (m, 1H), δ 2.48 (m, 1H), δ 2.75 (t, J=4 Hz, 2H), δ 4.27 (m, 1H), δ 5.09 (s, 2H), δ 5.65 (m, 1H), δ 6.85 (d, J=6 Hz, 1H), δ 7.12–7.62 (m, 14H), δ 7.77 (d, J=2 Hz, 2H), (C₃₃H₃₅N₃O₅);

pyrid-3-yl 3-methyl-1S-[1S-(5-phenyloxazol-2-ylcarbonyl)-3-phenylpropylcarbamoyl]butylcarbamate (Compound 319); MS (ESI) m/z=525 (M+1); ¹H-NMR (300 MHz, CDCl₃): δ 0.80–1.05 (m, 6H), δ 1.27 (m, 3H), δ 1.72 (m, 3H), δ 2.15 (m, 1H), δ 2.46 (m, 1H), δ 2.77 (t, J=4 Hz, 2H), δ 4.75 (m, 1H), δ 5.65 (m, 1H), δ 6.95 (d, J=4 Hz, 1H), δ 7.02 (d, J=4 Hz, 1H), δ 7.09–7.35 (m, 5H), δ 7.37–7.62 (m, 3H), δ 7.80 (d, J=4 Hz, 1H), δ 8.15 (d, J=6 Hz, 1H), δ 8.75 (m, 1H), δ 9.09 (s, 1H), (C₃₁H₃₂N₄O₄);

benzyl 1S-[1S-(5-phenyloxazol-2-ylcarbonyl)-3-phenylpropylsulfamoylmethyl]-2R-methylbutylcarbamate (Compound 320); MS (ESI) m/z=604 (M+1); ¹H-NMR (300 MHz, CDCl₃): δ 0.95 (m, 6H), δ 1.25 (m, 1H), δ 1.49 (m, 1H), δ 1.65 (m, 1H), δ 2.15 (m, 1H), δ 2.48 (m, 1H), δ 2.85 (m, 2H), δ 3.12 (m, 2H), δ 4.46 (m, 1H), δ 4.99 (d, J=8 Hz, 1H), δ 5.12 (m, 3H), δ 6.32 (d, J=6 Hz, 1H), δ 7.19–7.55 (m, 14H), δ 7.76 (m, 2H), (C₃₃H₃₇N₃O₆S);

benzyl 3-methyl-1-{2-hydroxy-1-phenethyl-2-[4-(3-phenylpropylcarbamoyl)oxazol-2-yl]ethylcarbamoyl}butylcarbamate (Compound 321);

benzyl 1-{2-hydroxy-2-[4-(2-indol-3-ylethylcarbamoyl)oxazol-2-yl]-1-phenethylethylcarbamoyl}-3-methylbutylcarbamate (Compound 322); MS (ESI) m/z=666 (M+1); ¹H-NMR (300 MHz, CDCl₃): δ 0.90 (d, J=6 Hz, 6H), δ 1.40–1.80 (m, 6H), δ 2.00 (m, 1H), δ 2.67 (m, 2H), δ 3.09 (m, 2H), δ 3.52–3.85 (m, 2H), δ 3.99–4.20 (m, 2H), δ 4.26–4.44 (m, 1H), δ 4.81 (s, 1H), δ 5.09 (s, 2H), δ 5.50 (m, 1H), δ 6.72 (d, J=6 Hz, 1H), δ 6.99–7.41 (m, 14H), δ 8.18 (s, 1H), δ 8.39 (s, 1H), (C₃₈H₄₃N₅O₆);

benzyl 3-methyl-1-[2-hydroxy-2-(4-methylcarbamoyloxazol-2-yl)-1-phenethylethylcarbamoyl]butylcarbamate (Compound 323); MS (ESI) m/z=537 (M+1); ¹H-NMR (300 MHz, CDCl₃): δ 0.90 (d, J=6 Hz, 6H), δ 1.33–1.80 (m, 6H), δ 2.00 (m, 1H), δ 2.67 (m, 2H), 2.89 (m, 3H), δ 4.10 (m, 1H), δ 4.25 (m, 1H), δ 4.81 (s, 1H), δ 5.09 (m, 3H), δ 6.68 (d, J=4 Hz, 1H), δ 7.09–7.38 (m, 10H), δ 8.18 (s, 1H), (C₂₉H₃₆N₄O₆);

benzyl 2-{2-[2-(2-benzyloxycarbonylamino-4-methylvalerylanino)-1-hydroxy-4-phenylbutyl]oxazol-2-ylcarbonylamino}valerate (Compound 324); MS (ESI) m/z= 727 (m+1); ¹H-NMR (300 MHz, CDCl₃): δ 0.95 (m, 12H), δ 1.45–1.80 (m, 9H), δ 2.00 (m, 1H), δ 2.67 (m, 2H), δ

3.99–4.15 (m, 2H), δ 4.85 (m, 2H), δ 5.09 (m, 4H), δ 5.50 (m, 1H), δ 6.88 (m, 1H), 7.12–7.45 (m, 15H), δ 8.18 (s, 1H), ($C_{41}H_{50}N_4O_8$);

benzyl 1S-{2-[4-(4-benzylpiperidin-1-ylcarbonyl)oxazol-2-yl]-2-hydroxy-1S-phenethylethylcarbamoyl}-3-methylbutylcarbamate (Compound 325);

benzyl 1S-[2-(4-fur-2-ylmethylcarbamoyloxazol-2-yl)-2-hydroxy-1S-phenethylethylcarbamoyl]-3-methylbutylcarbamate (Compound 326);

benzyl 3-methyl-1S-[2-hydroxy-1S-phenethyl-2-(4-pyrid-2-ylmethylcarbamoyloxazol-2-yl)ethylcarbamoyl]butylcarbamate (Compound 327);

benzyl 3-methyl-1S-[2-hydroxy-1S-phenethyl-2-(4-pyrid-3-ylmethylcarbamoyloxazol-2-yl)ethylcarbamoyl]butylcarbamate (Compound 328);

benzyl 3-methyl-1S-[2-hydroxy-1S-phenethyl-2-(4-pyrid-4-ylmethylcarbamoyloxazol-2-yl)ethylcarbamoyl]butylcarbamate (Compound 329);

benzyl 3-methyl-1S-{2-[4-(2-chlorobenzylcarbamoyl)oxazol-2-yl]-2-hydroxy-1S-phenethylethylcarbamoyl}butylcarbamate (Compound 330);

benzyl 3-methyl-1S-{2-[4-(3-chlorobenzylcarbamoyl)oxazol-2-yl]-2-hydroxy-1S-phenethylethylcarbamoyl}butylcarbamate (Compound 331);

benzyl 3-methyl-1S-{2-[4-(4-chlorobenzylcarbamoyl)oxazol-2-yl]-2-hydroxy-1S-phenethylethylcarbamoyl}butylcarbamate (Compound 332);

benzyl 3-methyl-1S-{2-hydroxy-1S-phenethyl-2-[4-(2R-phenylcycloprop-1S-ylcarbamoyl)oxazol-2-yl]ethylcarbamoyl}butylcarbamate (Compound 333);

benzyl 1S-[2-(4-adamantan-1-ylmethylcarbamoyloxazol-2-yl)-2-hydroxy-methyl)-1S-phenethylethylcarbamoyl]-3-methylbutylcarbamate (Compound 334);

benzyl 3-methyl-1S-[2-hydroxy-1S-phenethyl-2-(4-diphenylmethylcarbamoyloxazol-2-yl)ethylcarbamoyl]butylcarbamate (Compound 335);

benzyl 3-methyl-1-{2-hydroxy-2-[4-(1-methylethylcarbamoyl)oxazol-2-yl]-1-phenethylethylcarbamoyl}butylcarbamate (Compound 336);

benzyl 3-methyl-1-{2-hydroxy-1-phenethyl-2-[4-(2S-phenyethylcarbamoyl)oxazol-2-yl]ethylcarbamoyl}butylcarbamate (Compound 337);

benzyl 3-methyl-1-{2-hydroxy-1-phenethyl-2-[4-(2R-phenyethylcarbamoyl)oxazol-2-yl]ethylcarbamoyl}butylcarbamate (Compound 338);

benzyl 3-methyl-1-{2-[4-(N-benzyl-N-methylcarbamoyl)oxazol-2-yl]-2-hydroxy-1-phenethylethylcarbamoyl}butylcarbamate (Compound 339);

benzyl 3-methyl-1-[2-hydroxy-1-phenethyl-2-(4-pyrrolidin-1-ylcarbonyloxazol-2-yl)ethylcarbamoyl]butylcarbamate (Compound 340);

benzyl 3-methyl-1-[2-hydroxy-1-phenethyl-2-(4-piperidin-1-ylcarbonyloxazol-2-yl)ethylcarbamoyl]butylcarbamate (Compound 341);

benzyl 3-methyl-1-{2-[4-(2,3-dihydroindol-1-ylcarbonyl)oxazol-2-yl]-2-hydroxy-1-phenethylethylcarbamoyl}butylcarbamate (Compound 342);

benzyl 3-methyl-1-{2-[4-(3,4-dihydro-1H-isoquinol-2-ylcarbonyl)oxazol-2-yl]-2-hydroxy-1-phenethylethylcarbamoyl}butylcarbamate (Compound 343);

benzyl 3-methyl-1-{2-[4-(3,4-dihydro-1H-isoquinol-1-ylcarbonyl)oxazol-2-yl]-2-hydroxy-1-phenethylethylcarbamoyl}butylcarbamate (Compound 344);

benzyl 3-methyl-1-[2-hydroxy-2-(4-naphth-1-ylmethylcarbonyloxazol-2-yl)-1-phenethylethylcarbamoyl]butylcarbamate (Compound 345); and benzyl 1S-{2-[4-(3,4-dihydro-2H-quinol-1-ylcarbonyl)oxazol-2-yl]-2-hydroxy-1S-methylethlcarbamoyl}-3-methylbutylcarbamate (Compound 346).

Proceeding by methods analogous to those described above provided the following compounds of Formula I:

N-[3-methyl-1S-(1S-thiazol-2-ylcarbonylethylcarbamoyl)butyl]-4-morpholin-4-ylbenzamide (Compound 347); and N-[1S-(2-benzooxazol-2-yl-1,1-dimethyl-2-oxoethylcarbamoyl)-3-methylbutyl]-4-(4-methylpiperazin-1-yl)benzamide (Compound 348).

Proceeding by methods analogous to those set forth in this Application compounds of Formula I are provided which are comprised by the elements A, B, C and D listed in the following Table 1.

TABLE 1

TABLE 1-continued

TABLE 1-continued
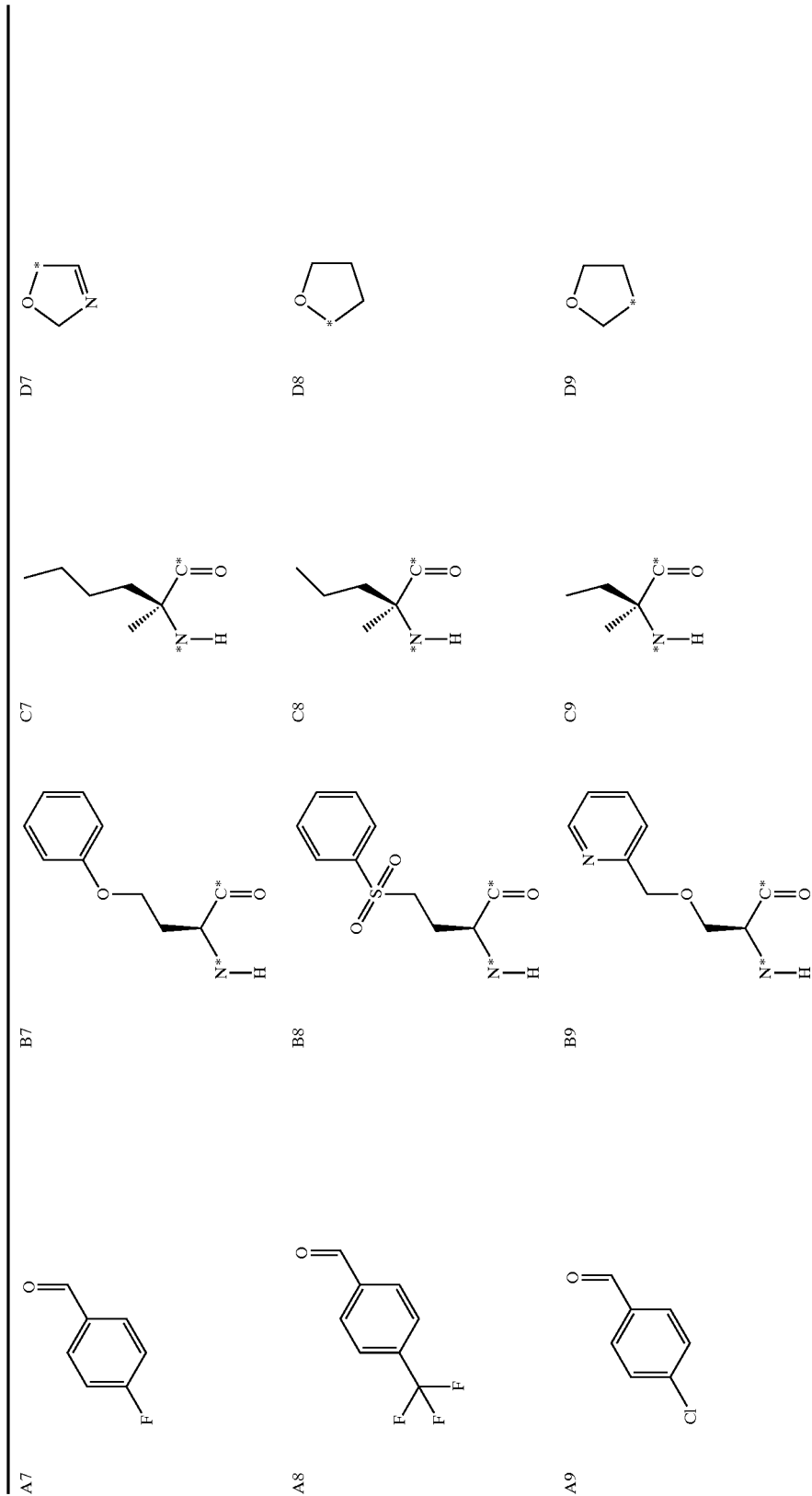

TABLE 1-continued

| A10 | B10 | C10 | D10 |
| A11 | B11 | C11 | D11 |
| A12 | B12 | C12 | D12 |
| A13 | B13 | C13 | D13 |

TABLE 1-continued

| A | B | C | D |
|---|---|---|---|
| A14 | B14 | C14 | D14 |
| A15 | B15 | C15 | D15 |
| A16 | B16 | C16 | D16 |
| A17 | B17 | C17 | D17 |

TABLE 1-continued
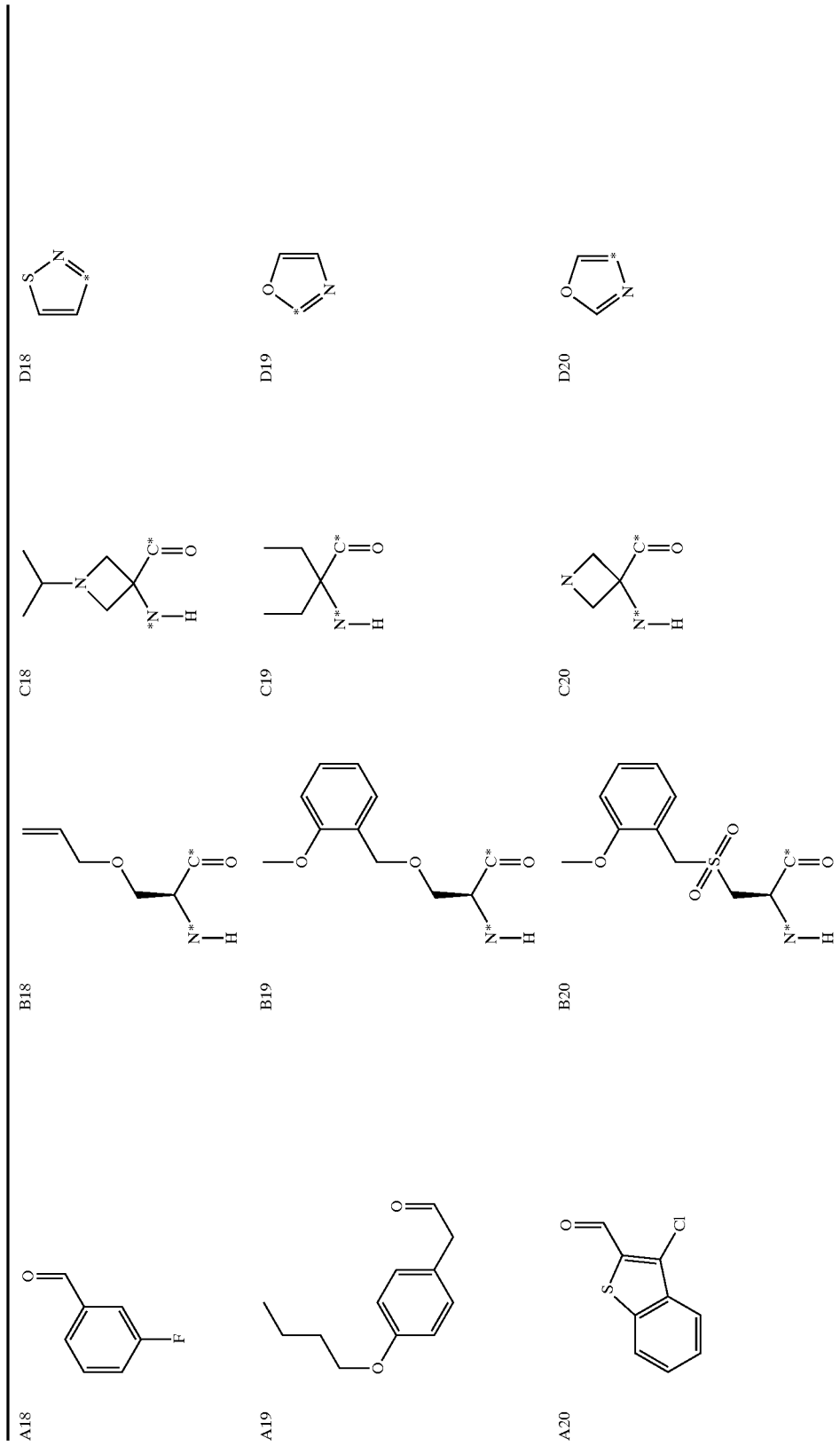

TABLE 1-continued

TABLE 1-continued
| A | B | C | D |
|---|---|---|---|
| 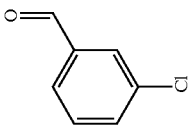 A24 | 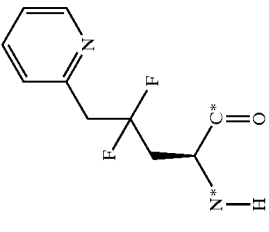 B24 | 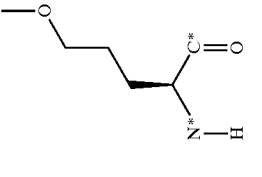 C24 | 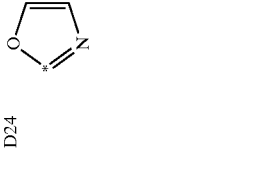 D24 |
|  A25 | 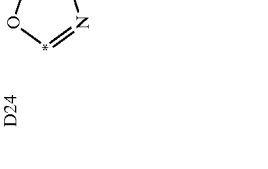 B25 | 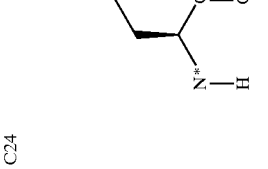 C25 | 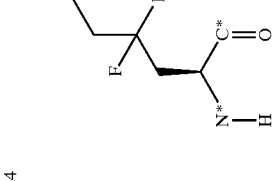 D25 |
|  A26 | 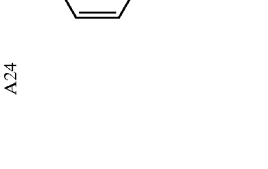 B26 | C26 | D26 |

TABLE 1-continued
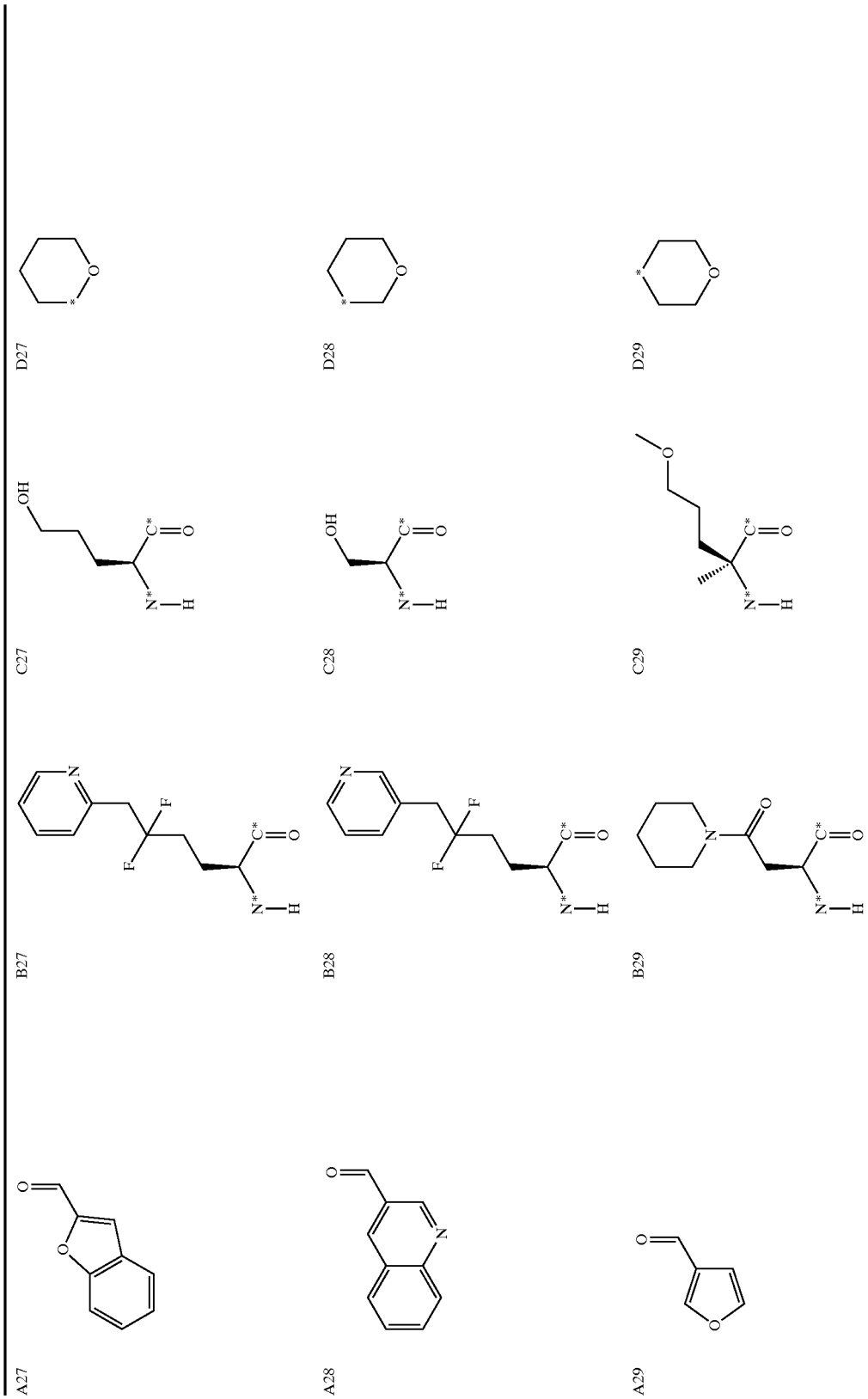

TABLE 1-continued

TABLE 1-continued

TABLE 1-continued

| A | B | C | D |
|---|---|---|---|
| A36 (4-CF3-benzaldehyde) | B36 (cyclohexylmethyl-aminomethyl amino acid) | C36 (methylsulfonyl amino acid) | D36 (pyrimidine) |
| A37 (thiophene-3-carbaldehyde) | B37 (isobutyramide amino acid) | | D37 (pyrazine) |
| A38 (thiophene-2-carbaldehyde) | B38 (isobutyramide amino acid) | | D38 (acridine) |

TABLE 1-continued

TABLE 1-continued
| A42 | B42 | D42 |
| A43 | B43 | D43 |
| A44 | B44 | D44 |
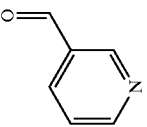

TABLE 1-continued

| | | |
|---|---|---|
| A45 | B45 | D45 |
| A46 | B46 | D46 |
| A47 | B47 | D47 |

TABLE 1-continued

| A48 | B48 | D48 |
| A49 | B49 | D49 |
| A50 | B50 | D50 |

TABLE 1-continued
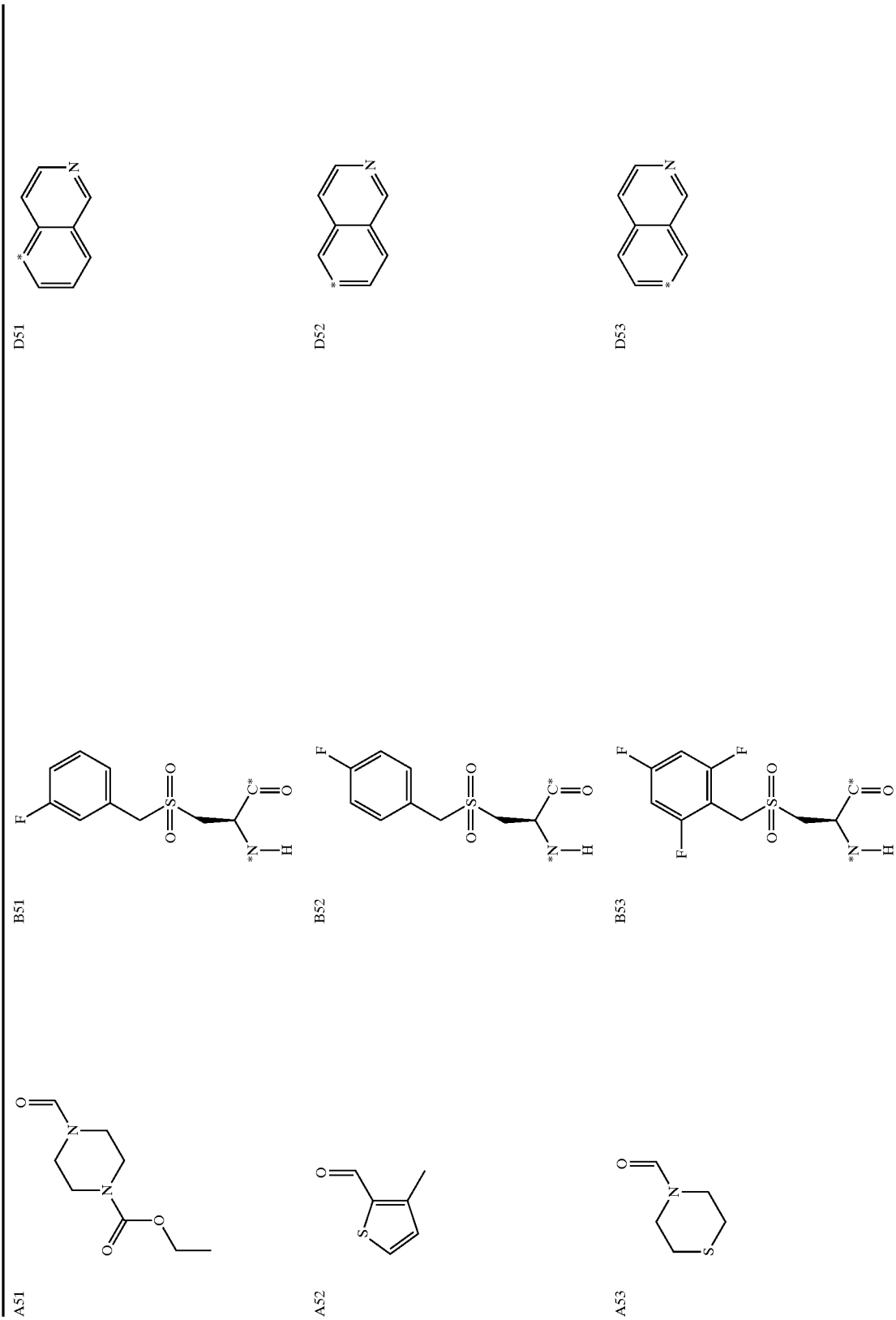

TABLE 1-continued

TABLE 1-continued

| | | |
|---|---|---|
| D59 | | A59 |
| D60 | | A60 |
| D61 | | A61 |
| D62 | | A62 |
| D63 | | A63 |
| D64 | | A64 |

TABLE 1-continued

| | |
|---|---|
| D65 | (structure) |
| D66 | (structure) |
| D67 | (structure) |
| D68 | (structure) |
| D69 | (structure) |
| D70 | (structure) |
| D71 | (structure) |
| A65 | (structure) |
| A66 | (structure) |
| A67 | (structure) |
| A68 | (structure) |
| A69 | (structure) |
| A70 | (structure) |
| A71 | (structure) |

TABLE 1-continued

TABLE 1-continued

TABLE 1-continued

| | |
|---|---|
| A84 | D84 |
| A85 | D85 |
| A86 | D86 |
| A87 | D87 |
| A88 | D88 |
| A89 | D89 |

TABLE 1-continued
| | | |
|---|---|---|
| D90 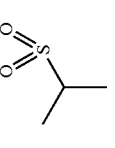 | D91 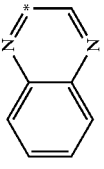 | D92 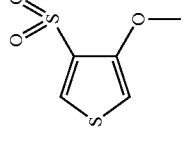 |
| D93 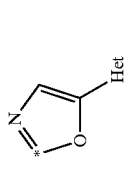 | D94 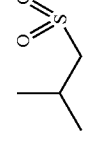 | D95 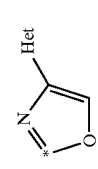 |
| A90 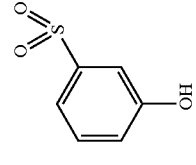 | A91 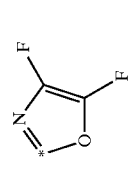 | A92 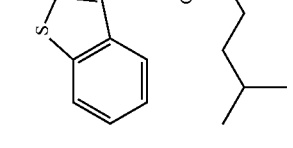 |
| A93 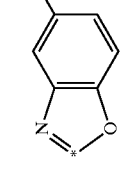 | A94 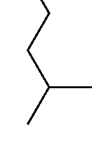 | A95 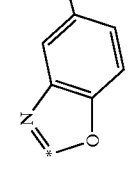 |

TABLE 1-continued
| | | |
|---|---|---|
| A96 | 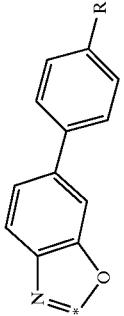 | D96 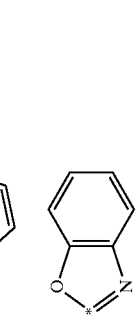 |
| A97 | 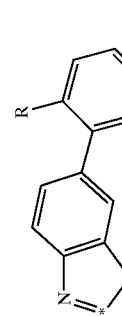 | D97 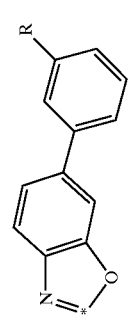 |
| A98 | 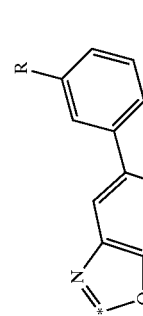 | D98 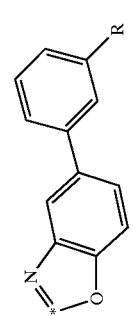 |
| A99 |  | D99 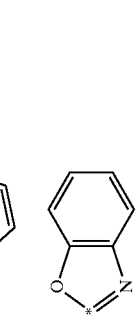 |
| A100 | 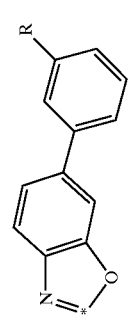 | D100 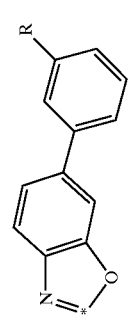 |
| A101 | 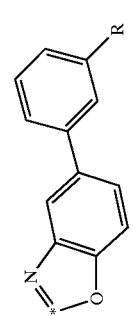 | D101 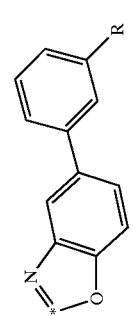 |

TABLE 1-continued

| | | | | | |
|---|---|---|---|---|---|
| D102 | D103 | D104 | D105 | D106 | D107 |
| A102 | A103 | A104 | A105 | A106 | A107 |

TABLE 1-continued

TABLE 1-continued

| | |
|---|---|
| A114 | D114 |
| A115 | D115 |
| A116 | D116 |
| A117 | D117 |
| A118 | D118 |
| A119 | D119 |

TABLE 1-continued

TABLE 1-continued
| A126 | A127 | A128 | A129 | A130 |
|---|---|---|---|---|
| 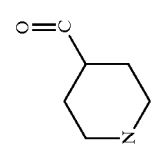 | 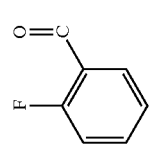 | 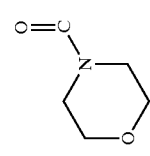 | 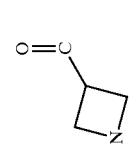 | 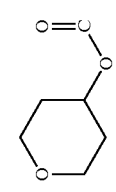 |

TABLE 1-continued
A131 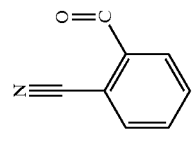
A132 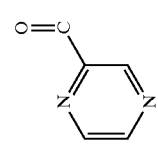
A133 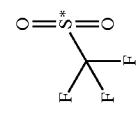

While any combination of the elements A, B and C may comprise the compounds of the Invention, certain combinations are preferred. For example, the following combinations Compounds of the invention were tested by the above-described assay and observed to exhibit cathepsin B inhibitory activity with a $K_i$ of less than or equal to 10 μM.

| | | | |
|---|---|---|---|
| A11-B5-C4-D1 | A17-B5-C4-D1 | A66-B5-C4-D1 | A75-B5-C4-D1 |
| A128-B5-C4-D1 | A11-B6-C4-D1 | A17-B6-C4-D1 | A66-B6-C4-D1 |
| A75-B6-C4-D1 | A128-B6-C4-D1 | A11-B8-C4-D1 | A17-B8-C4-D1 |
| A66-B8-C4-D1 | A75-B8-C4-D1 | A128-B8-C4-D1 | A11-B12-C4-D1 |
| A17-B12-C4-D1 | A66-B12-C4-D1 | A75-B12-C4-D1 | A128-B12-C4-D1 |
| A11-B11-C4-D1 | A17-B11-C4-D1 | A66-B11-C4-D1 | A75-B11-C4-D1 |
| A128-B11-C4-D1 | A11-B14-C4-D1 | A17-B14-C4-D1 | A66-B14-C4-D1 |
| A75-B14-C4-D1 | A128-B14-C4-D1 | A11-B5-C4-D2 | A17-B5-C4-D2 |
| A66-B5-C4-D2 | A75-B5-C4-D2 | A128-B5-C4-D2 | A11-B6-C4-D2 |
| A17-B6-C4-D2 | A66-B6-C4-D2 | A75-B6-C4-D2 | A128-B6-C4-D2 |
| A11-B8-C4-D2 | A17-B8-C4-D2 | A66-B8-C4-D2 | A75-B8-C4-D2 |
| A128-B8-C4-D2 | A11-B12-C4-D2 | A17-B12-C4-D2 | A66-B12-C4-D2 |
| A75-B12-C4-D2 | A128-B12-C4-D2 | A11-B11-C4-D2 | A17-B11-C4-D2 |
| A66-B11-C4-D2 | A75-B11-C4-D2 | A128-B11-C4-D2 | A11-B14-C4-D2 |
| A17-B14-C4-D2 | A66-B14-C4-D2 | A75-B14-C4-D2 | A128-B14-C4-D2 |
| A61-B5-C4-D1 | A64-B5-C4-D1 | A37-B5-C4-D1 | A38-B5-C4-D1 |
| A90-B5-C4-D1 | A92-B5-C4-D1 | A133-B5-C4-D1 | A61-B6-C4-D1 |
| A64-B6-C4-D1 | A37-B6-C4-D1 | A38-B6-C4-D1 | A90-B6-C4-D1 |
| A92-B6-C4-D1 | A133-B6-C4-D1 | A61-B12-C4-D1 | A64-B12-C4-D1 |
| A37-B12-C4-D1 | A38-B12-C4-D1 | A90-B12-C4-D1 | A92-B12-C4-D1 |
| A133-B12-C4-D1 | | | |
| A11-B31-C4-D1 | A75-B31-C4-D1 | A128-B31-C4-D1 | A11-B13-C4-D1 |
| A75-B13-C4-D1 | A128-B13-C4-D1 | A11-B21-C4-D1 | A75-B21-C4-D1 |
| A128-B21-C4-D1 | A11-B46-C4-D1 | A75-B46-C4-D1 | A128-B46-C4-D1 |
| A11-B49-C4-D1 | A75-B49-C4-D1 | A128-B49-C4-D1 | A11-B50-C4-D1 |
| A75-B50-C4-D1 | A128-B50-C4-D1 | A11-B51-C4-D1 | A75-B51-C4-D1 |
| A128-B51-C4-D1 | A11-B52-C4-D1 | A75-B52-C4-D1 | A128-B52-C4-D1 |
| A11-B53-C4-D1 | A75-B53-C4-D1 | A128-B53-C4-D1 | |
| A11-B5-C36-D1 | A75-B5-C36-D1 | A128-B5-C36-D1 | A11-B6-C36-D1 |
| A75-B6-C36-D1 | A128-B6-C36-D1 | A11-B12-C36-D1 | A75-B12-C36-D1 |
| A128-B12-C36-D1 | A11-B5-C11-D1 | A75-B5-C11-D1 | A128-B5-C11-D1 |
| A11-B6-C11-D1 | A75-B6-C11-D1 | A128-B6-C11-D1 | A11-B12-C11-D1 |
| A75-B12-C11-D1 | A128-B12-C11-D1 | A11-B5-C10-D1 | A75-B5-C10-D1 |
| A128-B5-C10-D1 | A11-B6-C10-D1 | A75-B6-C10-D1 | A128-B6-C10-D1 |
| A11-B12-C10-D1 | A75-B12-C10-D1 | A128-B12-C10-D1 | A11-B5-C35-D1 |
| A75-B5-C35-D1 | A128-B5-C35-D1 | A11-B6-C35-D1 | A75-B6-C35-D1 |
| A128-B6-C35-D1 | A11-B12-C35-D1 | A75-B12-C35-D1 | A128-B12-C35-D1 |
| A11-B5-C4-D33 | A75-B5-C4-D33 | A128-B5-C4-D33 | A11-B6-C4-D33 |
| A75-B6-C4-D33 | A128-B6-C4-D33 | A11-B12-C4-D33 | A75-B12-C4-D33 |
| A128-B12-C4-D33 | A11-B5-C4-D83 | A75-B5-C4-D83 | A128-B5-C4-D83 |
| A11-B6-C4-D83 | A75-B6-C4-D83 | A128-B6-C4-D83 | A11-B12-C4-D83 |
| A75-B12-C4-D83 | A128-B12-C4-D83 | A11-B5-C4-D86 | A75-B5-C4-D86 |
| A128-B5-C4-D86 | A11-B6-C4-D86 | A75-B6-C4-D86 | A128-B6-C4-D86 |
| A11-B12-C4-D86 | A75-B12-C4-D86 | A128-B12-C4-D86 | A11-B5-C4-D123 |
| A75-B5-C4-D123 | A128-B5-C4-D123 | A11-B6-C4-D123 | A75-B6-C4-D123 |
| A128-B6-C4-D123 | A11-B12-C4-D123 | A75-B12-C4-D123 | A128-B12-C4-D123 |

Example 28

Cathepsin B Assay

Solutions of test compounds in varying concentrations were prepared in 10 μL of dimethyl sulfoxide (DMSO) and then diluted into assay buffer (40 μL, comprising: N,N-bis (2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5–10 seconds on a shaker plate, covered and incubated for 30 minutes at room temperature. Z-FR-AMC (20 nMoles in 25 μL of assay buffer) was added to the assay solutions and hydrolysis was followed spectrophotometrically at (λ 460 nm) for 5 minutes. Apparent inhibition constants ($K_j$) were calculated from the enzyme progress curves using standard mathematical models.

Example 29

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at room temperature. Z-Phe-Arg-AMC (4 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested by the above-described assay and observed to exhibit cathepsin K inhibitory activity with a $K_i$ of less than or equal to 10 μM.

Example 30

Cathepsin L Assay

Solutions of test compounds in varying concentrations were prepared in 10 µL of dimethyl sulfoxide (DMSO) and then diluted into assay buffer (40 µL, comprising: MES, 50 mM (pH 5.5); EDTA, 2.5 mM; and DTT, 2.5 mM). Human cathepsin L (0.05 pMoles in 25 µL of assay buffer) was added to the dilutions. The assay solutions were mixed for 5–10 seconds on a shaker plate, covered and incubated for 30 minutes at room temperature. Z-Phe-Arg-AMC (1 nMoles in 25 µL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Compounds of the invention were tested by the above-described assay and observed to exhibit cathepsin L inhibitory activity with a $K_i$ of less than or equal to 10 µM.

Example 31

Cathepsin S Assay

Solutions of test compounds in varying concentrations were prepared in 10 µL of dimethyl sulfoxide (DMSO) and then diluted into assay buffer (40 µL, comprising: MES, 50 mM (pH 6.5); EDTA, 2.5 mM; and NaCl, 100 mM). Human cathepsin S (0.158 pMoles in 25 µL of assay buffer) was added to the dilutions. The assay solutions were mixed for 5–10 seconds on a shaker plate, covered and incubated for 30 minutes at room temperature. Z-Val-Val-Arg-AMC (9 nMoles in 25 µL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Compounds of the invention were tested by the above-described assay and observed to exhibit cathepsin S inhibitory activity with a $K_i$ of less than or equal to 10 µM.

Example 32

Ovalbumin Challenge Mouse

C57 mice (female) were sensitised with ovalbumin (10 µg, i.p.) administered together with aluminium hydroxide adjuvant (20 mg, i.p.) on days 0 and 12. Mice are challenged on either day 22, 23 or 24 by exposure for 60 minutes to an aerosol of ovalbumin (10 g/l) twice, 4 hours apart. Mice are dosed p.o. with either vehicle 5 ml/kg (0.5% MC/0.2% Tween 80 in $H_2O$) or test compound at 0, 8, 23.5 29, 33, 48 and 56 hours.

Mice were euthanized with pentobarbitone i.p. after 86 hours (72 hours after the first challenge). The lungs were insufflated for histological examination as soon as possible after euthanization. Lungs were insufflated with 10% neutral buffered formalin (NBF), at 30 cm water pressure. The lungs were removed and placed in pots of 10% NBF. After fixation in 10% NBF for a minimum of 24 hours the lungs were processed through graded alcohols to wax. The lungs were blocked longitudinally and one 2 µm section for each animal was cut at the level of the main bronchi. Sections then were stained with haematoxylin and eosin. Pathological assessment of sections is performed and a grading is assigned.

Histopathological evaluation of the lung tissue demonstrate a dose dependant anti-inflammatory effect on vascular and mucosal beds after treatment with compounds of the invention between 0.03 and 30 mg/kg.

Example 32

Representative Pharmaceutical Formulations Containing a Compound of Formula I

| ORAL FORMULATION | |
|---|---|
| Compound of Formula I | 10–100 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| Compound of Formula I | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of Formula I | 1% |
| Microcrystalline Cellulose | 73% |
| Stearic Acid | 25% |
| Colloidal Silica | 1%. |

The resulting tablets are useful for administration in accordance with the methods of this invention for treating or preventing a cathepsin mediated disease state, such as osteoporosis, juvenile onset diabetes, multiple sclerosis, pemphigus vulgaris, Graves' disease, myasthenia gravis, systemic lupus erythemotasus, rheumatoid arthritis, Hashimoto's thyroiditis, asthma, organ transplant or tissue graft rejections, chronic obstructive pulmonary disease, bronchiolitis, excessive airway elastolysis in asthma and bronchitis, pneumonities, plaque rupture, atheroma and systemic amyloidosis.

We claim:

1. A compound of Formula I:

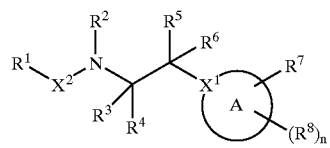

in which:

A comprises a benzooxazole or naphthooxazole ring, each substituted by a group $R^7$ and optionally substituted with a group $R^8$, wherein $R^7$ is hydrogen, halo, $(C_{1-4})$alkoxy, $(C_{1-4})$alkoxycarbonyl, nitro or phenyl, $R^8$ at each occurrence independently is halo, $(C_{1-4})$alkoxy, $(C_{1-4})$alkoxycarbonyl, nitro or trifluoromethyl;

n is 0, 1, 2 or 3;

$X^1$ is =C—;

$X^2$ is a bond or a divalent group of Formula (a):

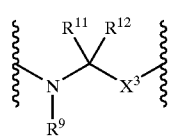

wherein within Formula (a) CR$^9$ is hydrogen, R$^{11}$ is hydrogen or methyl and R$^{12}$ is (C$_{1-6}$)alkyl substituted with —SR$^{14}$, —S(O)R$^{14}$ or —S(O)$_2$R$^{14}$, wherein R$^{14}$ is (C$_{6-12}$)aryl(C$_{0-6}$)alkyl or hetero(C$_{5-12}$)aryl(C$_{0-6}$)alkyl; wherein within R$^{12}$ the aromatic ring system present may be substituted further by 1 to 5 radicals independently selected from (C$_{1-6}$)alkyl, (C$_{1-6}$)alkylidene, cyano, halo, halo-substituted (C$_{1-4}$)alkyl, nitro, —X$^5$NR$^{14}$R$^{14}$, —X$^5$NR$^{14}$C(O)OR$^{14}$, —X$^5$NR$^{14}$C(O)NR$^{14}$R$^{14}$, —X$^5$NR$^{14}$C(NR$^{14}$)NR$^{14}$R$^{14}$, —X$^5$OR$^{14}$, —X$^5$SR$^{14}$, —$^5$C(O)OR$^{14}$, —X$^5$C(O)NR$^{14}$R$^{14}$, —X$^5$S(O)$_2$NR$^{14}$R$^{14}$, —X$^5$P(O)(OR$^{14}$)OR$^{14}$, —X$^5$OP(O)(OR$^{14}$)OR$^{14}$, —X$^5$NR$^{14}$C(O)R$^{15}$, —X$^5$S(O)R$^{15}$, —X$^5$S(O)$_2$R$^{13}$ and —X$^5$C(O)R$^{15}$, wherein X$^5$ is a bond or (C$_{1-6}$)alkylene, R$^{14}$ at each occurrence independently is hydrogen, (C$_{1-6}$)alkyl or halo-substituted (C$_{1-3}$)alkyl and R$^{15}$ is (C$_{1-6}$)alkyl or halo-substituted (C$_{1-3}$)alkyl;

R$^1$ is —X$^6$X$^7$R$^{20}$, wherein X$^6$ is —C(O)— or —S(O)$_2$—, X$^7$ is a bond, —O— or —NR$^{21}$—, wherein R$^{21}$ is hydrogen or (C$_{1-6}$)alkyl, and R$^{20}$ is (i) (C$_{1-6}$)alkyl optionally substituted by —C(O)OR$^{14}$ or (ii) (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl or hetero(C$_{5-12}$)aryl(C$_{0-6}$)alkyl or (iii) (C$_{3-6}$)cycloalkyl(C$_{0-6}$)alkyl, hetero(C$_{3-6}$)cycloalkyl(C$_{0-6}$)alkyl, phenyl(C$_{0-6}$)alkyl or hetero(C$_{5-6}$)aryl(C$_{0-6}$)alkyl, wherein said cycloalkyl, heterocycloalkyl, phenyl or heteroaryl is substituted by —X$^5$OR$^{24}$, —X$^5$C(O)R$^{24}$, —X$^5$C(O)OR$^{24}$, —X$^5$C(O)NR$^{24}$R$^{25}$, —X$^5$NR$^{24}$R$^{25}$, —X$^5$NR$^{25}$C(O)R$^{24}$, —X$^5$NR$^{25}$C(O)OR$^{24}$, —X$^5$NR$^{25}$C(O)NR$^{24}$R$^{25}$ or —X$^5$NR$^{25}$C(NR$^{25}$)NR$^{24}$R$^{25}$, wherein X$^5$ is a bond or (C$_{1-6}$)alkylene, R$^{24}$ is (C$_{3-6}$)cycloalkyl(C$_{0-6}$)alkyl, hetero(C$_{3-6}$)cycloalkyl(C$_{0-6}$)alkyl, phenyl(C$_{0-6}$)alkyl or hetero(C$_{5-6}$)aryl(C$_{0-6}$)alkyl and R$^{25}$ is hydrogen or (C$_{1-6}$)alkyl; wherein within R$^1$ any alicyclic or aromatic ring system present may be substituted further by 1 to 5 substituents independently selected from (C$_{1-6}$)alkyl, halo, halo-substituted (C$_{1-4}$)alkyl, —OR$^{14}$ and —C(O)OR$^{14}$ wherein R$^{14}$ is as defined above, or when X$^2$ is a divalent group of formula (a) then R$^1$ may be, but is not limited to, hydrogen or oxalo;

R$^2$ is hydrogen;

R$^3$ is hydrogen, (C$_{1-6}$)alkyl (optionally substituted with cyano, halo, nitro, —SR$^{24}$, —C(O)OR$^{24}$, —C(O)NR$^{24}$R$^{24}$, —P(O)(OR$^{24}$)OR$^{24}$, —OP(O)(OR$^{24}$)OR$^{24}$, —S(O)R$^{25}$, —S(O)$_2$R$^{25}$ or —C(O)R$^{25}$, wherein R$^{24}$ at each occurrence independently is hydrogen, (C$_{1-6}$)alkyl or halo-substituted (C$_{1-3}$)alkyl and R$^{25}$ is halo, (C$_{1-6}$)alkyl or halo-substituted (C$_{1-3}$)alkyl) or (C$_{6-12}$)aryl(C$_{2-3}$)alkyl, wherein said aryl optionally is substituted further with 1 to 5 radicals independently selected from (C$_{1-6}$)alkyl, (C$_{1-6}$)alkylidene, cyano, halo, halo-substituted (C$_{1-4}$)alkyl, nitro, —X$^5$NR$^{14}$C(O)OR$^{14}$, —X$^5$NR$^{14}$C(O)NR$^{14}$R$^{14}$, —X$^5$NR$^{14}$C(NR$^{14}$)NR$^{14}$R$^{14}$, —X$^5$OR$^{14}$, —X$^5$SR$^{14}$, —X$^5$C(O)OR$^{14}$, —X$^5$C(O)NR$^{14}$R$^{14}$, —X$^5$S(O)$_2$NR$^{14}$R$^{14}$, —X$^5$P(O)(OR$^{14}$)OR$^{14}$, —X$^5$OP(O)(OR$^{14}$)OR$^{14}$, —X$^5$NR$^{14}$C(O)R$^{15}$, —X$^5$S(O)R$^{15}$, —X$^5$S(O)$_2$R$^{15}$ and —X$^5$C(O)R$^{15}$, wherein X$^5$ is a bond or (C$_{1-6}$)alkylene and R$^{14}$ and R$^{15}$ are as defined above, or R$^3$ and R$^4$ or R$^3$ and R$^4$ taken together with the carbon atom to which both R$^3$ and R$^4$ are attached form cyclopropylene, cyclobutylene, cyclopentylene or cyclohexylene;

R$^4$ is hydrogen or as defined above; and

R$^5$ and R$^6$ together form oxo; and the N-oxide derivatives, and individual stereoisomers and mixtures of stereoisomers thereof; and the pharmaceutically acceptable salts thereof.

2. The compound of claim 1 in which:

A is benzoxazol-2-yl substituted by R$^7$, wherein R$^7$ is hydrogen, halo, (C$_{1-4}$)alkoxy, (C$_{1-4}$)alkoxycarbonyl or nitro and R$^8$ at each occurrence independently is halo, (C$_{1-4}$)alkoxy, (C$_{1-4}$)alkoxycarbonyl, nitro or trifluoromethyl;

X$^2$ is a bond or a divalent group of Formula (a), wherein within Formula (a) X$^3$ is —C(O)—, R$^{11}$ is hydrogen and R$^{12}$ is a group having the following formula:

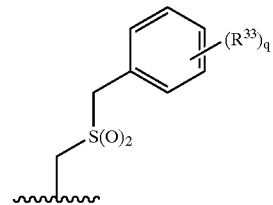

in which q is 0, 1, 2, 4 or 5 and R$^{33}$ at each occurrence independently is selected from a group consisting of (C$_{1-4}$)alkyl, cyano, halo, halo-substituted (C$_{1-4}$)alkyl, nitro, —X$^5$NR$^{14}$R$^{14}$, —X$^5$OR$^{14}$, —X$^5$SR$^{14}$, —X$^5$C(O)NR$^{14}$R$^{14}$, —X$^5$C(O)OR$^{14}$, —X$^5$S(O)R$^{15}$, —X$^5$S(O)$_2$R$^{15}$ and —X$^5$C(O)R$^{15}$, wherein X$^5$ is a bond or (C$_{1-6}$)alkylene, R$^{14}$ at each occurrence independently is hydrogen, (C$_{1-3}$)alkyl or halo-substituted (C$_{1-3}$)alkyl and R$^{15}$ is (C$_{1-3}$)alkyl or halo-substituted (C$_{1-3}$)alkyl;

R$^1$ is selected from a group consisting of acetyl, azetidin-3-ylcarbonyl, benzyloxycarbonyl, 1-benzyloxycarbonylpiperidin-4-ylcarbonyl, benzylsulfonyl, bicyclo[2.2.2]hept-2-ylcarbonyl, bicyclo[2.2.1]hept-2-ylcarbonyl, tert-butoxycarbonyl, carboxyacetyl, 2-carboxypropionyl, 3-carboxypropionyl, 2-cyclohexylacetyl, 4-cyclohexylbutyryl, 2-cyclohexylethylsulfonyl, cyclohexylmethoxycarbonyl, 3-cyclohexylpropionyl, 2-cyclopentylethylsulfonyl, 3-cyclopentylpropionyl, di(2-methoxyethyl)carbamoyl, dimethylcarbamoyl, 6-hydroxypyrid-3-ylcarbonyl, 1H-imidazol-4-ylcarbonyl, methoxycarbonyl, methylsulfonyl, 4-methylvaleryl, morpholin-4-ylcarbonyl, 2-morpholin-4-ylethylcarbonyl, naphth-1-ylacetyl, naphth-1-ylmethylcarbonyl, oxalo, 3-phenylpropionyl, piperazin-1-ylcarbonyl, piperidin-4-ylcarbonyl, pyrazin-2-ylcarbonyl, pyrid-3-ylcarbonyl, pyrid-4-ylcarbonyl, pyrid-3-ylaminocarbonyl, tetrahydropyran-4-ylcarbonyl and tetrahydropyran-4-yloxycarbonyl;

R$^3$ is selected from hydrogen, (C$_{1-4}$)alkyl, phenyl(C$_{2-3}$)alkyl or (C$_{1-4}$)alkylsulfonyl(C$_{2-4}$)alkyl or R$^3$ and R$^4$ taken together with the carbon atom to which both R$^3$ and R$^4$ are attached form (C$_{3-6}$)cycloalkylene;

R$^4$ is hydrogen or as defined above; and the N-oxide derivatives, and individual stereoisomers and mixtures of stereoisomers thereof; and the pharmaceutically acceptable salts thereof.

3. The compound of claim 2 in which q is 0, 1 or 2, R$^1$ is morpholin-4-ylcarbonyl, methoxycarbonyl, methylsulfonyl, piperidin-4-ylcarbonyl, pyrazin-2-ylcarbonyl pyrid-3-ylcarbonyl, pyrid-4-ylcarbonyl, tetrahydropyran-4-ylcarbonyl or tetrahydropyran-4-yloxycarbonyl, R$^3$ is methyl, ethyl, n-propyl, n-butyl, 2-methylsulfonylethyl or phenyethyl or R$^3$ and R$^4$ taken together with the carbon atom to which both R$^3$ and R$^4$ are attached form cyclobutylene and R$^{33}$ at each occurrence independently is (C$_{1-4}$)alkyl, cyano, halo, halo-subsituted $(C_{1-4})$alkyl, nitro, —$OR^{14}$, —$SR^{14}$ or –$C(O)OR^{14}$, wherein $R^{14}$ at each occurrence independently is hydrogen, $(C_{1-3})$alkyl or halo-substituted $(C_{1-3})$alkyl; and the N-oxide derivatives, and individual stereoisomers and mixtures of stereoisomers thereof; and the pharmaceutically acceptable salts thereof.

4. The compound of claim 3 in which $R^{33}$ at each occurrence independently is selected from a group consisting of $(C_{1-4})$alkyl, bromo, carboxy, chloro, cyano, difluoromethoxy, fluoro, iodo, methoxy, nitro, trifluoromethoxy, trifluoromethyl and trifluorosulfanyl; and the N-oxide derivatives, and individual stereoisomers and mixtures of stereoisomers thereof; and the pharmaceutically acceptable salts thereof.

5. The compound of claim 1 in which within Formula (a) $R^{12}$ is benzylsulfonylmethyl, 2-chlorobenzylsulfonylmethyl, 2-cyanobenzylsulfonylmethyl, 2-difluoromethoxybenzylsulfonylmethyl, 3,5-dimethylisooxazol-4-ylmethylsulfonylmethyl, 2-methoxybenzylsulfonylmethyl, 6-methylpyrid-2-ylmethylsulfonylmethyl, 2-nitrobenzylsulfonylmethyl, pyrid-2-ylmethylsulfonylmethyl, o-tolylmethylsulfonylmethyl or 2-trifluoromethylbenzylsulfonylmethyl; and the N-oxide derivatives, and individual stereoisomers and mixtures of stereoisomers thereof; and the pharmaceutically acceptable salts thereof.

6. A compound of Formula II:

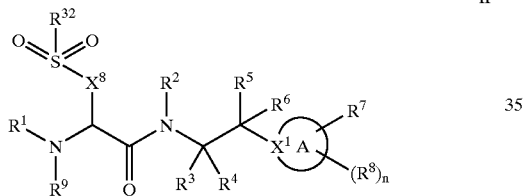

II in which:

A comprises a benzooxazole or naphthooxazolering wherein $X^1$ is a ring member carbon atom;

n is 0, 1, 2 or 3;

$X^1$ is =C— or —CH—;

$X^8$ is $(C_{1-2})$alkylene;

$R^1$ is hydrogen, carboxy, oxalo, carbamoyl or —$X^6X^7R^{20}$, wherein $X^6$ is —C(O)—, —C(O)C(O)— or —S(O)$_2$—, $X^7$ is a bond, —O— or —$NR^{21}$—, wherein $R^{21}$ is hydrogen or $(C_{1-6})$alkyl, and $R^{20}$ is (i) $(C_{1-6})$alkyl optionally substituted by cyano, halo, nitro, —$NR^{14}R$, —$NR^{14}C(O)OR^{14}$, —$NR^{14}C(O)NR^{14}R^{14}$, —$NR^{14}C(NR^{14})NR^{14}R^{14}$, —$OR^{14}$, —$SR^{14}$, —$C(O)OR^{14}$, —$C(O)NR^{14}R^{14}$, —$S(O)_2NR^{14}R^{14}$, —$P(O)(OR^{14})OR^{14}$, —$OP(O)(OR^{14})OR^{14}$, —$NR^{14}C(O)R^{15}$, —$S(O)R^{15}$, —$S(O)_2R^{15}$, —$C(O)R^{15}$, —$OR^{22}$, —$SR^{22}$, —$S(O)R^{22}$, —$S(O)_2R^{22}$, —$C(O)R^{22}$, —$C(O)OR^{22}$, —$C(O)NR^{22}R^{23}$, —$NR^{22}R^{23}$, —$NR^{23}C(O)R^{22}$, $NR^{23}C(O)OR^{22}$, $NR^{23}C(O)NR^{22}R^{23}$ or —$NR^{23}C(NR^{23})NR^{22}R^{23}$, wherein $R^{14}$ at each occurrence independently is hydrogen, $(C_{1-6})$alkyl or halo-substituted $(C_{1-3})$alkyl, $R^{15}$ is $(C_{1-6})$alkyl or halo-substituted $(C_{1-3})$alkyl, $R^{22}$ is $(C_{3-2})$cycloalkyl$(C_{0-6})$alkyl, hetero$(C_{3-2})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-6})$alkyl or hetero$(C_{8-12})$bicycloaryl$(C_{0-6})$alkyl and $R^{23}$ at each occurrence independently is hydrogen or $(C_{1-6})$alkyl, or (ii) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-6})$alkyl or hetero$(C_{8-12})$bicycloaryl$(C_{0-6})$alkyl or (iii) $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl substituted by —$X^5OR^{24}$, —$X^5SR^{24}$, —$X^5S(O)R^{24}$, —$X^5S(O)_2R^{24}$, —$X^5C(O)R^{24}$, —$X^5C(O)OR^{24}$, —$X^5C(O)NR^{24}R^{25}$, —$X^5NR^{24}R^{25}$, —$X^5NR^{25}C(O)R^{24}$, —$X^5NR^{25}C(O)OR^{24}$, —$X^5NR^{25}C(O)NR^{24}R^{25}$ or —$X^5NR^{25}C(NR^{25})NR^{24}R^{25}$, wherein $X^5$ is a bond or $(C_{1-6})$alkylene, $R^{24}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl and $R^{25}$ at each occurrence independently is hydrogen or $(C_{1-6})$alkyl; wherein within $R^1$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above;

$R^2$ is hydrogen or $(C_{1-6})$alkyl;

$R^3$ is (i) $(C_{1-6})$alkyl optionally substituted with cyano, halo, nitro, —$NR^{14}R^{14}$, —$NR^{14}C(O)OR^{14}$, —$NR^{14}C(O)NR^{14}R^{14}$, —$NR^{14}C(NR^{14})NR^{14}R^{14}$, —$OR^{14}$, —$SR^{14}$, —$C(O)OR^{14}$, —$C(O)NR^{14}R^{14}$, —$S(O)_2NR^{14}R^{14}$, —$P(O)(OR^{14})OR^{14}$, —$OP(O)(OR^{14})OR^{14}$, —$NR^{14}C(O)R^{15}$, —$S(O)R^{15}$, —$S(O)_2R^{15}$, —$C(O)R^{15}$, —$OR^{16}$, —$SR^{16}$, —$S(O)R^{16}$, —$S(O)_2R^{16}$, —$C(O)R^{16}$, —$C(O)OR^{16}$, —$OC(O)R^{16}$, —$NR^{16}R^{17}$, —$NR^{17}C(O)R^{16}$, —$NR^{17}C(O)OR^{16}$, —$C(O)NR^{16}R^{17}$, —$S(O)_2NR^{16}R^{17}$, —$NR^{17}C(O)NR^{16}R^{17}$ or —$NR^{17}C(NR^{17})NR^{16}R^{17}$, wherein $R^{14}$ at each occurrence independently is hydrogen, $(C_{1-6})$alkyl or halo-substituted $(C_{1-3})$alkyl, $R^{15}$ is $(C_{1-6})$alkyl or halo-substituted $(C_{1-3})$alkyl, $R^{16}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl and $R^{17}$ is hydrogen or $(C_{1-6})$alkyl, and wherein within $R^{16}$ said cycloalkyl, heterocycloalkyl, aryl, heteroaryl, polycycloaryl or heterpolycycloaryl ring optionally is substituted by a group selected from —$R^{18}$, —$X^5OR^{18}$, —$X^5SR^{18}$, —$X^5S(O)R^{18}$, —$X^5S(O)_2R^{18}$, —$X^5C(O)R^{18}$, —$X^5C(O)OR^{18}$, —$X^5OC(O)R^{18}$, —$X^5NR^{18}R^{19}$, —$X^5NR^{19}C(O)R^{18}$, —$X^5NR^{19}C(O)OR^{18}$, —$X^5C(O)NR^{18}R^{19}$, —$X^5S(O)_2NR^{18}R^{19}$, —$X^5NR^{19}C(O)NR^{18}R^{19}$ or —$X^5NR^{19}C(NR^{19})NR^{18}R^{19}$, wherein $X^5$ is as defined above, $R^{18}$ is hydrogen or $(C_{1-6})$alkyl and $R^{19}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl, or (ii) a group selected from $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl and hetero$(C_{8-12})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from —$R^{18}$, —$X^5OR^{18}$, —$X^5SR^{18}$, —$X^5S(O)R^{18}$, —$X^5S(O)_2R^{18}$, —$X^5C(O)R^{18}$, —$X^5C$ $(O)OR^{18}$, —$X^5OC(O)R^{18}$, —$X^5NR^{18}R^{19}$, —$X^5NR^{19}C(O)R^{18}$, —$X^5NR^{19}C(O)OR^{18}$, —$X^5C(O)NR^{18}R^{19}$, —$X^5S(O)_2NR^{18}R^{19}$, —$X^5NR^{19}C(O)NR^{18}R^{19}$ or —$X^5NR^{19}C(NR^{19})NR^{18}R^{19}$, wherein $X^5$, $R^{18}$ and $R^{19}$ are as defined above; wherein within $R^{12}$ and/or $R^{13}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above, or $R^3$ and $R^4$ taken together with the carbon atom to which both $R^3$ and $R^4$ are attached form $(C_{3-8})$cycloalkylene or $(C_{3-8})$heterocycloalkylene, wherein said cycloalkylene or heterocycloalkylene is optionally substituted with 1 to 3 radicals independently selected from $(C_{1-6})$alkyl, $(C_{1-6})$alkylidene, cyano, halo, halo-substituted $(C_{1-4})$alkyl, nitro, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above;

$R^4$ is hydrogen, $(C_{1-6})$alkyl or as defined above;

$R^5$ is hydrogen and $R^6$ is hydroxy or $R^5$ and $R^6$ together form oxo;

$R^7$ is a group selected from cyano, halo, nitro, —$R^{29}$, —$X^5NR^{29}R^{30}$, —$X^5NR^{30}C(O)OR^{29}$, —$X^5NR^{30}C(O)NR^{29}R^{30}$, —$X^5NR^{30}C(NR^{30})NR^{29}R^{30}$, —$X^5OR^{29}$, —$X^5SR^{29}$, —$X^5C(O)OR^{29}$, —$X^5C(O)NR^{29}R^{30}$, —$X^5S(O)_2NR^{29}R^{30}$, —$X^5P(O)(OR^{30})OR^{29}$, —$X^5OP(O)(OR^{29})OR^{29}$, —$X^5NR^{30}C(O)R^{31}$, —$X^5S(O)R^{31}$, —$X^5S(O)_2R^{31}$ and —$X^5C(O)R^{31}$, wherein $X^5$ is as defined above, $R^{29}$ is hydrogen or —$R^{31}$, $R^{30}$ at each occurrence is hydrogen or $(C_{1-6})$alkyl and $R^{31}$ is $(C_{1-6})$alkyl, $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl or hetero$(C_{5-12})$aryl$(C_{0-6})$alkyl, wherein within $R^7$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$x^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above; and $R^8$ at each occurrence independently is selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)N^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above;

$R^9$ is hydrogen or $(C_{1-6})$alkyl; and $R^{32}$ is $(C_{1-8})$alkyl, $(C_{3-12})$cycloalkyl$(C_{0-6})$alkyl, hetero$(C_{3-12})$cycloalkyl $(C_{0-6})$alkyl, $(C_{6-12})$aryl$(C_{0-6})$alkyl, hetero$(C_{5-12})$aryl $(C_{0-6})$alkyl, $(C_{9-12})$polycycloaryl$(C_{0-6})$alkyl or hetero $(C_{8-12})$polycycloaryl$(C_{0-6})$alkyl, wherein within $R^{32}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above; and the N-oxide derivatives and individual stereoisomers and mixtures of stereoisomers thereof; and the pharmaceutically acceptable salts thereof.

7. The compound of claim 6 in which:

A is benzooxazol-2-yl substituted by a group R and optionally substituted with a group $R^8$, wherein $R^7$ is hydrogen, halo, $(C_{1-4})$alkoxy, $(C_{1-4})$alkoxycarbonyl, nitro or phenyl, $R^8$ at each occurrence independently is halo, $(C_{1-4})$alkoxy, $(C_{1-4})$alkoxycarbonyl, nitro or trifluoromethyl;

$X^1$ is =C—

$X^8$ is methylene or ethylene;

$R^1$ is —$X^6X^7R^{20}$, wherein $X^6$ is —C(O)— or —S(O)$_2$—, —$X^7$ is a bond, —O— or —NR$^{21}$—, wherein $R^{21}$ is hydrogen or $(C_{1-6})$alkyl, and $R^{20}$ is (i) $(C_{1-6})$alkyl optionally substituted by —C(O)OR$^{14}$ or (ii) $(C_{3-12})$cycloalkyl$(C_{0-6})$alkyl, hetero$(C_{3-12})$cycloalkyl$(C_{0-6})$alkyl, $(C_{6-12})$aryl$(C_{0-6}$alkyl or hetero$(C_{5-12})$aryl$(C_{0-6})$alkyl or (iii) $(C_{3-6})$cycloalkyl$(C_{0-6})$alkyl, hetero$(C_{3-6})$cycloalkyl$(C_{0-6})$alkyl, phenyl$(C_{0-6})$alkyl or hetero $(C_{5-6})$aryl$(C_{0-6})$alkyl, wherein said cycloalkyl, heterocycloalkyl, phenyl or heteroaryl is substituted by —$X^5OR^{24}$, —$X^5C(O)R^{24}$, —$X^5C(O)OR^{24}$, —$X^5C(O)NR^{24}R^{25}$, —$X^5NR^{24}R^{25}$, —$X^5NR^2C(O)R^{24}$, —$X^5NR^{25}C(O)OR^{24}$, —$X^5NR^{25}C(O)NR^{24}R^{25}$ or —$X^5NR^{25}C(NR^{25})NR^{24}R^{25}$, wherein $X^5$ is a bond or $(C_{1-6})$alkylene, $R^{24}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl and $R^{25}$ is hydrogen or $(C_{1-6})$alkyl; wherein within $R^1$ any alicyclic or aromatic ring system present may be substituted further by 1 to 5 substituents independently selected from $(C_{1-6})$alkyl, halo, halo-substituted $(C_{1-4})$alkyl, —OR$^{14}$ and —C(O)OR$^{14}$wherein R$^{14}$is as defined above, or when $X^2$ is a divalent group of formula (a) then $R^1$ may be, but is not limited to, hydrogen or oxalo;

$R^2$ and $R^9$ each are hydrogen;

$R^3$ is hydrogen, $(C_{1-6})$alkyl (optionally substituted with cyano, halo, nitro, —SR$^{24}$, —C(O)OR$^{24}$, —C(O)NR$^{24}R^{24}$, —P(O)(OR$^{24}$)OR$^{24}$, —OP(O)(OR$^{24}$)OR$^{24}$, S(O)R$^{25}$, —S(O)$_2$R$^{25}$ or —C(O)R$^{25}$, wherein R$^{24}$ at each occurrence independently is hydrogen, $(C_{1-6})$alkyl or halo-substituted $(C_{1-3})$alkyl and R$^{25}$ is $(C_{1-6})$alkyl or halo-substituted $(C_{1-3})$alkyl) or $(C_{6-12})$aryl $(C_{2-3})$alkyl, wherein said aryl optionally is substituted further with 1 to 5 radicals independently selected from $(C_{1-6})$alkyl, $(C_{1-6})$alkylidene, cyano, halo, halo-substituted $(C_{1-4})$alkyl, nitro, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$, $R^{14}$ and $R^{15}$ are as defined above, or $R^3$ and $R^4$ taken together with the carbon atom to which both $R^3$ and $R^4$ are attached form cyclopropylene, cyclobutylene, cyclopentylene or cyclohexylene;

$R^4$ is hydrogen or as defined above;

$R^5$ and $R^6$ together form oxo; and $R^{32}$ is —$X^9R^{34}$, wherein $X^9$ is methylene when $X^8$ is methylene or is a bond when $X^8$ is ethylene, $R^{34}$ is —$CR^{35}$=$CHR^{36}$ or —$CR^{37}$=$NR^{38}$, wherein $R^{35}$ and $R^{36}$ together with the atoms to which $R^{35}$ and $R^{36}$ are attached form $(C_{2-6})$alkenyl, $(C_{5-12})$cycloalkenyl, hetero$(C_{5-12})$cycloalkenyl, $(C_{6-12})$aryl, hetero$(C_{6-12})$aryl, $(C_{9-12})$bicycloaryl or hetero$(C_{8-12})$bicycloaryl and $R^{37}$ and $R^{38}$ together with the atoms to which $R^{37}$ and $R^{38}$ are attached form hetero$(C_{5-12})$cycloalkenyl, hetero$(C_{6-12})$aryl or hetero$(C_{8-12})$bicycloaryl, wherein within $R^{34}$ said cycloalkenyl, heterocycloalkenyl, aryl, heteroaryl, bicycloaryl or heterobicycloaryl may be substituted further by 1 to 5 radicals independently selected from $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^{14})OR^{14}$, —$X^5NR^{14}C(O)R^{15}$, —$X^5S(O)R^{15}$, —$X^5S(O)_2R^{15}$ and —$X^5C(O)R^{15}$, wherein $X^5$ is a bond or $(C_{1-6})$alkylene, $R^{14}$ at each occurrence independently is hydrogen, $(C_{1-6})$alkyl or halo-substituted $(C_{1-3})$alkyl and $R^{15}$ is $(C_{1-6})$alkyl or halo-substituted $(C_{1-3})$alkyl; and the N-oxide derivatives and individual stereoisomers and mixtures of stereoisomers thereof; and the pharmaceutically acceptable salts thereof.

8. The compound of claim 7 in which:

A is benzooxazol-2-yl, wherein $R^7$ is hydrogen, halo, $(C_{1-4})$alkoxy, $(C_{1-4})$alkoxycarbonyl or nitro and $R^8$ at each occurrence independently is halo, $(C_{1-4})$alkoxy, $(C_{1-4})$alkoxycarbonyl, nitro or trifluoromethyl;

—$X^8S(O)_2R^{32}$ is a group having the following formula:

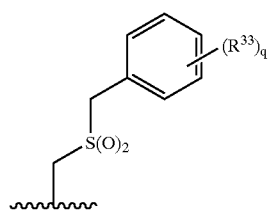

in which q is 0, 1, 2, 4 or 5 and $R^{33}$ at each occurrence independently is selected from a group consisting of $(C_{1-4})$alkyl, cyano, halo, halo-substituted $(C_{1-4})$alkyl, nitro, —$X^5NR^{14}R^{14}$, —$X^5OR^{14}$, —$X^5SR^{14}$, —$X^5C(O)NR^{14}R^{14}$, —$X^5C(O)OR^{14}$, —$X^5S(O)R^{15}$, —$X^5S(O)_2R^{15}$ and —$X^5C(O)R^{15}$, wherein $X^5$ is a bond or $(C_{1-2})$alkylene, $R^{14}$ at each occurrence independently is hydrogen, $(C_{1-3})$alkyl or halo-substituted $(C_{1-3})$alkyl and $R^{15}$ is $(C_{1-3})$alkyl or halo-substituted $(C_{1-3})$alkyl;

$R^1$ is selected from a group consisting of acetyl, azetidin-3-ylcarbonyl, benzyloxycarbonyl, 1-benzyloxycarbonylpiperidin-4-ylcarbonyl, benzylsulfonyl, bicyclo[2.2.2]hept-2-ylcarbonyl, bicyclo[2.2.1]hept-2-ylcarbonyl, tert-butoxycarbonyl, carboxyacetyl, 2-carboxypropionyl, 3-carboxypropionyl, 2-cyclohexylacetyl, 4-cyclohexylbutyryl, 2-cyclohexylethylsulfonyl, cyclohexylmethoxycarbonyl, 3-cyclohexylpropionyl, 2-cyclopentylethylsulfonyl, 3-cyclopentylpropionyl, di(2-methoxyethyl)carbamoyl, dimethylcarbamoyl, 6-hydroxypyrid-3-ylcarbonyl, 1H-imidazol-4-ylcarbonyl, methoxycarbonyl, methylsulfonyl, 4-methylvaleryl, morpholin-4-ylcarbonyl, 2-morpholin-4-ylethylcarbonyl, naphth-1-ylacetyl, naphth-1-ylmethylcarbonyl, oxalo, 3-phenylpropionyl, piperazin-1-ylcarbonyl, piperidin-4-ylcarbonyl, pyrazin-2-ylcarbonyl, pyrid-3-ylcarbonyl, pyrid-4-ylcarbonyl, pyrid-3-ylaminocarbonyl, tetrahydropyran-4-ylcarbonyl and tetrahydropyran-4-yloxycarbonyl;

$R^3$ is selected from hydrogen, $(C_{1-4})$alkyl, phenyl$(C_{2-3})$alkyl or $(C_{1-4})$alkylsulfonyl$(C_{2-4})$alkyl or $R^3$ and $R^4$ taken together with the carbon atom to which both $R^3$ and $R^4$ are attached form $(C_{3-6})$cycloalkylene;

$R^4$ is hydrogen or as defined above; and $R^{34}$ is $(C_{6-12})$aryl or hetero$(C_{5-12})$aryl, each optionally substituted by 1 to 5 radicals selected from a group consisting of $(C_{1-4})$alkyl, cyano, halo, halo-substituted $(C_{1-4})$alkyl, nitro, —$X^5NR^{14}R^{14}$, —$X^5OR^{14}$, —$X^5SR^{14}$, —$X^5C(O)NR^{14}R^{14}$, —$X^5C(O)OR^{14}$, —$X^5S(O)R^{15}$, —$X^5S(O)_2R^{15}$ and —$X^5C(O)R^{15}$, wherein $X^5$, $R^{14}$ and $R^{15}$ are as defined above; and the N-oxide derivatives and individual stereoisomers and mixtures of stereoisomers thereof; and the pharmaceutically acceptable salts thereof.

9. The compound of claim 6 in which q is 0, 1 or 2, $R^1$ is morpholin-4-ylcarbonyl, methoxycarbonyl, methylsulfonyl, piperidin-4-ylcarbonyl, pyrazin-2-ylcarbonyl, pyrid-3-ylcarbonyl, pyrid-4-ylcarbonyl, tetrahydropyran-4-ylcarbonyl or tetrahydropyran-4-yloxycarbonyl, $R^3$ is ethyl, butyl, 2-methylsulfonylethyl, phenethyl or propyl and —$X^8S(O)_2R^{32}$ is benzylsulfonylmethyl, 2-chlorobenzylsulfonylmethyl, 2-cyanobenzylsulfonylmethyl, 2-difluoromethoxybenzylsulfonylmethyl, 3,5-dimethylisooxazol-4-ylmethylsulfonylmethyl, 2-methoxybenzylsulfonylmethyl, 6-methylpyrid-2-ylmethylsulfonylmethyl, 2-nitrobenzylsulfonylmethyl, pyrid-2-ylmethylsulfonylmethyl, o-tolylmethylsulfonylmethyl or 2-trifluoromethylbenzylsulfonylmethyl; and the N-oxide derivatives and individual stereoisomers and mixtures of stereoisomers thereof; and the pharmaceutically acceptable salts thereof.

10. The compound of claim 9 selected from a group consisting of:

N-[1R-(1S-benzooxazol-2-ylcarbonylbutylcarbamoyl)-2-benzylsulfonylethyl]morpholine-4-carboxamide;

methyl 1R-(1S-benzooxazol-2-ylcarbonylbutylcarbamoyl)-2-benzylsulfonylethylcarbamate;

N-(1S-benzooxazol-2-ylcarbonylbutyl)-2R-methylsulfonylamino-3-benzylsulfonylpropionamide;

N-(1S-benzooxazol-2-ylcarbonylbutylcarbamoyl)-2R-(3,3-dimethylureido)-3-(2-methoxybenzylsulfonyl) propionamide;

N-[1R-(1S-benzooxazol-2-ylcarbonylbutylcarbamoyl)-2-(2-difluoromethoxybenzylsulfonyl)ethyl]morpholine-4-carboxamide;

N-[1R-(1S-benzooxazol-2-ylcarbonylbutylcarbamoyl)-2-(2-methoxybenzylsulfonyl)ethyl]morpholine-4-carboxamide;

N-[1R-(1S-benzooxazol-2-ylcarbonylpentylcarbamoyl)-2-benzylsulfonylethyl]morpholine-4-carboxamide;

N-[1R-(1S-benzooxazol-2-ylcarbonylpentylcarbamoyl)-2-(2-chlorobenzylsulfonyl)ethyl]morpholine-4-carboxamide;

1R-(1S-benzooxazol-2-ylcarbonylpentylcarbamoyl)-2-(2-difluoromethoxybenzylsulfonyl)ethylcarbamate;

N-[1R-(1S-benzooxazol-2-ylcarbonylpentylcarbamoyl)-2-(2-difluoromethoxybenzylsulfonyl)ethyl]morpholine-4-carboxyamide;

N-[1R-(1S-benzooxazol-2-ylcarbonylpentylcarbamoyl)-2-(3,5-dimethylisoxazol-4-ylmethylsulfonylethyl]isonicotinamide;

N-[1R-(1S-benzooxazol-2-ylcarbonylpentylcarbamoyl)-2-(2-nitrobenzylsulfonyl)ethyl]morpholine-4-carboxamide;

N-[1R-(1S-benzooxazol-2-ylcarbonylpentylcarbamoyl)-2-pyridin-2-ylmethylsulfonylethyl]morpholine-4-carboxamide;

N-[1R-(1S-benzooxazol-2-ylcarbonylpentylcarbamoyl)-2-o-tolylmethylsulfonylethyl]morpholine-4-carboxamide;

N-[1R-(1S-benzooxazol-2-ylcarbonylpentylcarbamoyl)-2-(2-trifluoromethylbenzylsulfonyl)ethyl]morpholine-4-carboxamide;

N-[1R-(1S-benzooxazol-2-ylcarbonyl-3-phenylpropylcarbamoyl)-2-benzylsulfonylethyl]nicotinamide;

N-[1R-(1S-benzooxazol-2-ylcarbonyl-3-phenylpropylcarbamoyl)-2-benzylsulfonylethyl]pyrazine-2-carboxamide;

N-[1R-(1S-benzooxazol-2-ylcarbonyl-3-phenylpropylcarbamoyl)-2-(2-chlorobenzylsulfonyl)ethyl]morpholine-4-carboxamide;

N-[1R-(1S-benzooxazol-2-ylcarbonyl-3-phenylpropylcarbamoyl)-2-(2-cyanobenzylsulfonyl)ethyl]isonicotinamide;

N-[1R-(1S-benzooxazol-2-ylcarbonyl-3-methylsulfonylpropylcarbamoyl)-2-(2-difluoromethoxybenzylsulfonyl)ethyl]morpholine-4-carboxamide;

N-[1R-(1S-benzooxazol-2-ylcarbonylpentylcarbamoyl)-2-(2-difluoromethoxybenzylsulfonyl)ethyl]isonicotinamide;

N-[1R-(1S-benzooxazol-2-ylcarbonyl)-3-phenylpropylcarbamoyl)-2-benzylsulfonylethyl]morpholine-4-carboxamide;

N-[1R-(1S-benzooxazol-2-ylcarbonyl-3-phenylpropylcarbamoyl)-2-(6-methylpyrid-2-ylmethylsulfonyl)ethyl]isonicotinamide;

N-[1R-(1S-benzooxazol-2-ylcarbonyl-3-phenylpropylcarbamoyl)-2-(2-nitrobenzylsulfonyl)ethyl]morpholine-4-carboxamide;

N-[1R-(1S-benzooxazol-2-ylcarbonyl-3-phenylpropylcarbamoyl)-2-pyrid-2-ylmethylsulfonylethyl]morpholine-4-carboxamide;

N-[1R-(1S-benzooxazol-2-ylcarbonyl-3-phenylpropylcarbamoyl)-2-o-tolylmethylsulfonylethyl]morpholine-4-carboxamide;

N-[1R-(1S-benzooxazol-2-ylcarbonyl-3-phenylpropylcarbamoyl)-2-(2-trifluoromethylbenzylsulfonyl)ethyl]tetrahydropyran-4-carboxamide;

tetrahydropyran-4-yl 1R-(1S-benzooxazol-2-ylcarbonyl-3-phenylpropylcarbamoyl)-2-benzylsulfonylethylcarbamate; and N-[1R-(1S-benzooxazol-2-ylcarbonyl-3-phenylpropylcarbamoyl)-2-(2-cyanobenzylsulfonyl)ethyl]piperidine-4-carboxamide; and the N-oxide derivatives and individual stereoisomers and mixtures of stereoisomers thereof; and the pharmaceutically acceptable salts thereof.

11. The compound of claim 6 which is A128-B14-C4-D1 of Table 1 and having the structure:

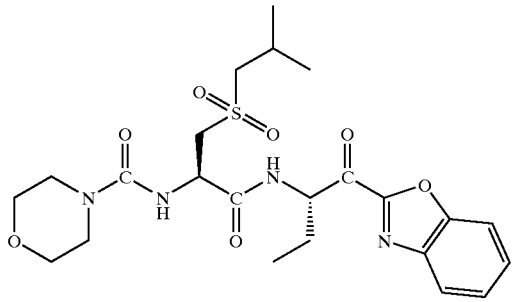

namely N-[1R-(1S-benzooxazol-2-ylcarbonylprop-1-ylcarbamoyl)-2-(2-methylprop-1-ylsulfonyl)ethyl]morpholine-4-carboxamide; and the pharmaceutically acceptable salts thereof.

12. The compound of claim 6 designated as A128-B46-C4-D1 of Table 1 and having the structure:

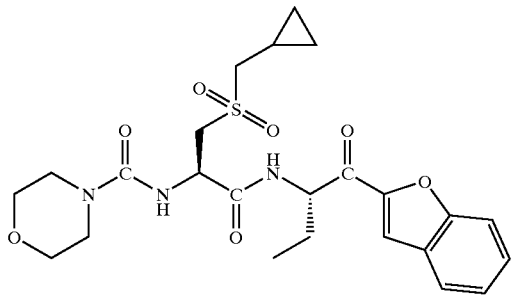

namely N-[1R-(1S-benzooxazol-2-ylcarbonylprop-1-ylcarbamoyl)-2-cyclopropylmethylsulfonylethyl]morpholine-4-carboxamide; and the pharmaceutically acceptable salts thereof.

13. A pharmaceutical composition comprising a compound of claim 6 or a N-oxide derivative thereof, or an individual stereoisomer or mixture of stereoisomers thereof; or a pharmaceutically acceptable salt thereof in admixture with one or more suitable excipients.

14. A pharmaceutical composition comprising a compound of claim 1, or a N-oxide derivative, individual stereoisomer, or mixture of stereoisomers thereof, or a pharmaceutically acceptable salt thereof in admixture with one or more suitable excipients.

15. A method of treating a disease selected from juvenile onset diabetes, multiple sclerosis, pemphigus vulgaris, rheumatoid arthritis, Hashimoto's thyroiditis, asthma, organ transplant or tissue graft rejections, chronic obstructive pulmonary disease, bronchiolitis, excessive airway elastolysis in asthma and bronchitis, pneumonities, plaque rupture and atheroma in an animal in need of such treatment, which method comprises administering a compound of claim 1 the animal; or a N-oxide derivative thereof; or an individual stereoisomer or mixture of stereoisomers thereof; or a pharmaceutically acceptable salt thereof.

16. A method of treating a disease selected from juvenile onset diabetes, multiple sclerosis, pemphigus vulgaris, rheumatoid arthritis, Hashimoto's thyroiditis, asthma, organ transplant or tissue graft rejections, chronic obstructive pulmonary disease, bronchiolitis, excessive airway elastolysis in asthma and bronchitis, pneumonities, plaque rupture and atheroma in an animal in need of such treatment, which method comprises administering a compound of claim 8 to the animal; or a N-oxide derivative thereof; or an individual stereoisomer or mixture of stereoisomers thereof; or a pharmaceutically acceptable salt thereof.

* * * * *

UNITED STATES PATENT AND TRADEMARK OFFICE
CERTIFICATE OF CORRECTION

PATENT NO. : 6,576,630 B1
APPLICATION NO. : 09/525507
DATED : June 10, 2003
INVENTOR(S) : Link et al.

It is certified that error appears in the above-identified patent and that said Letters Patent is hereby corrected as shown below:

Column 169, line 1, after the phrase "Formula (a)" beneath the structure (a), insert -- $X^3$ is -C-(O) or -CH$_2$S(O)$_2$-;--; column 169, line 1, "CR$^9$" should read --R$^9$--; line 12, "-$^5$C(O)OR$^{14}$" should read ---X$^5$C(O)OR$^{14}$--; line 15, "-X$^5$S(O)$_2$R$^{13}$" should read ---X$^5$S(O)$_2$R$^{15}$--.

Column 170, line 67, "(C$_{1\ 4}$)alkyl" should read --(C$_{1-4}$)alkyl--.

Column 171, line 52, "-NR$^{14}$R" should read ---NR$^{14}$R$^{14}$--; line 58, "-NR$^{23}$ C(O)R$^{22}$" should read ---NR$^{23}$C(O)R$^{22}$--; line 59, "NR$^{23}$C(O)OR$^{22}$" should read ---NR$^{23}$C(O)OR$^{22}$--; "NR$^{23}$C(O)NR$^{22}$R$^{23}$" should read ---NR$^{23}$C(O)NR$^{22}$R$^{23}$--; line 63, "(C$_{3-2}$)cycloalkyl(C$_{0-6}$)alkyl" should read --(C$_{3-12}$)cycloalkyl(C$_{0-6}$)alkyl--; line 63-64, "hetero(C$_{3-2}$)cycloalkyl(C$_{0-6}$)alkyl" should read --hetero(C$_{3-12}$)cycloalkyl (C$_{0-6}$)alkyl--; column 173, line 59, "-X$^5$NR$^{14}$C(O)N$^{14}$R$^{14}$" should read ---X$^5$NR$^{14}$C(O)NR$^{14}$R$^{14}$--.

Column 174, line 39, "-X$^5$NR$^2$C(O)R$^{24}$" should read ---X$^5$NR$^{25}$C(O)R$^{24}$--.

UNITED STATES PATENT AND TRADEMARK OFFICE
CERTIFICATE OF CORRECTION

PATENT NO.        : 6,576,630 B1
APPLICATION NO.   : 09/525507
DATED             : June 10, 2003
INVENTOR(S)       : Link et al.

It is certified that error appears in the above-identified patent and that said Letters Patent is hereby corrected as shown below:

Column 178, lines 21-32, the structure

"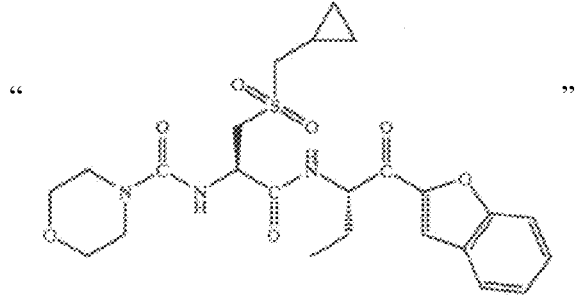"

should read

--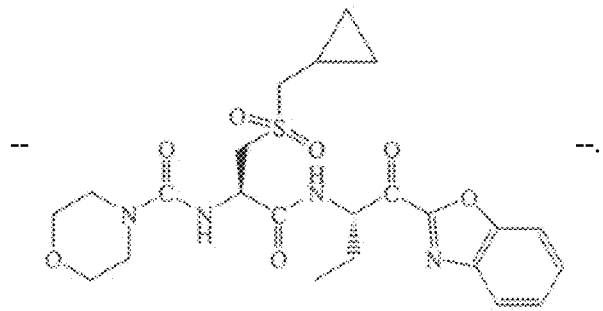--.

Column 178, line 53, after the phrase "a compound of claim 1" insert --to--.

Signed and Sealed this

Twenty-fourth Day of October, 2006

JON W. DUDAS
*Director of the United States Patent and Trademark Office*